US011427840B2

(12) United States Patent
Liao et al.

(10) Patent No.: US 11,427,840 B2
(45) Date of Patent: Aug. 30, 2022

(54) OLIVETOLIC ACID CYCLASE VARIANTS WITH IMPROVED ACTIVITY FOR USE IN PRODUCTION OF PHYTOCANNABINOIDS

(71) Applicant: Hyasynth Biologicals Inc., Montréal (CA)

(72) Inventors: Timothy S. Liao, Montréal (CA); Letian Song, Montréal (CA); Louis Hom, Ithaca, NY (US); Curtis Walton, Montréal (CA); Daniel Furlong, Montréal (CA); Mindy Melgar, Montréal (CA); Devanshi Bhargava, Montréal (CA)

(73) Assignee: Hyasynth Biologicals Inc., Montreal (CA)

( * ) Notice: Subject to any disclaimer, the term of this patent is extended or adjusted under 35 U.S.C. 154(b) by 0 days.

(21) Appl. No.: 16/953,638

(22) Filed: Nov. 20, 2020

(65) Prior Publication Data

US 2022/0170055 A1 Jun. 2, 2022

(51) Int. Cl.
*C12P 7/42* (2006.01)

(52) U.S. Cl.
CPC .................................... *C12P 7/42* (2013.01)

(58) Field of Classification Search
CPC ........................................................ C12P 7/42
See application file for complete search history.

(56) References Cited

U.S. PATENT DOCUMENTS

| | | | | |
|---|---|---|---|---|
| 7,361,482 B2 | 4/2008 | Chang et al. | | |
| 8,884,100 B2 | 11/2014 | Page et al. | | |
| 10,837,031 B2 * | 11/2020 | Barr | ........................ | C12N 9/88 |

FOREIGN PATENT DOCUMENTS

| | | | | |
|---|---|---|---|---|
| WO | 2017161041 A1 | 9/2017 | | |
| WO | 2018148848 A1 | 8/2018 | | |
| WO | 2018148849 A1 | 8/2018 | | |
| WO | 2018209143 A1 | 11/2018 | | |
| WO | WO 2020/214951 A1 * | 10/2020 | ................ | C12P 7/22 |

OTHER PUBLICATIONS

Broun et al., Catalytic plasticity of fatty acid modification enzymes underlying chemical diversity of plant lipids. Science, 1998, vol. 282: 1315-1317. (Year: 1998).*

Devos et al., Practical limits of function prediction. Proteins: Structure, Function, and Genetics. 2000, vol. 41: 98-107. (Year: 2000).*

Seffernick et al., Melamine deaminase and Atrazine chlorohydrolase: 98 percent identical but functionally different. J. Bacteriol., 2001, vol. 183 (8): 2405-2410. (Year: 2001).*

Whisstock et al., Prediction of protein function from protein sequence. Q. Rev. Biophysics., 2003, vol. 36 (3): 307-340. (Year: 2003).*

Witkowski et al., Conversion of b-ketoacyl synthase to a Malonyl Decarboxylase by replacement of the active cysteine with glutamine. Biochemistry, 1999, vol. 38: 11643-11650. (Year: 1999).*

Eisenberg et al., "Analysis of Membrane and Surface Protein Sequences With the Hydrophobic Moment Plot," Journal of Molecular Biology, 1984, vol. 179, pp. 125-142.

Flagfeldt et al., "Characterization of Chromosomal Integration Sites for Heterologous Gene Expression in *Saccharomyces cerevisiae*," Yeast, Oct. 2009, vol. 26 (10), pp. 545-551.

Gagne et al., "Identification of Olivetolic Acid Cyclase From Cannabis Sativa Reveals a Unique Catalytic Route to Plant Polyketides," Proceedings of the National Academy of Sciences of the United States of America, Jul. 2012, vol. 109 (31), pp. 12811-12816.

Ghosh et al., "Dissecting the Functional Role of Polyketide Synthases in Dictyostelium Discoideum: Biosynthesis of the Differentiation Regulating Factor 4-methyl-5-pentylbenzene-1,3-diol," The Journal of Biological Chemistry, Apr. 2008, vol. 283 (17), pp. 11348-11354, ISSN 0021-9258.

Gieiz et al., "High-Efficiency Yeast Transformation Using the LiAc/SS Carrier DNA/PEG Method," Nature Protocols, 2007, vol. 2(1), pp. 31-34.

Gietz et al., "Yeast Transformation by the LiAc/SS Carrier DNA/PEG Method," Methods in Molecular Biology, 2014, vol. 1205. https://doi.org/10.1007/978-1-4939-1363-3_1.

Jensen et al., "EasyClone: Method for Iterative Chromosomal Integration of Multiple Genes in *Saccharomyces cerevisiae*," FEMS Yeast Research, Mar. 2014, vol. 14(2), pp. 238-248. https://doi.org/10.1111/1567-1364.12118.

Kim et al., "Characterization of NpgA, a 4'-Phosphopantetheinyl Transferase of Aspergillus Nidulans, and Evidence of Its Involvement in Fungal Growth and Formation of Conidia and Cleistothecia for Development," Journal of Microbiology, Jan. 2015, vol. 53 (1), pp. 21-31.

Kuzuyama et al., "Structural Basis for the Promiscuous Biosynthetic Prenylation of Aromatic Natural Products," Nature, Jun. 2005, vol. 435 (7044), pp. 983-987.

Liu et al., "Overproduction of Geraniol by Enhanced Precursor Supply in *Saccharomyces cerevisiae*," Journal of Biotechnology, Dec. 2013, vol. 168 (4), pp. 446-451.

Luo et al., "Complete Biosynthesis of Cannabinoids and Their Unnatural Analogues in Yeast," Nature, Mar. 2019, vol. 567(7746), pp. 123-126.

(Continued)

*Primary Examiner* — Ganapathirama Raghu
(74) *Attorney, Agent, or Firm* — Borden Ladner Gervais LLP; Kathleen E. Marsman

(57) ABSTRACT

The present disclosure relates generally to methods, isolated polypeptides and polynucleotides, expression vectors, and host cells for the production of olivetolic acid and phytocannabinoids. A method of producing olivetolic acid (OVLa) and/or a phytocannabinoid in a heterologous host cell having OVLa-producing or phytocannabinoid-producing capacity comprises transforming the host cell with a nucleotide encoding a variant olivetolic acid cyclase (OAC) protein having at least 6 amino acid mutations relative to the wild type OAC protein, and culturing the transformed host cell to produce OVLa and/or phytocannabinoids therefrom. The variant OAC protein (SEQ ID NO:92) has at least 85% sequence identity with the wild type OAC protein (SEQ ID NO:91). Exemplary variants having improved OVLa or phytocannabinoid production capacity are described.

14 Claims, 5 Drawing Sheets

Specification includes a Sequence Listing.

(56) References Cited

OTHER PUBLICATIONS

Oswald et al., "Monoterpenoid Biosynthesis in *Saccharomyces cerevisiae*," FEMS Yeast Research, May 2007, vol. 7(3), pp. 413-421. https://doi.org/10.1111/j.1567-1364.2006.00172.x.
Peng et al., "Engineered Protein Degradation of Farnesyl Pyrophosphate Synthase is an Effective Regulatory Mechanism to Increase Monoterpene Production in *Saccharomyces cerevisiae*," Metabolic Engineering, May 2018, vol. 47, pp. 83-93. https://doi.org/10.1016/J.YMBEN.2018.02.005.
Ro et al., "Production of the Antimalarial Drug Precursor Artemisinic Acid in Engineered Yeast," Nature Letters, Apr. 2006, vol. 440(7086), pp. 940-943.
Ryan et al., "CRISPR-Cas9 Genome Engineering in *Saccharomyces cerevisiae* Cells," Cold Spring Harbor Protocols, Jun. 2016, vol. 2016(6). https://doi.org/10.1101/pdb.prot086827.
Saeki et al., "An Aromatic Farnesyltransferase Functions in Biosynthesis of the Anti-HIV Meroterpenoid Daurichromenic Acid," Plant Physiology, Oct. 2018, vol. 178(2), pp. 535-551. https://doi.org/10.1104/PP.18.00655.
Shi et al., "Improving Production of Malonyl Coenzyme A-Derived Metabolites by Abolishing Snf1-Dependent Regulation of Acc1" American Society for Microbiology, May 2014, vol. 5 (3), pp. e01130-14.
Shiba et al., "Engineering of the Pyruvate Dehydrogenase Bypass in *Saccharomyces cerevisiae* for High-Level Production of Isoprenoids," Metabolic Engineering, Mar. 2007, vol. 9 (2), pp. 160-168.
Sirikantaramas et al., "Tetrahydrocannabinolic Acid Synthase, the Enzyme Controlling Marijuana Psychoactivity, is Secreted Into the Storage Cavity of the Glandular Trichomes," Plant & Cell Physiology, 2005, vol. 46(9), pp. 1578-1582.
Stout et al., "The Hexanoyl-CoA Precursor for Cannabinoid Biosynthesis is Formed by an Acyl-activating Enzyme in *Cannabis sativa* Trichomes," The Plant Journal, Aug. 2012, vol. 71 (3), pp. 353-365.
Taura et al., "Characterization of Olivetol Synthase, A Polyketide Synthase Putatively Involved in Cannabinoid Biosynthetic Pathway," FEBS Letters, Jun. 2009, vol. 583 (12), pp. 2061-2066, ISSN 0014-5793.
Varshavsky., "The N-End Rule Pathway and Regulation by Proteolysis," Protein Science, Jun. 2011, vol. 20, pp. 1298-1345.
GenBank NCBI Reference Sequence XM _030652929.1, "Predicted: *Cannabis sativa* olivetolic acid cyclase (LOC 115723438), mRNA", Aug. 28, 2019 [online] [retrieved on Jan. 21, 2022]. Retrieved from the internet: https:/ /www .nc bi.nlm.nih.gov /nuccore/ 1731724904 ?sat=48&satkey=813 31592.
International Patent Application No. PCT/CA2021/051626, International Search Report and Written Opinion dated Feb. 3, 2022.
Yang et al., "Structural Basis for Olivetolic Acid Formation by a Polyketide Cyclase From *Cannabis sativa*," The FEBS Journal, Mar. 2016, vol. 283 (6), pp. 1088-1106.

* cited by examiner

1: Hexanoyl-coA Synthase

2: Olivetolic Acid Synthase

3: Olivetolic Acid Cyclase

4: Prenyltransferase

5: Cannabidiolic Acid Synthase

6: Tetrahydrocannabinolic Acid Synthase

1: DiPKS

2: Olivetolic Acid Cyclase

3: Prenyltransferase

4: Cannabidiolic Acid Synthase

5: Tetrahydrocannabinolic Acid Synthase

OLIVETOLIC ACID CYCLASE VARIANTS WITH IMPROVED ACTIVITY FOR USE IN PRODUCTION OF PHYTOCANNABINOIDS

CROSS REFERENCE TO RELATED APPLICATIONS

None.

FIELD

The present disclosure relates generally to proteins having olivetolic acid cyclase activity, useful in production of phytocannabinoids.

BACKGROUND

Phytocannabinoids are a large class of compounds with over 100 different known structures that are produced in the *Cannabis sativa* plant. Phytocannabinoids are known to be biosynthesized in *C. sativa*, or may result from thermal or other decomposition from phytocannabinoids biosynthesized in *C. sativa*. These bio-active molecules, such as tetrahydrocannabinol (THC) and cannabidiol (CBD), can be extracted from plant material for medical and recreational purposes. However, the synthesis of plant material is costly, not readily scalable to large volumes, and requires lengthy growing periods to produce sufficient quantities of phytocannabinoids. While the *C. sativa* plant is also a valuable source of grain, fiber, and other material, growing *C. sativa* for phytocannabinoid production, particularly indoors, is costly in terms of energy and labour. Subsequent extraction, purification, and fractionation of phytocannabinoids from the *C. sativa* plant is also labour and energy intensive.

Phytocannabinoids are pharmacologically active molecules that contribute to the medical and psychotropic effects of *C. sativa*. Biosynthesis of phytocannabinoids in the *C. sativa* plant scales similarly to other agricultural projects. As with other agricultural projects, large scale production of phytocannabinoids by growing *C. sativa* requires a variety of inputs (e.g. nutrients, light, pest control, CO, etc.). The inputs required for cultivating *C. sativa* must be provided. In addition, cultivation of *C. sativa*, where allowed, is currently subject to heavy regulation, taxation, and rigorous quality control where products prepared from the plant are for commercial use, further increasing costs.

Phytocannabinoid analogues are pharmacologically active molecules that are structurally similar to phytocannabinoids. Phytocannabinoid analogues are often synthesized chemically, which can be labour intensive and costly. As a result, it may be economical to produce the phytocannabinoids and phytocannabinoid analogues in a robust and scalable, fermentable organism. *Saccharomyces cerevisiae* is an example of a fermentable organism that has been used to produce industrial scales of similar molecules.

The extensive time, energy, and labour involved in growing *C. sativa* for production of naturally-occurring phytocannabinoids provides a motivation to produce transgenic cell lines for production of phytocannabinoids by other means. Polyketides, including olivetolic acid and its analogues are valuable precursors to phytocannabinoids.

It is desirable to find alternative enzymes and methods for the production of phytocannabinoids, and/or for the production of compounds useful in phytocannabinoid biosynthesis as intermediate or precursor compounds.

SUMMARY

Olivetolic Acid Cyclase (OAC) variants are described herein which are capable of producing olivetolic acid (OVLa). These variants are useful in the production of olivetolic acid and relevant phytocannabinoids in a heterologous host. Methods of production are described. The described OAC variants that can produce olivetolic acid and downstream metabolites in a modified yeast cell can be applied to any host and used in phytocannabinoid production.

In certain aspects described, OAC variants comprise 6 or greater non-conservative substitution amino acid mutations relative to the wild type enzyme. Certain OAC variants described have improved activity and/or show improved ratios of olivetol to olivetolic acid compared to the wild type enzyme.

A method of producing OVLa or a phytocannabinoid derived therefrom in a heterologous host cell having OVLa-producing or phytocannabinoid-producing capacity is described. The method comprises: transforming the host cell with a nucleotide encoding a variant olivetolic acid cyclase (OAC) protein having at least 6 amino acid mutations relative to the wild type OAC protein, and culturing said transformed host cell to produce olivetolic acid and/or phytocannabinoids therefrom, wherein the variant OAC protein comprises at least 85% sequence identity with the wild type OAC protein sequence according to SEQ ID NO:91.

An isolated polypeptide having olivetolic acid cyclase activity is described, comprising an amino acid sequence according to SEQ ID NO: 92, wherein 6 or more amino acid residues comprise mutations relative to SEQ ID NO:91, located at 6 or more of residues 28, 31, 41, 43, 44, 68, 74, 84, 100 or 102 of SEQ ID NO:91.

An isolated polynucleotide is described, comprising: (a) a nucleotide sequence according to SEQ ID NO:3-SEQ ID NO:39; (b) a nucleotide sequence having at least 85% identity with the nucleotide sequence of (a), or (c) a nucleotide sequence that hybridizes with the complementary strand of the nucleotide having the sequence of (a). Expression vectors comprising the polynucleotide, and host cells transformed with such expression vectors are described.

Other aspects and features of the present disclosure will become apparent to those ordinarily skilled in the art upon review of the following description of specific embodiments in conjunction with the accompanying figures.

BRIEF DESCRIPTION OF THE FIGURES

Embodiments of the present disclosure will now be described, by way of example only, with reference to the attached Figures.

DETAILED DESCRIPTION

Figure 1:
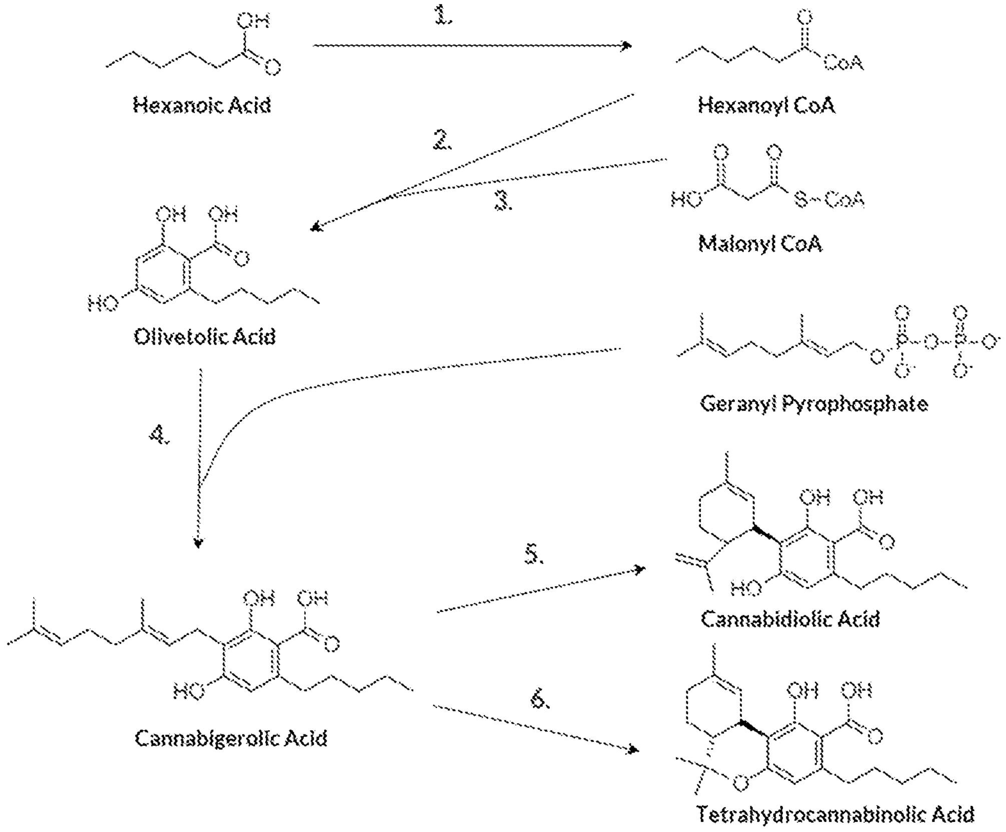
FIG. 1 illustrates a cannabinoid biosynthesis pathway in *Cannabis sativa.*

A method of producing olivetolic acid (OVLa) or a phytocannabinoid produced therefrom is described herein. A heterologous host cell comprising OVLa-producing or phytocannabinoid-producing capacity is transformed with a nucleotide encoding a variant olivetolic acid cyclase (OAC) protein having at least 6 amino acid mutations relative to the wild type OAC protein and culturing said transformed host cell to produce olivetolic acid and/or phytocannabinoids therefrom, wherein the variant OAC protein comprises at least 85% sequence identity with the wild type OAC protein sequence according to SEQ ID NO: 91. Exemplary variant proteins may result in improved OVLa or phytocannabinoid production over wild type according to the method described.

In some embodiments, at least 4 of the at least 6 amino acid mutations of the OAC protein are in residues 28, 31, 41, 43, 44, 68, 74, 84, 100 or 102 of the wild type OAC protein (SEQ ID NO:91), with other mutations being located elsewhere in the sequence. When a mutation is present at residue 28, 31, 41, 43, 44, 68, 74, 84, 100 or 102, it can be either a conservative or non-conservative amino acid substitution, but may advantageously be a non-conservative amino acid substitution. While at least 4 of the 6 amino acid mutations are present in the specified residue locations, in exemplary embodiments, more than 4 may be present in the specified residues, such as 6, 7, 8, 9 or 10 of the amino acid mutations may be found at positions 28, 31, 41, 43, 44, 68, 74, 84, 100 or 102, relative to the wild type sequence. In certain embodiments, mutations other than those located at residue 28, 31, 41, 43, 44, 68, 74, 84, 100 or 102 may be limited to conservative amino acid substitutions, such that the variant OAC protein remains within 85% sequence identity with the wild type OAC protein.

The method may encompass transformation of the host cell with a nucleotide encoding the variant olivetolic acid cyclase (OAC) protein, which nucleotide has a sequence comprising: (a) a nucleotide sequence according to SEQ ID NO:3-SEQ ID NO:39; (b) a nucleotide sequence having at least 85% identity with the sequence of (a); or (c) a nucleotide sequence that hybridizes with the complementary strand of the nucleotide having the sequence of (a). For example, the variant OAC protein may comprise a according to any one of SEQ ID NO:40 to SEQ ID NO:76.

In certain embodiments, at least 4 of the at least 6 amino acid mutations relative to the wild type OAC protein are selected from the group consisting of: V28A; V31G; Y41T, Y41S or Y41V; K44V; T68L or T68R; I74E, I74R, I74D or I74G; V84R; R100M or R100E; and G102R, G102S, or G102STOP.

In the method, the production of a phytocannabinoid by the transformed host cell may involve production of phytocannabinoids including but not limited to cannabigerol (CBG), cannabigerolic acid (CBGa), cannabigerovarin (CBGV), cannabigerovarinic acid (CBGVa), cannabigerocin (CBGO), cannabigerocinic acid (CBGOa), a cannabivarin, tetrahydrocannabinol (THC), or tetrahydrocannabinolic acid (THCa). Further, using the OAC variants described, in combination with a divarinic acid synthase within the host cell, the host cell may produce a cannabivarin, such as divarinic acid.

The host cell transformed in the method described may be a bacterial cell, a fungal cell, a protist cell, or a plant cell. Exemplary organisms include *S. cerevisiae, E. coli, Yarrowia lipolytica*, or *Komagataella phaffii*, as well as others described herein. The transformed host cell may additionally comprise, or be transformed with, other enzymes useful in phytocannabinoid production. For example, a polynucleotide encoding a polyketide synthase enzyme and/or a polynucleotide encoding a prenyltransferase enzyme may also be included in the host cell. Further options for polynucleotides and methods, such as described in Applicant's co-pending International Application No. PCT/CA2020/050687 (hereby incorporated by reference) are envisioned.

An isolated polypeptide is described herein, which has olivetolic acid cyclase (OAC) activity. The polypeptide activity comprises an amino acid sequence according to SEQ ID NO: 92, wherein 6 or more amino acid residues comprise mutations relative to SEQ ID NO: 91 (wild type OAC) which are mutations at residues 28, 31, 41, 43, 44, 68, 74, 84, 100 or 102 of SEQ ID NO:91. The isolated polypeptide may have an amino acid sequence according to one of SEQ ID NO:40 to SEQ ID NO:76.

An isolated polynucleotide is described, which may have (a) a nucleotide sequence according to SEQ ID NO:3-SEQ ID NO:39; (b) a nucleotide sequence having at least 85% identity with the nucleotide sequence of (a), or (c) a nucleotide sequence that hybridizes with the complementary strand of the nucleotide having the sequence of (a).

An expression vector is described, comprising a polynucleotide encoding a variant olivetolic acid cyclase (OAC) protein having the sequence of SEQ ID NO: 92, in which 6 or more amino acid mutations are present relative to the wild type OAC protein. In such an expression vector, the polynucleotide encoding the variant OAC protein may have at least 85% sequence identity with any one of SEQ ID NO:3 to SEQ ID NO:39.

A host cell transformed with the above-described expression vector is also encompassed herein. Such a host cell may additionally comprise a polynucleotide encoding other enzymes useful in synthesis of olivetolic acid and/or phytocannabinoids, such as encoding a polyketide synthase enzyme and/or a prenyltransferase enzyme. Such a host cell may be a bacterial cell, a fungal cell, a protist cell, or a plant cell, for example: *S. cerevisiae, E. coli, Yarrowia lipolytica*, or *Komagataella phaffii*.

Definitions

Certain terms used herein are described below.

The term "cannabinoid" as used herein refers to a chemical compound that shows direct or indirect activity at a cannabinoid receptor. Non limiting examples of cannabinoids include tetrahydrocannabinol (THC), cannabidiol (CBD), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), and cannabigerol monomethyl ether (CBGM).

The term "phytocannabinoid" as used herein refers to a cannabinoid that typically occurs in a plant species. Exemplary phytocannabinoids produced according to the invention include cannabigerol (CBG), cannabigerolic acid (CBGa), cannabigerovarin (CBGV), cannabigerovarinic acid (CBGVa), cannabigerocin (CBGo), or cannabigerocinic acid (CBGoa).

Cannabinoids and phytocannabinoids may contain or may lack one or more carboxylic acid functional groups. Non limiting examples of such cannabinoids or phytocannabinoids containing carboxylic acid function groups or phytocannabinoids include tetrahydrocannabinolic acid (THCA), cannabidiolic acid (CBDA), and cannabichromenic acid (CBCA).

The term "homologue" includes homologous sequences from the same and other species and orthologous sequences from the same and other species. Different polynucleotides or polypeptides having homology may be referred to as homologues.

The term "homology" may refer to the level of similarity between two or more polynucleotide and/or polypeptide sequences in terms of percent of positional identity (i.e., sequence similarity or identity). Homology also refers to the concept of similar functional properties among different polynucleotide or polypeptides. Thus, the compositions and methods herein may further comprise homologues to the polypeptide and polynucleotide sequences described herein.

The term "orthologous," as used herein, refers to homologous polypeptide sequences and/or polynucleotide sequences in different species that arose from a common ancestral gene during speciation.

As used herein, a "homologue" may have a significant sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% and/or 100%) to the polynucleotide sequences herein.

As used herein "sequence identity" refers to the extent to which two optimally aligned polynucleotide or peptide sequences are invariant throughout a window of alignment of components, e.g., nucleotides or amino acids. "Identity" can be readily calculated by known methods.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

The terms "fatty acid-CoA", "fatty acyl-CoA", or "CoA donors" as used herein may refer to compounds useful in polyketide synthesis as primer molecules which react in a condensation reaction with an extender unit (such as malonyl-CoA) to form a polyketide. Examples of fatty acid-CoA molecules (also referred to herein as primer molecules or CoA donors), useful in the synthetic routes described herein include but are not limited to: acetyl-CoA, butyryl-CoA, hexanoyl-CoA. These fatty acid-CoA molecules may be provided to host cells or may be synthesized by the host cells for biosynthesis of polyketides, as described herein.

Two nucleotide sequences can be considered to be substantially "complementary" when the two sequences hybridize to each other under stringent conditions. In some examples, two nucleotide sequences considered to be substantially complementary hybridize to each other under highly stringent conditions.

The terms "stringent hybridization conditions" and "stringent hybridization wash conditions" in the context of nucleic acid hybridization experiments, for example in Southern hybridizations and Northern hybridizations are sequence dependent, and are different under different environmental parameters. In some examples, generally, highly stringent hybridization and wash conditions are selected to be about 5° C. lower than the thermal melting point (Tm) for the specific sequence at a defined ionic strength and pH.

In some examples, polynucleotides include polynucleotides or "variants" having at least about 50%, 55%, 60%, 65%, 70%, 75%, 80%, 85%, 90%, 95%, 96%, 97%, 98%, 99% or 100% sequence identity to any of the reference sequences described herein, typically where the variant maintains at least one biological activity of the reference sequence.

As used herein, the terms "polynucleotide variant" and "variant" and the like refer to polynucleotides displaying substantial sequence identity with a reference polynucleotide sequence or polynucleotides that hybridize with a reference sequence under, for example, stringent conditions. These terms may include polynucleotides in which one or more nucleotides have been added or deleted, or replaced with different nucleotides compared to a reference polynucleotide. It will be understood that that certain alterations inclusive of mutations, additions, deletions and substitutions can be made to a reference polynucleotide whereby the altered polynucleotide retains the biological function or activity of the reference polynucleotide.

In some examples, the polynucleotides described herein may be included within "vectors" and/or "expression cassettes".

In some embodiments, the nucleotide sequences and/or nucleic acid molecules described herein may be "operably" or "operatively" linked to a variety of promoters for expression in host cells. Thus, in some examples, the invention provides transformed host cells and transformed organisms comprising the transformed host cells, wherein the host cells and organisms are transformed with one or more nucleic acid molecules/nucleotide sequences of the invention. As used herein, "operably linked to," when referring to a first nucleic acid sequence that is operably linked to a second nucleic acid sequence, means a situation when the first nucleic acid sequence is placed in a functional relationship with the second nucleic acid sequence. For instance, a promoter is operably associated with a coding sequence if the promoter effects the transcription or expression of the coding sequence.

In the context of a polypeptide, "operably linked to," when referring to a first polypeptide sequence that is operably linked to a second polypeptide sequence, refers to a situation when the first polypeptide sequence is placed in a functional relationship with the second polypeptide sequence.

The term a "promoter," as used herein, refers to a nucleotide sequence that controls or regulates the transcription of a nucleotide sequence (i.e., a coding sequence) that is operably associated with the promoter. Typically, a "promoter" refers to a nucleotide sequence that contains a binding site for RNA polymerase II and directs the initiation of transcription. In general, promoters are found 5', or upstream, relative to the start of the coding region of the corresponding coding sequence. The promoter region may comprise other elements that act as regulators of gene expression.

Promoters can include, for example, constitutive, inducible, temporally regulated, developmentally regulated, chemically regulated, tissue-preferred and tissue-specific promoters for use in the preparation of recombinant nucleic acid molecules, i.e., chimeric genes.

The choice of promoter will vary depending on the temporal and spatial requirements for expression, and also depending on the host cell to be transformed. Thus, for example, where expression in response to a stimulus is desired a promoter inducible by stimuli or chemicals can be used. Where continuous expression at a relatively constant level is desired throughout the cells or tissues of an organism a constitutive promoter can be chosen.

In some examples, vectors may be used.

In some examples, the polynucleotide molecules and nucleotide sequences described herein can be used in connection with vectors.

The term "vector" refers to a composition for transferring, delivering or introducing a nucleic acid or polynucleotide into a host cell. A vector may comprise a polynucleotide molecule comprising the nucleotide sequence(s) to be transferred, delivered or introduced. Non-limiting examples of general classes of vectors include, but are not limited to, a viral vector, a plasmid vector, a phage vector, a phagemid vector, a cosmid, a fosmid, a bacteriophage, or an artificial chromosome. The selection of a vector will depend upon the preferred transformation technique and the target species for transformation.

As used herein, "expression vectors" refers to a nucleic acid molecule comprising a nucleotide sequence of interest, wherein said nucleotide sequence is operatively associated with at least a control sequence (e.g., a promoter). Thus, some examples provide expression vectors designed to express the polynucleotide sequences of described herein.

An expression vector comprising a polynucleotide sequence of interest may be "chimeric", meaning that at least one of its components is heterologous with respect to at least one of its other components. An expression cassette may also be one that is naturally occurring but has been obtained in a recombinant form useful for heterologous expression. In some examples, however, the expression vector is heterologous with respect to the host. For example, the particular polynucleotide sequence of the expression vector does not occur naturally in the host cell and must have been introduced into the host cell or an ancestor of the host cell by a transformation event.

In some examples, an expression vector may also include other regulatory sequences. As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. Regulatory sequences include, but are not limited to, promoters, enhancers, introns, 5' and 3' untranslated regions, translation leader sequences, termination signals, and polyadenylation signal sequences.

An expression vector may also include a nucleotide sequence for a selectable marker, which can be used to select a transformed host cell.

As used herein, "selectable marker" means a nucleotide sequence that when expressed imparts a distinct phenotype to the host cell expressing the marker and thus allows such transformed host cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, a sugar, a carbon source, or the like), or on whether the marker is simply a trait that one can identify through observation or testing, such as by screening. Examples of suitable selectable markers are known in the art and can be used in the expression vectors described herein.

The vector and/or expression vectors and/or polynucleotides may be introduced in to a cell.

The term "introducing," in the context of a nucleotide sequence of interest (e.g., the nucleic acid molecules/constructs/expression vectors), refers to presenting the nucleotide sequence of interest to cell host in such a manner that the nucleotide sequence gains access to the interior of a cell. Where more than one nucleotide sequence is to be introduced these nucleotide sequences can be assembled as part of a single polynucleotide or nucleic acid construct, or as separate polynucleotide or nucleic acid constructs, and can be located on the same or different transformation vectors. Accordingly, these polynucleotides may be introduced into host cells in a single transformation event, or in separate transformation events.

As used herein, the term "contacting" refers to a process by which, for example, a compound may be delivered to a cell. The compound may be administered in a number of ways, including, but not limited to, direct introduction into a cell (i.e., intracellularly) and/or extracellular introduction into a cavity, interstitial space, or into the circulation of the organism.

The term "transformation" or "transfection" as used herein refers to the introduction of a polynucleotide or heterologous nucleic acid into a cell. Transformation of a cell may be stable or transient.

The term "transient transformation" as used herein in the context of a polynucleotide refers to a polynucleotide introduced into the cell and does not integrate into the genome of the cell.

The terms "stably introducing" or "stably introduced" in the context of a polynucleotide introduced into a cell is intended to represent that the introduced polynucleotide is stably incorporated into the genome of the cell, and thus the cell is stably transformed with the polynucleotide.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transformed in vivo or in vitro with a recombinant vector or a polynucleotide of the invention. A host cell which comprises a recombinant vector of the invention is a recombinant host cell.

In some examples, a host cell may be a bacterial cell, a fungal cell, a protist cell, or a plant cell. Specific examples of host cells are described below.

"Conversion" refers to the enzymatic transformation of a substrate to the corresponding product. "Percent conversion" refers to the percent of the substrate that is converted to the product within a period of time under specified conditions. Thus, for example, the "activity" or "conversion rate" of a ketoreductase polypeptide can be expressed as "percent conversion" of the substrate to the product.

"Hydrophilic Amino Acid or Residue" refers to an amino acid or residue having a side chain exhibiting a hydrophobicity of less than zero according to the normalized consensus hydrophobicity scale Eisenberg et al., 1984. Genetically encoded hydrophilic amino acids include L-Thr (T), L-Ser (S), L-His (H), L-Glu (E), L-Asn (N), L-Gln (Q), L-Asp (D), L-Lys (K) and L-Arg (R).

"Acidic Amino Acid or Residue" refers to a hydrophilic amino acid or residue having a side chain exhibiting a pKa value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic Amino Acid or Residue" refers to a hydrophilic amino acid or residue having a side chain exhibiting a pKa value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Polar Amino Acid or Residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S) and L-Thr (T).

"Hydrophobic Amino Acid or Residue" refers to an amino acid or residue having a side chain exhibiting a hydrophobicity of greater than zero according to the normalized consensus hydrophobicity scale (Eisenberg et al., 1984). Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic Amino Acid or Residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (V). Although owing to the pKa of its heteroaromatic nitrogen atom L His (H) it is sometimes classified as a basic residue, or as an aromatic residue as its side chain includes a heteroaromatic ring, herein histidine is classified as a hydrophilic residue.

"Constrained amino acid or residue" refers to an amino acid or residue that has a constrained geometry. Herein, constrained residues include L-Pro (P) and L-His (H). Histidine has a constrained geometry because it has a relatively small imidazole ring. Proline has a constrained geometry because it also has a five membered ring.

"Non-polar Amino Acid or Residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Aliphatic Amino Acid or Residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Small Amino Acid or Residue" refers to an amino acid or residue having a side chain that is composed of a total three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

A "conservative" amino acid substitution (or mutation) refers to the substitution of a residue with a residue having a similar side chain, and thus typically involves substitution of the amino acid in the polypeptide with amino acids within the same or similar defined class of amino acids. For the following residues, the possible conservative mutations are provided in parentheses: A, L, V, I (Other aliphatic residues: A, L, V, I); A, L, V, I, G, M (Other non-polar residues: A, L, V, I, G, M); D, E (Other acidic residues: D, E); K, R (Other basic residues: K, R); P, H (Other constrained residues: P, H); N, Q, S, T (Other polar residues: N, Q, S, T); Y, W, F (Other aromatic residues: Y, W, F); and C (none).

Phytocannabinoids are a large class of compounds with over 100 different known structures that are produced in the *Cannabis* plant. These bio-active molecules, such as tetrahydrocannabinol (THC) and cannabidiol (CBD), can be extracted from plant material for medical and psychotropic purposes. However, the synthesis of plant material is costly, not readily scalable to large volumes, and requires lengthy growth periods to produce sufficient quantities of phytocannabinoids. A fermentable organism such as *Saccharomyces cerevisiae* capable of producing cannabinoids would provide an economical route to producing these compounds on an industrial scale. The extensive time, energy, and labour involved in growing *C. sativa* for phytocannabinoid production provides a motivation to produce transgenic cell lines for production of phytocannabinoids in yeast. One example of such efforts is provided in PCT application by Mookerjee et al WO2018/148848. Aromatic prenyltransferase from *cannabis* are described by Page et al. in U.S. Pat. No. 8,884,100.

FIG. 1 illustrates a cannabinoid biosynthesis pathway in *Cannabis sativa*. As expression and functionality of the *C. sativa* pathway in *S. cerevisiae* is hindered by problems of toxic precursors and poor expression, a novel biosynthetic route for cannabinoid production was developed that overcomes said issues. This pathway is described in FIG. 1 and comprises a multi-enzyme system. DiPKS from *D. discoideum* and OAC from *C. sativa* are used to produce olivetolic acid directly from glucose. GPP from the yeast terpenoid pathway and OLA are subsequently converted to cannabigerolic acid catalyzed by using a prenyltransferase. Then, *C. sativa* THCa synthase or CBDa synthase is used to further cyclize cannabigerolic acid to form THCa or CBDa respectively.

Figure 2:
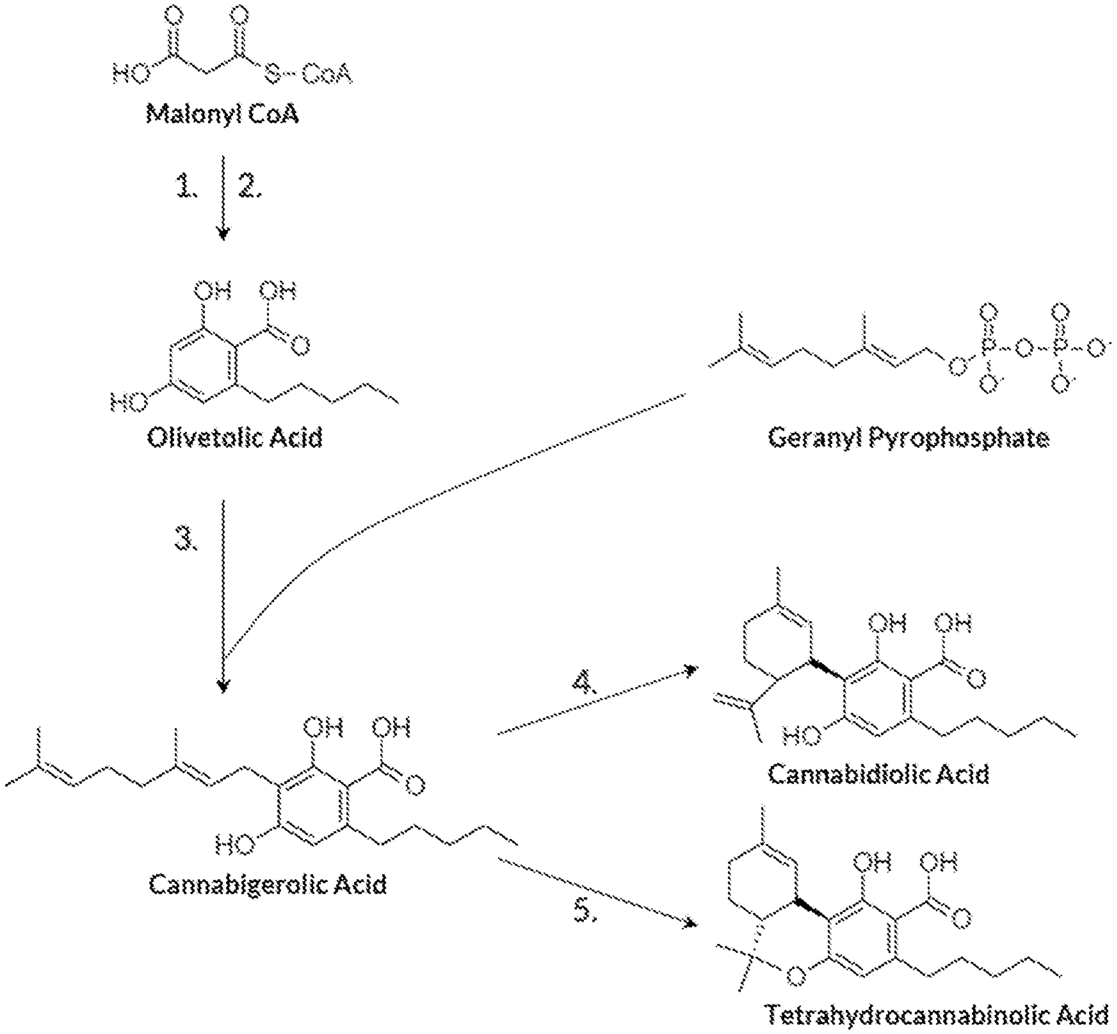
FIG. 2 illustrates a cannabinoid biosynthesis pathway as described in Applicant's co-pending International Application No. PCT/CA2020/050687.

FIG. 2 illustrates a cannabinoid biosynthesis pathway as described in Applicant's co-pending PCT Application No. CA2020/050687 (Bourgeois et al., filed May 21, 2019), which is herein incorporated by reference.

The first committed step in the cannabinoid biosynthesis pathway is the biosynthesis of olivetolic acid. This is done using a polyketide synthase such as DiPKS (Ghosh et al., 2008) from *D. discoideum* or OAS (Taura et al., 2009) from *C. sativa* and also requires the use of an olivetolic acid cyclase (OAC) (Gagne et al., 2012). The process begins with the polyketide synthase condensing three units of malonyl-CoA to form a linear tetraketide. Olivetolic acid cyclase can then cyclize the tetraketide backbone to form olivetolic acid. In the absence of OAC, the tetraketide can spontaneously cyclize to form olivetol, an unwanted byproduct in the cannabinoid biosynthesis pathway. In order to improve enzyme performance in a heterologous host, the authors subjected OAC to an enzyme engineering regimen.

Enzyme engineering is the process of improving a desired phenotype of the enzyme by making modifications to the amino acid sequence of the polypeptide. As the functionality of the enzyme is dependent on the structure of the enzyme and the structure of the enzyme is dependent, partially, on the primary amino acid sequence; modification of the amino acid sequence of the enzyme could lead to a beneficial impact on the desired phenotype. This principle was applied to olivetolic acid cyclase (OAC) and modifications were made to its amino acid sequence using a directed evolution approach. This allowed for the identification of amino acid residues that improved olivetolic acid production in a strain of recombinant *S. cerevisiae*. Beneficial mutations were then tested in conjunction to identify combinations of mutations that improve enzyme performance.

Sequences are described herein that have multiple residues modified as compared to the wild type OAC sequence. Certain mutations produce over 2x more olivetolic acid than the wild type OAC when expressed in *S. cerevisiae*. Improvements to one or more enzyme properties as exhibited in the engineered OACs may include increases in enzyme activity, improved enzyme kinetics and turnover, higher tolerance to increased levels of substrate, and improved tolerance to increased product levels.

The modifications of the amino acid residues, as compared to the wild type OAC sequence may be conservative modifications or non-conservative modifications. Insertions or deletions may be used to modify the residues, relative to wild type OAC. Note that in the OAC described herein, the protein may end at position 101 instead of 102, as in other reports of wild type OAC sequences. In embodiments described herein, the residues represented as X{#} may be modified, where {#} represents the sequence position in the amino acid position of the wild type OAC sequence referenced herein as (SEQ ID NO:91). Thus, SEQ ID NO:92 comprises the option of mutations at X{28}, X{31}, X{41}, X{43}, X{44}, X{68}, X{74}, X{84}, X{100}, and X{102}, as outlined below:

SEQ ID NO:91 represents wild type OAC protein:

```
MAVKHLIVLK FKDEITEAQK EEFFKTYVNL VNIIPAMKDV YWGKDVTQKN    50

KEEGYTHIVE VTFESVETIQ DYIIHPAHVG FGDVYRSFWE KLLIFDYTPR   100

KG                                                       102
```

SEQ ID NO:92 represents the generalized variant OAC protein, wherein X represents candidate locations for mutated residues (where X represents any amino acid):

```
MAVKHLIVLK FKDEITEAQK EEFFKTYXNL XNIIPAMKDV XWXXDVTQKN    50

KEEGYTHIVE VTFESVEXIQ DYIXHPAHVG FGDXYRSFWE KLLIFDYTPX   100

KX                                                       102
```

Materials and Methods:

Genetic Manipulations:

Vector VB40 was used to construct all expression plasmids encoding enzyme proteins disclosed herein, including OAC and variants.

The OAC variants were constructed in a combinatorial library using mutations that were initially selected in a site-saturation mutagenesis library screen. Plasmid VB40_OAC was used as the template in all library construction.

Figure 3:
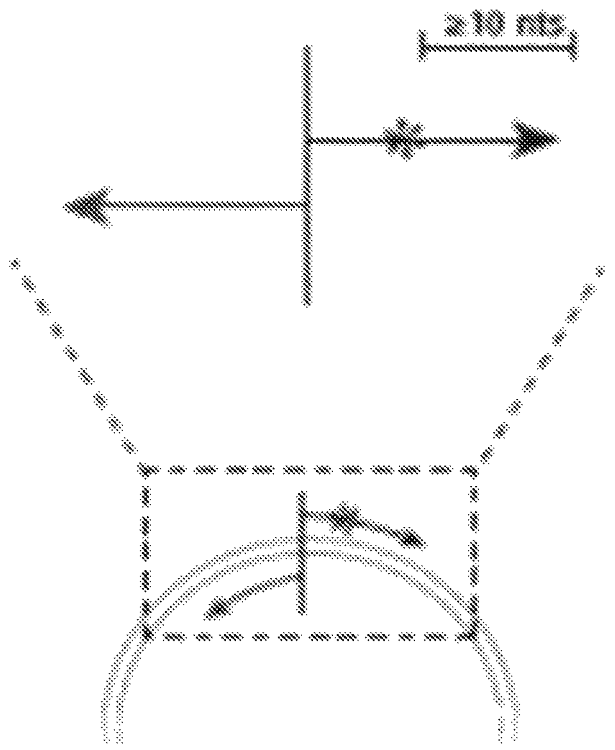
FIG. 3 illustrates PCR primers used in site-saturation mutagenesis protocol.

Site-saturation mutagenesis was conducted at each amino acid position by a PCR reaction using a forward degenerate NNK primer and a ‘back-to-back’ reverse non-mutagenic primer (FIG. 3). The PCR products were then processed through in vitro kinase-ligase-Dpnl reactions and transformed into *Escherichia coli* DH5alpha strain for amplification.

FIG. 3 illustrates PCR primers used in site-saturation mutagenesis protocol. Right-facing arrows represents forward degenerate NNK primer, symbol * denotes the mutational position, and the left-facing arrows represent reverse primer designed ‘back-to-back’ in the opposite direction of the forward primer.

Figure 4:
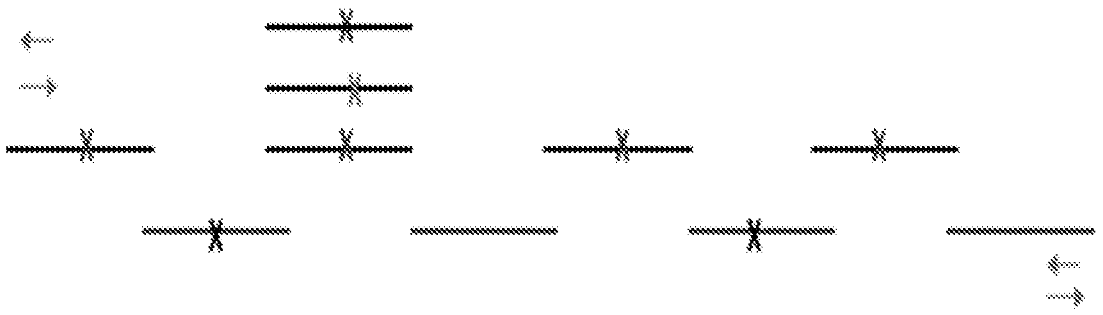
FIG. 4 shows an overlap-extension approach that was used to assemble mutagenic oligonucleotides for combinatorial library construction. The symbol x represents a point mutation.

The combinatorial library was constructed by an in-house protocol. Selected mutations were combined through an overlap-extension PCR of a batch of mutagenic oligonucleotides that were generated using targeted mutagenic primers. (FIG. 4). Double-stranded DNA of the assembled combinatorial mutant variants were cloned into a vector with complementary overlapping sequences, which resulted in a pool of OAC combinatorial variants. FIG. 4 shows an overlap-extension assembly of mutagenic oligonucleotides for combinatorial library construction. The symbol x represents a point mutation.

The plasmids encoding OAC and variant proteins as disclosed herein were transformed and expressed in *Saccharomyces cerevisiae*, with the host strain H B1416. All DNA was transformed into background strains using the Gietz et al. transformation protocol (Gietz 2014).

Strain Growth and Media:

Strains were grown in yeast synthetic complete media with a composition of 1.7 g/L YNB without ammonium sulfate, 1.92 g/L URA dropout amino acid supplement, 1.5 g/L magnesium L-glutamate, with 2% w/v galactose, 2% w/v raffinose, 200 μg/l geneticin, and 200 μg/L ampicillin (Sigma-Aldrich Canada). The culture was incubated at 30° C. for four days (96 hours). Strain HB1891 and HB1892 were respectively used as wild type control and negative control in all of the screenings.

Variant Screening Conditions:

Each variant was tested in three replicates and each replicate was clonally derived from single colonies. All strains were grown in 500 μl of media for 96 hours in 96-well deepwell plates. The 96-well deepwell plates were incubated at 30° C. and shaken at 950 rpm for 96 hrs.

Metabolite extraction was performed by adding 30 μl of culture to 270 μl of 56% acetonitrile in a new 96-well microtiter plate. The solutions were mixed thoroughly, then centrifuged at 3750 rpm for 10 mins. 200 μl of the soluble layer was removed and stored in a 96-well v-bottom microtiter plate. Samples were stored at −20° C. until analysis.

Quantification Protocol:

The quantification of olivetolic acid was performed using HPLC-MS/MS on a Waters Acquity UPLC-TQD MS. The chromatography and MS conditions are described below.

HPLC Conditions

Column: ACQUITY HSS C18 UPLC 50×1 mm, 1.8 μm particle size (PN: 186003529); Column temperature: 45° C.; Flow rate: 0.350 mL/min; Eluent A: Water+0.1% Formic Acid; Eluent B: Acetonitrile+0.1% Formic Acid; Gradient is shown in Table 1.

TABLE 1

| Gradient | |
|---|---|
| Time (min) | % B |
| 0 | 20 |
| 0.60 | 98 |
| 1.10 | 98 |
| 1.11 | 20 |
| 1.60 | 20 |

ESI-MS Conditions

The following conditions were utilized: Capillary: 2.90 (kV); Source temperature: 150° C.; Desolvation gas temperature: 250° C.; Desolvation gas flow (nitrogen): 500 L/hour; Cone gas flow (nitrogen): 1 L/hour; Detection parameters are shown in Table 2.

TABLE 2

| Detection Parameters | | | | |
|---|---|---|---|---|
| | OVLa | OVL | CBGa | THCa |
| Retention time (min) | 0.70 | 0.72 | 0.98 | 1.12 |
| Parent (m/z) | 223.0 | 181.1 | 359.2 | 357.2 |
| Daughter (m/z) | 179.0 | 71.0 | 341.2 | 313.2 |
| Mode | ES−, MRM | ES+, MRM | ES−, MRM | ES−, MRM |
| Cone (V) | 35 | 20 | 40 | 45 |
| Collision (V) | 20 | 12 | 25 | 30 |

Strains used are described in Table 3.

TABLE 3

| Strains Used | | | | |
|---|---|---|---|---|
| Strain # | Background | Plasmids | Genotype | Notes |
| HB1416 | -URA, -LEU | None | *Saccharomyces cerevisiae* CEN.PK2; ΔLEU2; ΔURA3; Erg2 0K197E::KanMx; ALD6; ASC1L6 41P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Parent strain for olivetolic acid production screen |
| HB1891 | -URA, -LEU | PLAS-417 | *Saccharomyces cerevisiae* CEN.PK2; ΔLEU2; ΔURA3; Erg2 0K197E::KanMx; ALD6; ASC1L6 41P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses OAC; positive control for olivetolic acid production screen |
| HB1892 | -URA, -LEU | PLAS-416 | *Saccharomyces cerevisiae* CEN.PK2; ΔLEU2; ΔURA3; Erg2 0K197E::KanMx; ALD6; ASC1L6 41P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses non-catalytic mScarlet; negative control for olivetolic acid production screen |
| PLT1577-D10 | -URA, -LEU | PLAS-527 | *Saccharomyces cerevisiae* CEN.PK2; ΔLEU2; ΔURA3; Erg2 0K197E::KanMx; ALD6; ASC1L6 41P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1575-D12 | -URA, -LEU | PLAS-528 | *Saccharomyces cerevisiae* CEN.PK2; ΔLEU2; ΔURA3; Erg2 0K197E::KanMx; ALD6; ASC1L6 41P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1576-B9 | -URA, -LEU | PLAS-529 | *Saccharomyces cerevisiae* CEN.PK2; ΔLEU2; ΔURA3; Erg2 0K197E::KanMx; ALD6; ASC1L6 41P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1575-C12 | -URA, -LEU | PLAS-530 | *Saccharomyces cerevisiae* CEN.PK2; ΔLEU2; ΔURA3; Erg2 0K197E::KanMx; ALD6; ASC1L6 41P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1575-D2 | -URA, -LEU | PLAS-531 | *Saccharomyces cerevisiae* CEN.PK2; ΔLEU2; ΔURA3; Erg2 0K197E::KanMx; ALD6; ASC1L6 41P; NPGA; MAF1; PGK1p:Acc1; tHMGR1; IDI; DiPKS_G1516R X | Expresses mutant OAC |

TABLE 3-continued

| Strains Used | | | | |
|---|---|---|---|---|
| Strain # | Background | Plasmids | Genotype | Notes |
| | | | 5; ACC1_S659A_S1157A; UB14 p:ERG20; PT254-R2S; Ost1-pro-alpha-f(I)-OXC53 | |
| PLT1572-B10 | -URA, -LEU | PLAS-532 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14p:ERG20; PT254-R2S; Ost1-pro-alpha-f(I)-OXC53 | Expresses mutant OAC |
| PLT1576-A9 | -URA, -LEU | PLAS-533 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14p:ERG20; PT254-R2S; Ost1-pro-alpha-f(I)-OXC53 | Expresses mutant OAC |
| PLT1577-D1 | -URA, -LEU | PLAS-534 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14p:ERG20; PT254-R2S; Ost1-pro-alpha-f(I)-OXC53 | Expresses mutant OAC |
| PLT1577-B7 | -URA, -LEU | PLAS-535 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14p:ERG20; PT254-R2S; Ost1-pro-alpha-f(I)-OXC53 | Expresses mutant OAC |
| PLT1575-F8 | -URA, -LEU | PLAS-536 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14p:ERG20; PT254-R2S; Ost1-pro-alpha-f(I)-OXC53 | Expresses mutant OAC |
| PLT1574-H11 | -URA, -LEU | PLAS-537 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14p:ERG20; PT254-R2S; Ost1-pro-alpha-f(I)-OXC53 | Expresses mutant OAC |
| PLT1575-E1 | -URA, -LEU | PLAS-538 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14p:ERG20; PT254-R2S; Ost1-pro-alpha-f(I)-OXC53 | Expresses mutant OAC |
| PLT1575-G1 | -URA, -LEU | PLAS-539 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14p:ERG20; PT254-R2S; Ost1-pro-alpha-f(I)-OXC53 | Expresses mutant OAC |
| PLT1576-A2 | -URA, -LEU | PLAS-540 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14p:ERG20; PT254-R2S; Ost1-pro-alpha-f(I)-OXC53 | Expresses mutant OAC |

TABLE 3-continued

| Strains Used | | | | |
|---|---|---|---|---|
| Strain # | Background | Plasmids | Genotype | Notes |
| PLT1576-B10 | -URA, -LEU | PLAS-541 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1573-D7 | -URA, -LEU | PLAS-542 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1575-H10 | -URA, -LEU | PLAS-543 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1574-F5 | -URA, -LEU | PLAS-544 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1573-D8 | -URA, -LEU | PLAS-545 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1574-A11 | -URA, -LEU | PLAS-546 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1574-B9 | -URA, -LEU | PLAS-547 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1576-B5 | -URA, -LEU | PLAS-548 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1573-F2 | -URA, -LEU | PLAS-549 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1572-H10 | -URA, -LEU | PLAS-550 | *Saccharomyces cerevisiae* CEN.PK2; ΔLEU2; ΔURA3; Erg20K197E::KanMx; ALD6; ASC1L641P; NPGA; MAF1; PGK1p:Acc1; | Expresses mutant OAC |

TABLE 3-continued

| Strains Used | | | | |
|---|---|---|---|---|
| Strain # | Background | Plasmids | Genotype | Notes |
| | | | tHMGR1; IDI; DiPKS_G1516R X 5; ACC1_S659A_S1157A; UB14 p:ERG20; PT254-R2S; Ost1-pro-alpha-f(I)-OXC53 | |
| PLT1573-E12 | -URA, -LEU | PLAS-551 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1573-D12 | -URA, -LEU | PLAS-552 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1573-B8 | -URA, -LEU | PLAS-553 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1573-A2 | -URA, -LEU | PLAS-554 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1576-B4 | -URA, -LEU | PLAS-555 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1573-G12 | -URA, -LEU | PLAS-556 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1576-G12 | -URA, -LEU | PLAS-557 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1575-H5 | -URA, -LEU | PLAS-558 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |
| PLT1576-A6 | -URA, -LEU | PLAS-559 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14 p:ERG20; PT254-R2S; Ost1-pro-alpha-f(I)-OXC53 | Expresses mutant OAC |

TABLE 3-continued

| Strains Used | | | | |
|---|---|---|---|---|
| Strain # | Background | Plasmids | Genotype | Notes |
| PLT1576-D1 | -URA, -LEU | PLAS-560 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14p:ERG20; PT254-R2S; Ost1-pro-alpha-f(I)-OXC53 | Expresses mutant OAC |
| PLT1572-E8 | -URA, -LEU | PLAS-561 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14p:ERG20; PT254-R2S; Ost1-pro-alpha-f(I)-OXC53 | Expresses mutant OAC |
| PLT1572-H9 | -URA, -LEU | PLAS-562 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14p:ERG20; PT254-R2S; Ost1-pro-alpha-f(I)-OXC53 | Expresses mutant OAC |
| PLT1575-F9 | -URA, -LEU | PLAS-563 | *Saccharomyces cerevisiae* CEN.PK2; ΔLEU2; ΔURA3; Erg20K197E::KanMx; ALD6; ASC1L641P; NPGA; MAF1; PGK1p:Acc1; tHMGR1; IDI; DiPKS_G1516R X 5; ACC1_S659A_S1157A; UB14p:ERG20; PT254-R2S; Ost1-pro-alpha-f(I)-OXC53 | Expresses mutant OAC |

The following plasmids were used, as described in Table 4.

TABLE 4

| Plasmids | | | | |
|---|---|---|---|---|
| # | Plasmid Name | SEQ ID NO. | Description | Selection |
| 1 | PLAS-416 | 001 | Gal1p:mScarlet:Cyc1t | Uracil |
| 2 | PLAS-417 | 002 | Gal1p:OAC:Cyc1t | Uracil |
| 3 | PLAS-527 | 003 | Gal1p:OAC-V28A/Y41T/G43SILENT(=GGG)/T68L/I74E/V84 R/R100M/G102R: Cyc1t | Uracil<br>Uracil |
| 4 | PLAS-528 | 004 | Gal1p:OAC-Y41S/G43SILENT(=GGG)/K44V/T68R/I74R/V84R:Cyc1t | Uracil |
| 5 | PLAS-529 | 005 | Gal1p:OAC-V28A/V31G/Y41S/G43SILENT(=GGG)/K44V/T68L/I74R/V84R/R100E/G102R:Cyc1t | Uracil |
| 6 | PLAS-530 | 006 | Gal1p:OAC-V28A/Y41T/G43SILENT(=GGG)/T68L/I74G/V84R/R100E:Cyc1t | Uracil |
| 7 | PLAS-531 | 007 | Gal1p:OAC-V28A/Y41T/G43SILENT(=GGG)/K44V/T68L/I74D/V84R/R100M/G102R:Cyc1t | Uracil |
| 8 | PLAS-532 | 008 | Gal1p:OAC-V28A/Y41T/G43SILENT(=GGG)/T68L/I74D/V84R/G102R:Cyc1t | Uracil |
| 9 | PLAS-533 | 009 | Gal1p:OAC-V28A/Y41T/G43SILENT(=GGG)/K44V/T68L/I74R/V84R/R100E/G10R:Cyc1t | Uracil<br>Uracil |
| 10 | PLAS-534 | 010 | Gal1p:OAC-Y41T/G43SILENT(=GGG)/T68R/I74R/V84R/R100M/G102STOP:Cyc1t | |
| 11 | PLAS-535 | 011 | Gal1p:OAC-V28A/Y41V/G43SILENT(=GGG)/K44V/T68L/I74G/V84R/R100E/G102R:Cyc1t | Uracil |

TABLE 4-continued

| Plasmids | | | | |
|---|---|---|---|---|
| # | Plasmid Name | SEQ ID NO. | Description | Selection |
| 12 | PLAS-536 | 012 | Gal1p:OAC-V28A/Y41T/G43SILENT(=GGG)/K44V/T68R/I74G/V84R/G102STOP: Cyc1t | Uracil |
| 13 | PLAS-537 | 013 | Gal1p:OAC-V28A/Y41V/G43SILENT(=GGG)/K44V/T68L/I74R/V84R/R100E/G102STOP:Cyc1t | Uracil |
| 14 | PLAS-538 | 014 | Gal1p:OAC-V28A/V31G/Y41T/G43SILENT(=GGG)/K44V/T68R/I74E/V84R/R100E:Cyc1t | Uracil |
| 15 | PLAS-539 | 015 | Gal1p:OAC-V28A/Y41S/G43SILENT(=GGG)/T68R/I74R/V84R/R100M/G102STOP:Cyc1t | Uracil |
| 16 | PLAS-540 | 016 | Gal1p:OAC-Y41T/G43SILENT(=GGG)/K44V/T68L/I74G/V84R/G102R:Cyc1t | Uracil |
| 17 | PLAS-541 | 017 | Gal1p:OAC-V28A/Y41T/G43SILENT(=GGG)/K44V/T68R/I74R/V84R/R100E/G102R:Cyc1t | Uracil |
| 18 | PLAS-542 | 018 | Gal1p:OAC-V28A/V31G/Y41S/G43SILENT(=GGG)/K44V/T68R/I74 R/V84 R: Cyc1t | Uracil |
| 19 | PLAS-543 | 019 | Gal1p:OAC-V28A/G43SILENT(=GGG)/K44V/I74D/V84R/R100E/G102R(=CGC): Cyc1t | Uracil |
| 20 | PLAS-544 | 020 | Gal1p:OAC-V28A/Y41V/G43SILENT(=GGG)/K44V/T68L/I74G/V84RIG102 R: Cyc1t | Uracil |
| 21 | PLAS-545 | 021 | Gal1p:OAC-Y41T/G43SILENT(=GGG)/T68L/I74G/V84R/R100M/G102 R:Cyc1t | Uracil |
| 22 | PLAS-546 | 022 | Gal1p:OAC-V28A/V31G/Y41T/G43SILENT(=GGG)/K44V/T68R/I74R/V84R/R100E/G102R:Cyc1t | Uracil |
| 23 | PLAS-547 | 023 | Gal1p:OAC-V31G/Y41S/G43SILENT(=GGG)/K44V/T68R/V84R/R100E:Cyc1t | Uracil |
| 24 | PLAS-548 | 024 | Gal1p:OAC-V28A/Y41V/G43SILENT(=GGG)/T68L/I74D/R100E/G102STOP:Cyc1t | Uracil |
| 25 | PLAS-549 | 025 | Gal1p:OAC-V28A/Y41V/G43SILENT(=GGG)/T68R/I74G/V84 R/R100M/G 102R: Cyc1t | Uracil |
| 26 | PLAS-550 | 026 | Gal1p:OAC-V31G/G43SILENT(=GGG)/I74G/V84R/R100E:Cyc1t | Uracil |
| 27 | PLAS-551 | 027 | Gal1p:OAC-V28A/Y41S/G43SILENT(=GGG)/K44V/T68R/I74R/V84 R/R100M/G102R:Cyc1t | Uracil |
| 28 | PLAS-552 | 028 | Gal1p:OAC-V28A/V31G/Y41V/G43SILENT(=GGG)/K44V/T68UI74G/V84R: Cyc1t | Uracil |
| 29 | PLAS-553 | 029 | Gal1p:OAC-V28A/Y41V/G43SILENT(=GGG)/K44V/T68L/I74G/V84R/R100M/G102R:Cyc1t | Uracil |
| 30 | PLAS-554 | 030 | Gal1p:OAC-V28A/V31G/G43SILENT(=GGG)/T68L/I74R/V84R/R100E/G102R:Cyc1t | Uracil |
| 31 | PLAS-555 | 031 | Gal1p:OAC-V31G/Y41V/G43SILENT(=GGG)/K44V/T68L/I 74R/V84 R/R100 E/G102STOP: Cyc1t | Uracil |
| 32 | PLAS-556 | 032 | Gal1p:OAC-V31G/Y41T/G43SILENT(=GGG)/K44V/T68 R/I74D/V84R/G 102 R: Cyc1t | Uracil |
| 33 | PLAS-557 | 033 | Gal1p:OAC-V31G/Y41T/G43SILENT(=GGG)/K44V/T68R/174D/V84R/R100 E/G102R:Cyc1t | Uracil |
| 34 | PLAS-558 | 034 | Gal1p:OAC-V28A/Y41S/G43SILENT(=GGG)/K44V/T68R/I74G/V84 R/R100M/G102R:Cyc1t | Uracil |
| 35 | PLAS-559 | 035 | Gal1p:OAC-V28A/Y41V/G43SILENT(=GGG)/K44V/I74R/R100E/G102STOP:Cyc1t | Uracil |

TABLE 4-continued

| Plasmids | | | | |
|---|---|---|---|---|
| # | Plasmid Name | SEQ ID NO. | Description | Selection |
| 36 | PLAS-560 | 036 | Gal1p:OAC-V28A/V31G/Y41T/G43SILENT(=GGG)/K44V/I74E/V84R/R100M/G102R:Cyc1t | Uracil |
| 37 | PLAS-561 | 037 | Gal1p:OAC-V28A/G43SILENT(=GGG)/K44V/T68R/I74E/V84R/R100E/G102STOP:Cyc1t | Uracil |
| 38 | PLAS-562 | 038 | Gal1p:OAC-V31G/Y41T/G43SILENT(=GGG)/K44V/T68L/I74D/V84R/G102R:Cyc1t | Uracil |
| 39 | PLAS-563 | 039 | Gal1p:OAC-Y41V/G43SILENT(=GGG)/K44V/T 68L/I74R/V84R/G102R:Cyc1t | Uracil |

The following sequences are described herein (Table 5)

TABLE 5

| Sequences | | | | | |
|---|---|---|---|---|---|
| SEQ ID NO: | Plasmid Name | Description | DNA/ Protein | Length of sequence | Position of coding sequence |
| 001 | PLAS-416 | Gal1p:mScarlet:Cyc1t | DNA | 6114 | 2649 to 3347 |
| 002 | PLAS-417 | Gal1p:OAC:Cyc1t | DNA | 5724 | 2649 to 2957 |
| 003 | PLAS-527 | Gal1p:OAC-V28A/Y41T/G43SILENT(=GGG)/T68L/I74E/V84R/R100M/G102R:Cyc1t | DNA | 5724 | 2648 to 2957 |
| 004 | PLAS-528 | Gal1p:OAC-Y41S/G43SILENT(=GGG)/K44V/T68R/I74R/V84R:Cyc1t | DNA | 5724 | 2648 to 2957 |
| 005 | PLAS-529 | Gal1p:OAC-V28A/V31G/Y41S/G43SILENT(=GGG)/K44V/T68L/I74R/V84R/R100E/G102R:Cyc1t | DNA | 5724 | 2648 to 2957 |
| 006 | PLAS-530 | Gal1p:OAC-V28A/Y41T/G43SILENT(=GGG)/T68L/I74G/V84R/R100E:Cyc1t | DNA | 5724 | 2648 to 2957 |
| 007 | PLAS-531 | Gal1p:OAC-V28A/Y41T/G43SILENT(=GGG)/K44V/T68L/I74D/V84R/R100M/G102R:Cyc1t | DNA | 5724 | 2648 to 2957 |
| 008 | PLAS-532 | Gal1p:OAC-V28A/Y41T/G43SILENT(=GGG)/T68L/I74D/V84R/G102R:Cyc1t | DNA | 5724 | 2648 to 2957 |
| 009 | PLAS-533 | Gal1p:OAC-V28A/Y41T/G43SILENT(=GGG)/K44V/T68L/I74R/V84R/R100E/G102R:Cyc1t | DNA | 5724 | 2648 to 2957 |
| 010 | PLAS-534 | Gal1p:OAC-Y41T/G43SILENT(=GGG)/T68R/I74R/V84R/R100/G102STOP:Cyc1t | DNA | 5724 | 2648 to 2954 |
| 011 | PLAS-535 | Gal1p:OAC-V28A/Y41V/G43SILENT(=GGG)/K44V/T68L/I74G/V84R/R100E/G102R:Cyc1t | DNA | 5724 | 2648 to 2957 |

TABLE 5-continued

Sequences

| SEQ ID NO: | Plasmid Name | Description | DNA/ Protein | Length of sequence | Position of coding sequence |
|---|---|---|---|---|---|
| 012 | PLAS-536 | Gal1p:OAC-V28A/Y41T/G43SILENT(=GGG)/K44V/T68R/I74G/V84R/G102STOP:Cyc1t | DNA | 5724 | 2648 to 2954 |
| 013 | PLAS-537 | Gal1p:OAC-V28A/Y41V/G43SILENT(=GGG)/K44V/T68L/I74R/V84R/R100E/G102STOP:Cyc1t | DNA | 5724 | 2648 to 2954 |
| 014 | PLAS-538 | Gal1p:OAC-V28A/V31G/Y41T/G43SILENT(=GGG)/K44V/T68R/I74E/V84R/R100E:Cyc1t | DNA | 5724 | 2648 to 2957 |
| 015 | PLAS-539 | Gal1p:OAC-V28A/Y41S/G43SILENT(=GGG)/T68R/I74R/V84R/R100M/G102STOP:Cyc1t | DNA | 5724 | 2648 to 2954 |
| 016 | PLAS-540 | Gal1p:OAC-Y41T/G43SILENT(=GGG)/K44V/T68L/I74G/V84R/G102R:Cyc1t | DNA | 5724 | 2648 to 2957 |
| 017 | PLAS-541 | Gal1p:OAC-V28A/Y41T/G43SILENT(=GGG)/K44V/T68R/I74R/V84R/R100E/G102R:Cyc1t | DNA | 5724 | 2648 to 2957 |
| 018 | PLAS-542 | Gal1p:OAC-V28A/V31G/Y41S/G43SILENT(=GGG)/K44V/T68R/I74R/V84R:Cyc1t | DNA | 5724 | 2648 to 2957 |
| 019 | PLAS-543 | Gal1p:OAC-V28A/G43SILENT(=GGG)/K44V/I74D/V84R/R100E/G102R(=CGC):Cyc1t | DNA | 5724 | 2648 to 2957 |
| 020 | PLAS-544 | Gal1p:OAC-V28A/Y41V/G43SILENT(=GGG)/K44V/T68L/I74G/V84R/G102R:Cyc1t | DNA | 5724 | 2648 to 2957 |
| 021 | PLAS-545 | Gal1p:OAC-Y41T/G43SILENT(=GGG)/T68L/I74G/V84R/R100M/G102R:Cyc1t | DNA | 5724 | 2648 to 2957 |
| 022 | PLAS-546 | Gal1p:OAC-V28A/V31G/Y41T/G43SILENT(=GGG)/K44V/T68R/I74R/V84R/R100E/G102R:Cyc1t | DNA | 5724 | 2648 to 2957 |
| 023 | PLAS-547 | Gal1p:OAC-V31G/Y41S/G43SILENT(=GGG)/K44V/T68R/V84R/R100E:Cyc1t | DNA | 5724 | 2648 to 2957 |
| 024 | PLAS-548 | Gal1p:OAC-V28A/Y41V/G43SILENT(=GGG)/T68L/I74D/R100E/G102STOP:Cyc1t | DNA | 5724 | 2648 to 2954 |

TABLE 5-continued

| Sequences | | | | | |
|---|---|---|---|---|---|
| SEQ ID NO: | Plasmid Name | Description | DNA/ Protein | Length of sequence | Position of coding sequence |
| 025 | PLAS-549 | Gal1p:OAC-V28A/Y41V/G43SILENT(=GGG)/T68R/I74G/V84R/R100M/G102R: Cyc1t | DNA | 5724 | 2648 to 2957 |
| 026 | PLAS-550 | Gal1p:OAC-V31G/G43SILENT(=GGG)/I74G/V84R/R100E:Cyc1t | DNA | 5724 | 2648 to 2957 |
| 027 | PLAS-551 | Gal1p:OAC-V28A/Y41S/G43SILENT(=GGG)/K44V/T68RI74R/V84R/R100M/G102R:Cyc1t | DNA | 5724 | 2648 to 2957 |
| 028 | PLAS-552 | Gal1p:OAC-V28A/V31G/Y41V/G43SILENT(=GGG)/K44V/T68L/I74G/V84R:Cyc1t | DNA | 5724 | 2648 to 2957 |
| 029 | PLAS-553 | Gal1p:OAC-V28A/Y41V/G43SILENT(=GGG)/K44V/T68L/I74G/V84R/R100M/G102R:Cyc1t | DNA | 5724 | 2648 to 2957 |
| 030 | PLAS-554 | Gal1p:OAC-V28A/V31G/G43SILENT(=GGG)/T68L/I74R/V84R/R100E/G102R:Cyc1t | DNA | 5724 | 2648 to 2957 |
| 031 | PLAS-555 | Gal1p:OAC-V31G/Y41V/G43SILENT(=GGG)/K44V/T68L/I74R/V84R/R100E/G102STOP:Cyc1t | DNA | 5724 | 2648 to 2954 |
| 032 | PLAS-556 | Gal1p:OAC-V31G/Y41T/G43SILENT(=GGG)/K44V/T68R/I74D/V84R/G102R:Cyc1t | DNA | 5724 | 2648 to 2957 |
| 033 | PLAS-557 | Gal1p:OAC-V31G/Y41T/G43SILENT(=GGG)/K44V/T68R/I74D/V84R/R100E/G102R:Cyc1t | DNA | 5724 | 2648 to 2957 |
| 034 | PLAS-558 | Gal1p:OAC-V28A/Y41S/G43SILENT(=GGG)/K44V/T68R/I74G/V84R/R100M/G102R:Cyc1t | DNA | 5724 | 2648 to 2957 |
| 035 | PLAS-559 | Gal1p:OAC-V28A/Y41V/G43SILENT(=GGG)/K44V/I74R/R100E/G102STOP:Cyc1t | DNA | 5724 | 2648 to 2954 |
| 036 | PLAS-560 | Gal1p:OAC-V28A/V31G/Y41T/G43SILENT(=GGG)/K44V/I74E/V84R/R100M/G102R:Cyc1t | DNA | 5724 | 2648 to 2957 |
| 037 | PLAS-561 | Gal1p:OAC-V28A/G43SILENT(=GGG)/K44V/T68R/I74E/V84R/R100E/G102STOP:Cyc1t | DNA | 5724 | 2648 to 2954 |

TABLE 5-continued

| Sequences | | | | | |
|---|---|---|---|---|---|
| SEQ ID NO: | Plasmid Name | Description | DNA/ Protein | Length of sequence | Position of coding sequence |
| 038 | PLAS-562 | Gal1p:OAC-V31G/Y41T/G43SILENT(=GGG)/K44V/T68L/I74D/V84R/G102R:Cyc1t | DNA | 5724 | 2648 to 2957 |
| 039 | PLAS-563 | Gal1p:OAC-Y41V/G43SILENT(=GGG)/K44V/T68L/I74R/V84R/G102R:Cyc1t | DNA | 5724 | 2648 to 2957 |
| 40 | PLAS-527 | Gal1p:OAC-V28A/Y41T/G43SILENT(=GGG)/T68L/I74E/V84R/R100M/G102R:Cyc1t | Protein | 102 | All |
| 41 | PLAS-528 | Gal1p:OAC-Y41S/G43SILENT(=GGG)/K44V/T68R/I74R/V84R:Cyc1t | Protein | 102 | All |
| 42 | PLAS-529 | Gal1p:OAC-V28A/V31G/Y41S/G43SILENT(=GGG)/K44V/T68L/I74R/V84R/R100E/G102R: Cyc1t | Protein | 102 | All |
| 43 | PLAS-530 | Gal1p:OAC-V28A/Y41T/G43SILENT(=GGG)/T68L/I74G/V84R/R100E:Cyc1t | Protein | 102 | All |
| 44 | PLAS-531 | Gal1p:OAC-V28A/Y41T/G43SILENT(=GGG)/K44V/T68L/I74D/V84R/R100M/G102R:Cyc1t | Protein | 102 | All |
| 45 | PLAS-532 | Gal1p:OAC-V28A/Y41T/G43SILENT(=GGG)/T68L/I74D/V84R/G102R:Cyc1t | Protein | 102 | All |
| 46 | PLAS-533 | Gal1p:OAC-V28A/Y41T/G43SILENT(=GGG)/K44V/T68L/I74R/V84R/R100E/G102R:Cyc1t | Protein | 102 | All |
| 47 | PLAS-534 | Gal1p:OAC-Y41T/G43SILENT(=GGG)/T68R/I74R/V84R/R100M/G102STOP:Cyc1t | Protein | 101 | All |
| 48 | PLAS-535 | Gal1p:OAC-V28A/Y41V/G43SILENT(=GGG)/K44V/T68L/I74G/V84R/R100E/G102R:Cyc1t | Protein | 102 | All |
| 49 | PLAS-536 | Gal1p:OAC-V28A/Y41T/G43SILENT(=GGG)/K44V/T68R/I74G/V84R/G102STOP:Cyc1t | Protein | 101 | All |
| 50 | PLAS-537 | Gal1p:OAC-V28A/Y41V/G43SILENT(=GGG)/K44V/T68L/I74R/V84R/R100E/G102STOP:Cyc1t | Protein | 101 | All |

TABLE 5-continued

| Sequences | | | | | |
|---|---|---|---|---|---|
| SEQ ID NO: | Plasmid Name | Description | DNA/ Protein | Length of sequence | Position of coding sequence |
| 51 | PLAS-538 | Gal1p:OAC-V28A/V31G/Y41T/G43SILENT(=GGG)/K44V/T68R/I74E/V84R/R100E: Cyc1t | Protein | 102 | All |
| 52 | PLAS-539 | Gal1p:OAC-V28A/Y41S/G43SILENT(=GGG)/T68R/I74R/V84R/R100M/G102STOP:Cyc1t | Protein | 101 | All |
| 53 | PLAS-540 | Gal1p:OAC-Y41T/G43SILENT(=GGG)/K44V/T68L/I74G/V84R/G102R:Cyc1t | Protein | 102 | All |
| 54 | PLAS-541 | Gal1p:OAC-V28A/Y41T/G43SILENT(=GGG)/K44V/T68R/I74R/V84R/R100E/G102R:Cyc1t | Protein | 102 | All |
| 55 | PLAS-542 | Gal1p:OAC-V28A/V31G/Y41S/G43SILENT(=GGG)/K44V/T68R/I74R/V84R:Cyc1t | Protein | 102 | All |
| 56 | PLAS-543 | Gal1p:OAC-V28A/G43SILENT(=GGG)/K44V/I74D/V84R/R100E/G102R(=CGC):Cyc1t | Protein | 102 | All |
| 57 | PLAS-544 | Gal1p:OAC-V28A/Y41V/G43 SILENT(=GGG)/K44V/T68L/I74G/V84R/G102R:Cyc1t | Protein | 102 | All |
| 58 | PLAS-545 | Gal1p:OAC-Y41T/G43SILENT(=GGG)/T68L/I74G/V84R/R100M/G102R:Cyc1t | Protein | 102 | All |
| 59 | PLAS-546 | Gal1p:OAC-V28A/V31G/Y41T/G43SILENT(=GGG)/K44V/T68R/I74R/V84R/R100E/G102R:Cyc1t | Protein | 102 | All |
| 60 | PLAS-547 | Gal1p:OAC-V31G/Y41S/G43SILENT(=GGG)/K44V/T68R/V84R/R100E:Cyc1t | Protein | 102 | All |
| 61 | PLAS-548 | Gal1p:OAC-V28A/Y41V/G43SILENT(=GGG)/T68L/I74D/R100E/G102STOP:Cyc1t | Protein | 101 | All |
| 62 | PLAS-549 | Gal1p:OAC-V28A/Y41V/G43SILENT(=GGG)/T68R/I74G/V84R/R100M/G102R:Cyc1t | Protein | 102 | All |
| 63 | PLAS-550 | Gal1p:OAC-V31G/G43SILENT(=GGG)/I74G/V84R/R100E:Cyc1t | Protein | 102 | All |

TABLE 5-continued

| Sequences | | | | | |
|---|---|---|---|---|---|
| SEQ ID NO: | Plasmid Name | Description | DNA/ Protein | Length of sequence | Position of coding sequence |
| 64 | PLAS-551 | Gal1p:OAC-V28A/Y41S/G43SILENT(=GGG)/K44V/T68R/I74R/V84R/R100M/G02R:Cyc1t | Protein | 102 | All |
| 65 | PLAS-552 | Gal1p:OAC-V28A/V31G/Y41V/G43SILENT(=GGG)/K44V/T68L/I74G/V84R:Cyc1t | Protein | 102 | All |
| 66 | PLAS-553 | Gal1p:OAC-V28A/Y41V/G43SILENT(=GGG)/K44V/T68L/I74G/V84R/R100M/G02R:Cyc1t | Protein | 102 | All |
| 67 | PLAS-554 | Gal1p:OAC-V28A/V31G/G43SILENT(=GGG)/T68L/I74R/V84R/R100E/G102R:Cyc1t | Protein | 102 | All |
| 68 | PLAS-555 | Gal1p:OAC-V31G/Y41V/G43SILENT(=GGG)/K44V/T68L/I74R/V84R/R100E/G102STOP:Cyc1t | Protein | 101 | All |
| 69 | PLAS-556 | Gal1p:OAC-V31G/Y41T/G43SILENT(=GGG)/K44V/T68R/I74D/V84R/G102R:Cyc1t | Protein | 102 | All |
| 70 | PLAS-557 | Gal1p:OAC-V31G/Y41T/G43SILENT(=GGG)/K44V/T68R/I74D/V84R/R100E/G102R:Cyc1t | Protein | 102 | All |
| 71 | PLAS-558 | Gal1p:OAC-V28A/Y41S/G43SILENT(=GGG)/K44V/T68R/I74G/V84R/R100M/G102R:Cyc1t | Protein | 102 | All |
| 72 | PLAS-559 | Gal1p:OAC-V28A/Y41V/G43SILENT(=GGG)/K44V/I74R/R100E/G102STOP:Cyc1t | Protein | 101 | All |
| 73 | PLAS-560 | Gal1p:OAC-V28A/V31G/Y41T/G43SILENT(=GGG)/K44V/I74E/V84R/R100M/G102R:Cyc1t | Protein | 102 | All |
| 74 | PLAS-561 | Gal1p:OAC-V28A/G43SILENT(=GGG)/K44V/T68R/I74E/V84R/R100E/G102STOP:Cyc1t | Protein | 101 | All |
| 75 | PLAS-562 | Gal1p:OAC-V31G/Y41T/G43SILENT(=GGG)/K44V/T68L/I74D/V84R/G102R:Cyc1t | Protein | 102 | All |
| 76 | PLAS-563 | Gal1p:OAC-Y41V/G43SILENT(=GGG)/K44V/T68L/I74R/V84R/G102R:Cyc1t | Protein | 102 | All |

TABLE 5-continued

| Sequences | | | | | |
|---|---|---|---|---|---|
| SEQ ID NO: | Plasmid Name | Description | DNA/ Protein | Length of sequence | Position of coding sequence |
| 77 | | NpgA | DNA | 3564 | 1170 - 2201 |
| 78 | | DiPKS-1 | DNA | 11114 | 849 - 10292 |
| 79 | | DiPKS-2 | DNA | 10890 | 717 - 10160 |
| 80 | | DiPKS-3 | DNA | 11300 | 795 - 10238 |
| 81 | | DiPKS-4 | DNA | 11140 | 794 - 10237 |
| 82 | | DiPKS-5 | DNA | 11637 | 1172 - 10615 |
| 83 | | PDH | DNA | 7114 | Ald6: 1444 - 2949 ACS: 3888 - 5843 |
| 84 | | Maf1 | DNA | 3256 | 936 - 2123 |
| 85 | | Erg20K197E | DNA | 4254 (4538) | 2842 - 3900 |
| 86 | | Erg1p:UB14-Erg20:deg | DNA | 3503 | 1364 - 2701 |
| 87 | | tHMGr-IDI | DNA | 4843 | tHMGR1: 885 - 2393 IDI1: 3209 - 4075 |
| 88 | | PGK1p:ACC1$^{S659A, S1157A}$ | DNA | 7673 | Pgk1p: 222 - 971 Acc1mut: 972 - 7673 |
| 89 | | PT254-R2S | DNA | 4707 | 1957-2925 |
| 90 | | Ost1-pro-alpha-f(I)-OXC53 | DNA | 4137 | 1615-3168 |
| 91 | PLAS-417 | Wild Type OAC | Protein | 102 | All |
| 92 | PLAS-417 | Variant OAC | Protein | 102 | All |
| 93 | PLAS-416 | mScarlet | Protein | 232 | All |

Modifications to base strains used herein are outlined below in Table 6.

TABLE 6

| Modifications to Base Strains | | | | | |
|---|---|---|---|---|---|
| # | Modification name | SEQ ID NO. | Integration Region/Plasmid | Description | Genetic Structure of Sequence |
| 1 | NpgA | 77 | Flagfeldt Site14 integration | Phosphopantetheinyl Transferase from *Aspergillus niger.* Accessory Protein for DiPKS (Kim et al., 2015) | Site14Up::Tef1p: NpgA:Prm9t: Site 14Down |
| 2 | DiPKS-1 | 78 | USER Site XII-1 integration | Type 1 FAS fused to Type 3 PKS from *D. discoideum.* Produces Olivetol from malonyl-coA | XII-1up::Gal1p:DiPKSG1516R: Prm9t::XII1-down |
| 3 | DiPKS-2 | 79 | Wu site 1 integration | Type 1 FAS fused to Type 3 PKS from *D. discoideum.* Produces Olivetol from malonyl-coA | Wu1up::Gal1t: DiPKSG1516R: Prm9t::Wu1down |
| 4 | DiPKS-3 | 80 | Wu site 3 integration | Type 1 FAS fused to Type 3 PKS from *D. discoideum.* Produces Olivetol from malonyl-coA | Wu3up::Gal1p: DiPKSG1516R: Prm9t::Wu3down |
| 5 | DiPKS-4 | 81 | Wu site 6 integration | Type 1 FAS fused to Type 3 PKS from *D. discoideum.* Produces Olivetol from malonyl-coA | Wu6up::Gal1p: DiPKSG1516R: Prm9t::Wu6down |
| 6 | DiPKS-5 | 82 | Wu site 18 integration | Type 1 FAS fused to Type 3 PKS from *D. discoideum.* Produces Olivetol from malonyl-coA | Wu18up::Gal1p: DiPKSG1516R: Prm9t::Wu18down |

TABLE 6-continued

| Modifications to Base Strains | | | | | |
|---|---|---|---|---|---|
| # | Modification name | SEQ ID NO. | Integration Region/Plasmid | Description | Genetic Structure of Sequence |
| 7 | PDH | 83 | Flagfeldt Site 19 integration | Acetaldehyde dehydrogenase (ALD6) from *S. cerevisiae* and acetoacetyl coA synthase (AscL641P) from *Salmonella enterica*. Will allow greater accumulation of acetyl-coA in the cell (Shiba et al., 2007). | 19Up::Tdh3p:Ald6: Adh1::Tef1p: seACS1$^{L641P}$: Prm9t::19Down |
| 8 | Maf1 | 84 | Flagfeldt Site 5 integration | Maf1 is a regulator of tRNA biosynthesis. Overexpression in *S. cerevisiae* has demonstrated higher monoterpene (GPP) yields (Liu et al., 2013). | Site5Up::Tef1p: Maf1:Prm9t:Site 5Down |
| 9 | Erg20K197E | 85 | Chromosomal modification | Mutant of Erg20 protein that diminishes FPP synthase activity creating greater pool of GPP precursor. Negatively affects growth phenotype (Oswald et al., 2007). | Tpi1t:ERG20K197E: Cyc1t::Tef1p: KanMX:Tef1t |
| 10 | Erg1p:UB14-Erg20: deg | 86 | Flagfeldt Site 18 integration | Sterol responsive promoter controlling Erg20 protein activity. Allows for regular FPP synthase activity and uninhibited growth phenotype until accumulation of sterols which leads to a suppression of expression of enzyme (Peng et al., 2018). | Site18Up::Erg1p: UB14deg:ERG20: Adh1t:Site18down |
| 11 | tHMGr-ID1 | 87 | USER Site X-3 integration | Overexpression of truncated HMGr1 and IDI1 proteins that have been previously identified to be bottlenecks in the *S. cerevisiae* terpenoid pathway responsible for GPP production (Ro et al., 206). | X3up::Tdh3p: tHMGR1: Adh1t::Tef1p:IDI1: Prm9t::X3down |
| 12 | PGK1p: ACC1$^{S659A,\ S1157A}$ | 88 | Chromosomal modification | Mutations in the native *S. cerevisiae* acetyl-coA carboxylase that removes post-translational modification based down-regulation. Leads to greater malonyl-coA pools. The promoter of Acc1 was also changed to a constitutive promoter for higher expression (Shi et al., 2014). | Pgkt1: ACC1$^{S659A,\ S1157A}$: Acc1t |
| 13 | PT254-R25 | 89 | Flagfeldt Site 18 integration | The *Cannabis sativa* prenyltransferase PT254 allows CBGa to be produced from olivetolic acid and geranyl pyrophosphate (Luo et al., 2019). The N terminal arginine of this enzyme has been replaced with a serine in order to enhance protein stability in accordance with N-end rule (Varshaysky 1996). | FgF18up::Tef1p: R2S-PT254:Cyct:: FgF20down |
| 14 | Ost1-pro-f(I)-alpha-OXC53 | 90 | Apel-3 | ΔA28THCa synthase (OX053) from *C. sativa*. (Sirikantaramas et al., 2005). Fused with a Ost1-pro-alpha-f(I) tag. Produces THCa from CBGa | Apel3up::Tef1p: Ost1-pro-alpha-f(I)-OXC53t:Cyct:: Apel3down |

Results:

Identification of Variants that Demonstrate Improved Production of Olivetolic Acid (OVLa) and Downstream Cannabinoids An OAC mutants library was constructed in a plasmid regulated by the Gal1p promoter, and expressed in an olivetol-producing background strain (HB1416) harboring downstream enzymes of the cannabinoid production pathway. The strains expressing wild type OAC (HB1891) and mScarlet fluorescent protein (HB1892) were utilized as control in the screening to facilitate identification of OAC mutant hits with improved activity.

Figure 5:
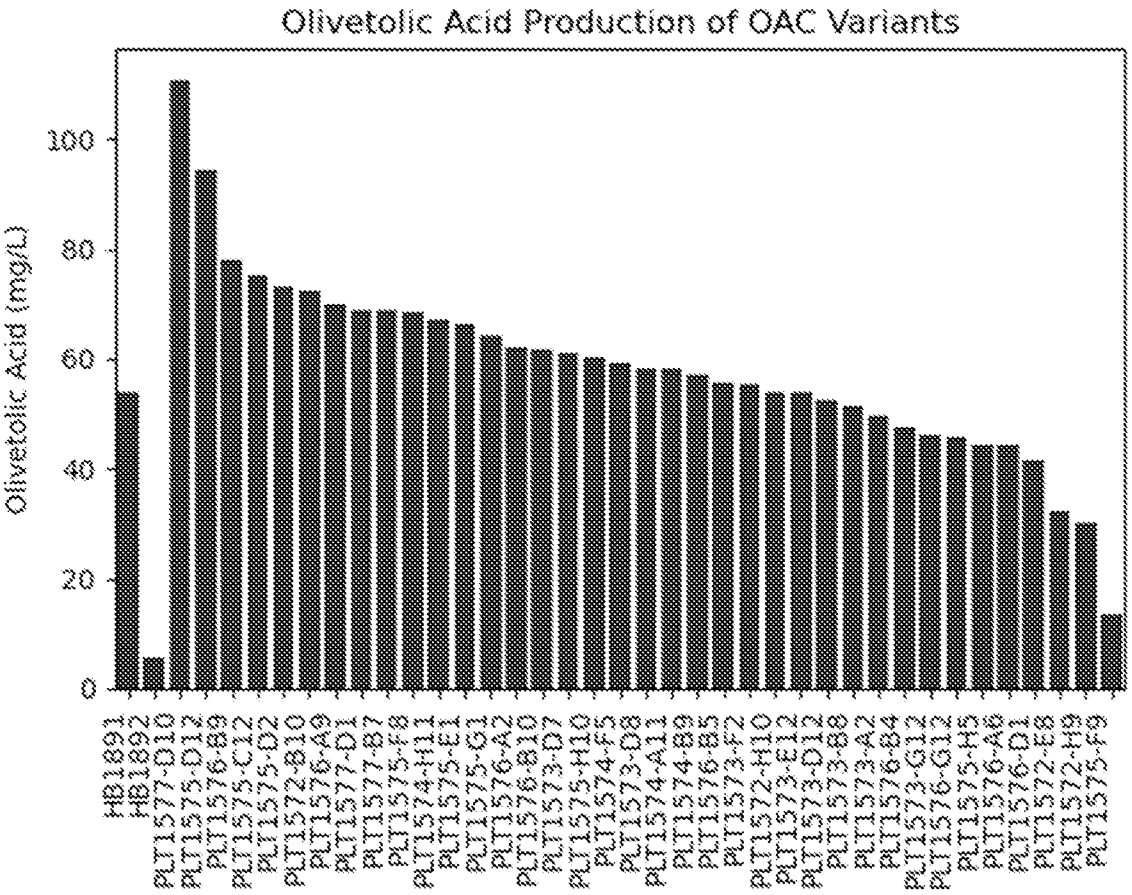
FIG. 5 shows olivetolic acid production with mutant OAC variants.

FIG. 5 shows olivetolic acid production by engineered OACs strains. The measured values of each cannabinoid are shown in FIG. 5. The mutants tested had the silent mutation G43G(GGG) present, which is an artifact of the plasmid construction process and not relevant to increased enzyme performance.

Table 7 shows production of olivetol, olivetolic acid and downstream cannabinoids in OAC wild type and engineered OACs strains.

TABLE 7

Production of Olivetol, Olivetolic Acid and Downstream Cannabinoids

| Strain | OAC mutant | Olivetol (mg/L) | Olivetolic Acid (mg/L) | CBGa (mg/L) | THCa (mg/L) | Total Downstream Metabolites (OVLa, CBGa, THCa) | # of non-conservative mutations |
|---|---|---|---|---|---|---|---|
| HB1891 | Wild type OAC | 53.367 | 53.850 | 8.283 | 2.367 | 64.500 | NA |
| HB1892 | RFP negative -- no OAC | 84.833 | 5.717 | 0.517 | 0.150 | 6.383 | NA |
| PLT1577-D10 | Gal1p: OAC-V28A/Y41T/G43 SILENT(=GGG)/ T68L/I74E/V84R/ R100M/G102R: Cyc1t | 70.633 | 110.800 | 13.933 | 2.700 | 127.433 | 6 |
| PLT1575-D12 | Gal1p: OAC-Y41S/G43SILENT (=GGG)/K44V/ T68R/I74R/V84R: Cyc1t | 77.200 | 94.367 | 13.200 | 4.133 | 111.700 | 5 |
| PLT1576-B9 | Gal1p: OAC-V28A/V31G/Y41S/ G43SILENT(=GGG)/ K44V/T68L/I74R/V84R/ R100E/G102R: Cyc1t | 52.500 | 78.167 | 14.933 | 3.367 | 96.467 | 7 |
| PLT1575-C12 | Gal1p: OAC-V28A/Y41T/G43 SILENT(=GGG)/ T68L/I74G/V84R/ R100E: Cyc1t | 75.333 | 75.400 | 12.600 | 3.500 | 91.500 | 5 |
| PLT1575-D2 | Gal1p: OAC-V28A/Y41T/G43 SILENT(=GGG)/ K44V/T68L/I74D/ V84R/R100M/ G102R: Cyc1t | 81.400 | 73.267 | 12.800 | 2.700 | 88.767 | 7 |
| PLT1572-B10 | Gal1p: OAC-V28A/Y41T/G43 SILENT(=GGG)/ T68L/I74D/V84R/ G102R: Cyc1t | 45.433 | 72.400 | 8.433 | 2.867 | 83.700 | 5 |
| PLT1576-A9 | Gal1p: OAC-V28A/Y41T/G43 SILENT(=GGG)/ K44V/T68L/I74R/ V84R/R100E/ G102R: Cyc1t | 66.633 | 69.767 | 10.800 | 2.733 | 83.300 | 7 |
| PLT1577-D1 | Gal1p: OAC-Y41T/G43SILENT (=GGG)/T68R/ I74R/V84R/R100M/ G102STOP: Cyc1t | 71.567 | 68.833 | 12.933 | 2.967 | 84.733 | 5 |
| PLT1577-B7 | Gal1p: OAC-V28A/Y41V/ G43SILENT(=GGG)/ K44V/T68L/I74G/V84R/ R100E/G102R: Cyc1t | 77.800 | 68.800 | 10.767 | 2.533 | 82.100 | 7 |
| PLT1575-F8 | Gal1p: OAC-V28A/Y41T/ G43SILENT(=GGG)/ K44V/T68R/I74G/V84R/ G102STOP: Cyc1t | 81.667 | 68.533 | 12.167 | 3.067 | 83.767 | 5 |
| PLT1574-H11 | Gal1p: OAC-V28A/Y41V/ G43SILENT(=GGG)/ K44V/T68L/I74R/ V84R/R100E/ G102STOP: Cyc1t | 72.833 | 67.200 | 11.533 | 3.333 | 82.067 | 6 |
| PLT1575-E1 | Gal1p: OAC-V28A/V31G/Y41T/ G43SILENT(=GGG)/ K44V/T68R/ I74E/V84R/R100E: Cyc1t | 85.100 | 66.433 | 11.500 | 3.467 | 81.400 | 6 |

TABLE 7-continued

Production of Olivetol, Olivetolic Acid and Downstream Cannabinoids

| Strain | OAC mutant | Olivetol (mg/L) | Olivetolic Acid (mg/L) | CBGa (mg/L) | THCa (mg/L) | Total Downstream Metabolites (OVLa, CBGa, THCa) | # of non-conserative mutations |
|---|---|---|---|---|---|---|---|
| PLT1575-G1 | Gal1p: OAC-V28A/Y41S/G43SILENT(=GGG)/T68R/I74R/V84R/R100M/G102STOP: Cyc1t | 71.200 | 64.200 | 9.300 | 2.367 | 75.867 | 5 |
| PLT1576-A2 | Gal1p: OAC-Y41T/G43SILENT(=GGG)/K44V/T68L/I74G/V84R/G102R: Cyc1t | 56.633 | 62.267 | 12.300 | 3.067 | 77.633 | 6 |
| PLT1576-B10 | Gal1p: OAC-V28A/Y41T/G43SILENT(=GGG)/K44V/T68R/I74R/V84R/R100E/G102R: Cyc1t | 63.633 | 61.600 | 12.533 | 2.967 | 77.100 | 7 |
| PLT1573-D7 | Gal1p: OAC-V28A/V31G/Y41S/G43SILENT(=GGG)/K44V/T68R/I74R/V84R: Cyc1t | 58.467 | 61.033 | 8.767 | 2.833 | 72.633 | 5 |
| PLT1575-H10 | Gal1p: OAC-V28A/G43SILENT(=GGG)/K44V/I74D/V84R/R100E/G102R(=CGC): Cyc1t | 72.533 | 60.400 | 11.467 | 2.600 | 74.467 | 5 |
| PLT1574-F5 | Gal1p: OAC-V28A/Y41V/G43SILENT(=GGG)/K44V/T68L/I74G/V84R/G102R: Cyc1t | 71.300 | 59.400 | 10.767 | 2.867 | 73.033 | 6 |
| PLT1573-D8 | Gal1p: OAC-Y41T/G43SILENT(=GGG)/T68L/I74G/V84R/R100M/G102R: Cyc1t | 58.367 | 58.167 | 7.733 | 2.800 | 68.700 | 6 |
| PLT1574-A11 | Gal1p: OAC-V28A/V31G/Y41T/G43SILENT(=GGG)/K44V/T68R/I74R/V84R/R100E/G102R: Cyc1t | 65.033 | 58.133 | 8.167 | 3.067 | 69.367 | 7 |
| PLT1574-B9 | Gal1p: OAC-V31G/Y41S/G43SILENT(=GGG)/K44V/T68R/V84R/R100E: Cyc1t | 75.800 | 57.133 | 9.600 | 2.700 | 69.433 | 5 |
| PLT1576-B5 | Gal1p: OAC-V28A/Y41V/G43SILENT(=GGG)/T68L/I74D/R100E/G102STOP: Cyc1t | 72.900 | 55.833 | 9.900 | 2.467 | 68.200 | 4 |
| PLT1573-F2 | Gal1p: OAC-V28A/Y41V/G43SILENT(=GGG)/T68R/I74G/V84R/R100M/G102R: Cyc1t | 71.900 | 55.433 | 8.367 | 2.567 | 66.367 | 6 |
| PLT1572-H10 | Gal1p: OAC-V31G/G43SILENT(=GGG)/I74G/V84R/R100E: Cyc1t | 49.733 | 54.100 | 6.700 | 2.433 | 63.233 | 3 |
| PLT1573-E12 | Gal1p: OAC-V28A/Y41S/G43SILENT(=GGG)/K44V/T68R/I74R/V84R/R100M/G102R: Cyc1t | 56.833 | 54.000 | 7.100 | 2.433 | 63.533 | 7 |

TABLE 7-continued

Production of Olivetol, Olivetolic Acid and Downstream Cannabinoids

| Strain | OAC mutant | Olivetol (mg/L) | Olivetolic Acid (mg/L) | CBGa (mg/L) | THCa (mg/L) | Total Downstream Metabolites (OVLa, CBGa, THCa) | # of non-conserative mutations |
|---|---|---|---|---|---|---|---|
| PLT1573-D12 | Gal1p: OAC-V28A/V31G/Y41V/G43SILENT(=GGG)/K44V/T68L/I74G/V84R: Cyc1t | 57.633 | 52.500 | 6.967 | 2.467 | 61.933 | 5 |
| PLT1573-B8 | Gal1p: OAC-V28A/Y41V/G43SILENT(=GGG)/K44V/T68L/I74G/V84R/R100M/G102R: Cyc1t | 53.267 | 51.367 | 6.733 | 2.133 | 60.233 | 7 |
| PLT1573-A2 | Gal1p: OAC-V28A/V31G/G43SILENT(=GGG)/T68L/I74R/V84R/R100E/G102R: Cyc1t | 66.700 | 49.600 | 6.900 | 2.467 | 58.967 | 5 |
| PLT1576-B4 | Gal1p: OAC-V31G/Y41V/G43SILENT(=GGG)/K44V/T68L/I74R/V84R/R100E/G102STOP: Cyc1t | 70.700 | 47.633 | 10.833 | 2.600 | 61.067 | 6 |
| PLT1573-G12 | Gal1p: OAC-V31G/Y41T/G43SILENT(=GGG)/K44V/T68R/I74D/V84R/G102R: Cyc1t | 71.933 | 46.133 | 7.600 | 2.400 | 56.133 | 6 |
| PLT1576-G12 | Gal1p: OAC-V31G/Y41T/G43SILENT(=GGG)/K44V/T68R/I74D/V84R/R100E/G102R: Cyc1t | 56.133 | 45.800 | 10.667 | 2.467 | 58.933 | 7 |
| PLT1575-H5 | Gal1p: OAC-V28A/Y41S/G43SILENT(=GGG)/K44V/T68R/I74G/V84R/R100M/G102R: Cyc1t | 59.733 | 44.533 | 10.500 | 2.467 | 57.500 | 7 |
| PLT1576-A6 | Gal1p: OAC-V28A/Y41V/G43SILENT(=GGG)/K44V/I74R/R100E/G102STOP: Cyc1t | 63.500 | 44.400 | 9.533 | 2.367 | 56.300 | 4 |
| PLT1576-D1 | Gal1p: OAC-V28A/V31G/Y41T/G43SILENT(=GGG)/K44V/I74E/V84R/R100M/G102R: Cyc1t | 67.767 | 41.500 | 9.867 | 2.533 | 53.900 | 6 |
| PLT1572-E8 | Gal1p: OAC-V28A/G43SILENT(=GGG)/K44V/T68R/I74E/V84R/R100E/G102STOP: Cyc1t | 29.467 | 32.433 | 2.833 | 1.167 | 36.433 | 5 |
| PLT1572-H9 | Gal1p: OAC-V31G/Y41T/G43SILENT(=GGG)/K44V/T68L/I74D/V84R/G102R: Cyc1t | 43.067 | 30.200 | 3.333 | 1.233 | 34.767 | 6 |
| PLT1575-F9 | Gal1p: OAC-Y41V/G43SILENT(=GGG)/K44V/T68L/I74R/V84R/G102R: Cyc1t | 106.267 | 13.633 | 2.033 | 0.533 | 16.200 | 6 |

Table 8 illustrates the ratio of OVLa or downstream metabolites (CBGa, CBDa, THCa) to OVL in OAC variants.

TABLE 8

Ratio of OVLa or Downstream Metabolites (CBGa, CBDa, THCa) to OVL in OAC Variants

| Strain | OAC mutant | # of non-conservative mutations | OVLa:OVL ratio | Total Downstream:OVL |
|---|---|---|---|---|
| HB1891 | Wild type OAC | NA | 1.105 | 1.301 |
| HB1892 | RFP negative: no OAC | NA | 0.076 | 0.083 |
| PLT1577-D10 | Gal1p:OAC-V28A/Y41T/G43 SILENT(=GGG)/T68L/I74E/V84R/R100M/G102R: Cyc1t | 6 | 1.569 | 1.804 |
| PLT1575-D12 | Gal1p:OAC-Y415/G43SI LENT(=GGG)/K44V/T68R/I74R/V84R: Cyc1t | 5 | 1.227 | 1.451 |
| PLT1576-B9 | Gal1p:OAC-V28A/V31G/Y41S/G43SILENT(=GGG)/K44V/T68L/I74R/V84R/R100E/G102R:Cyc1t | 7 | 1.485 | 1.839 |
| PLT1575-C12 | Gal1p:OAC-V28A/Y41T/G43SILENT(=GGG)/T68L/I74G/V84R/R100E: Cyc1t | 5 | 1.003 | 1.218 |
| PLT1575-D2 | Gal1p:OAC-V28A/Y41T/G43SILENT(=GGG)/K44V/T68L/I74D/V84R/R100M/G102R:Cyc1t | 7 | 0.901 | 1.091 |
| PLT1572-B10 | Gal1p:OAC-V28A/Y41T/G43SILENT(=GGG)/T68L/I74D/V84R/G102R:Cyc1t | 5 | 1.609 | 1.856 |
| PLT1576-A9 | Gal1p:OAC-V28A/Y41T/G43SILENT(=GGG)/K44V/T68L/I74R/V84R/R100E/G102R:Cyc1t | 7 | 1.053 | 1.259 |
| PLT1577-D1 | Gal1p:OAC-Y41T/G43SILENT(=GGG)/T68R/I74R/V84R/R100M/G102STOP:Cyc1t | 5 | 0.961 | 1.184 |
| PLT1577-B7 | Gal1p:OAC-V28A/Y41V/G43SILENT(=GGG)/K44V/T68L/I74G/V84R/R100E/G102R:Cyc1t | 7 | 0.907 | 1.084 |
| PLT1575-F8 | Gal1p:OAC-V28A/Y41T/G43SILENT(=GGG)/K44V/T68R/I74G/V84R/G102STOP:Cyc1t | 5 | 0.839 | 1.027 |
| PLT1574-H11 | Gal1p:OAC-V28A/Y41V/G43SILENT(=GGG)/K44V/T68L/I74R/V84R/R100E/G102STOP:Cyc1t | 6 | 0.929 | 1.136 |
| PLT1575-E1 | Gal1p:OAC-V28A/V31G/Y41T/G43SILENT(=GGG)/K44V/T68R/I74E/V84R/R100E:Cyc1t | 6 | 0.783 | 0.959 |
| PLT1575-G1 | Gal1p:OAC-V28A/Y41S/G43SILENT(=GGG)/T68R/I74R/V84R/R100M/G102 STOP: Cyc1t | 5 | 0.904 | 1.068 |

TABLE 8-continued

Ratio of OVLa or Downstream Metabolites (CBGa, CBDa, THCa) to OVL in OAC Variants

| Strain | OAC mutant | # of non-conservative mutations | OVLa:OVL ratio | Total Downstream:OVL |
|---|---|---|---|---|
| PLT1576-A2 | Gal1p:OAC-Y41T/G43SILENT(=GGG)/K44V/T68L/I74G/V84R/G102R:Cyc1t | 6 | 1.107 | 1.378 |
| PLT1576-B10 | Gal1p:OAC-V28A/Y41T/G43SILENT(=GGG)/K44V/T68R/I74R/V84R/R100E/G102R:Cyc1t | 7 | 0.981 | 1.227 |
| PLT1573-D7 | Gal1p:OAC-V28A/V31G/Y41S/G43SILENT(=GGG)/K44V/T68R/I74R/V84R:Cyc1t | 5 | 1.046 | 1.247 |
| PLT1575-H10 | Gal1p:OAC-V28A/G43SILENT(=GGG)/K44V/I74D/V84R/R100E/G102R(=CGC):Cyc1t | 5 | 0.834 | 1.031 |
| PLT1574-F5 | Gal1p:OAC-V28A/Y41V/G43 SILENT(=GGG)/K44V/T68L/I74G/V84R/G102R:Cyc1t | 6 | 0.838 | 1.030 |
| PLT1573-D8 | Gal1p:OAC-Y41T/G43SILENT(=GGG)/T68L/I74G/V84R/R100M/G102R:Cyc1t | 6 | 0.994 | 1.174 |
| PLT1574-A11 | Gal1p:OAC-V28A/V31G/Y41T/G43SILENT(=GGG)/K44V/T68R/I74R/V84R/R100E/G102R:Cyc1t | 7 | 0.890 | 1.061 |
| PLT1574-B9 | Gal1p:OAC-V31G/Y41S/G43SILENT(=GGG)/K44V/T68R/V84R/R100E:Cyc1t | 5 | 0.757 | 0.921 |
| PLT1576-B5 | Gal1p:OAC-V28A/Y41V/G43SILENT(=GGG)/T68L/I74D/R100E/G102STOP:Cyc1t | 4 | 0.767 | 0.937 |
| PLT1573-F2 | Gal1p:OAC-V28A/Y41V/G43SILENT(=GGG)/T68R/I74G/V84R/R100M/G102R:Cyc1t | 6 | 0.783 | 0.936 |
| PLT1572-H10 | Gal1p:OAC-V31G/G43SILENT(=GGG)/I74G/V84R/R100E:Cyc1t | 3 | 1.102 | 1.287 |
| PLT1573-E12 | Gal1p:OAC-V28A/Y41S/G43SILENT(=GGG)/K44V/T68R/I74R/V84R/R100M/G102R:Cyc1t | 7 | 0.951 | 1.119 |
| PLT1573-D12 | Gal1p:OAC-V28A/V31G/Y41V/G43SILENT(=GGG)/K44V/T68L/I74G/V84R:Cyc1t | 5 | 1.082 | 1.267 |
| PLT1573-B8 | Gal1p:OAC-V28A/Y41V/G43SILENT(=GGG)/K44V/T68L/I74G/V84R/R100M/G102R:Cyc1t | 7 | 0.986 | 1.152 |

TABLE 8-continued

Ratio of OVLa or Downstream Metabolites (CBGa, CBDa, THCa) to OVL in OAC Variants

| Strain | OAC mutant | # of non-conservative mutations | OVLa:OVL ratio | Total Downstream:OVL |
|---|---|---|---|---|
| PLT1573-A2 | Gal1p:OAC-V28A/V31G//G43SILENT(=GGG) T68L/I74R/V84R/R100E/G102R:Cyc1t | 5 | 0.753 | 0.894 |
| PLT1576-B4 | Gal1p:OAC-V31G/Y41V/G43SILENT(=GGG)/K44V/T68L/I74R/V84R/R100E/G102STOP:Cyc1t | 6 | 0.679 | 0.873 |
| PLT1573-G12 | Gal1p:OAC-V31G/Y41T/G43SILENT(=GGG)/K44V/T68R/I74D/V84R/G102R:Cyc1t | 6 | 0.638 | 0.777 |
| PLT1576-G12 | Gal1p:OAC-V31G/Y41T/G43SILENT(=GGG)/K44V/T68R/I74D/V84R/R100E/G102R:Cyc1t | 7 | 0.824 | 1.064 |
| PLT1575-H5 | Gal1p:OAC-V28A/Y41S/G43SILENT(=GGG)/K44V/T68R/I74G/V84R/R100M/G102R:Cyc1t | 7 | 0.748 | 0.966 |
| PLT1576-A6 | Gal1p:OAC-V28A/Y41V/G43SILENT(=GGG)/K44V/I74R/R100E/G102STOP:Cyc1t | 4 | 0.703 | 0.891 |
| PLT1576-D1 | Gal1p:OAC-V28A/V31G/Y41T/G43SILENT(=GGG)/K44V/I74E/V84R/R100M/G102R:Cyc1t | 6 | 0.614 | 0.798 |
| PLT1572-E8 | Gal1p:OAC-V28A/G43SILENT(=GGG)/K44V/T68R/I74E/V84R/R100E/G102STOP:Cyc1t | 5 | 1.101 | 1.236 |
| PLT1572-H9 | Gal1p:OAC-V31G/Y41T/G43SILENT(=GGG)/K44V/T68L/I74D/V84R/G102R:Cyc1t | 6 | 0.729 | 0.838 |
| PLT1575-F9 | Gal1p:OAC-Y41V/G43SILENT(=GGG)/K44V/T68L/I74R/V84R/G102R:Cyc1t | 6 | 0.138 | 0.164 |

Table 9 provides a summary of mutational frequency data.

TABLE 9

Mutational Frequency Data

| Mutation | mutational type | Total occurrences in sequence set (/37) | Occurrences in best 10 improved olivetolic acid producers (/10) | Occurrences in strains with improved total downstream metabolites vs WT (/24) | Occurrences in strains with improved OVLa:OVL ratios vs WT (/5) |
|---|---|---|---|---|---|
| V28A | Conservative | 26 | 8 | 18 | 3 |
| Y41T | Non-conservative | 16 | 7 | 12 | 3 |
| T68L | Non-conservative | 18 | 7 | 12 | 4 |
| I74E | Non-conservative | 4 | 1 | 2 | 1 |

TABLE 9-continued

Mutational Frequency Data

| Mutation | mutational type | Total occurrences in sequence set (/37) | Occurrences in best 10 improved olivetolic acid producers (/10) | Occurrences in strains with improved total downstream metabolites vs WT (/24) | Occurrences in strains with improved OVLa:OVL ratios vs WT (/5) |
|---|---|---|---|---|---|
| V84R | Non-conservative | 35 | 10 | 22 | 5 |
| R100M | Non-conservative | 10 | 3 | 6 | 1 |
| G102R | Non-conservative | 22 | 6 | 13 | 5 |
| K44V | Non-conservative | 27 | 6 | 15 | 3 |
| T68R | Non-conservative | 15 | 3 | 10 | 1 |
| V31G | Conservative | 13 | 2 | 5 | 1 |
| I74R | Non-conservative | 14 | 4 | 9 | 2 |
| R100E | Non-conservative | 17 | 4 | 11 | 1 |
| I74D | Non-conservative | 7 | 2 | 4 | 1 |
| G102S | Non-conservative | 8 | 2 | 5 | 0 |
| Y41S | Non-conservative | 7 | 1 | 5 | 2 |
| Y41V | Non-conservative | 10 | 1 | 5 | 0 |
| I74G | Conservative | 11 | 3 | 7 | 2 |
| G102STOP | Conservative | 8 | 2 | 6 | 0 |
| G43SILENT (=GGG | Conservative | 37 | 10 | 24 | 5 |

Use in Host Cells

Phytocannabinoids, such as tetrahydrocannabinol (THC) and cannabidiol (CBD), can be extracted from plant material for medical and psychotropic purposes. However, the synthesis of plant material is costly, not readily scalable to large volumes, and requires a lengthy grow periods to produce sufficient quantities of phytocannabinoids. An organism capable of fermentation, such as *Saccharomyces cerevisiae*, that is capable of producing cannabinoids would provide an economical route to producing these compounds on an industrial scale.

The early stages of the cannabinoid pathway proceeds via the generation of olivetolic acid by the type III PKS olivetolic acid synthase (OAS) and cyclase olivetolic acid cyclase (OAC). This reaction uses a hexanoyl-CoA starter as well as three units of malonyl-CoA. Olivetolic acid is the backbone of most classical cannabinoids and can be prenylated to form CBGA, which is ultimately converted to CBDA or THCA by an oxidocyclase. Production of olivetolic acid in *S. cerevisiae* is challenging as OAS generates significant by-products such as HTAL, PDAL and olivetol. These by-products can be reduced in a recombinant organism by the introduction of olivetolic acid cyclase (OAC) but even with this enzyme by-products can account for up to 80% of the total carbon in the reaction.

Table 10 lists specific examples of host cell organisms in which the described OAC variants may be utilized for preparation of cannabinoids in the described pathways.

TABLE 10

List of Host Cell Organisms

| Type | Organisms |
|---|---|
| Bacteria | *Escherichia coli, Streptomyces coelicolor and other species., Bacillus subtilis, Mycoplasma genitalium, Synechocytis, Zymomonas mobilis, Corynebacterium glutamicum, Synechococcus* sp., *Salmonella typhi, Shigella flexneri, Shigella sonnei,* and *Shigella disenteriae, Pseudomonas putida, Pseudomonas aeruginosa, Pseudomonas mevalonii, Rhodobacter sphaeroides, Rhodobacter capsulatus, Rhodospirillum rubrum, Rhodococcus* sp. |
| Fungi | *Saccharomyces cerevisiae, Ogataea polymorpha, Komagataella phaffii, Kluyveromyces lactis, Neurospora crassa, Aspergillus niger, Aspergillus nidulans, Schizosaccharomyces pombe, Yarrowia lipolytica, Myceliophthora thermophila, Aspergillus oryzae, Trichoderma reesei, Chrysosporium lucknowense, Fusarium* sp., *Fusarium gramineum, Fusarium venenatum, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stipitis, Pichia methanolica, Hansenula polymorpha.* |
| Protists | *Chlamydomonas reinhardtii, Dictyostelium discoideum, Chlorella* sp., *Haematococcus pluvialis, Arthrospira platensis, Dunaliella* sp., *Nannochloropsis oceanica.* |

TABLE 10-continued

| List of Host Cell Organisms | |
|---|---|
| Type | Organisms |
| Plants | *Cannabis sativa, Arabidopsis thaliana, Theobroma cacao*, maize, banana, peanut, field peas, sunflower, *Nicotiana* sp., tomato, canola, wheat, barley, oats, potato, soybeans, cotton, *sorghum*, lupin, rice. |

Phytocannabinoids may be produced in a host cell involving Dictyostelium discoideum polyketide synthase (DiPKS), olivetolic acid cyclase (OAC), prenyltransferases, and/or mutants of these, as described in Applicant's co-pending International Application No. PCT/CA2020/050687 (herein incorporated by reference). For example, a host cell transformed with a polyketide synthase coding sequence, an olivetolic acid cyclase coding sequence, and a prenyltransferase coding sequence may be prepared. The polyketide synthase and the olivetolic acid cyclase catalyze synthesis of olivetolic acid from malonyl CoA. The olivetolic acid cyclase may include wild type, or any of the functional mutants described herein. The host cell may include a yeast cell, a bacterial cell, a protest cell or a plant cell, selected from among those listed in Table 10.

Combinations of the methods, nucleotides, and expression vectors described herein as well as in Applicant's co-pending International Application No. PCT/CA2020/050687 may be employed together to produce phytocannabinoids, phytocannabinoid precursors such as polyketides. Depending on the desired product, selections of characteristics of the cells and methods employed may be selected to achieve production of the cannabinoid, cannabinoid precursor, or intermediate of interest.

Methods of producing a phytocannabinoid may comprising culturing a host cell under suitable culture conditions to form a phytocannabinoid, said host cell comprising: a polynucleotide encoding a polyketide synthase (PKS) enzyme; a polynucleotide encoding an olivetolic acid cyclase (OAC) enzyme mutants as described herein; and a polynucleotide encoding a prenyltransferase (PT) enzyme; and optionally comprising: a polynucleotide encoding an acyl-CoA synthase (Alk) enzyme; a polynucleotide encoding a fatty acyl CoA activating (CsAAE) enzyme; and/or a polynucleotide encoding a THCa synthase (OXC) enzyme.

An expression vector can be prepared comprising a polynucleotide encoding a polyketide synthase (PKS) enzyme; a polynucleotide encoding an olivetolic acid cyclase (OAC) enzyme mutants as described herein; and a polynucleotide encoding a prenyltransferase (PT) enzyme. The expression vector can optionally comprise a polynucleotide encoding an acyl-CoA synthase (Alk) enzyme; a polynucleotide encoding CsAAE1; and/or a polynucleotide encoding a THCa synthase (OXC) enzyme.

Examples Only

In the preceding description, for purposes of explanation, numerous details are set forth in order to provide a thorough understanding of the embodiments. However, it will be apparent to one skilled in the art that these specific details are not required.

The embodiments described herein are intended to be examples only. Alterations, modifications and variations can be effected to the particular embodiments by those of skill in the art. The scope of the claims should not be limited by the particular embodiments set forth herein, but should be construed in a manner consistent with the specification as a whole.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

REFERENCES

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

Patent Publications

U.S. Pat. No. 7,361,482

U.S. Pat. No. 8,884,100 (Page et al.) Aromatic Prenyltransferase from *Cannabis.*

WO2018148848 (Mookerjee et al.) publication of PCT/CA2018/050189, METHOD AND CELL LINE FOR PRODUCTION OF PHYTOCANNABINOIDS AND PHYTOCANNABINOID ANALOGUES IN YEAST WO2018148849 (Mookerjee et al.) publication of PCT/CA2018/050190, METHOD AND CELL LINE FOR PRODUCTION OF POLYKETIDES IN YEAST

Non-Patent Literature

Bai Flagfeldt, D., Siewers, V., Huang, L. and Nielsen, J. (2009) "Characterization of chromosomal integration sites for heterologous gene expression in *Saccharomyces cerevisiae" Yeast,* 26, 545-551.

Eisenberg, D., Schwarz, E., Komaromy, M., & Wall, R. (1984). "Analysis of membrane and surface protein sequences with the hydrophobic moment plot". *Journal of Molecular Biology,* 179(1), 125-142. https://doi.org/10.1016/0022-2836(84)90309-7.

Gagne, S. J., et al. (2012) "Identification of Olivetolic Acid Cyclase from *Cannabis Sativa* Reveals a Unique Catalytic Route to Plant Polyketides." *Proceedings of the National Academy of Sciences*, vol. 109, no. 31, 2012, pp. 12811-12816. doi:10.1073/pnas.1200330109.

Ghosh, R., A. Chhabra, P. A. Phatale, S. K. Samrat, J. Sharma, A. Gosain, D. Mohanty, S. Saran and R. S. Gokhale (2008) "Dissecting the Functional Role of Polyketide Synthases in Dictyostelium discoideum biosynthesis of the differentiation regulating factor 4-methyl-5-pentylbenzene-1,3-diol" *Journal of Biological Chemistry,* 283(17), 11348-11354.

Gietz, R. D. and Schiestl, R. H., (2007) "High-efficiency yeast transformation using the LiAc/SS carrier DNA/PEG method." *Nat. Protoc.* 2, 31-34.

Gietz R. D. (2014) Yeast Transformation by the LiAc/SS Carrier DNA/PEG Method (pp 1-12). In: Smith J., Burke D. (eds) Yeast Genetics. Methods in Molecular Biology (Methods and Protocols), vol 1205. Humana Press, New York, N.Y. https://doi.org/10.1007/978-1-4939-1363-3_1.

Jensen, N. B., Strucko, T., Kildegaard, K. R., David, F., et al., (2014). EasyClone: method for iterative chromosomal integration of multiple genes in *Saccharomyces cerevi-* siae. *FEMS Yeast Research*, Volume 14, Issue 2, pages 238-248; https://doi.org/10.1111/1567-1364.12118.

Kim, J.-M., Song, H.-Y., Choi, H.-J., So, K.-K., Kim, D.-H., Chae, K.-S., . . . Jahng, K.-Y. (2015). "Characterization of NpgA, a 4'-phosphopantetheinyl transferase of *Aspergillus nidulans*, and evidence of its involvement in fungal growth and formation of conidia and cleistothecia for development." *Journal of Microbiology,* 53(1), 21-31 https://doi.org/10.1007/s12275-015-4657-8.

Kuzuyama et al. (2005) Structural basis for the promiscuous biosynthetic prenylation of aromatic natural products, Nature, volume 435, pages 983-987; doi: 10.1038/nature03668.

Liu, J., Zhang, W., Du, G., Chen, J., & Zhou, J. (2013). "Overproduction of geraniol by enhanced precursor supply in *Saccharomyces cerevisiae." Journal of Biotechnology,* 168(4), 446-451. https://doi.org/10.1016/J.JBIOTEC.2013.10.017.

Luo, X., Reiter, M., d'Espaux, L., Wong, J., Denby, C., Lechner, A., Zhang, Y., Grzybowski, A., Harth, S., Lin, W., Lee, H., Yu, C., Shin, J., Deng, K., Benites, V., Wang, G., Baidoo, E., Chen, Y., Dev, I., Petzold, C. and Keasling, J. (2019). "Complete biosynthesis of cannabinoids and their unnatural analogues in yeast." *Nature,* 567(7746), pp. 123-126.

Oswald, Marilyne; Marc Fischer, Nicole Dirninger, Francis Karst, (2007) "Monoterpenoid biosynthesis in *Saccharomyces cerevisiae." FEMS Yeast Research,* 7(3), 413-421. https://doi.org/10.1111/j.1567-1364.2006.00172.x Peng, B., Nielsen, L. K., Kampranis, S. C., & Vickers, C. E. (2018). Engineered protein degradation of farnesyl pyrophosphate synthase is an effective regulatory mechanism to increase monoterpene production in *Saccharomyces cerevisiae. Metabolic Engineering,* 47, 83-93. https://doi.org/10.1016/J.YMBEN.2018.02.005.

Ro, D.-K., Paradise, E. M., Ouellet, M., Fisher, K. J., Newman, K. L., Ndungu, J. M., Keasling, J. D. (2006). Production of the antimalarial drug precursor artemisinic acid in engineered yeast. *Nature,* 440(7086), 940-943. JOUR. https://doi.org/10.1038/nature04640.

Ryan, O. W., Poddar, S., & Cate, J. H. D. (2016). CRISPR-Cas9 Genome Engineering in *Saccharomyces cerevisiae* Cells. Cold Spring Harbor Protocols, 2016(6), pdb. prot086827. https://doi.org/10.1101/pdb.prot086827.

Saeki, H., Hara, R., Takahashi, H., Iijima, M., Munakata, R., Kenmoku, H., . . . Taura, F. (2018). An Aromatic Farnesyltransferase Functions in Biosynthesis of the Anti-HIV Meroterpenoid Daurichromenic Acid. Plant Physiology, 178(2), 535-551; https://doi.org/10.1104/PP.18.00655.

Shi, S., Chen, Y., Siewers, V., & Nielsen, J. (2014). "Improving Production of Malonyl Coenzyme A-Derived Metabolites by Abolishing Snf1-Dependent Regulation of Acc1." *mBio,* 5(3), e01130-14. https://doi.org/10.1128/mBio.01130-14.

Shiba, Y., Paradise, E. M., Kirby, J., Ro, D.-K., & Keasling, J. D. (2007). "Engineering of the pyruvate dehydrogenase bypass in *Saccharomyces cerevisiae* for high-level production of isoprenoids." *Metabolic Engineering,* 9(2), 160-168. https://doi.org/10.1016/J.YMBEN.2006.10.005.

Sirikantaramas, S., Taura, F., Tanaka, Y., Ishikawa, Y., Morimoto, S., & Shoyama, Y. (2005). "Tetrahydrocannabinolic acid synthase, the enzyme controlling marijuana psychoactivity, is secreted into the storage cavity of the glandular trichomes". *Plant and Cell Physiology,* 46(9), 1578-1582.

Stout, J. M., Boubakir, Z., Ambrose, S. J., Purves, R. W., & Page, J. E. (2012). The hexanoyl-CoA precursor for cannabinoid biosynthesis is formed by an acyl-activating enzyme in *Cannabis sativa* trichomes. *The Plant Journal,* 71(3), 353-365.

Taura, Futoshi, et al. (2009) "Characterization of olivetol synthase, a polyketide synthase putatively involved in cannabinoid biosynthetic pathway." *FEBS letters,* 583.12 (2009): 2061-2066.

Varshaysky, A. (2011). The N-end rule pathway and regulation by proteolysis. *Protein Science* 20(8):1285-1476. https://doi.org/10.1002/pro.666.

What is claimed is:

1. A method of producing olivetolic acid (OVLa) or a phytocannabinoid produced therefrom in a heterologous host cell comprising OVLa-producing or phytocannabinoid-producing capacity, said method comprising:

transforming said host cell with a nucleotide encoding a variant olivetolic acid cyclase (OAC) protein of at least 95% sequence identity with the amino acid sequence of SEQ ID NO:42, and having at least 6 amino acid mutations relative to the wild type OAC protein sequence of SEQ ID NO:91, said at least 6 mutations being selected from the group consisting of:

V28A;
V31G;
Y41T, Y41S or Y41V;
K44V;
T68L or T68R;
I74E, I74R, I74D or I74G;
V84R;
R100M or R100E; and
G102R, or G102S, and culturing said transformed host cell to produce olivetolic acid or phytocannabinoids therefrom.

2. The method of claim 1, wherein said variant OAC protein has 7, 8, or 9 amino acid mutations relative to the wild type OAC protein sequence of SEQ ID NO:91 selected from the group consisting of:

V28A;
V31G;
Y41T, Y41S or Y41V;
K44V;
T68L or T68R;
I74E, I74R, I74D or I74G;
V84R;
R100M or R100E; and
G102R, or G102S.

3. The method according to claim 1, wherein the nucleotide encoding the variant olivetolic acid cyclase (OAC) protein has a sequence comprising:

(a) a nucleotide sequence of SEQ ID NO:5; or (b) a nucleotide sequence having at least 95% sequence identity with the sequence of (a).

4. The method according to claim 1, wherein the variant OAC protein comprises the sequence of SEQ ID NO: 42.

5. The method of claim 1, wherein said phytocannabinoid is cannabigerol (CBG), cannabigerolic acid (CBGa), cannabigerovarin (CBGV), cannabigerovarinic acid (CBGVa), cannabigerocin (CBGO), cannabigerocinic acid (CBGOa), a cannabivarin, tetrahydrocannabinol (THC), or tetrahydrocannabinolic acid (THCa).

6. The method of claim 1, wherein the host cell additionally comprises a divarinic acid synthase and produces divarinic acid.

7. The method of claim 1, wherein said host cell is *S. cerevisiae.*

8. The method of claim 1, wherein said transformed host cell additionally comprises a polynucleotide encoding a polyketide synthase enzyme or a polynucleotide encoding a prenyltransferase enzyme.

9. An isolated polypeptide having olivetolic acid cyclase (OAC) activity comprising an amino acid sequence of at least 95% sequence identity with the amino acid sequence of SEQ ID NO: 42, and having at least 6 amino acid mutations relative to the wild type OAC protein sequence of SEQ ID NO:91, said at least 6 mutations being selected from the group consisting of:

V28A;
V31G;
Y41T, Y41S or Y41V;
K44V;
T68L or T68R;
I74E, I74R, I74D or I74G;
V84R;
R100M or R100E; and
G102R, or G102S.

10. The isolated polypeptide of claim 9, wherein said variant OAC protein has 7, 8, or 9 of the amino acid mutations relative to the wild type OAC protein sequence.

11. The isolated polypeptide of claim 9, having the amino acid sequence of SEQ ID NO:42.

12. An isolated polynucleotide encoding the isolated polypeptide of claim 9 having (a) the nucleotide sequence of SEQ ID NO:5; or (b) a nucleotide sequence having at least 95% sequence identity with the nucleotide sequence of (a).

13. An expression vector comprising the polynucleotide according to claim 12.

14. An isolated host cell transformed with the expression vector of claim 12.

* * * * *

SEQUENCE LISTING

```
<160> NUMBER OF SEQ ID NOS: 93

<210> SEQ ID NO 1
<211> LENGTH: 6114
<212> TYPE: DNA
<213> ORGANISM: Artificial Sequence
<220> FEATURE:
<223> OTHER INFORMATION: mScarlet nucleotide sequence

<400> SEQUENCE: 1

aagagtaaaa aattgtactt ggcggataat gcctttagcg gcttaactgt gccctccatg      60

gaaaaatcag tcaagatatc cacatgtgtt tttagtaaac aaattttggg acctaatgct     120

tcaactaact ccagtaattc cttggtggta cgaacatcca atgaagcaca caagtttgtt     180

tgcttttcgt gcatgatatt aaatagcttg gcagcaacag gactaggatg agtagcagca     240

cgttccttat atgtagcttt cgacatgatt tatcttcgtt tcctgcaggt ttttgttctg     300

tgcagttggg ttaagaatac tgggcaattt catgtttctt caacactaca tatgcgtata     360

tataccaatc taagtctgtg ctccttcctt cgttcttcct tctgttcgga gattaccgaa     420

tcaaaaaaat ttcaaagaaa ccgaaatcaa aaaaaagaat aaaaaaaaaa tgatgaattg     480

aattgaaaag ctagcttatc gatgataagc tgtcaaagat gagaattaat tccacggact     540
```

-continued

```
atagactata ctagatactc cgtctactgt acgatacact tccgctcagg tccttgtcct    600
ttaacgaggc cttaccactc ttttgttact ctattgatcc agctcagcaa aggcagtgtg    660
atctaagatt ctatcttcgc gatgtagtaa aactagctag accgagaaag agactagaaa    720
tgcaaaaggc acttctacaa tggctgccat cattattatc cgatgtgacg ctgcagcttc    780
tcaatgatat tcgaatacgc tttgaggaga tacagcctaa tatccgacaa actgttttac    840
agatttacga tcgtacttgt tacccatcat tgaattttga acatccgaac ctgggagttt    900
tccctgaaac agatagtata tttgaacctg tataataata tatagtctag cgctttacgg    960
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc tttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcatttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gtttttttggg  1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggtgtctaaa ggtgaagccg tcatcaaaga attcatgaga ttcaaggttc   2700
acatggaagg ttctatgaat ggtcacgaat tcgaaattga aggtgaaggt gagggtagac   2760
catatgaagg tactcaaact gctaagttga aggttacaaa aggtggtcca ttgccattct   2820
cttgggatat tttgtctcca caattcatgt acggttctag agcttttaca aaacacccag   2880
ctgatatccc agattactac aagcaatcat ttccagaggg tttcaagtgg gaaagagtta   2940
```

```
tgaattttga agatggtggt gccgttactg ttactcaaga tacttctttg gaagatggca   3000
ccttgatcta caaggttaag ttgagaggta ctaatttccc accagatggt ccagttatgc   3060
aaaaaaagac tatgggttgg gaagctagta ctgaaagatt atatccagag gatggtgttt   3120
tgaagggtga tattaagatg gccttgagat tgaaagacgg tggtagatat ttggctgatt   3180
tcaagactac ttacaaggcc aaaaagccag ttcaaatgcc aggtgcttat aacgttgata   3240
gaaagttgga tatcacctct cacaacgaag attacaccgt tgttgaacag tacgaaagat   3300
ctgaaggtag acattctact ggtggtatgg atgagttgta caagtaactc gagcatgcat   3360
ctagagggcc gcatcatgta attagttatg tcacgcttac attcacgccc tccccccaca   3420
tccgctctaa ccgaaaagga aggagttaga caacctgaag tctaggtccc tatttatttt   3480
tttatagtta tgttagtatt aagaacgtta tttatatttc aaatttttct ttttttctg    3540
tacagacgcg tgtacgcatg taacattata ctgaaaacct tgcttgagaa ggttttggga   3600
cgctcgaagg ctttaatttg cggccctgca ttaatgaatc ggccaacgcg cggggagagg   3660
cggtttgcgt attgggcgct cttccgcttc ctcgctcact gactcgctgc gctcggtcgt   3720
tcggctgcgg cgagcggtat cagctcactc aaaggcggta atacggttat ccacagaatc   3780
aggggataac gcaggaaaga acatgtgagc aaaaggccag caaaagccca ggaaccgtaa   3840
aaaggccgcg ttgctggcgt ttttccatag gctccgcccc cctgacgagc atcacaaaaa   3900
tcgacgctca agtcagaggt ggcgaaaccc gacaggacta taaagatacc aggcgtttcc   3960
ccctggaagc tccctcgtgc gctctcctgt tccgaccctg ccgcttaccg gatacctgtc   4020
cgcctttctc ccttcgggaa gcgtggcgct ttctcatagc tcacgctgta ggtatctcag   4080
ttcggtgtag gtcgttcgct ccaagctggg ctgtgtgcac gaaccccccg ttcagcccga   4140
ccgctgcgcc ttatccggta actatcgtct tgagtccaac ccggtaagac acgacttatc   4200
gccactggca gcagccactg gtaacaggat tagcagagcg aggtatgtag gcggtgctac   4260
agagttcttg aagtggtggc ctaactacgg ctacactaga agaacagtat ttggtatctg   4320
cgctctgctg aagccagtta ccttcggaaa aagagttggt agctcttgat ccggcaaaca   4380
aaccaccgct ggtagcggtg gtttttttgt ttgcaagcag cagattacgc gcagaaaaaa   4440
aggatctcaa gaagatcctt tgatcttttc tacggggtct gacgctcagt ggaacgaaaa   4500
ctcacgttaa gggattttgg tcatgagatt atcaaaaagg atcttcacct agatcctttt   4560
aaattaaaaa tgaagtttta aatcaatcta aagtatatat gagtaaactt ggtctgacag   4620
ttaccaatgc ttaatcagtg aggcacctat ctcagcgatc tgtctatttc gttcatccat   4680
agttgcctga ctccccgtcg tgtagataac tacgatacgg gagcgcttac catctggccc   4740
cagtgctgca atgataccgc gagacccacg ctcaccggct ccagatttat cagcaataaa   4800
ccagccagcc ggaagggccg agcgcagaag tggtcctgca actttatccg cctccattca   4860
gtctattaat tgttgccggg aagctagagt aagtagttcg ccagttaata gtttgcgcaa   4920
cgttgttggc attgctacag gcatcgtggt gtcactctcg tcgtttggta tggcttcatt   4980
cagctccggt tcccaacgat caaggcgagt tacatgatcc cccatgttgt gcaaaaaagc   5040
ggttagctcc ttcggtcctc cgatcgttgt cagaagtaag ttggccgcag tgttatcact   5100
catggttatg gcagcactgc ataattctct tactgtcatg ccatccgtaa gatgcttttc   5160
tgtgactggt gagtactcaa ccaagtcatt ctgagaatag tgtatgcggc gaccgagttg   5220
ctcttgcccg gcgtcaatac gggataatag tgtatcacat agcagaactt taaaagtgct   5280
```

```
catcattgga aaacgttctt cggggcgaaa actctcaagg atcttaccgc tgttgagatc   5340
cagttcgatg taacccactc gtgcacccaa ctgatcttca gcatctttta ctttcaccag   5400
cgtttctggg tgagcaaaaa caggaaggca aaatgccgca aaaaagggaa taagggcgac   5460
acggaaatgt tgaatactca tactcttcct ttttcaatgg gtaataactg atataattaa   5520
attgaagctc taatttgtga gtttagtata catgcattta cttataatac agttttttag   5580
ttttgctggc cgcatcttct caaatatgct tcccagcctg cttttctgta acgttcaccc   5640
tctaccttag catcccttcc ctttgcaaat agtcctcttc caacaataat aatgtcagat   5700
cctgtagaga ccacatcatc cacggttcta tactgttgac ccaatgcgtc tcccttgtca   5760
tctaaaccca caccgggtgt cataatcaac caatcgtaac cttcatctct tccacccatg   5820
tctctttgag caataaagcc gataacaaaa tctttgtcgc tcttcgcaat gtcaacagta   5880
cccttagtat attctccagt agatagggag cccttgcatg acaattctgc taacatcaaa   5940
aggcctctag gttcctttgt tacttcttct gccgcctgct tcaaaccgct aacaatacct   6000
gggcccacca caccgtgtgc attcgtaatg tctgcccatt ctgctattct gtatacaccc   6060
gcagagtact gcaatttgac tgtattacca atgtcagcaa attttctgtc ttcg         6114
```

<210> SEQ ID NO 2
<211> LENGTH: 5724
<212> TYPE: DNA
<213> ORGANISM: Artificial Sequence
<220> FEATURE:
<223> OTHER INFORMATION: OAC wild type nucleotide sequence

<400> SEQUENCE: 2

```
aagagtaaaa aattgtactt ggcggataat gcctttagcg gcttaactgt gccctccatg     60
gaaaaatcag tcaagatatc cacatgtgtt tttagtaaac aaattttggg acctaatgct    120
tcaactaact ccagtaattc cttggtggta cgaacatcca atgaagcaca caagtttgtt    180
tgcttttcgt gcatgatatt aaatagcttg gcagcaacag gactaggatg agtagcagca    240
cgttccttat atgtagcttt cgacatgatt tatcttcgtt tcctgcaggt ttttgttctg    300
tgcagttggg ttaagaatac tgggcaattt catgtttctt caacactaca tatgcgtata    360
tataccaatc taagtctgtg ctccttcctt cgttcttcct tctgttcgga gattaccgaa    420
tcaaaaaaat ttcaaagaaa ccgaaatcaa aaaaaagaat aaaaaaaaaa tgatgaattg    480
aattgaaaag ctagcttatc gatgataagc tgtcaaagat gagaattaat tccacggact    540
atagactata ctagatactc cgtctactgt acgatacact tccgctcagg tccttgtcct    600
ttaacgaggc cttaccactc ttttgttact ctattgatcc agctcagcaa aggcagtgtg    660
atctaagatt ctatcttcgc gatgtagtaa aactagctag accgagaaag agactagaaa    720
tgcaaaaggc acttctacaa tggctgccat cattattatc cgatgtgacg ctgcagcttc    780
tcaatgatat tcgaatacgc tttgaggaga tacagcctaa tatccgacaa actgttttac    840
agatttacga tcgtacttgt tacccatcat tgaattttga acatccgaac ctgggagttt    900
tccctgaaac agatagtata tttgaacctg tataataata tatagtctag cgctttacgg    960
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
```

```
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc tttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcatttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg ttaacttggt taacatcatt cctgctatga   2760
aggacgtcta ctggggtaag gatgtcactc aaaaaaacaa ggaagaaggt tatacccaca   2820
tcgttgaagt caccttcgaa tctgttgaaa ctattcaaga ctacatcatt cacccagctc   2880
acgtcggttt cggtgatgtt tacagatctt tctgggaaaa attgttgatc ttcgactaca   2940
ccccaagaaa gggctaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct tttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
```

```
tccgaccctg ccgcttaccg gatacctgtc cgcctttctc ccttcgggaa gcgtggcgct   3660

ttctcatagc tcacgctgta ggtatctcag ttcggtgtag gtcgttcgct ccaagctggg   3720

ctgtgtgcac gaaccccccg ttcagcccga ccgctgcgcc ttatccggta actatcgtct   3780

tgagtccaac ccggtaagac acgacttatc gccactggca gcagccactg gtaacaggat   3840

tagcagagcg aggtatgtag gcggtgctac agagttcttg aagtggtggc ctaactacgg   3900

ctacactaga agaacagtat ttggtatctg cgctctgctg aagccagtta ccttcggaaa   3960

aagagttggt agctcttgat ccggcaaaca aaccaccgct ggtagcggtg gtttttttgt   4020

ttgcaagcag cagattacgc gcagaaaaaa aggatctcaa gaagatcctt tgatcttttc   4080

tacggggtct gacgctcagt ggaacgaaaa ctcacgttaa gggattttgg tcatgagatt   4140

atcaaaaagg atcttcacct agatcctttt aaattaaaaa tgaagtttta aatcaatcta   4200

aagtatatat gagtaaactt ggtctgacag ttaccaatgc ttaatcagtg aggcacctat   4260

ctcagcgatc tgtctatttc gttcatccat agttgcctga ctccccgtcg tgtagataac   4320

tacgatacgg gagcgcttac catctggccc cagtgctgca atgataccgc gagacccacg   4380

ctcaccggct ccagatttat cagcaataaa ccagccagcc ggaagggccg agcgcagaag   4440

tggtcctgca actttatccg cctccattca gtctattaat tgttgccggg aagctagagt   4500

aagtagttcg ccagttaata gtttgcgcaa cgttgttggc attgctacag gcatcgtggt   4560

gtcactctcg tcgtttggta tggcttcatt cagctccggt tcccaacgat caaggcgagt   4620

tacatgatcc cccatgttgt gcaaaaaagc ggttagctcc ttcggtcctc cgatcgttgt   4680

cagaagtaag ttggccgcag tgttatcact catggttatg gcagcactgc ataattctct   4740

tactgtcatg ccatccgtaa gatgcttttc tgtgactggt gagtactcaa ccaagtcatt   4800

ctgagaatag tgtatgcggc gaccgagttg ctcttgcccg gcgtcaatac gggataatag   4860

tgtatcacat agcagaactt taaaagtgct catcattgga aaacgttctt cggggcgaaa   4920

actctcaagg atcttaccgc tgttgagatc cagttcgatg taacccactc gtgcacccaa   4980

ctgatcttca gcatctttta ctttcaccag cgtttctggg tgagcaaaaa caggaaggca   5040

aaatgccgca aaaaagggaa taagggcgac acggaaatgt tgaatactca tactcttcct   5100

ttttcaatgg gtaataactg atataattaa attgaagctc taatttgtga gtttagtata   5160

catgcattta cttataatac agtttttttag ttttgctggc cgcatcttct caaatatgct   5220

tcccagcctg cttttctgta acgttcaccc tctaccttag catcccttcc ctttgcaaat   5280

agtcctcttc caacaataat aatgtcagat cctgtagaga ccacatcatc cacggttcta   5340

tactgttgac ccaatgcgtc tcccttgtca tctaaaccca caccgggtgt cataatcaac   5400

caatcgtaac cttcatctct tccacccatg tctctttgag caataaagcc gataacaaaa   5460

tctttgtcgc tcttcgcaat gtcaacagta cccttagtat attctccagt agatagggag   5520

cccttgcatg acaattctgc taacatcaaa aggcctctag gttcctttgt tacttcttct   5580

gccgcctgct tcaaaccgct aacaatacct gggcccacca caccgtgtgc attcgtaatg   5640

tctgcccatt ctgctattct gtatacaccc gcagagtact gcaatttgac tgtattacca   5700

atgtcagcaa attttctgtc ttcg                                         5724
```

<210> SEQ ID NO 3
<211> LENGTH: 5724
<212> TYPE: DNA
<213> ORGANISM: Artificial Sequence
<220> FEATURE:
<223> OTHER INFORMATION: OAC-V28A/Y41T/G43SILENT(=GGG)/T68L/I74E/V84R/

-continued

R100M/G102R

<400> SEQUENCE: 3

```
aagagtaaaa aattgtactt ggcggataat gcctttagcg gcttaactgt gccctccatg     60
gaaaaatcag tcaagatatc cacatgtgtt tttagtaaac aaattttggg acctaatgct    120
tcaactaact ccagtaattc cttggtggta cgaacatcca atgaagcaca caagtttgtt    180
tgcttttcgt gcatgatatt aaatagcttg gcagcaacag gactaggatg agtagcagca    240
cgttccttat atgtagcttt cgacatgatt tatcttcgtt tcctgcaggt tttgttctg     300
tgcagttggg ttaagaatac tgggcaattt catgtttctt caacactaca tatgcgtata    360
tataccaatc taagtctgtg ctccttcctt cgttcttcct tctgttcgga gattaccgaa    420
tcaaaaaaat ttcaaagaaa ccgaaatcaa aaaaaagaat aaaaaaaaaa tgatgaattg    480
aattgaaaag ctagcttatc gatgataagc tgtcaaagat gagaattaat tccacggact    540
atagactata ctagatactc cgtctactgt acgatacact tccgctcagg tccttgtcct    600
ttaacgaggc cttaccactc ttttgttact ctattgatcc agctcagcaa aggcagtgtg    660
atctaagatt ctatcttcgc gatgtagtaa aactagctag accgagaaag agactagaaa    720
tgcaaaaggc acttctacaa tggctgccat cattattatc cgatgtgacg ctgcagcttc    780
tcaatgatat tcgaatacgc tttgaggaga tacagcctaa tatccgacaa actgttttac    840
agatttacga tcgtacttgt tacccatcat tgaattttga acatccgaac ctgggagttt    900
tccctgaaac agatagtata tttgaacctg tataataata tatagtctag cgctttacgg    960
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc tttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcattttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gtttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
```

gcttttatgg ttatgaagag gaaaaattgg cagtaacctg gccccacaaa ccttcaaatg 2340
aacgaatcaa attaacaacc ataggatgat aatgcgatta gtttttagc cttatttctg 2400
gggtaattaa tcagcgaagc gatgattttt gatctattaa cagatatata aatgcaaaaa 2460
ctgcataacc actttaacta atactttcaa cattttcggt ttgtattact tcttattcaa 2520
atgtaataaa agtatcaaca aaaaattgtt aatatacctc tatactttaa cgtcaaggag 2580
aaaaaacccc ggatcggact actagcagct gtaatacgac tcactatagg gaatattaag 2640
cttaaacaat ggccgtcaag cacttgatcg tcttaaagtt taaggacgag atcactgaag 2700
cccaaaagga agaattcttc aaaacttacg cgaacttggt taacatcatt cctgctatga 2760
aggacgtcac gtgggggaag gatgtcactc aaaaaaacaa ggaagaaggt tatacccaca 2820
tcgttgaagt caccttcgaa tctgttgaac tgattcaaga ctacatcgag cacccagctc 2880
acgtcggttt cggtgatagg tacagatctt tctgggaaaa attgttgatc ttcgactaca 2940
ccccaatgaa gcggtaactc gagcatgcat ctagagggcc gcatcatgta attagttatg 3000
tcacgcttac attcacgccc tccccccaca tccgctctaa ccgaaaagga aggagttaga 3060
caacctgaag tctaggtccc tatttatttt tttatagtta tgttagtatt aagaacgtta 3120
tttatatttc aaatttttct tttttttctg tacagacgcg tgtacgcatg taacattata 3180
ctgaaaacct tgcttgagaa ggttttggga cgctcgaagg ctttaatttg cggccctgca 3240
ttaatgaatc ggccaacgcg cggggagagg cggtttgcgt attgggcgct cttccgcttc 3300
ctcgctcact gactcgctgc gctcggtcgt tcggctgcgg cgagcggtat cagctcactc 3360
aaaggcggta atacggttat ccacagaatc aggggataac gcaggaaaga acatgtgagc 3420
aaaaggccag caaaagccca ggaaccgtaa aaaggccgcg ttgctggcgt ttttccatag 3480
gctccgcccc cctgacgagc atcacaaaaa tcgacgctca agtcagaggt ggcgaaaccc 3540
gacaggacta taaagatacc aggcgtttcc ccctggaagc tccctcgtgc gctctcctgt 3600
tccgaccctg ccgcttaccg gatacctgtc cgcctttctc ccttcgggaa gcgtggcgct 3660
ttctcatagc tcacgctgta ggtatctcag ttcggtgtag gtcgttcgct ccaagctggg 3720
ctgtgtgcac gaaccccccg ttcagcccga ccgctgcgcc ttatccggta actatcgtct 3780
tgagtccaac ccggtaagac acgacttatc gccactggca gcagccactg gtaacaggat 3840
tagcagagcg aggtatgtag gcggtgctac agagttcttg aagtggtggc ctaactacgg 3900
ctacactaga agaacagtat ttggtatctg cgctctgctg aagccagtta ccttcggaaa 3960
aagagttggt agctcttgat ccggcaaaca aaccaccgct ggtagcggtg gtttttttgt 4020
ttgcaagcag cagattacgc gcagaaaaaa aggatctcaa gaagatcctt tgatcttttc 4080
tacggggtct gacgctcagt ggaacgaaaa ctcacgttaa gggattttgg tcatgagatt 4140
atcaaaaagg atcttcacct agatcctttt aaattaaaaa tgaagtttta aatcaatcta 4200
aagtatatat gagtaaactt ggtctgacag ttaccaatgc ttaatcagtg aggcacctat 4260
ctcagcgatc tgtctatttc gttcatccat agttgcctga ctccccgtcg tgtagataac 4320
tacgatacgg gagcgcttac catctggccc cagtgctgca atgataccgc gagacccacg 4380
ctcaccggct ccagatttat cagcaataaa ccagccagcc ggaagggccg agcgcagaag 4440
tggtcctgca actttatccg cctccattca gtctattaat tgttgccggg aagctagagt 4500
aagtagttcg ccagttaata gtttgcgcaa cgttgttggc attgctacag gcatcgtggt 4560
gtcactctcg tcgtttggta tggcttcatt cagctccggt tcccaacgat caaggcgagt 4620

-continued tacatgatcc cccatgttgt gcaaaaaagc ggttagctcc ttcggtcctc cgatcgttgt 4680
cagaagtaag ttggccgcag tgttatcact catggttatg gcagcactgc ataattctct 4740
tactgtcatg ccatccgtaa gatgcttttc tgtgactggt gagtactcaa ccaagtcatt 4800
ctgagaatag tgtatgcggc gaccgagttg ctcttgcccg gcgtcaatac gggataatag 4860
tgtatcacat agcagaactt taaaagtgct catcattgga aaacgttctt cggggcgaaa 4920
actctcaagg atcttaccgc tgttgagatc cagttcgatg taacccactc gtgcacccaa 4980
ctgatcttca gcatctttta ctttcaccag cgtttctggg tgagcaaaaa caggaaggca 5040
aaatgccgca aaaaagggaa taagggcgac acggaaatgt tgaatactca tactcttcct 5100
ttttcaatgg gtaataactg atataattaa attgaagctc taatttgtga gtttagtata 5160
catgcattta cttataatac agttttttag ttttgctggc cgcatcttct caaatatgct 5220
tcccagcctg cttttctgta acgttcaccc tctaccttag catcccttcc ctttgcaaat 5280
agtcctcttc caacaataat aatgtcagat cctgtagaga ccacatcatc cacggttcta 5340
tactgttgac ccaatgcgtc tcccttgtca tctaaaccca caccgggtgt cataatcaac 5400
caatcgtaac cttcatctct tccacccatg tctctttgag caataaagcc gataacaaaa 5460
tctttgtcgc tcttcgcaat gtcaacagta cccttagtat attctccagt agatagggag 5520
cccttgcatg acaattctgc taacatcaaa aggcctctag gttcctttgt tacttcttct 5580
gccgcctgct tcaaaccgct aacaatacct gggcccacca caccgtgtgc attcgtaatg 5640
tctgcccatt ctgctattct gtatacaccc gcagagtact gcaatttgac tgtattacca 5700
atgtcagcaa atttctgtc ttcg 5724

<210> SEQ ID NO 4
<211> LENGTH: 5724
<212> TYPE: DNA
<213> ORGANISM: Artificial Sequence
<220> FEATURE:
<223> OTHER INFORMATION: OAC-Y41S/G43SILENT(=GGG)/K44V/T68R/I74R/V84R

<400> SEQUENCE: 4
aagagtaaaa aattgtactt ggcggataat gcctttagcg gcttaactgt gccctccatg 60
gaaaaatcag tcaagatatc cacatgtgtt tttagtaaac aaattttggg acctaatgct 120
tcaactaact ccagtaattc cttggtggta cgaacatcca atgaagcaca caagtttgtt 180
tgcttttcgt gcatgatatt aaatagcttg gcagcaacag gactaggatg agtagcagca 240
cgttccttat atgtagcttt cgacatgatt tatcttcgtt tcctgcaggt ttttgttctg 300
tgcagttggg ttaagaatac tgggcaattt catgtttctt caacactaca tatgcgtata 360
tataccaatc taagtctgtg ctccttcctt cgttcttcct tctgttcgga gattaccgaa 420
tcaaaaaaat ttcaaagaaa ccgaaatcaa aaaaaagaat aaaaaaaaaa tgatgaattg 480
aattgaaaag ctagcttatc gatgataagc tgtcaaagat gagaattaat tccacggact 540
atagactata ctagatactc cgtctactgt acgatacact tccgctcagg tccttgtcct 600
ttaacgaggc cttaccactc ttttgttact ctattgatcc agctcagcaa aggcagtgtg 660
atctaagatt ctatcttcgc gatgtagtaa aactagctag accgagaaag agactagaaa 720
tgcaaaaggc acttctacaa tggctgccat cattattatc cgatgtgacg ctgcagcttc 780
tcaatgatat tcgaatacgc tttgaggaga tacagcctaa tatccgacaa actgttttac 840
agatttacga tcgtacttgt tacccatcat tgaattttga acatccgaac ctgggagttt 900
tccctgaaac agatagtata tttgaacctg tataataata tatagtctag cgctttacgg 960

-continued

```
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc tttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcatttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg ttaacttggt taacatcatt cctgctatga   2760
aggacgtctc ctggggggtg gatgtcactc aaaaaaacaa ggaagaaggt tatacccaca   2820
tcgttgaagt caccttcgaa tctgttgaac ggattcaaga ctacatcagg cacccagctc   2880
acgtcggttt cggtgatagg tacagatctt tctgggaaaa attgttgatc ttcgactaca   2940
ccccaagaaa gggctaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct tttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
```

```
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
tactgtcatg ccatccgtaa gatgcttttc tgtgactggt gagtactcaa ccaagtcatt   4800
ctgagaatag tgtatgcggc gaccgagttg ctcttgcccg gcgtcaatac gggataatag   4860
tgtatcacat agcagaactt taaaagtgct catcattgga aaacgttctt cggggcgaaa   4920
actctcaagg atcttaccgc tgttgagatc cagttcgatg taacccactc gtgcacccaa   4980
ctgatcttca gcatctttta ctttcaccag cgtttctggg tgagcaaaaa caggaaggca   5040
aaatgccgca aaaaagggaa taagggcgac acggaaatgt tgaatactca tactcttcct   5100
ttttcaatgg gtaataactg atataattaa attgaagctc taatttgtga gtttagtata   5160
catgcattta cttataatac agttttttag ttttgctggc cgcatcttct caaatatgct   5220
tcccagcctg cttttctgta acgttcaccc tctaccttag catcccttcc ctttgcaaat   5280
agtcctcttc caacaataat aatgtcagat cctgtagaga ccacatcatc cacggttcta   5340
tactgttgac ccaatgcgtc tcccttgtca tctaaaccca caccgggtgt cataatcaac   5400
caatcgtaac cttcatctct tccacccatg tctctttgag caataaagcc gataacaaaa   5460
tctttgtcgc tcttcgcaat gtcaacagta cccttagtat attctccagt agatagggag   5520
cccttgcatg acaattctgc taacatcaaa aggcctctag gttcctttgt tacttcttct   5580
gccgcctgct tcaaaccgct aacaatacct gggcccacca caccgtgtgc attcgtaatg   5640
tctgcccatt ctgctattct gtatacaccc gcagagtact gcaatttgac tgtattacca   5700
```

atgtcagcaa atttctgtc ttcg 5724

<210> SEQ ID NO 5
<211> LENGTH: 5724
<212> TYPE: DNA
<213> ORGANISM: Artificial Sequence
<220> FEATURE:
<223> OTHER INFORMATION: OAC-V28A/V31G/Y41S/G43SILENT(=GGG)/K44V/T68L/
I74R/V84R/R100E/G102R

<400> SEQUENCE: 5
aagagtaaaa aattgtactt ggcggataat gcctttagcg gcttaactgt gccctccatg 60
gaaaaatcag tcaagatatc cacatgtgtt tttagtaaac aaattttggg acctaatgct 120
tcaactaact ccagtaattc cttggtggta cgaacatcca atgaagcaca caagtttgtt 180
tgcttttcgt gcatgatatt aaatagcttg gcagcaacag gactaggatg agtagcagca 240
cgttccttat atgtagcttt cgacatgatt tatcttcgtt tcctgcaggt tttgttctg 300
tgcagttggg ttaagaatac tggcaattt catgtttctt caacactaca tatgcgtata 360
tataccaatc taagtctgtg ctccttcctt cgttcttcct tctgttcgga gattaccgaa 420
tcaaaaaaat ttcaaagaaa ccgaaatcaa aaaaaagaat aaaaaaaaaa tgatgaattg 480
aattgaaaag ctagcttatc gatgataagc tgtcaaagat gagaattaat tccacggact 540
atagactata ctagatactc cgtctactgt acgatacact tccgctcagg tccttgtcct 600
ttaacgaggc cttaccactc ttttgttact ctattgatcc agctcagcaa aggcagtgtg 660
atctaagatt ctatcttcgc gatgtagtaa aactagctag accgagaaag agactagaaa 720
tgcaaaaggc acttctacaa tggctgccat cattattatc cgatgtgacg ctgcagcttc 780
tcaatgatat tcgaatacgc tttgaggaga tacagcctaa tatccgacaa actgttttac 840
agatttacga tcgtacttgt tacccatcat tgaattttga acatccgaac ctgggagttt 900
tccctgaaac agatagtata tttgaacctg tataataata tatagtctag cgctttacgg 960
aagacaatgt atgtatttcg gttcctggag aaactattgc atctattgca taggtaatct 1020
tgcacgtcgc atccccggtt cattttctgc gtttccatct tgcacttcaa tagcatatct 1080
ttgttcgctt gcctgtaact tacacgcgcc tcgtatcttt taatgatgga ataatttggg 1140
aatttactct gtgtttattt atttttatgt tttgtatttg gattttagaa agtaaataaa 1200
gaaggtagaa gagttacgga atgaagaaaa aaaaataaac aaaggtttaa aaaatttcaa 1260
caaaaagcgt actttacata tatatttatt agacaagaaa agcagattaa atagatatac 1320
attcgattaa cgataagtaa aatgtaaaat cacaggattt tcgtgtgtgg tcttctacac 1380
agacaagatg aaacaattcg gcattaatac ctgagagcag gaagagcaag ataaaaggta 1440
gtatttgttg gcgatccccc tagagtcttt tacatcttcg gaaaacaaaa actatttttt 1500
ctttaatttc ttttttact ttctattttt aatttatata tttatattaa aaaatttaaa 1560
ttataattat ttttatagca cgtgatgaaa aggaccggga agctccaccc cggttgataa 1620
tcagaaaagc cccaaaaaca ggaagattgt ataagcaaat atttaaattg taaacgttaa 1680
tattttgtta aaattcgcgt taaatttttg ttaaatcagc tcattttta acgaatagcc 1740
cgaaatcggc aaaatccctt ataaatcaaa agaatagacc gagatagggt tgagtgttgt 1800
tccagtttcc aacaagagtc cactattaaa gaacgtggac tccaacgtca aagggcgaaa 1860
aagggtctat cagggcgatg gcccactacg tgaaccatca ccctaatcaa gtttttggg 1920
gtcgaggtgc cgtaaagcag taaatcggaa gggtaaacgg atgcccccat ttagagcttg 1980

```
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggg gaacatcatt cctgctatga   2760
aggacgtctc ctggggggtg gatgtcactc aaaaaaacaa ggaagaaggt tatacccaca   2820
tcgttgaagt caccttcgaa tctgttgaac tgattcaaga ctacatcagg cacccagctc   2880
acgtcggttt cggtgatagg tacagatctt tctgggaaaa attgttgatc ttcgactaca   2940
ccccagagaa gcggtaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct ttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
```

tacgatacgg gagcgcttac catctggccc cagtgctgca atgataccgc gagacccacg 4380
ctcaccggct ccagatttat cagcaataaa ccagccagcc ggaagggccg agcgcagaag 4440
tggtcctgca actttatccg cctccattca gtctattaat tgttgccggg aagctagagt 4500
aagtagttcg ccagttaata gtttgcgcaa cgttgttggc attgctacag gcatcgtggt 4560
gtcactctcg tcgtttggta tggcttcatt cagctccggt tcccaacgat caaggcgagt 4620
tacatgatcc cccatgttgt gcaaaaaagc ggttagctcc ttcggtcctc cgatcgttgt 4680
cagaagtaag ttggccgcag tgttatcact catggttatg gcagcactgc ataattctct 4740
tactgtcatg ccatccgtaa gatgcttttc tgtgactggt gagtactcaa ccaagtcatt 4800
ctgagaatag tgtatgcggc gaccgagttg ctcttgcccg gcgtcaatac gggataatag 4860
tgtatcacat agcagaactt taaaagtgct catcattgga aaacgttctt cggggcgaaa 4920
actctcaagg atcttaccgc tgttgagatc cagttcgatg taacccactc gtgcacccaa 4980
ctgatcttca gcatctttta ctttcaccag cgtttctggg tgagcaaaaa caggaaggca 5040
aaatgccgca aaaaagggaa taagggcgac acggaaatgt tgaatactca tactcttcct 5100
ttttcaatgg gtaataactg atataattaa attgaagctc taatttgtga gtttagtata 5160
catgcattta cttataatac agtttttag ttttgctggc cgcatcttct caaatatgct 5220
tcccagcctg cttttctgta acgttcaccc tctaccttag catcccttcc ctttgcaaat 5280
agtcctcttc caacaataat aatgtcagat cctgtagaga ccacatcatc cacggttcta 5340
tactgttgac ccaatgcgtc tcccttgtca tctaaaccca caccgggtgt cataatcaac 5400
caatcgtaac cttcatctct tccacccatg tctctttgag caataaagcc gataacaaaa 5460
tctttgtcgc tcttcgcaat gtcaacagta cccttagtat attctccagt agatagggag 5520
cccttgcatg acaattctgc taacatcaaa aggcctctag gttcctttgt tacttcttct 5580
gccgcctgct tcaaaccgct aacaatacct gggcccacca caccgtgtgc attcgtaatg 5640
tctgcccatt ctgctattct gtatacaccc gcagagtact gcaatttgac tgtattacca 5700
atgtcagcaa attttctgtc ttcg 5724

<210> SEQ ID NO 6
<211> LENGTH: 5724
<212> TYPE: DNA
<213> ORGANISM: Artificial Sequence
<220> FEATURE:
<223> OTHER INFORMATION: OAC-V28A/Y41T/G43SILENT(=GGG)/T68L/I74G/V84R/
R100E

<400> SEQUENCE: 6
aagagtaaaa aattgtactt ggcggataat gcctttagcg gcttaactgt gccctccatg 60
gaaaaatcag tcaagatatc cacatgtgtt tttagtaaac aaattttggg acctaatgct 120
tcaactaact ccagtaattc cttggtggta cgaacatcca atgaagcaca caagtttgtt 180
tgcttttcgt gcatgatatt aaatagcttg gcagcaacag gactaggatg agtagcagca 240
cgttccttat atgtagcttt cgacatgatt tatcttcgtt tcctgcaggt ttttgttctg 300
tgcagttggg ttaagaatac tgggcaattt catgtttctt caacactaca tatgcgtata 360
tataccaatc taagtctgtg ctccttcctt cgttcttcct tctgttcgga gattaccgaa 420
tcaaaaaaat ttcaaagaaa ccgaaatcaa aaaaaagaat aaaaaaaaaa tgatgaattg 480
aattgaaaag ctagcttatc gatgataagc tgtcaaagat gagaattaat tccacggact 540
atagactata ctagatactc cgtctactgt acgatacact tccgctcagg tccttgtcct 600

-continued

```
ttaacgaggc cttaccactc ttttgttact ctattgatcc agctcagcaa aggcagtgtg    660
atctaagatt ctatcttcgc gatgtagtaa aactagctag accgagaaag agactagaaa    720
tgcaaaaggc acttctacaa tggctgccat cattattatc cgatgtgacg ctgcagcttc    780
tcaatgatat tcgaatacgc tttgaggaga tacagcctaa tatccgacaa actgttttac    840
agatttacga tcgtacttgt tacccatcat tgaattttga acatccgaac ctgggagttt    900
tccctgaaac agatagtata tttgaacctg tataataata tatagtctag cgctttacgg    960
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc tttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcattttta acgaatagcc    1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gtttttggg    1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttagc cttatttctg    2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggt taacatcatt cctgctatga   2760
aggacgtcac gtgggggaag gatgtcactc aaaaaaacaa ggaagaaggt tatacccaca   2820
tcgttgaagt caccttcgaa tctgttgaac tgattcaaga ctacatcggg cacccagctc   2880
acgtcggttt cggtgatagg tacagatctt tctgggaaaa attgttgatc ttcgactaca   2940
ccccagagaa gggctaactc gagcatgcat ctagagggcc gcatcatgta attagttatg   3000
```

```
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct tttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
tactgtcatg ccatccgtaa gatgcttttc tgtgactggt gagtactcaa ccaagtcatt   4800
ctgagaatag tgtatgcggc gaccgagttg ctcttgcccg gcgtcaatac gggataatag   4860
tgtatcacat agcagaactt taaaagtgct catcattgga aaacgttctt cggggcgaaa   4920
actctcaagg atcttaccgc tgttgagatc cagttcgatg taacccactc gtgcacccaa   4980
ctgatcttca gcatctttta ctttcaccag cgtttctggg tgagcaaaaa caggaaggca   5040
aaatgccgca aaaaagggaa taagggcgac acggaaatgt tgaatactca tactcttcct   5100
ttttcaatgg gtaataactg atataattaa attgaagctc taatttgtga gtttagtata   5160
catgcattta cttataatac agttttttag ttttgctggc cgcatcttct caaatatgct   5220
tcccagcctg cttttctgta acgttcaccc tctaccttag catcccttcc ctttgcaaat   5280
agtcctcttc caacaataat aatgtcagat cctgtagaga ccacatcatc cacggttcta   5340
```

```
tactgttgac ccaatgcgtc tcccttgtca tctaaaccca caccgggtgt cataatcaac   5400
caatcgtaac cttcatctct tccacccatg tctctttgag caataaagcc gataacaaaa   5460
tctttgtcgc tcttcgcaat gtcaacagta cccttagtat attctccagt agatagggag   5520
cccttgcatg acaattctgc taacatcaaa aggcctctag gttcctttgt tacttcttct   5580
gccgcctgct tcaaaccgct aacaatacct gggcccacca caccgtgtgc attcgtaatg   5640
tctgcccatt ctgctattct gtatacaccc gcagagtact gcaatttgac tgtattacca   5700
atgtcagcaa atttctgtc ttcg                                           5724
```

<210> SEQ ID NO 7
<211> LENGTH: 5724
<212> TYPE: DNA
<213> ORGANISM: Artificial Sequence
<220> FEATURE:
<223> OTHER INFORMATION: OAC-V28A/Y41T/G43SILENT(=GGG)/K44V/T68L/I74D/ V84R/R100M/G102R

<400> SEQUENCE: 7

```
aagagtaaaa aattgtactt ggcggataat gcctttagcg gcttaactgt gccctccatg     60
gaaaaatcag tcaagatatc cacatgtgtt tttagtaaac aaattttggg acctaatgct    120
tcaactaact ccagtaattc cttggtggta cgaacatcca atgaagcaca caagtttgtt    180
tgcttttcgt gcatgatatt aaatagcttg gcagcaacag gactaggatg agtagcagca    240
cgttccttat atgtagcttt cgacatgatt tatcttcgtt tcctgcaggt ttttgttctg    300
tgcagttggg ttaagaatac tgggcaattt catgtttctt caacactaca tatgcgtata    360
tataccaatc taagtctgtg ctccttcctt cgttcttcct tctgttcgga gattaccgaa    420
tcaaaaaaat ttcaaagaaa ccgaaatcaa aaaaaagaat aaaaaaaaaa tgatgaattg    480
aattgaaaag ctagcttatc gatgataagc tgtcaaagat gagaattaat tccacggact    540
atagactata ctagatactc cgtctactgt acgatacact tccgctcagg tccttgtcct    600
ttaacgaggc cttaccactc ttttgttact ctattgatcc agctcagcaa aggcagtgtg    660
atctaagatt ctatcttcgc gatgtagtaa aactagctag accgagaaag agactagaaa    720
tgcaaaaggc acttctacaa tggctgccat cattattatc cgatgtgacg ctgcagcttc    780
tcaatgatat tcgaatacgc tttgaggaga tacagcctaa tatccgacaa actgttttac    840
agatttacga tcgtacttgt tacccatcat tgaattttga acatccgaac ctgggagttt    900
tccctgaaac agatagtata tttgaacctg tataataata tatagtctag cgctttacgg    960
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc tttttttact ttctattttt aatttatata tttatattaa aaaatttaaa   1560
ttataattat ttttatagca cgtgatgaaa aggaccggga agctccaccc cggttgataa   1620
```

-continued

```
tcagaaaagc cccaaaaaca ggaagattgt ataagcaaat atttaaattg taaacgttaa   1680
tattttgtta aaattcgcgt taaatttttg ttaaatcagc tcatttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggt taacatcatt cctgctatga   2760
aggacgtcac gtggggggtg gatgtcactc aaaaaaacaa ggaagaaggt tatacccaca   2820
tcgttgaagt caccttcgaa tctgttgaac tgattcaaga ctacatcgac cacccagctc   2880
acgtcggttt cggtgatagg tacagatctt tctgggaaaa attgttgatc ttcgactaca   2940
ccccaatgaa gcggtaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct ttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
```

ttgcaagcag cagattacgc gcagaaaaaa aggatctcaa gaagatcctt tgatcttttc 4080
tacggggtct gacgctcagt ggaacgaaaa ctcacgttaa gggattttgg tcatgagatt 4140
atcaaaaagg atcttcacct agatcctttt aaattaaaaa tgaagtttta aatcaatcta 4200
aagtatatat gagtaaactt ggtctgacag ttaccaatgc ttaatcagtg aggcacctat 4260
ctcagcgatc tgtctatttc gttcatccat agttgcctga ctccccgtcg tgtagataac 4320
tacgatacgg gagcgcttac catctggccc cagtgctgca atgataccgc gagacccacg 4380
ctcaccggct ccagatttat cagcaataaa ccagccagcc ggaagggccg agcgcagaag 4440
tggtcctgca actttatccg cctccattca gtctattaat tgttgccggg aagctagagt 4500
aagtagttcg ccagttaata gtttgcgcaa cgttgttggc attgctacag gcatcgtggt 4560
gtcactctcg tcgtttggta tggcttcatt cagctccggt tcccaacgat caaggcgagt 4620
tacatgatcc cccatgttgt gcaaaaaagc ggttagctcc ttcggtcctc cgatcgttgt 4680
cagaagtaag ttggccgcag tgttatcact catggttatg gcagcactgc ataattctct 4740
tactgtcatg ccatccgtaa gatgcttttc tgtgactggt gagtactcaa ccaagtcatt 4800
ctgagaatag tgtatgcggc gaccgagttg ctcttgcccg gcgtcaatac gggataatag 4860
tgtatcacat agcagaactt taaaagtgct catcattgga aaacgttctt cggggcgaaa 4920
actctcaagg atcttaccgc tgttgagatc cagttcgatg taacccactc gtgcacccaa 4980
ctgatcttca gcatctttta ctttcaccag cgtttctggg tgagcaaaaa caggaaggca 5040
aaatgccgca aaaaagggaa taagggcgac acggaaatgt tgaatactca tactcttcct 5100
ttttcaatgg gtaataactg atataattaa attgaagctc taatttgtga gtttagtata 5160
catgcattta cttataatac agttttttag ttttgctggc cgcatcttct caaatatgct 5220
tcccagcctg cttttctgta acgttcaccc tctaccttag catcccttcc ctttgcaaat 5280
agtcctcttc caacaataat aatgtcagat cctgtagaga ccacatcatc cacggttcta 5340
tactgttgac ccaatgcgtc tcccttgtca tctaaaccca caccgggtgt cataatcaac 5400
caatcgtaac cttcatctct tccacccatg tctctttgag caataaagcc gataacaaaa 5460
tctttgtcgc tcttcgcaat gtcaacagta cccttagtat attctccagt agatagggag 5520
cccttgcatg acaattctgc taacatcaaa aggcctctag gttcctttgt tacttcttct 5580
gccgcctgct tcaaaccgct aacaatacct gggcccacca caccgtgtgc attcgtaatg 5640
tctgcccatt ctgctattct gtatacaccc gcagagtact gcaatttgac tgtattacca 5700
atgtcagcaa attttctgtc ttcg 5724

<210> SEQ ID NO 8
<211> LENGTH: 5724
<212> TYPE: DNA
<213> ORGANISM: Artificial Sequence
<220> FEATURE:
<223> OTHER INFORMATION: OAC-V28A/Y41T/G43SILENT(=GGG)/T68L/I74D/V84R/
G102R

<400> SEQUENCE: 8
aagagtaaaa aattgtactt ggcggataat gcctttagcg gcttaactgt gccctccatg 60
gaaaaatcag tcaagatatc cacatgtgtt tttagtaaac aaattttggg acctaatgct 120
tcaactaact ccagtaattc cttggtggta cgaacatcca atgaagcaca caagtttgtt 180
tgcttttcgt gcatgatatt aaatagcttg gcagcaacag gactaggatg agtagcagca 240
cgttccttat atgtagcttt cgacatgatt tatcttcgtt tcctgcaggt ttttgttctg 300

```
tgcagttggg ttaagaatac tgggcaattt catgtttctt caacactaca tatgcgtata    360
tataccaatc taagtctgtg ctccttcctt cgttcttcct tctgttcgga gattaccgaa    420
tcaaaaaaat ttcaaagaaa ccgaaatcaa aaaaaagaat aaaaaaaaaa tgatgaattg    480
aattgaaaag ctagcttatc gatgataagc tgtcaaagat gagaattaat tccacggact    540
atagactata ctagatactc cgtctactgt acgatacact tccgctcagg tccttgtcct    600
ttaacgaggc cttaccactc ttttgttact ctattgatcc agctcagcaa aggcagtgtg    660
atctaagatt ctatcttcgc gatgtagtaa aactagctag accgagaaag agactagaaa    720
tgcaaaaggc acttctacaa tggctgccat cattattatc cgatgtgacg ctgcagcttc    780
tcaatgatat tcgaatacgc tttgaggaga tacagcctaa tatccgacaa actgttttac    840
agatttacga tcgtacttgt tacccatcat tgaattttga acatccgaac ctgggagttt    900
tccctgaaac agatagtata tttgaacctg tataataata tatagtctag cgctttacgg    960
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc ttttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcattttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
```

-continued

```
cttaaacaat ggccgtcaag cacttgatcg tcttaaagtt taaggacgag atcactgaag   2700
cccaaaagga agaattcttc aaaacttacg cgaacttggt taacatcatt cctgctatga   2760
aggacgtcac gtgggggaag gatgtcactc aaaaaaacaa ggaagaaggt tatacccaca   2820
tcgttgaagt caccttcgaa tctgttgaac tgattcaaga ctacatcgac cacccagctc   2880
acgtcggttt cggtgatagg tacagatctt tctgggaaaa attgttgatc ttcgactaca   2940
ccccaagaaa gcggtaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct tttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
tactgtcatg ccatccgtaa gatgcttttc tgtgactggt gagtactcaa ccaagtcatt   4800
ctgagaatag tgtatgcggc gaccgagttg ctcttgcccg gcgtcaatac gggataatag   4860
tgtatcacat agcagaactt taaaagtgct catcattgga aaacgttctt cggggcgaaa   4920
actctcaagg atcttaccgc tgttgagatc cagttcgatg taacccactc gtgcacccaa   4980
ctgatcttca gcatctttta ctttcaccag cgtttctggg tgagcaaaaa caggaaggca   5040
```

```
aaatgccgca aaaaagggaa taagggcgac acggaaatgt tgaatactca tactcttcct   5100

ttttcaatgg gtaataactg atataattaa attgaagctc taatttgtga gtttagtata   5160

catgcattta cttataatac agttttttag ttttgctggc cgcatcttct caaatatgct   5220

tcccagcctg cttttctgta acgttcaccc tctaccttag catcccttcc ctttgcaaat   5280

agtcctcttc caacaataat aatgtcagat cctgtagaga ccacatcatc cacggttcta   5340

tactgttgac ccaatgcgtc tcccttgtca tctaaaccca caccgggtgt cataatcaac   5400

caatcgtaac cttcatctct tccacccatg tctctttgag caataaagcc gataacaaaa   5460

tctttgtcgc tcttcgcaat gtcaacagta cccttagtat attctccagt agatagggag   5520

cccttgcatg acaattctgc taacatcaaa aggcctctag gttcctttgt tacttcttct   5580

gccgcctgct tcaaaccgct aacaatacct gggcccacca caccgtgtgc attcgtaatg   5640

tctgcccatt ctgctattct gtatacaccc gcagagtact gcaatttgac tgtattacca   5700

atgtcagcaa attttctgtc ttcg                                          5724
```

<210> SEQ ID NO 9
<211> LENGTH: 5724
<212> TYPE: DNA
<213> ORGANISM: Artificial Sequence
<220> FEATURE:
<223> OTHER INFORMATION: OAC-V28A/Y41T/G43SILENT(=GGG)/K44V/T68L/I74R/
      V84R/R100E/G102R

<400> SEQUENCE: 9

```
aagagtaaaa aattgtactt ggcggataat gcctttagcg gcttaactgt gccctccatg     60

gaaaaatcag tcaagatatc cacatgtgtt tttagtaaac aaattttggg acctaatgct    120

tcaactaact ccagtaattc cttggtggta cgaacatcca atgaagcaca caagtttgtt    180

tgcttttcgt gcatgatatt aaatagcttg gcagcaacag gactaggatg agtagcagca    240

cgttccttat atgtagcttt cgacatgatt tatcttcgtt tcctgcaggt ttttgttctg    300

tgcagttggg ttaagaatac tgggcaattt catgtttctt caacactaca tatgcgtata    360

tataccaatc taagtctgtg ctccttcctt cgttcttcct tctgttcgga gattaccgaa    420

tcaaaaaaat ttcaaagaaa ccgaaatcaa aaaaaagaat aaaaaaaaaa tgatgaattg    480

aattgaaaag ctagcttatc gatgataagc tgtcaaagat gagaattaat tccacggact    540

atagactata ctagatactc cgtctactgt acgatacact tccgctcagg tccttgtcct    600

ttaacgaggc cttaccactc ttttgttact ctattgatcc agctcagcaa aggcagtgtg    660

atctaagatt ctatcttcgc gatgtagtaa aactagctag accgagaaag agactagaaa    720

tgcaaaaggc acttctacaa tggctgccat cattattatc cgatgtgacg ctgcagcttc    780

tcaatgatat tcgaatacgc tttgaggaga tacagcctaa tatccgacaa actgttttac    840

agatttacga tcgtacttgt tacccatcat tgaattttga acatccgaac ctgggagttt    900

tccctgaaac agatagtata tttgaacctg tataataata tatagtctag cgctttacgg    960

aagacaatgt atgtatttcg gttcctggag aaactattgc atctattgca taggtaatct   1020

tgcacgtcgc atccccggtt cattttctgc gtttccatct tgcacttcaa tagcatatct   1080

ttgttcgctt gcctgtaact tacacgcgcc tcgtatcttt taatgatgga ataatttggg   1140

aatttactct gtgtttattt atttttatgt tttgtatttg gattttagaa agtaaataaa   1200

gaaggtagaa gagttacgga atgaagaaaa aaaaataaac aaaggtttaa aaaatttcaa   1260

caaaaagcgt actttacata tatatttatt agacaagaaa agcagattaa atagatatac   1320
```

-continued

```
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc ttttttact ttctattttt aatttatata tttatattaa aaaatttaaa    1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcatttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggt taacatcatt cctgctatga   2760
aggacgtcac gtgggggtg gatgtcactc aaaaaaacaa ggaagaaggt tatacccaca    2820
tcgttgaagt caccttcgaa tctgttgaac tgattcaaga ctacatcagg cacccagctc   2880
acgtcggttt cggtgatagg tacagatctt tctgggaaaa attgttgatc ttcgactaca   2940
ccccagagaa gcggtaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaattttttct ttttttctg tacagacgcg tgtacgcatg taacattata  3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
```

-continued

```
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
tactgtcatg ccatccgtaa gatgcttttc tgtgactggt gagtactcaa ccaagtcatt   4800
ctgagaatag tgtatgcggc gaccgagttg ctcttgcccg gcgtcaatac gggataatag   4860
tgtatcacat agcagaactt taaaagtgct catcattgga aaacgttctt cggggcgaaa   4920
actctcaagg atcttaccgc tgttgagatc cagttcgatg taacccactc gtgcacccaa   4980
ctgatcttca gcatctttta ctttcaccag cgtttctggg tgagcaaaaa caggaaggca   5040
aaatgccgca aaaaagggaa taagggcgac acggaaatgt tgaatactca tactcttcct   5100
ttttcaatgg gtaataactg atataattaa attgaagctc taatttgtga gtttagtata   5160
catgcattta cttataatac agttttttag ttttgctggc cgcatcttct caaatatgct   5220
tcccagcctg cttttctgta acgttcaccc tctaccttag catcccttcc ctttgcaaat   5280
agtcctcttc caacaataat aatgtcagat cctgtagaga ccacatcatc cacggttcta   5340
tactgttgac ccaatgcgtc tcccttgtca tctaaaccca caccgggtgt cataatcaac   5400
caatcgtaac cttcatctct tccacccatg tctctttgag caataaagcc gataacaaaa   5460
tctttgtcgc tcttcgcaat gtcaacagta cccttagtat attctccagt agatagggag   5520
cccttgcatg acaattctgc taacatcaaa aggcctctag gttcctttgt tacttcttct   5580
gccgcctgct tcaaaccgct aacaatacct gggcccacca caccgtgtgc attcgtaatg   5640
tctgcccatt ctgctattct gtatacaccc gcagagtact gcaatttgac tgtattacca   5700
atgtcagcaa attttctgtc ttcg                                          5724
```

<210> SEQ ID NO 10
<211> LENGTH: 5724
<212> TYPE: DNA
<213> ORGANISM: Artificial Sequence
<220> FEATURE:
<223> OTHER INFORMATION: OAC-Y41T/G43SILENT(=GGG)/T68R/I74R/V84R/R100M/
G102STOP

<400> SEQUENCE: 10

```
aagagtaaaa aattgtactt ggcggataat gcctttagcg gcttaactgt gccctccatg      60
gaaaaatcag tcaagatatc cacatgtgtt tttagtaaac aaattttggg acctaatgct     120
tcaactaact ccagtaattc cttggtggta cgaacatcca atgaagcaca caagtttgtt     180
tgcttttcgt gcatgatatt aaatagcttg gcagcaacag gactaggatg agtagcagca     240
cgttccttat atgtagcttt cgacatgatt tatcttcgtt tcctgcaggt ttttgttctg     300
tgcagttggg ttaagaatac tgggcaattt catgtttctt caacactaca tatgcgtata     360
tataccaatc taagtctgtg ctccttcctt cgttcttcct tctgttcgga gattaccgaa     420
tcaaaaaaat ttcaaagaaa ccgaaatcaa aaaaaagaat aaaaaaaaaa tgatgaattg     480
aattgaaaag ctagcttatc gatgataagc tgtcaaagat gagaattaat tccacggact     540
atagactata ctagatactc cgtctactgt acgatacact tccgctcagg tccttgtcct     600
ttaacgaggc cttaccactc ttttgttact ctattgatcc agctcagcaa aggcagtgtg     660
atctaagatt ctatcttcgc gatgtagtaa aactagctag accgagaaag agactagaaa     720
tgcaaaaggc acttctacaa tggctgccat cattattatc cgatgtgacg ctgcagcttc     780
tcaatgatat tcgaatacgc tttgaggaga tacagcctaa tatccgacaa actgttttac     840
agatttacga tcgtacttgt tacccatcat tgaattttga acatccgaac ctgggagttt     900
tccctgaaac agatagtata tttgaacctg tataataata tatagtctag cgctttacgg     960
aagacaatgt atgtatttcg gttcctggag aaactattgc atctattgca taggtaatct    1020
tgcacgtcgc atccccggtt cattttctgc gtttccatct tgcacttcaa tagcatatct    1080
ttgttcgctt gcctgtaact tacacgcgcc tcgtatcttt taatgatgga ataatttggg    1140
aatttactct gtgtttattt atttttatgt tttgtatttg gattttagaa agtaaataaa    1200
gaaggtagaa gagttacgga atgaagaaaa aaaaataaac aaaggtttaa aaaatttcaa    1260
caaaaagcgt actttacata tatatttatt agacaagaaa agcagattaa atagatatac    1320
attcgattaa cgataagtaa aatgtaaaat cacaggattt tcgtgtgtgg tcttctacac    1380
agacaagatg aaacaattcg gcattaatac ctgagagcag gaagagcaag ataaaaggta    1440
gtatttgttg gcgatccccc tagagtcttt tacatcttcg gaaaacaaaa actatttttt    1500
ctttaatttc ttttttttact ttctattttt aatttatata tttatattaa aaaatttaaa    1560
ttataattat ttttatagca cgtgatgaaa aggaccggga agctccaccc cggttgataa    1620
tcagaaaagc cccaaaaaca ggaagattgt ataagcaaat atttaaattg taaacgttaa    1680
tattttgtta aaattcgcgt taaatttttg ttaaatcagc tcattttttta acgaatagcc    1740
cgaaatcggc aaaatccctt ataaatcaaa agaatagacc gagatagggt tgagtgttgt    1800
tccagtttcc aacaagagtc cactattaaa gaacgtggac tccaacgtca aagggcgaaa    1860
aagggtctat cagggcgatg gcccactacg tgaaccatca ccctaatcaa gtttttttggg    1920
gtcgaggtgc cgtaaagcag taaatcggaa gggtaaacgg atgcccccat ttagagcttg    1980
acggggaaag ccggcgaacg tggcgagaaa ggaagggaag aaagcgaaag gagcgggggc    2040
tagggcggtg ggaagtgtag gggtcacgct gggcgtaacc accacacccg ccgcgcttaa    2100
tggggcgcta cagggcgcgt ggggatgatc cactagtacg gattagaagc cgccgagcgg    2160
gtgacagccc tccgaaggaa gactctcctc cgtgcgtcct cgtcttcacc ggtcgcgttc    2220
ctgaaacgca gatgtgcctc gcgccgcact gctccgaaca ataaagattc tacaatacta    2280
gcttttatgg ttatgaagag gaaaaattgg cagtaacctg gccccacaaa ccttcaaatg    2340
```

-continued

```
aacgaatcaa attaacaacc ataggatgat aatgcgatta gtttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg ttaacttggt taacatcatt cctgctatga   2760
aggacgtcac gtgggggaag gatgtcactc aaaaaaacaa ggaagaaggt tatacccaca   2820
tcgttgaagt caccttcgaa tctgttgaac ggattcaaga ctacatcagg cacccagctc   2880
acgtcggttt cggtgatagg tacagatctt tctgggaaaa attgttgatc ttcgactaca   2940
ccccaatgaa gtaataactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct tttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
```

-continued

```
cagaagtaag ttggccgcag tgttatcact catggttatg gcagcactgc ataattctct   4740

tactgtcatg ccatccgtaa gatgcttttc tgtgactggt gagtactcaa ccaagtcatt   4800

ctgagaatag tgtatgcggc gaccgagttg ctcttgcccg gcgtcaatac gggataatag   4860

tgtatcacat agcagaactt taaaagtgct catcattgga aaacgttctt cggggcgaaa   4920

actctcaagg atcttaccgc tgttgagatc cagttcgatg taacccactc gtgcacccaa   4980

ctgatcttca gcatctttta ctttcaccag cgtttctggg tgagcaaaaa caggaaggca   5040

aaatgccgca aaaaagggaa taagggcgac acggaaatgt tgaatactca tactcttcct   5100

ttttcaatgg gtaataactg atataattaa attgaagctc taatttgtga gtttagtata   5160

catgcattta cttataatac agttttttag ttttgctggc cgcatcttct caaatatgct   5220

tcccagcctg cttttctgta acgttcaccc tctaccttag catcccttcc ctttgcaaat   5280

agtcctcttc caacaataat aatgtcagat cctgtagaga ccacatcatc cacggttcta   5340

tactgttgac ccaatgcgtc tcccttgtca tctaaaccca caccgggtgt cataatcaac   5400

caatcgtaac cttcatctct tccacccatg tctctttgag caataaagcc gataacaaaa   5460

tctttgtcgc tcttcgcaat gtcaacagta cccttagtat attctccagt agatagggag   5520

cccttgcatg acaattctgc taacatcaaa aggcctctag gttcctttgt tacttcttct   5580

gccgcctgct tcaaaccgct aacaatacct gggcccacca caccgtgtgc attcgtaatg   5640

tctgcccatt ctgctattct gtatacaccc gcagagtact gcaatttgac tgtattacca   5700

atgtcagcaa attttctgtc ttcg                                         5724
```

```
<210> SEQ ID NO 11
<211> LENGTH: 5724
<212> TYPE: DNA
<213> ORGANISM: Artificial Sequence
<220> FEATURE:
<223> OTHER INFORMATION: OAC-V28A/Y41V/G43SILENT(=GGG)/K44V/T68L/I74G/
      V84R/R100E/G102R

<400> SEQUENCE: 11

aagagtaaaa aattgtactt ggcggataat gcctttagcg gcttaactgt gccctccatg     60

gaaaaatcag tcaagatatc cacatgtgtt tttagtaaac aaattttggg acctaatgct    120

tcaactaact ccagtaattc cttggtggta cgaacatcca atgaagcaca caagtttgtt    180

tgcttttcgt gcatgatatt aaatagcttg gcagcaacag gactaggatg agtagcagca    240

cgttccttat atgtagcttt cgacatgatt tatcttcgtt tcctgcaggt tttgttctg    300

tgcagttggg ttaagaatac tggcaatttt catgtttctt caacactaca tatgcgtata    360

tataccaatc taagtctgtg ctccttcctt cgttcttcct tctgttcgga gattaccgaa    420

tcaaaaaaat ttcaaagaaa ccgaaatcaa aaaaaagaat aaaaaaaaaa tgatgaattg    480

aattgaaaag ctagcttatc gatgataagc tgtcaaagat gagaattaat tccacggact    540

atagactata ctagatactc cgtctactgt acgatacact tccgctcagg tccttgtcct    600

ttaacgaggc cttaccactc ttttgttact ctattgatcc agctcagcaa aggcagtgtg    660

atctaagatt ctatcttcgc gatgtagtaa aactagctag accgagaaag agactagaaa    720

tgcaaaaggc acttctacaa tggctgccat cattattatc cgatgtgacg ctgcagcttc    780

tcaatgatat tcgaatacgc tttgaggaga tacagcctaa tatccgacaa actgttttac    840

agatttacga tcgtacttgt tacccatcat tgaattttga acatccgaac ctgggagttt    900

tccctgaaac agatagtata tttgaacctg tataataata tatagtctag cgctttacgg    960
```

-continued

```
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc ttttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcatttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggt taacatcatt cctgctatga   2760
aggacgtcgt gtggggggtg gatgtcactc aaaaaaacaa ggaagaaggt tatacccaca   2820
tcgttgaagt caccttcgaa tctgttgaac tgattcaaga ctacatcggg cacccagctc   2880
acgtcggttt cggtgatagg tacagatctt tctgggaaaa attgttgatc ttcgactaca   2940
ccccagagaa gcggtaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct tttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
```

```
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
tactgtcatg ccatccgtaa gatgcttttc tgtgactggt gagtactcaa ccaagtcatt   4800
ctgagaatag tgtatgcggc gaccgagttg ctcttgcccg gcgtcaatac gggataatag   4860
tgtatcacat agcagaactt taaaagtgct catcattgga aaacgttctt cggggcgaaa   4920
actctcaagg atcttaccgc tgttgagatc cagttcgatg taacccactc gtgcacccaa   4980
ctgatcttca gcatctttta ctttcaccag cgtttctggg tgagcaaaaa caggaaggca   5040
aaatgccgca aaaaagggaa taagggcgac acggaaatgt tgaatactca tactcttcct   5100
ttttcaatgg gtaataactg atataattaa attgaagctc taatttgtga gtttagtata   5160
catgcattta cttataatac agtttttttag ttttgctggc cgcatcttct caaatatgct   5220
tcccagcctg cttttctgta acgttcaccc tctaccttag catcccttcc ctttgcaaat   5280
agtcctcttc caacaataat aatgtcagat cctgtagaga ccacatcatc cacggttcta   5340
tactgttgac ccaatgcgtc tcccttgtca tctaaaccca caccgggtgt cataatcaac   5400
caatcgtaac cttcatctct tccacccatg tctctttgag caataaagcc gataacaaaa   5460
tctttgtcgc tcttcgcaat gtcaacagta cccttagtat attctccagt agatagggag   5520
cccttgcatg acaattctgc taacatcaaa aggcctctag gttcctttgt tacttcttct   5580
gccgcctgct tcaaaccgct aacaatacct gggcccacca caccgtgtgc attcgtaatg   5640
tctgcccatt ctgctattct gtatacaccc gcagagtact gcaatttgac tgtattacca   5700
```

```
atgtcagcaa atttctgtc ttcg                                          5724


<210> SEQ ID NO 12
<211> LENGTH: 5724
<212> TYPE: DNA
<213> ORGANISM: Artificial Sequence
<220> FEATURE:
<223> OTHER INFORMATION: OAC-V28A/Y41T/G43SILENT(=GGG)/K44V/T68R/I74G/
      V84R/G102STOP

<400> SEQUENCE: 12

aagagtaaaa aattgtactt ggcggataat gcctttagcg gcttaactgt gccctccatg     60

gaaaaatcag tcaagatatc cacatgtgtt tttagtaaac aaattttggg acctaatgct    120

tcaactaact ccagtaattc cttggtggta cgaacatcca atgaagcaca caagtttgtt    180

tgcttttcgt gcatgatatt aaatagcttg gcagcaacag gactaggatg agtagcagca    240

cgttccttat atgtagcttt cgacatgatt tatcttcgtt tcctgcaggt ttttgttctg    300

tgcagttggg ttaagaatac tgggcaattt catgtttctt caacactaca tatgcgtata    360

tataccaatc taagtctgtg ctccttcctt cgttcttcct tctgttcgga gattaccgaa    420

tcaaaaaaat ttcaaagaaa ccgaaatcaa aaaaaagaat aaaaaaaaaa tgatgaattg    480

aattgaaaag ctagcttatc gatgataagc tgtcaaagat gagaattaat tccacggact    540

atagactata ctagatactc cgtctactgt acgatacact tccgctcagg tccttgtcct    600

ttaacgaggc cttaccactc ttttgttact ctattgatcc agctcagcaa aggcagtgtg    660

atctaagatt ctatcttcgc gatgtagtaa aactagctag accgagaaag agactagaaa    720

tgcaaaaggc acttctacaa tggctgccat cattattatc cgatgtgacg ctgcagcttc    780

tcaatgatat tcgaatacgc tttgaggaga tacagcctaa tatccgacaa actgttttac    840

agatttacga tcgtacttgt tacccatcat tgaattttga acatccgaac ctgggagttt    900

tccctgaaac agatagtata tttgaacctg tataataata tatagtctag cgctttacgg    960

aagacaatgt atgtatttcg gttcctggag aaactattgc atctattgca taggtaatct   1020

tgcacgtcgc atccccggtt cattttctgc gtttccatct tgcacttcaa tagcatatct   1080

ttgttcgctt gcctgtaact tacacgcgcc tcgtatcttt taatgatgga ataatttggg   1140

aatttactct gtgtttattt atttttatgt tttgtatttg gattttagaa agtaaataaa   1200

gaaggtagaa gagttacgga atgaagaaaa aaaaataaac aaaggtttaa aaaatttcaa   1260

caaaaagcgt actttacata tatatttatt agacaagaaa agcagattaa atagatatac   1320

attcgattaa cgataagtaa aatgtaaaat cacaggattt tcgtgtgtgg tcttctacac   1380

agacaagatg aaacaattcg gcattaatac ctgagagcag gaagagcaag ataaaaggta   1440

gtatttgttg gcgatccccc tagagtcttt tacatcttcg gaaaacaaaa actatttttt   1500

ctttaatttc tttttttact ttctattttt aatttatata tttatattaa aaaatttaaa   1560

ttataattat ttttatagca cgtgatgaaa aggaccggga agctccaccc cggttgataa   1620

tcagaaaagc cccaaaaaca ggaagattgt ataagcaaat atttaaattg taaacgttaa   1680

tattttgtta aaattcgcgt taaatttttg ttaaatcagc tcattttta acgaatagcc     1740

cgaaatcggc aaaatccctt ataaatcaaa agaatagacc gagatagggt tgagtgttgt   1800

tccagtttcc aacaagagtc cactattaaa gaacgtggac tccaacgtca aagggcgaaa   1860

aagggtctat cagggcgatg gcccactacg tgaaccatca ccctaatcaa gtttttggg    1920

gtcgaggtgc cgtaaagcag taaatcggaa gggtaaacgg atgcccccat ttagagcttg   1980
```

-continued

```
acggggaaag ccggcgaacg tggcgagaaa ggaagggaag aaagcgaaag gagcgggggc   2040

tagggcggtg ggaagtgtag gggtcacgct gggcgtaacc accacacccg ccgcgcttaa   2100

tggggcgcta cagggcgcgt ggggatgatc cactagtacg gattagaagc cgccgagcgg   2160

gtgacagccc tccgaaggaa gactctcctc cgtgcgtcct cgtcttcacc ggtcgcgttc   2220

ctgaaacgca gatgtgcctc gcgccgcact gctccgaaca ataaagattc tacaatacta   2280

gcttttatgg ttatgaagag gaaaaattgg cagtaacctg gccccacaaa ccttcaaatg   2340

aacgaatcaa attaacaacc ataggatgat aatgcgatta gtttttttagc cttatttctg   2400

gggtaattaa tcagcgaagc gatgattttt gatctattaa cagatatata aatgcaaaaa   2460

ctgcataacc actttaacta atactttcaa cattttcggt ttgtattact tcttattcaa   2520

atgtaataaa agtatcaaca aaaaattgtt aatatacctc tatactttaa cgtcaaggag   2580

aaaaaacccc ggatcggact actagcagct gtaatacgac tcactatagg gaatattaag   2640

cttaaacaat ggccgtcaag cacttgatcg tcttaaagtt taaggacgag atcactgaag   2700

cccaaaagga agaattcttc aaaacttacg cgaacttggt taacatcatt cctgctatga   2760

aggacgtcac gtggggggtg gatgtcactc aaaaaaacaa ggaagaaggt tatacccaca   2820

tcgttgaagt caccttcgaa tctgttgaac ggattcaaga ctacatcggg cacccagctc   2880

acgtcggttt cggtgatagg tacagatctt tctgggaaaa attgttgatc ttcgactaca   2940

ccccaagaaa gtaataactc gagcatgcat ctagagggcc gcatcatgta attagttatg   3000

tcacgcttac attcacgccc tccccccaca tccgctctaa ccgaaaagga aggagttaga   3060

caacctgaag tctaggtccc tatttatttt tttatagtta tgttagtatt aagaacgtta   3120

tttatatttc aaatttttct tttttttctg tacagacgcg tgtacgcatg taacattata   3180

ctgaaaacct tgcttgagaa ggttttggga cgctcgaagg ctttaatttg cggccctgca   3240

ttaatgaatc ggccaacgcg cggggagagg cggtttgcgt attgggcgct cttccgcttc   3300

ctcgctcact gactcgctgc gctcggtcgt tcggctgcgg cgagcggtat cagctcactc   3360

aaaggcggta atacggttat ccacagaatc aggggataac gcaggaaaga acatgtgagc   3420

aaaaggccag caaaagccca ggaaccgtaa aaaggccgcg ttgctggcgt ttttccatag   3480

gctccgcccc cctgacgagc atcacaaaaa tcgacgctca agtcagaggt ggcgaaaccc   3540

gacaggacta taaagatacc aggcgtttcc ccctggaagc tccctcgtgc gctctcctgt   3600

tccgaccctg ccgcttaccg gatacctgtc cgcctttctc ccttcgggaa gcgtggcgct   3660

ttctcatagc tcacgctgta ggtatctcag ttcggtgtag gtcgttcgct ccaagctggg   3720

ctgtgtgcac gaaccccccg ttcagcccga ccgctgcgcc ttatccggta actatcgtct   3780

tgagtccaac ccggtaagac acgacttatc gccactggca gcagccactg gtaacaggat   3840

tagcagagcg aggtatgtag gcggtgctac agagttcttg aagtggtggc ctaactacgg   3900

ctacactaga agaacagtat ttggtatctg cgctctgctg aagccagtta ccttcggaaa   3960

aagagttggt agctcttgat ccggcaaaca aaccaccgct ggtagcggtg gtttttttgt   4020

ttgcaagcag cagattacgc gcagaaaaaa aggatctcaa gaagatcctt tgatcttttc   4080

tacggggtct gacgctcagt ggaacgaaaa ctcacgttaa gggattttgg tcatgagatt   4140

atcaaaaagg atcttcacct agatcctttt aaattaaaaa tgaagtttta aatcaatcta   4200

aagtatatat gagtaaactt ggtctgacag ttaccaatgc ttaatcagtg aggcacctat   4260

ctcagcgatc tgtctatttc gttcatccat agttgcctga ctccccgtcg tgtagataac   4320

tacgatacgg gagcgcttac catctggccc cagtgctgca atgataccgc gagacccacg   4380
```

ctcaccggct ccagatttat cagcaataaa ccagccagcc ggaagggccg agcgcagaag 4440
tggtcctgca actttatccg cctccattca gtctattaat tgttgccggg aagctagagt 4500
aagtagttcg ccagttaata gtttgcgcaa cgttgttggc attgctacag gcatcgtggt 4560
gtcactctcg tcgtttggta tggcttcatt cagctccggt tcccaacgat caaggcgagt 4620
tacatgatcc cccatgttgt gcaaaaaagc ggttagctcc ttcggtcctc cgatcgttgt 4680
cagaagtaag ttggccgcag tgttatcact catggttatg gcagcactgc ataattctct 4740
tactgtcatg ccatccgtaa gatgcttttc tgtgactggt gagtactcaa ccaagtcatt 4800
ctgagaatag tgtatgcggc gaccgagttg ctcttgcccg gcgtcaatac gggataatag 4860
tgtatcacat agcagaactt taaaagtgct catcattgga aaacgttctt cggggcgaaa 4920
actctcaagg atcttaccgc tgttgagatc cagttcgatg taacccactc gtgcacccaa 4980
ctgatcttca gcatctttta ctttcaccag cgtttctggg tgagcaaaaa caggaaggca 5040
aaatgccgca aaaaagggaa taagggcgac acggaaatgt tgaatactca tactcttcct 5100
ttttcaatgg gtaataactg atataattaa attgaagctc taatttgtga gtttagtata 5160
catgcattta cttataatac agttttttag ttttgctggc cgcatcttct caaatatgct 5220
tcccagcctg cttttctgta acgttcaccc tctaccttag catcccttcc ctttgcaaat 5280
agtcctcttc caacaataat aatgtcagat cctgtagaga ccacatcatc cacggttcta 5340
tactgttgac ccaatgcgtc tcccttgtca tctaaaccca caccgggtgt cataatcaac 5400
caatcgtaac cttcatctct tccacccatg tctctttgag caataaagcc gataacaaaa 5460
tctttgtcgc tcttcgcaat gtcaacagta cccttagtat attctccagt agatagggag 5520
cccttgcatg acaattctgc taacatcaaa aggcctctag gttcctttgt tacttcttct 5580
gccgcctgct tcaaaccgct aacaatacct gggcccacca caccgtgtgc attcgtaatg 5640
tctgcccatt ctgctattct gtatacaccc gcagagtact gcaatttgac tgtattacca 5700
atgtcagcaa attttctgtc ttcg 5724

<210> SEQ ID NO 13
<211> LENGTH: 5724
<212> TYPE: DNA
<213> ORGANISM: Artificial Sequence
<220> FEATURE:
<223> OTHER INFORMATION: OAC-V28A/Y41V/G43SILENT(=GGG)/K44V/T68L/I74R/
V84R/R100E/G102STOP

<400> SEQUENCE: 13
aagagtaaaa aattgtactt ggcggataat gcctttagcg gcttaactgt gccctccatg 60
gaaaaatcag tcaagatatc cacatgtgtt tttagtaaac aaattttggg acctaatgct 120
tcaactaact ccagtaattc cttggtggta cgaacatcca atgaagcaca caagtttgtt 180
tgcttttcgt gcatgatatt aaatagcttg gcagcaacag gactaggatg agtagcagca 240
cgttccttat atgtagcttt cgacatgatt tatcttcgtt tcctgcaggt tttgttctg 300 tgcagttggg ttaagaatac tgggcaattt catgtttctt caacactaca tatgcgtata 360
tataccaatc taagtctgtg ctccttcctt cgttcttcct tctgttcgga gattaccgaa 420
tcaaaaaaat ttcaaagaaa ccgaaatcaa aaaaaagaat aaaaaaaaaa tgatgaattg 480
aattgaaaag ctagcttatc gatgataagc tgtcaaagat gagaattaat tccacggact 540
atagactata ctagatactc cgtctactgt acgatacact tccgctcagg tccttgtcct 600
ttaacgaggc cttaccactc ttttgttact ctattgatcc agctcagcaa aggcagtgtg 660
atctaagatt ctatcttcgc gatgtagtaa aactagctag accgagaaag agactagaaa 720
tgcaaaaggc acttctacaa tggctgccat cattattatc cgatgtgacg ctgcagcttc 780
tcaatgatat tcgaatacgc tttgaggaga tacagcctaa tatccgacaa actgttttac 840
agatttacga tcgtacttgt tacccatcat tgaattttga acatccgaac ctgggagttt 900
tccctgaaac agatagtata tttgaacctg tataataata tatagtctag cgctttacgg 960
aagacaatgt atgtatttcg gttcctggag aaactattgc atctattgca taggtaatct 1020
tgcacgtcgc atccccggtt cattttctgc gtttccatct tgcacttcaa tagcatatct 1080
ttgttcgctt gcctgtaact tacacgcgcc tcgtatcttt taatgatgga ataatttggg 1140
aatttactct gtgtttattt atttttatgt tttgtatttg gattttagaa agtaaataaa 1200
gaaggtagaa gagttacgga atgaagaaaa aaaaataaac aaaggtttaa aaaatttcaa 1260
caaaaagcgt actttacata tatatttatt agacaagaaa agcagattaa atagatatac 1320
attcgattaa cgataagtaa aatgtaaaat cacaggattt tcgtgtgtgg tcttctacac 1380
agacaagatg aaacaattcg gcattaatac ctgagagcag gaagagcaag ataaaaggta 1440
gtatttgttg gcgatccccc tagagtcttt tacatcttcg gaaaacaaaa actatttttt 1500
ctttaatttc tttttttact ttctattttt aatttatata tttatattaa aaaatttaaa 1560
ttataattat ttttatagca cgtgatgaaa aggaccggga agctccaccc cggttgataa 1620
tcagaaaagc cccaaaaaca ggaagattgt ataagcaaat atttaaattg taaacgttaa 1680
tattttgtta aaattcgcgt taaatttttg ttaaatcagc tcattttta acgaatagcc 1740
cgaaatcggc aaaatccctt ataaatcaaa agaatagacc gagatagggt tgagtgttgt 1800
tccagtttcc aacaagagtc cactattaaa gaacgtggac tccaacgtca aagggcgaaa 1860
aagggtctat cagggcgatg gcccactacg tgaaccatca ccctaatcaa gtttttggg 1920
gtcgaggtgc cgtaaagcag taaatcggaa gggtaaacgg atgccccat ttagagcttg 1980
acggggaaag ccggcgaacg tggcgagaaa ggaagggaag aaagcgaaag gagcgggggc 2040
tagggcggtg ggaagtgtag gggtcacgct gggcgtaacc accacacccg ccgcgcttaa 2100
tggggcgcta cagggcgcgt ggggatgatc cactagtacg gattagaagc cgccgagcgg 2160
gtgacagccc tccgaaggaa gactctcctc cgtgcgtcct cgtcttcacc ggtcgcgttc 2220
ctgaaacgca gatgtgcctc gcgccgcact gctccgaaca ataaagattc tacaatacta 2280
gcttttatgg ttatgaagag gaaaaattgg cagtaacctg gccccacaaa ccttcaaatg 2340
aacgaatcaa attaacaacc ataggatgat aatgcgatta gtttttagc cttatttctg 2400
gggtaattaa tcagcgaagc gatgattttt gatctattaa cagatatata aatgcaaaaa 2460
ctgcataacc actttaacta atactttcaa cattttcggt ttgtattact tcttattcaa 2520
atgtaataaa agtatcaaca aaaaattgtt aatatacctc tatactttaa cgtcaaggag 2580
aaaaaacccc ggatcggact actagcagct gtaatacgac tcactatagg gaatattaag 2640
cttaaacaat ggccgtcaag cacttgatcg tcttaaagtt taaggacgag atcactgaag 2700
cccaaaagga agaattcttc aaaacttacg cgaacttggt taacatcatt cctgctatga 2760
aggacgtcgt gtgggggtg gatgtcactc aaaaaaacaa ggaagaaggt tatacccaca 2820
tcgttgaagt caccttcgaa tctgttgaac tgattcaaga ctacatcagg cacccagctc 2880
acgtcggttt cggtgatagg tacagatctt tctgggaaaa attgttgatc ttcgactaca 2940
ccccagagaa gtaataactc gagcatgcat ctagagggcc gcatcatgta attagttatg 3000

```
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct tttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
tactgtcatg ccatccgtaa gatgcttttc tgtgactggt gagtactcaa ccaagtcatt   4800
ctgagaatag tgtatgcggc gaccgagttg ctcttgcccg gcgtcaatac gggataatag   4860
tgtatcacat agcagaactt taaaagtgct catcattgga aaacgttctt cggggcgaaa   4920
actctcaagg atcttaccgc tgttgagatc cagttcgatg taacccactc gtgcacccaa   4980
ctgatcttca gcatctttta ctttcaccag cgtttctggg tgagcaaaaa caggaaggca   5040
aaatgccgca aaaaagggaa taagggcgac acggaaatgt tgaatactca tactcttcct   5100
ttttcaatgg gtaataactg atataattaa attgaagctc taatttgtga gtttagtata   5160
catgcattta cttataatac agttttttag ttttgctggc cgcatcttct caaatatgct   5220
tcccagcctg cttttctgta acgttcaccc tctaccttag catcccttcc ctttgcaaat   5280
agtcctcttc caacaataat aatgtcagat cctgtagaga ccacatcatc cacggttcta   5340
tactgttgac ccaatgcgtc tcccttgtca tctaaaccca caccgggtgt cataatcaac   5400
```

caatcgtaac cttcatctct tccacccatg tctctttgag caataaagcc gataacaaaa 5460
tctttgtcgc tcttcgcaat gtcaacagta cccttagtat attctccagt agatagggag 5520
cccttgcatg acaattctgc taacatcaaa aggcctctag gttcctttgt tacttcttct 5580
gccgcctgct tcaaaccgct aacaatacct gggcccacca caccgtgtgc attcgtaatg 5640
tctgcccatt ctgctattct gtatacaccc gcagagtact gcaatttgac tgtattacca 5700
atgtcagcaa attttctgtc ttcg 5724

<210> SEQ ID NO 14
<211> LENGTH: 5724
<212> TYPE: DNA
<213> ORGANISM: Artificial Sequence
<220> FEATURE:
<223> OTHER INFORMATION: OAC-V28A/V31G/Y41T/G43SILENT(=GGG)/K44V/T68R/
I74E/V84R/R100E

<400> SEQUENCE: 14
aagagtaaaa aattgtactt ggcggataat gcctttagcg gcttaactgt gccctccatg 60
gaaaaatcag tcaagatatc cacatgtgtt tttagtaaac aaattttggg acctaatgct 120
tcaactaact ccagtaattc cttggtggta cgaacatcca atgaagcaca caagtttgtt 180
tgcttttcgt gcatgatatt aaatagcttg gcagcaacag gactaggatg agtagcagca 240
cgttccttat atgtagcttt cgacatgatt tatcttcgtt tcctgcaggt ttttgttctg 300
tgcagttggg ttaagaatac tggcaattt catgtttctt caacactaca tatgcgtata 360
tataccaatc taagtctgtg ctccttcctt cgttcttcct tctgttcgga gattaccgaa 420
tcaaaaaaat ttcaaagaaa ccgaaatcaa aaaaaagaat aaaaaaaaaa tgatgaattg 480
aattgaaaag ctagcttatc gatgataagc tgtcaaagat gagaattaat tccacggact 540
atagactata ctagatactc cgtctactgt acgatacact tccgctcagg tccttgtcct 600
ttaacgaggc cttaccactc ttttgttact ctattgatcc agctcagcaa aggcagtgtg 660
atctaagatt ctatcttcgc gatgtagtaa aactagctag accgagaaag agactagaaa 720
tgcaaaaggc acttctacaa tggctgccat cattattatc cgatgtgacg ctgcagcttc 780
tcaatgatat tcgaatacgc tttgaggaga tacagcctaa tatccgacaa actgttttac 840
agatttacga tcgtacttgt tacccatcat tgaattttga acatccgaac ctgggagttt 900
tccctgaaac agatagtata tttgaacctg tataataata tatagtctag cgctttacgg 960
aagacaatgt atgtatttcg gttcctggag aaactattgc atctattgca taggtaatct 1020
tgcacgtcgc atccccggtt cattttctgc gtttccatct tgcacttcaa tagcatatct 1080
ttgttcgctt gcctgtaact tacacgcgcc tcgtatcttt taatgatgga ataatttggg 1140
aatttactct gtgtttattt atttttatgt tttgtatttg gattttagaa agtaaataaa 1200
gaaggtagaa gagttacgga atgaagaaaa aaaaataaac aaaggtttaa aaaatttcaa 1260
caaaaagcgt actttacata tatatttatt agacaagaaa agcagattaa atagatatac 1320
attcgattaa cgataagtaa aatgtaaaat cacaggattt tcgtgtgtgg tcttctacac 1380
agacaagatg aaacaattcg gcattaatac ctgagagcag gaagagcaag ataaaaggta 1440
gtatttgttg gcgatccccc tagagtcttt tacatcttcg gaaaacaaaa actatttttt 1500
ctttaatttc tttttttact ttctattttt aatttatata tttatattaa aaaatttaaa 1560
ttataattat ttttatagca cgtgatgaaa aggaccggga agctccaccc cggttgataa 1620
tcagaaaagc cccaaaaaca ggaagattgt ataagcaaat atttaaattg taaacgttaa 1680

```
tattttgtta aaattcgcgt taaatttttg ttaaatcagc tcatttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggg gaacatcatt cctgctatga   2760
aggacgtcac gtggggggtg gatgtcactc aaaaaaacaa ggaagaaggt tatacccaca   2820
tcgttgaagt caccttcgaa tctgttgaac ggattcaaga ctacatcgag cacccagctc   2880
acgtcggttt cggtgatagg tacagatctt tctgggaaaa attgttgatc ttcgactaca   2940
ccccagagaa gggctaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct ttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
```

ttgcaagcag cagattacgc gcagaaaaaa aggatctcaa gaagatcctt tgatcttttc 4080
tacggggtct gacgctcagt ggaacgaaaa ctcacgttaa gggattttgg tcatgagatt 4140
atcaaaaagg atcttcacct agatcctttt aaattaaaaa tgaagtttta aatcaatcta 4200
aagtatatat gagtaaactt ggtctgacag ttaccaatgc ttaatcagtg aggcacctat 4260
ctcagcgatc tgtctatttc gttcatccat agttgcctga ctccccgtcg tgtagataac 4320
tacgatacgg gagcgcttac catctggccc cagtgctgca atgataccgc gagacccacg 4380
ctcaccggct ccagatttat cagcaataaa ccagccagcc ggaagggccg agcgcagaag 4440
tggtcctgca actttatccg cctccattca gtctattaat tgttgccggg aagctagagt 4500
aagtagttcg ccagttaata gtttgcgcaa cgttgttggc attgctacag gcatcgtggt 4560
gtcactctcg tcgtttggta tggcttcatt cagctccggt tcccaacgat caaggcgagt 4620
tacatgatcc cccatgttgt gcaaaaaagc ggttagctcc ttcggtcctc cgatcgttgt 4680
cagaagtaag ttggccgcag tgttatcact catggttatg gcagcactgc ataattctct 4740
tactgtcatg ccatccgtaa gatgcttttc tgtgactggt gagtactcaa ccaagtcatt 4800
ctgagaatag tgtatgcggc gaccgagttg ctcttgcccg gcgtcaatac gggataatag 4860
tgtatcacat agcagaactt taaaagtgct catcattgga aaacgttctt cggggcgaaa 4920
actctcaagg atcttaccgc tgttgagatc cagttcgatg taacccactc gtgcacccaa 4980
ctgatcttca gcatctttta ctttcaccag cgtttctggg tgagcaaaaa caggaaggca 5040
aaatgccgca aaaaagggaa taagggcgac acggaaatgt tgaatactca tactcttcct 5100
ttttcaatgg gtaataactg atataattaa attgaagctc taatttgtga gtttagtata 5160
catgcattta cttataatac agtttttag ttttgctggc cgcatcttct caaatatgct 5220
tcccagcctg cttttctgta acgttcaccc tctaccttag catcccttcc ctttgcaaat 5280
agtcctcttc caacaataat aatgtcagat cctgtagaga ccacatcatc cacggttcta 5340
tactgttgac ccaatgcgtc tcccttgtca tctaaaccca caccgggtgt cataatcaac 5400
caatcgtaac cttcatctct tccacccatg tctctttgag caataaagcc gataacaaaa 5460
tctttgtcgc tcttcgcaat gtcaacagta cccttagtat attctccagt agatagggag 5520
cccttgcatg acaattctgc taacatcaaa aggcctctag gttcctttgt tacttcttct 5580
gccgcctgct tcaaaccgct aacaatacct gggcccacca caccgtgtgc attcgtaatg 5640
tctgcccatt ctgctattct gtatacaccc gcagagtact gcaatttgac tgtattacca 5700
atgtcagcaa atttctgtc ttcg 5724

<210> SEQ ID NO 15
<211> LENGTH: 5724
<212> TYPE: DNA
<213> ORGANISM: Artificial Sequence
<220> FEATURE:
<223> OTHER INFORMATION: OAC-V28A/Y41S/G43SILENT(=GGG)/T68R/I74R/V84R/
R100M/G102STOP

<400> SEQUENCE: 15
aagagtaaaa aattgtactt ggcggataat gcctttagcg gcttaactgt gccctccatg 60
gaaaaatcag tcaagatatc cacatgtgtt tttagtaaac aaattttggg acctaatgct 120
tcaactaact ccagtaattc cttggtggta cgaacatcca atgaagcaca caagtttgtt 180
tgcttttcgt gcatgatatt aaatagcttg gcagcaacag gactaggatg agtagcagca 240
cgttccttat atgtagcttt cgacatgatt tatcttcgtt tcctgcaggt tttgttctg 300

-continued

```
tgcagttggg ttaagaatac tgggcaattt catgtttctt caacactaca tatgcgtata    360
tataccaatc taagtctgtg ctccttcctt cgttcttcct tctgttcgga gattaccgaa    420
tcaaaaaaat ttcaaagaaa ccgaaatcaa aaaaaagaat aaaaaaaaaa tgatgaattg    480
aattgaaaag ctagcttatc gatgataagc tgtcaaagat gagaattaat tccacggact    540
atagactata ctagatactc cgtctactgt acgatacact tccgctcagg tccttgtcct    600
ttaacgaggc cttaccactc ttttgttact ctattgatcc agctcagcaa aggcagtgtg    660
atctaagatt ctatcttcgc gatgtagtaa aactagctag accgagaaag agactagaaa    720
tgcaaaaggc acttctacaa tggctgccat cattattatc cgatgtgacg ctgcagcttc    780
tcaatgatat tcgaatacgc tttgaggaga tacagcctaa tatccgacaa actgttttac    840
agatttacga tcgtacttgt tacccatcat tgaattttga acatccgaac ctgggagttt    900
tccctgaaac agatagtata tttgaacctg tataataata tatagtctag cgctttacgg    960
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc tttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcattttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gtttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttttagc cttatttctg   2400
gggtaattaa tcagcgaagc gatgattttt gatctattaa cagatatata aatgcaaaaa   2460
ctgcataacc actttaacta atactttcaa catttttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
```

cccaaaagga agaattcttc aaaacttacg cgaacttggt taacatcatt cctgctatga 2760
aggacgtctc ctgggggaag gatgtcactc aaaaaaacaa ggaagaaggt tatacccaca 2820
tcgttgaagt caccttcgaa tctgttgaac ggattcaaga ctacatcagg cacccagctc 2880
acgtcggttt cggtgatagg tacagatctt tctgggaaaa attgttgatc ttcgactaca 2940
ccccaatgaa gtaataactc gagcatgcat ctagagggcc gcatcatgta attagttatg 3000
tcacgcttac attcacgccc tccccccaca tccgctctaa ccgaaaagga aggagttaga 3060
caacctgaag tctaggtccc tatttatttt tttatagtta tgttagtatt aagaacgtta 3120
tttatatttc aaatttttct ttttttctg tacagacgcg tgtacgcatg taacattata 3180
ctgaaaacct tgcttgagaa ggttttggga cgctcgaagg ctttaatttg cggccctgca 3240
ttaatgaatc ggccaacgcg cggggagagg cggtttgcgt attgggcgct cttccgcttc 3300
ctcgctcact gactcgctgc gctcggtcgt tcggctgcgg cgagcggtat cagctcactc 3360
aaaggcggta atacggttat ccacagaatc aggggataac gcaggaaaga acatgtgagc 3420
aaaaggccag caaaagccca ggaaccgtaa aaaggccgcg ttgctggcgt ttttccatag 3480
gctccgcccc cctgacgagc atcacaaaaa tcgacgctca agtcagaggt ggcgaaaccc 3540
gacaggacta taaagatacc aggcgtttcc ccctggaagc tccctcgtgc gctctcctgt 3600
tccgaccctg ccgcttaccg gatacctgtc cgcctttctc ccttcgggaa gcgtggcgct 3660
ttctcatagc tcacgctgta ggtatctcag ttcggtgtag gtcgttcgct ccaagctggg 3720
ctgtgtgcac gaaccccccg ttcagcccga ccgctgcgcc ttatccggta actatcgtct 3780
tgagtccaac ccggtaagac acgacttatc gccactggca gcagccactg gtaacaggat 3840
tagcagagcg aggtatgtag gcggtgctac agagttcttg aagtggtggc ctaactacgg 3900
ctacactaga agaacagtat ttggtatctg cgctctgctg aagccagtta ccttcggaaa 3960
aagagttggt agctcttgat ccggcaaaca aaccaccgct ggtagcggtg gtttttttgt 4020
ttgcaagcag cagattacgc gcagaaaaaa aggatctcaa gaagatcctt tgatcttttc 4080
tacggggtct gacgctcagt ggaacgaaaa ctcacgttaa gggattttgg tcatgagatt 4140
atcaaaaagg atcttcacct agatcctttt aaattaaaaa tgaagtttta aatcaatcta 4200
aagtatatat gagtaaactt ggtctgacag ttaccaatgc ttaatcagtg aggcacctat 4260
ctcagcgatc tgtctatttc gttcatccat agttgcctga ctccccgtcg tgtagataac 4320
tacgatacgg gagcgcttac catctggccc cagtgctgca atgataccgc gagacccacg 4380
ctcaccggct ccagatttat cagcaataaa ccagccagcc ggaagggccg agcgcagaag 4440
tggtcctgca actttatccg cctccattca gtctattaat tgttgccggg aagctagagt 4500
aagtagttcg ccagttaata gtttgcgcaa cgttgttggc attgctacag gcatcgtggt 4560
gtcactctcg tcgtttggta tggcttcatt cagctccggt tcccaacgat caaggcgagt 4620
tacatgatcc cccatgttgt gcaaaaaagc ggttagctcc ttcggtcctc cgatcgttgt 4680
cagaagtaag ttggccgcag tgttatcact catggttatg gcagcactgc ataattctct 4740
tactgtcatg ccatccgtaa gatgcttttc tgtgactggt gagtactcaa ccaagtcatt 4800
ctgagaatag tgtatgcggc gaccgagttg ctcttgcccg gcgtcaatac gggataatag 4860
tgtatcacat agcagaactt taaaagtgct catcattgga aaacgttctt cggggcgaaa 4920
actctcaagg atcttaccgc tgttgagatc cagttcgatg taacccactc gtgcacccaa 4980
ctgatcttca gcatctttta ctttcaccag cgtttctggg tgagcaaaaa caggaaggca 5040

```
aaatgccgca aaaaagggaa taagggcgac acggaaatgt tgaatactca tactcttcct   5100

ttttcaatgg gtaataactg atataattaa attgaagctc taatttgtga gtttagtata   5160

catgcattta cttataatac agttttttag ttttgctggc cgcatcttct caaatatgct   5220

tcccagcctg cttttctgta acgttcaccc tctaccttag catcccttcc ctttgcaaat   5280

agtcctcttc caacaataat aatgtcagat cctgtagaga ccacatcatc cacggttcta   5340

tactgttgac ccaatgcgtc tcccttgtca tctaaaccca caccgggtgt cataatcaac   5400

caatcgtaac cttcatctct tccacccatg tctctttgag caataaagcc gataacaaaa   5460

tctttgtcgc tcttcgcaat gtcaacagta cccttagtat attctccagt agatagggag   5520

cccttgcatg acaattctgc taacatcaaa aggcctctag gttcctttgt tacttcttct   5580

gccgcctgct tcaaaccgct aacaatacct gggcccacca caccgtgtgc attcgtaatg   5640

tctgcccatt ctgctattct gtatacaccc gcagagtact gcaatttgac tgtattacca   5700

atgtcagcaa atttctgtc ttcg                                         5724
```

```
<210> SEQ ID NO 16
<211> LENGTH: 5724
<212> TYPE: DNA
<213> ORGANISM: Artificial Sequence
<220> FEATURE:
<223> OTHER INFORMATION: OAC-Y41T/G43SILENT(=GGG)/K44V/T68L/I74G/V84R/
      G102R

<400> SEQUENCE: 16

aagagtaaaa aattgtactt ggcggataat gcctttagcg gcttaactgt gccctccatg     60

gaaaaatcag tcaagatatc cacatgtgtt tttagtaaac aaattttggg acctaatgct    120

tcaactaact ccagtaattc cttggtggta cgaacatcca atgaagcaca caagtttgtt    180

tgcttttcgt gcatgatatt aaatagcttg gcagcaacag gactaggatg agtagcagca    240

cgttccttat atgtagcttt cgacatgatt tatcttcgtt tcctgcaggt ttttgttctg    300

tgcagttggg ttaagaatac tgggcaattt catgtttctt caacactaca tatgcgtata    360

tataccaatc taagtctgtg ctccttcctt cgttcttcct tctgttcgga gattaccgaa    420

tcaaaaaaat ttcaaagaaa ccgaaatcaa aaaaaagaat aaaaaaaaaa tgatgaattg    480

aattgaaaag ctagcttatc gatgataagc tgtcaaagat gagaattaat tccacggact    540

atagactata ctagatactc cgtctactgt acgatacact tccgctcagg tccttgtcct    600

ttaacgaggc cttaccactc ttttgttact ctattgatcc agctcagcaa aggcagtgtg    660

atctaagatt ctatcttcgc gatgtagtaa aactagctag accgagaaag agactagaaa    720

tgcaaaaggc acttctacaa tggctgccat cattattatc cgatgtgacg ctgcagcttc    780

tcaatgatat tcgaatacgc tttgaggaga tacagcctaa tatccgacaa actgttttac    840

agatttacga tcgtacttgt tacccatcat tgaattttga acatccgaac ctgggagttt    900

tccctgaaac agatagtata tttgaacctg tataataata tatagtctag cgctttacgg    960

aagacaatgt atgtatttcg gttcctggag aaactattgc atctattgca taggtaatct   1020

tgcacgtcgc atccccggtt cattttctgc gtttccatct tgcacttcaa tagcatatct   1080

ttgttcgctt gcctgtaact tacacgcgcc tcgtatcttt taatgatgga ataatttggg   1140

aatttactct gtgtttattt atttttatgt tttgtatttg gattttagaa agtaaataaa   1200

gaaggtagaa gagttacgga atgaagaaaa aaaaataaac aaaggtttaa aaaatttcaa   1260

caaaaagcgt actttacata tatatttatt agacaagaaa agcagattaa atagatatac   1320
```

```
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc tttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcatttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg ttaacttggt taacatcatt cctgctatga   2760
aggacgtcac gtggggggtg gatgtcactc aaaaaaacaa ggaagaaggt tatacccaca   2820
tcgttgaagt caccttcgaa tctgttgaac tgattcaaga ctacatcggg cacccagctc   2880
acgtcggttt cggtgatagg tacagatctt tctgggaaaa attgttgatc ttcgactaca   2940
ccccaagaaa gcggtaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct tttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
```

```
ctgtgtgcac gaaccccccg ttcagcccga ccgctgcgcc ttatccggta actatcgtct   3780

tgagtccaac ccggtaagac acgacttatc gccactggca gcagccactg gtaacaggat   3840

tagcagagcg aggtatgtag gcggtgctac agagttcttg aagtggtggc ctaactacgg   3900

ctacactaga agaacagtat ttggtatctg cgctctgctg aagccagtta ccttcggaaa   3960

aagagttggt agctcttgat ccggcaaaca aaccaccgct ggtagcggtg gtttttttgt   4020

ttgcaagcag cagattacgc gcagaaaaaa aggatctcaa gaagatcctt tgatcttttc   4080

tacggggtct gacgctcagt ggaacgaaaa ctcacgttaa gggattttgg tcatgagatt   4140

atcaaaaagg atcttcacct agatcctttt aaattaaaaa tgaagtttta aatcaatcta   4200

aagtatatat gagtaaactt ggtctgacag ttaccaatgc ttaatcagtg aggcacctat   4260

ctcagcgatc tgtctatttc gttcatccat agttgcctga ctccccgtcg tgtagataac   4320

tacgatacgg gagcgcttac catctggccc cagtgctgca atgataccgc gagacccacg   4380

ctcaccggct ccagatttat cagcaataaa ccagccagcc ggaagggccg agcgcagaag   4440

tggtcctgca actttatccg cctccattca gtctattaat tgttgccggg aagctagagt   4500

aagtagttcg ccagttaata gtttgcgcaa cgttgttggc attgctacag gcatcgtggt   4560

gtcactctcg tcgtttggta tggcttcatt cagctccggt tcccaacgat caaggcgagt   4620

tacatgatcc cccatgttgt gcaaaaaagc ggttagctcc ttcggtcctc cgatcgttgt   4680

cagaagtaag ttggccgcag tgttatcact catggttatg gcagcactgc ataattctct   4740

tactgtcatg ccatccgtaa gatgcttttc tgtgactggt gagtactcaa ccaagtcatt   4800

ctgagaatag tgtatgcggc gaccgagttg ctcttgcccg gcgtcaatac gggataatag   4860

tgtatcacat agcagaactt taaaagtgct catcattgga aaacgttctt cggggcgaaa   4920

actctcaagg atcttaccgc tgttgagatc cagttcgatg taacccactc gtgcacccaa   4980

ctgatcttca gcatctttta ctttcaccag cgtttctggg tgagcaaaaa caggaaggca   5040

aaatgccgca aaaaagggaa taagggcgac acggaaatgt tgaatactca tactcttcct   5100

ttttcaatgg gtaataactg atataattaa attgaagctc taatttgtga gtttagtata   5160

catgcattta cttataatac agttttttag ttttgctggc cgcatcttct caaatatgct   5220

tcccagcctg cttttctgta acgttcaccc tctaccttag catcccttcc ctttgcaaat   5280

agtcctcttc caacaataat aatgtcagat cctgtagaga ccacatcatc cacggttcta   5340

tactgttgac ccaatgcgtc tcccttgtca tctaaaccca caccgggtgt cataatcaac   5400

caatcgtaac cttcatctct tccacccatg tctctttgag caataaagcc gataacaaaa   5460

tctttgtcgc tcttcgcaat gtcaacagta ccccttagtat attctccagt agatagggag   5520

cccttgcatg acaattctgc taacatcaaa aggcctctag gttcctttgt tacttcttct   5580

gccgcctgct tcaaaccgct aacaatacct gggcccacca caccgtgtgc attcgtaatg   5640

tctgcccatt ctgctattct gtatacaccc gcagagtact gcaatttgac tgtattacca   5700

atgtcagcaa attttctgtc ttcg                                          5724
```

```
<210> SEQ ID NO 17
<211> LENGTH: 5724
<212> TYPE: DNA
<213> ORGANISM: Artificial Sequence
<220> FEATURE:
<223> OTHER INFORMATION: OAC-V28A/Y41T/G43SILENT(=GGG)/K44V/T68R/I74R/
      V84R/R100E/G102R

<400> SEQUENCE: 17
```

-continued

```
aagagtaaaa aattgtactt ggcggataat gcctttagcg gcttaactgt gccctccatg      60
gaaaaatcag tcaagatatc cacatgtgtt tttagtaaac aaattttggg acctaatgct     120
tcaactaact ccagtaattc cttggtggta cgaacatcca atgaagcaca caagtttgtt     180
tgcttttcgt gcatgatatt aaatagcttg gcagcaacag gactaggatg agtagcagca     240
cgttccttat atgtagcttt cgacatgatt tatcttcgtt tcctgcaggt tttgttctg      300
tgcagttggg ttaagaatac tgggcaattt catgtttctt caacactaca tatgcgtata     360
tataccaatc taagtctgtg ctccttcctt cgttcttcct tctgttcgga gattaccgaa     420
tcaaaaaaat ttcaaagaaa ccgaaatcaa aaaaaagaat aaaaaaaaaa tgatgaattg     480
aattgaaaag ctagcttatc gatgataagc tgtcaaagat gagaattaat tccacggact     540
atagactata ctagatactc cgtctactgt acgatacact tccgctcagg tccttgtcct     600
ttaacgaggc cttaccactc ttttgttact ctattgatcc agctcagcaa aggcagtgtg     660
atctaagatt ctatcttcgc gatgtagtaa aactagctag accgagaaag agactagaaa     720
tgcaaaaggc acttctacaa tggctgccat cattattatc cgatgtgacg ctgcagcttc     780
tcaatgatat tcgaatacgc tttgaggaga tacagcctaa tatccgacaa actgttttac     840
agatttacga tcgtacttgt tacccatcat tgaattttga acatccgaac ctgggagttt     900
tccctgaaac agatagtata tttgaacctg tataataata tatagtctag cgctttacgg     960
aagacaatgt atgtatttcg gttcctggag aaactattgc atctattgca taggtaatct    1020
tgcacgtcgc atccccggtt cattttctgc gtttccatct tgcacttcaa tagcatatct    1080
ttgttcgctt gcctgtaact tacacgcgcc tcgtatcttt taatgatgga ataatttggg    1140
aatttactct gtgtttattt atttttatgt tttgtatttg gattttagaa agtaaataaa    1200
gaaggtagaa gagttacgga atgaagaaaa aaaaataaac aaaggtttaa aaaatttcaa    1260
caaaaagcgt actttacata tatatttatt agacaagaaa agcagattaa atagatatac    1320
attcgattaa cgataagtaa aatgtaaaat cacaggattt tcgtgtgtgg tcttctacac    1380
agacaagatg aaacaattcg gcattaatac ctgagagcag gaagagcaag ataaaaggta    1440
gtatttgttg gcgatccccc tagagtcttt tacatcttcg gaaaacaaaa actattttt     1500
ctttaatttc tttttttact ttctattttt aatttatata tttatattaa aaaatttaaa    1560
ttataattat ttttatagca cgtgatgaaa aggaccggga agctccaccc cggttgataa    1620
tcagaaaagc cccaaaaaca ggaagattgt ataagcaaat atttaaattg taaacgttaa    1680
tattttgtta aaattcgcgt taaatttttg ttaaatcagc tcattttta acgaatagcc     1740
cgaaatcggc aaaatccctt ataaatcaaa agaatagacc gagatagggt tgagtgttgt    1800
tccagtttcc aacaagagtc cactattaaa gaacgtggac tccaacgtca aagggcgaaa    1860
aagggtctat cagggcgatg gcccactacg tgaaccatca ccctaatcaa gtttttggg     1920
gtcgaggtgc cgtaaagcag taaatcggaa gggtaaacgg atgcccccat ttagagcttg    1980
acggggaaag ccggcgaacg tggcgagaaa ggaagggaag aaagcgaaag gagcgggggc    2040
tagggcggtg ggaagtgtag gggtcacgct gggcgtaacc accacacccg ccgcgcttaa    2100
tggggcgcta cagggcgcgt ggggatgatc cactagtacg gattagaagc cgccgagcgg    2160
gtgacagccc tccgaaggaa gactctcctc cgtgcgtcct cgtcttcacc ggtcgcgttc    2220
ctgaaacgca gatgtgcctc gcgccgcact gctccgaaca ataaagattc tacaatacta    2280
gcttttatgg ttatgaagag gaaaaattgg cagtaacctg gccccacaaa ccttcaaatg    2340
```

-continued

```
aacgaatcaa attaacaacc ataggatgat aatgcgatta gtttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggt taacatcatt cctgctatga   2760
aggacgtcac gtgggggtg gatgtcactc aaaaaaacaa ggaagaaggt tatacccaca   2820
tcgttgaagt caccttcgaa tctgttgaac ggattcaaga ctacatcagg cacccagctc   2880
acgtcggttt cggtgatagg tacagatctt tctgggaaaa attgttgatc ttcgactaca   2940
ccccagagaa gcggtaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaattttct ttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
```

```
tactgtcatg ccatccgtaa gatgcttttc tgtgactggt gagtactcaa ccaagtcatt   4800

ctgagaatag tgtatgcggc gaccgagttg ctcttgcccg gcgtcaatac gggataatag   4860

tgtatcacat agcagaactt taaaagtgct catcattgga aaacgttctt cggggcgaaa   4920

actctcaagg atcttaccgc tgttgagatc cagttcgatg taacccactc gtgcacccaa   4980

ctgatcttca gcatctttta ctttcaccag cgtttctggg tgagcaaaaa caggaaggca   5040

aaatgccgca aaaaagggaa taagggcgac acggaaatgt tgaatactca tactcttcct   5100

ttttcaatgg gtaataactg atataattaa attgaagctc taatttgtga gtttagtata   5160

catgcattta cttataatac agttttttag ttttgctggc cgcatcttct caaatatgct   5220

tcccagcctg cttttctgta acgttcaccc tctaccttag catcccttcc ctttgcaaat   5280

agtcctcttc caacaataat aatgtcagat cctgtagaga ccacatcatc cacggttcta   5340

tactgttgac ccaatgcgtc tcccttgtca tctaaaccca caccgggtgt cataatcaac   5400

caatcgtaac cttcatctct tccacccatg tctctttgag caataaagcc gataacaaaa   5460

tctttgtcgc tcttcgcaat gtcaacagta cccttagtat attctccagt agatagggag   5520

cccttgcatg acaattctgc taacatcaaa aggcctctag gttcctttgt tacttcttct   5580

gccgcctgct tcaaaccgct aacaatacct gggcccacca caccgtgtgc attcgtaatg   5640

tctgcccatt ctgctattct gtatacaccc gcagagtact gcaatttgac tgtattacca   5700

atgtcagcaa atttctgtc ttcg                                          5724
```

<210> SEQ ID NO 18
<211> LENGTH: 5724
<212> TYPE: DNA
<213> ORGANISM: Artificial Sequence
<220> FEATURE:
<223> OTHER INFORMATION: OAC-V28A/V31G/Y41S/G43SILENT(=GGG)/K44V/T68R/
I74R/V84R

<400> SEQUENCE: 18

```
aagagtaaaa aattgtactt ggcggataat gcctttagcg gcttaactgt gccctccatg     60

gaaaaatcag tcaagatatc cacatgtgtt tttagtaaac aaattttggg acctaatgct    120

tcaactaact ccagtaattc cttggtggta cgaacatcca atgaagcaca caagtttgtt    180

tgcttttcgt gcatgatatt aaatagcttg gcagcaacag gactaggatg agtagcagca    240

cgttccttat atgtagcttt cgacatgatt tatcttcgtt tcctgcaggt ttttgttctg    300

tgcagttggg ttaagaatac tgggcaattt catgtttctt caacactaca tatgcgtata    360

tataccaatc taagtctgtg ctccttcctt cgttcttcct tctgttcgga gattaccgaa    420

tcaaaaaaat ttcaaagaaa ccgaaatcaa aaaaaagaat aaaaaaaaaa tgatgaattg    480

aattgaaaag ctagcttatc gatgataagc tgtcaaagat gagaattaat tccacggact    540

atagactata ctagatactc cgtctactgt acgatacact tccgctcagg tccttgtcct    600

ttaacgaggc cttaccactc ttttgttact ctattgatcc agctcagcaa aggcagtgtg    660

atctaagatt ctatcttcgc gatgtagtaa aactagctag accgagaaag agactagaaa    720

tgcaaaaggc acttctacaa tggctgccat cattattatc cgatgtgacg ctgcagcttc    780

tcaatgatat tcgaatacgc tttgaggaga tacagcctaa tatccgacaa actgttttac    840

agatttacga tcgtacttgt tacccatcat tgaattttga acatccgaac ctgggagttt    900

tccctgaaac agatagtata tttgaacctg tataataata tatagtctag cgctttacgg    960

aagacaatgt atgtatttcg gttcctggag aaactattgc atctattgca taggtaatct   1020
```

-continued

```
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc tttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcatttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gtttttggg    1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatataccte tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggg gaacatcatt cctgctatga   2760
aggacgtctc ctgggggtg gatgtcactc aaaaaaacaa ggaagaaggt tatacccaca    2820
tcgttgaagt caccttcgaa tctgttgaac ggattcaaga ctacatcagg cacccagctc   2880
acgtcggttt cggtgatagg tacagatctt tctgggaaaa attgttgatc ttcgactaca   2940
ccccaagaaa gggctaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct ttttttctg tacagacgcg tgtacgcatg taacattata    3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
```

```
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
tactgtcatg ccatccgtaa gatgcttttc tgtgactggt gagtactcaa ccaagtcatt   4800
ctgagaatag tgtatgcggc gaccgagttg ctcttgcccg gcgtcaatac gggataatag   4860
tgtatcacat agcagaactt taaaagtgct catcattgga aaacgttctt cggggcgaaa   4920
actctcaagg atcttaccgc tgttgagatc cagttcgatg taacccactc gtgcacccaa   4980
ctgatcttca gcatctttta ctttcaccag cgtttctggg tgagcaaaaa caggaaggca   5040
aaatgccgca aaaaagggaa taagggcgac acggaaatgt tgaatactca tactcttcct   5100
ttttcaatgg gtaataactg atataattaa attgaagctc taatttgtga gtttagtata   5160
catgcattta cttataatac agtttttag ttttgctggc cgcatcttct caaatatgct   5220
tcccagcctg cttttctgta acgttcaccc tctaccttag catcccttcc ctttgcaaat   5280
agtcctcttc caacaataat aatgtcagat cctgtagaga ccacatcatc cacggttcta   5340
tactgttgac ccaatgcgtc tcccttgtca tctaaaccca caccgggtgt cataatcaac   5400
caatcgtaac cttcatctct tccacccatg tctctttgag caataaagcc gataacaaaa   5460
tctttgtcgc tcttcgcaat gtcaacagta ccccttagtat attctccagt agatagggag   5520
cccttgcatg acaattctgc taacatcaaa aggcctctag gttcctttgt tacttcttct   5580
gccgcctgct tcaaaccgct aacaatacct gggcccacca caccgtgtgc attcgtaatg   5640
tctgcccatt ctgctattct gtatacaccc gcagagtact gcaatttgac tgtattacca   5700
atgtcagcaa atttctgtc ttcg                                           5724
```

<210> SEQ ID NO 19
<211> LENGTH: 5724
<212> TYPE: DNA
<213> ORGANISM: Artificial Sequence
<220> FEATURE:
<223> OTHER INFORMATION: OAC-V28A/G43SILENT(=GGG)/K44V/I74D/V84R/R100E/
G102R(=CGC)

<400> SEQUENCE: 19
aagagtaaaa aattgtactt ggcggataat gcctttagcg gcttaactgt gccctccatg 60
gaaaaatcag tcaagatatc cacatgtgtt tttagtaaac aaattttggg acctaatgct 120
tcaactaact ccagtaattc cttggtggta cgaacatcca atgaagcaca caagtttgtt 180
tgcttttcgt gcatgatatt aaatagcttg gcagcaacag gactaggatg agtagcagca 240
cgttccttat atgtagcttt cgacatgatt tatcttcgtt tcctgcaggt ttttgttctg 300
tgcagttggg ttaagaatac tgggcaattt catgtttctt caacactaca tatgcgtata 360
tataccaatc taagtctgtg ctccttcctt cgttcttcct tctgttcgga gattaccgaa 420
tcaaaaaaat ttcaaagaaa ccgaaatcaa aaaaaagaat aaaaaaaaaa tgatgaattg 480
aattgaaaag ctagcttatc gatgataagc tgtcaaagat gagaattaat tccacggact 540
atagactata ctagatactc cgtctactgt acgatacact tccgctcagg tccttgtcct 600
ttaacgaggc cttaccactc ttttgttact ctattgatcc agctcagcaa aggcagtgtg 660
atctaagatt ctatcttcgc gatgtagtaa aactagctag accgagaaag agactagaaa 720
tgcaaaaggc acttctacaa tggctgccat cattattatc cgatgtgacg ctgcagcttc 780
tcaatgatat tcgaatacgc tttgaggaga tacagcctaa tatccgacaa actgttttac 840
agatttacga tcgtacttgt tacccatcat tgaattttga acatccgaac ctgggagttt 900
tccctgaaac agatagtata tttgaacctg tataataata tatagtctag cgctttacgg 960
aagacaatgt atgtatttcg gttcctggag aaactattgc atctattgca taggtaatct 1020
tgcacgtcgc atccccggtt cattttctgc gtttccatct tgcacttcaa tagcatatct 1080
ttgttcgctt gcctgtaact tacacgcgcc tcgtatcttt taatgatgga ataatttggg 1140
aatttactct gtgtttattt atttttatgt tttgtatttg gattttagaa agtaaataaa 1200
gaaggtagaa gagttacgga atgaagaaaa aaaaataaac aaaggtttaa aaaatttcaa 1260
caaaaagcgt actttacata tatatttatt agacaagaaa agcagattaa atagatatac 1320
attcgattaa cgataagtaa aatgtaaaat cacaggattt tcgtgtgtgg tcttctacac 1380
agacaagatg aaacaattcg gcattaatac ctgagagcag gaagagcaag ataaaaggta 1440
gtatttgttg gcgatccccc tagagtcttt tacatcttcg gaaaacaaaa actatttttt 1500
ctttaatttc ttttttact ttctattttt aatttatata tttatattaa aaaatttaaa 1560
ttataattat ttttatagca cgtgatgaaa aggaccggga agctccaccc cggttgataa 1620
tcagaaaagc cccaaaaaca ggaagattgt ataagcaaat atttaaattg taaacgttaa 1680
tattttgtta aaattcgcgt taaatttttg ttaaatcagc tcattttta acgaatagcc 1740 cgaaatcggc aaaatccctt ataaatcaaa agaatagacc gagatagggt tgagtgttgt 1800
tccagtttcc aacaagagtc cactattaaa gaacgtggac tccaacgtca aagggcgaaa 1860
aagggtctat cagggcgatg gcccactacg tgaaccatca ccctaatcaa gtttttggg 1920 gtcgaggtgc cgtaaagcag taaatcggaa gggtaaacgg atgcccccat ttagagcttg 1980
acggggaaag ccggcgaacg tggcgagaaa ggaagggaag aaagcgaaag gagcgggggc 2040

```
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggt taacatcatt cctgctatga   2760
aggacgtcta ctgggggggtg gatgtcactc aaaaaaacaa ggaagaaggt tatacccaca   2820
tcgttgaagt caccttcgaa tctgttgaaa ctattcaaga ctacatcgac cacccagctc   2880
acgtcggttt cggtgatagg tacagatctt tctgggaaaa attgttgatc ttcgactaca   2940
ccccagagaa gcgctaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaattttttct ttttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaacccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
```

ctcaccggct ccagatttat cagcaataaa ccagccagcc ggaagggccg agcgcagaag 4440
tggtcctgca actttatccg cctccattca gtctattaat tgttgccggg aagctagagt 4500
aagtagttcg ccagttaata gtttgcgcaa cgttgttggc attgctacag gcatcgtggt 4560
gtcactctcg tcgtttggta tggcttcatt cagctccggt tcccaacgat caaggcgagt 4620
tacatgatcc cccatgttgt gcaaaaaagc ggttagctcc ttcggtcctc cgatcgttgt 4680
cagaagtaag ttggccgcag tgttatcact catggttatg gcagcactgc ataattctct 4740
tactgtcatg ccatccgtaa gatgcttttc tgtgactggt gagtactcaa ccaagtcatt 4800
ctgagaatag tgtatgcggc gaccgagttg ctcttgcccg gcgtcaatac gggataatag 4860
tgtatcacat agcagaactt taaaagtgct catcattgga aaacgttctt cggggcgaaa 4920
actctcaagg atcttaccgc tgttgagatc cagttcgatg taacccactc gtgcacccaa 4980
ctgatcttca gcatctttta ctttcaccag cgtttctggg tgagcaaaaa caggaaggca 5040
aaatgccgca aaaaagggaa taagggcgac acggaaatgt tgaatactca tactcttcct 5100
ttttcaatgg gtaataactg atataattaa attgaagctc taatttgtga gtttagtata 5160
catgcattta cttataatac agttttttag ttttgctggc cgcatcttct caaatatgct 5220
tcccagcctg cttttctgta acgttcaccc tctaccttag catcccttcc ctttgcaaat 5280
agtcctcttc caacaataat aatgtcagat cctgtagaga ccacatcatc cacggttcta 5340
tactgttgac ccaatgcgtc tcccttgtca tctaaaccca caccgggtgt cataatcaac 5400
caatcgtaac cttcatctct tccacccatg tctctttgag caataaagcc gataacaaaa 5460
tctttgtcgc tcttcgcaat gtcaacagta cccttagtat attctccagt agatagggag 5520
cccttgcatg acaattctgc taacatcaaa aggcctctag gttcctttgt tacttcttct 5580
gccgcctgct tcaaaccgct aacaatacct gggcccacca caccgtgtgc attcgtaatg 5640
tctgcccatt ctgctattct gtatacaccc gcagagtact gcaatttgac tgtattacca 5700
atgtcagcaa attttctgtc ttcg 5724

<210> SEQ ID NO 20
<211> LENGTH: 5724
<212> TYPE: DNA
<213> ORGANISM: Artificial Sequence
<220> FEATURE:
<223> OTHER INFORMATION: OAC-V28A/Y41V/G43SILENT(=GGG)/K44V/T68L/I74G/
V84R/G102R

<400> SEQUENCE: 20
aagagtaaaa aattgtactt ggcggataat gcctttagcg gcttaactgt gccctccatg 60
gaaaaatcag tcaagatatc cacatgtgtt tttagtaaac aaattttggg acctaatgct 120
tcaactaact ccagtaattc cttggtggta cgaacatcca atgaagcaca caagtttgtt 180
tgcttttcgt gcatgatatt aaatagcttg gcagcaacag gactaggatg agtagcagca 240
cgttccttat atgtagcttt cgacatgatt tatcttcgtt tcctgcaggt ttttgttctg 300
tgcagttggg ttaagaatac tgggcaattt catgtttctt caacactaca tatgcgtata 360
tataccaatc taagtctgtg ctccttcctt cgttcttcct tctgttcgga gattaccgaa 420
tcaaaaaaat ttcaaagaaa ccgaaatcaa aaaaaagaat aaaaaaaaaa tgatgaattg 480
aattgaaaag ctagcttatc gatgataagc tgtcaaagat gagaattaat tccacggact 540
atagactata ctagatactc cgtctactgt acgatacact tccgctcagg tccttgtcct 600
ttaacgaggc cttaccactc ttttgttact ctattgatcc agctcagcaa aggcagtgtg 660

-continued

```
atctaagatt ctatcttcgc gatgtagtaa aactagctag accgagaaag agactagaaa    720
tgcaaaaggc acttctacaa tggctgccat cattattatc cgatgtgacg ctgcagcttc    780
tcaatgatat tcgaatacgc tttgaggaga tacagcctaa tatccgacaa actgttttac    840
agatttacga tcgtacttgt tacccatcat tgaattttga acatccgaac ctgggagttt    900
tccctgaaac agatagtata tttgaacctg tataataata tatagtctag cgctttacgg    960
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc tttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcatttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gtttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggt taacatcatt cctgctatga   2760
aggacgtcgt gtggggggtg gatgtcactc aaaaaaacaa ggaagaaggt tatacccaca   2820
tcgttgaagt caccttcgaa tctgttgaac tgattcaaga ctacatcggg cacccagctc   2880
acgtcggttt cggtgatagg tacagatctt tctgggaaaa attgttgatc ttcgactaca   2940
ccccaagaaa gcggtaactc gagcatgcat ctagagggcc gcatcatgta attagttatg   3000
tcacgcttac attcacgccc tccccccaca tccgctctaa ccgaaaagga aggagttaga   3060
```

caacctgaag tctaggtccc tatttatttt tttatagtta tgttagtatt aagaacgtta 3120
tttatatttc aaatttttct tttttttctg tacagacgcg tgtacgcatg taacattata 3180
ctgaaaacct tgcttgagaa ggttttggga cgctcgaagg ctttaatttg cggccctgca 3240
ttaatgaatc ggccaacgcg cggggagagg cggtttgcgt attgggcgct cttccgcttc 3300
ctcgctcact gactcgctgc gctcggtcgt tcggctgcgg cgagcggtat cagctcactc 3360
aaaggcggta atacggttat ccacagaatc aggggataac gcaggaaaga acatgtgagc 3420
aaaaggccag caaaagccca ggaaccgtaa aaaggccgcg ttgctggcgt ttttccatag 3480
gctccgcccc cctgacgagc atcacaaaaa tcgacgctca agtcagaggt ggcgaaaccc 3540
gacaggacta taaagatacc aggcgtttcc ccctggaagc tccctcgtgc gctctcctgt 3600
tccgaccctg ccgcttaccg gatacctgtc cgcctttctc ccttcgggaa gcgtggcgct 3660
ttctcatagc tcacgctgta ggtatctcag ttcggtgtag gtcgttcgct ccaagctggg 3720
ctgtgtgcac gaaccccccg ttcagcccga ccgctgcgcc ttatccggta actatcgtct 3780
tgagtccaac ccggtaagac acgacttatc gccactggca gcagccactg gtaacaggat 3840
tagcagagcg aggtatgtag gcggtgctac agagttcttg aagtggtggc ctaactacgg 3900
ctacactaga agaacagtat ttggtatctg cgctctgctg aagccagtta ccttcggaaa 3960
aagagttggt agctcttgat ccggcaaaca aaccaccgct ggtagcggtg gtttttttgt 4020
ttgcaagcag cagattacgc gcagaaaaaa aggatctcaa gaagatcctt tgatcttttc 4080
tacggggtct gacgctcagt ggaacgaaaa ctcacgttaa gggattttgg tcatgagatt 4140
atcaaaaagg atcttcacct agatcctttt aaattaaaaa tgaagtttta aatcaatcta 4200
aagtatatat gagtaaactt ggtctgacag ttaccaatgc ttaatcagtg aggcacctat 4260
ctcagcgatc tgtctatttc gttcatccat agttgcctga ctccccgtcg tgtagataac 4320
tacgatacgg gagcgcttac catctggccc cagtgctgca atgataccgc gagacccacg 4380
ctcaccggct ccagatttat cagcaataaa ccagccagcc ggaagggccg agcgcagaag 4440
tggtcctgca actttatccg cctccattca gtctattaat tgttgccggg aagctagagt 4500
aagtagttcg ccagttaata gtttgcgcaa cgttgttggc attgctacag gcatcgtggt 4560
gtcactctcg tcgtttggta tggcttcatt cagctccggt tcccaacgat caaggcgagt 4620
tacatgatcc cccatgttgt gcaaaaaagc ggttagctcc ttcggtcctc cgatcgttgt 4680
cagaagtaag ttggccgcag tgttatcact catggttatg gcagcactgc ataattctct 4740
tactgtcatg ccatccgtaa gatgcttttc tgtgactggt gagtactcaa ccaagtcatt 4800
ctgagaatag tgtatgcggc gaccgagttg ctcttgcccg gcgtcaatac gggataatag 4860
tgtatcacat agcagaactt taaaagtgct catcattgga aaacgttctt cggggcgaaa 4920
actctcaagg atcttaccgc tgttgagatc cagttcgatg taacccactc gtgcacccaa 4980
ctgatcttca gcatctttta ctttcaccag cgtttctggg tgagcaaaaa caggaaggca 5040
aaatgccgca aaaaagggaa taagggcgac acggaaatgt tgaatactca tactcttcct 5100
ttttcaatgg gtaataactg atataattaa attgaagctc taatttgtga gtttagtata 5160
catgcattta cttataatac agtttttag ttttgctggc cgcatcttct caaatatgct 5220
tcccagcctg cttttctgta acgttcaccc tctaccttag catcccttcc ctttgcaaat 5280
agtcctcttc caacaataat aatgtcagat cctgtagaga ccacatcatc cacggttcta 5340
tactgttgac ccaatgcgtc tcccttgtca tctaaaccca caccgggtgt cataatcaac 5400
caatcgtaac cttcatctct tccacccatg tctctttgag caataaagcc gataacaaaa 5460
tctttgtcgc tcttcgcaat gtcaacagta cccttagtat attctccagt agatagggag 5520
cccttgcatg acaattctgc taacatcaaa aggcctctag gttcctttgt tacttcttct 5580
gccgcctgct tcaaaccgct aacaatacct gggcccacca caccgtgtgc attcgtaatg 5640
tctgcccatt ctgctattct gtatacaccc gcagagtact gcaatttgac tgtattacca 5700
atgtcagcaa attttctgtc ttcg 5724

<210> SEQ ID NO 21
<211> LENGTH: 5724
<212> TYPE: DNA
<213> ORGANISM: Artificial Sequence
<220> FEATURE:
<223> OTHER INFORMATION: OAC-Y41T/G43SILENT(=GGG)/T68L/I74G/V84R/R100M/ G102R

<400> SEQUENCE: 21
aagagtaaaa aattgtactt ggcggataat gcctttagcg gcttaactgt gccctccatg 60
gaaaaatcag tcaagatatc cacatgtgtt tttagtaaac aaattttggg acctaatgct 120
tcaactaact ccagtaattc cttggtggta cgaacatcca atgaagcaca caagtttgtt 180
tgcttttcgt gcatgatatt aaatagcttg gcagcaacag gactaggatg agtagcagca 240
cgttccttat atgtagcttt cgacatgatt tatcttcgtt tcctgcaggt ttttgttctg 300
tgcagttggg ttaagaatac tgggcaattt catgtttctt caacactaca tatgcgtata 360
tataccaatc taagtctgtg ctccttcctt cgttcttcct tctgttcgga gattaccgaa 420
tcaaaaaaat ttcaaagaaa ccgaaatcaa aaaaaagaat aaaaaaaaaa tgatgaattg 480
aattgaaaag ctagcttatc gatgataagc tgtcaaagat gagaattaat tccacggact 540
atagactata ctagatactc cgtctactgt acgatacact tccgctcagg tccttgtcct 600
ttaacgaggc cttaccactc ttttgttact ctattgatcc agctcagcaa aggcagtgtg 660
atctaagatt ctatcttcgc gatgtagtaa aactagctag accgagaaag agactagaaa 720
tgcaaaaggc acttctacaa tggctgccat cattattatc cgatgtgacg ctgcagcttc 780
tcaatgatat tcgaatacgc tttgaggaga tacagcctaa tatccgacaa actgttttac 840
agatttacga tcgtacttgt tacccatcat tgaattttga acatccgaac ctgggagttt 900
tccctgaaac agatagtata tttgaacctg tataataata tatagtctag cgctttacgg 960
aagacaatgt atgtatttcg gttcctggag aaactattgc atctattgca taggtaatct 1020
tgcacgtcgc atccccggtt cattttctgc gtttccatct tgcacttcaa tagcatatct 1080
ttgttcgctt gcctgtaact tacacgcgcc tcgtatcttt taatgatgga ataatttggg 1140
aatttactct gtgtttattt atttttatgt tttgtatttg gattttagaa agtaaataaa 1200
gaaggtagaa gagttacgga atgaagaaaa aaaaataaac aaaggtttaa aaaatttcaa 1260
caaaaagcgt actttacata tatatttatt agacaagaaa agcagattaa atagatatac 1320
attcgattaa cgataagtaa aatgtaaaat cacaggattt tcgtgtgtgg tcttctacac 1380
agacaagatg aaacaattcg gcattaatac ctgagagcag gaagagcaag ataaaaggta 1440
gtatttgttg gcgatccccc tagagtcttt tacatcttcg gaaaacaaaa actatttttt 1500
ctttaatttc tttttttact ttctattttt aatttatata tttatattaa aaaatttaaa 1560
ttataattat ttttatagca cgtgatgaaa aggaccggga agctccaccc cggttgataa 1620
tcagaaaagc cccaaaaaca ggaagattgt ataagcaaat atttaaattg taaacgttaa 1680

-continued tattttgtta aaattcgcgt taaatttttg ttaaatcagc tcatttttta acgaatagcc 1740
cgaaatcggc aaaatccctt ataaatcaaa agaatagacc gagatagggt tgagtgttgt 1800
tccagtttcc aacaagagtc cactattaaa gaacgtggac tccaacgtca aagggcgaaa 1860
aagggtctat cagggcgatg gcccactacg tgaaccatca ccctaatcaa gttttttggg 1920
gtcgaggtgc cgtaaagcag taaatcggaa gggtaaacgg atgcccccat ttagagcttg 1980
acggggaaag ccggcgaacg tggcgagaaa ggaagggaag aaagcgaaag gagcgggggc 2040
tagggcggtg ggaagtgtag gggtcacgct gggcgtaacc accacacccg ccgcgcttaa 2100
tggggcgcta cagggcgcgt ggggatgatc cactagtacg gattagaagc cgccgagcgg 2160
gtgacagccc tccgaaggaa gactctcctc cgtgcgtcct cgtcttcacc ggtcgcgttc 2220
ctgaaacgca gatgtgcctc gcgccgcact gctccgaaca ataaagattc tacaatacta 2280
gcttttatgg ttatgaagag gaaaaattgg cagtaacctg gccccacaaa ccttcaaatg 2340
aacgaatcaa attaacaacc ataggatgat aatgcgatta gtttttttagc cttatttctg 2400 gggtaattaa tcagcgaagc gatgattttt gatctattaa cagatatata aatgcaaaaa 2460
ctgcataacc actttaacta atactttcaa cattttcggt ttgtattact tcttattcaa 2520
atgtaataaa agtatcaaca aaaaattgtt aatatacctc tatactttaa cgtcaaggag 2580
aaaaaacccc ggatcggact actagcagct gtaatacgac tcactatagg gaatattaag 2640
cttaaacaat ggccgtcaag cacttgatcg tcttaaagtt taaggacgag atcactgaag 2700
cccaaaagga agaattcttc aaaacttacg ttaacttggt taacatcatt cctgctatga 2760
aggacgtcac gtgggggaag gatgtcactc aaaaaaacaa ggaagaaggt tatacccaca 2820
tcgttgaagt caccttcgaa tctgttgaac tgattcaaga ctacatcggg cacccagctc 2880
acgtcggttt cggtgatagg tacagatctt tctgggaaaa attgttgatc ttcgactaca 2940
ccccaatgaa gcggtaactc gagcatgcat ctagagggcc gcatcatgta attagttatg 3000
tcacgcttac attcacgccc tccccccaca tccgctctaa ccgaaaagga aggagttaga 3060
caacctgaag tctaggtccc tatttatttt tttatagtta tgttagtatt aagaacgtta 3120
tttatatttc aaatttttct tttttttctg tacagacgcg tgtacgcatg taacattata 3180
ctgaaaacct tgcttgagaa ggttttggga cgctcgaagg ctttaatttg cggccctgca 3240
ttaatgaatc ggccaacgcg cggggagagg cggtttgcgt attgggcgct cttccgcttc 3300
ctcgctcact gactcgctgc gctcggtcgt tcggctgcgg cgagcggtat cagctcactc 3360
aaaggcggta atacggttat ccacagaatc aggggataac gcaggaaaga acatgtgagc 3420
aaaaggccag caaaagccca ggaaccgtaa aaaggccgcg ttgctggcgt ttttccatag 3480
gctccgcccc cctgacgagc atcacaaaaa tcgacgctca agtcagaggt ggcgaaaccc 3540
gacaggacta taaagatacc aggcgtttcc ccctggaagc tccctcgtgc gctctcctgt 3600
tccgaccctg ccgcttaccg gatacctgtc cgcctttctc ccttcgggaa gcgtggcgct 3660
ttctcatagc tcacgctgta ggtatctcag ttcggtgtag gtcgttcgct ccaagctggg 3720
ctgtgtgcac gaaccccccg ttcagcccga ccgctgcgcc ttatccggta actatcgtct 3780
tgagtccaac ccggtaagac acgacttatc gccactggca gcagccactg gtaacaggat 3840
tagcagagcg aggtatgtag gcggtgctac agagttcttg aagtggtggc ctaactacgg 3900
ctacactaga agaacagtat ttggtatctg cgctctgctg aagccagtta ccttcggaaa 3960
aagagttggt agctcttgat ccggcaaaca aaccaccgct ggtagcggtg gtttttttgt 4020
ttgcaagcag cagattacgc gcagaaaaaa aggatctcaa gaagatcctt tgatcttttc 4080
tacggggtct gacgctcagt ggaacgaaaa ctcacgttaa gggattttgg tcatgagatt 4140
atcaaaaagg atcttcacct agatcctttt aaattaaaaa tgaagtttta aatcaatcta 4200
aagtatatat gagtaaactt ggtctgacag ttaccaatgc ttaatcagtg aggcacctat 4260
ctcagcgatc tgtctatttc gttcatccat agttgcctga ctccccgtcg tgtagataac 4320
tacgatacgg gagcgcttac catctggccc cagtgctgca atgataccgc gagacccacg 4380
ctcaccggct ccagatttat cagcaataaa ccagccagcc ggaagggccg agcgcagaag 4440
tggtcctgca actttatccg cctccattca gtctattaat tgttgccggg aagctagagt 4500
aagtagttcg ccagttaata gtttgcgcaa cgttgttggc attgctacag gcatcgtggt 4560
gtcactctcg tcgtttggta tggcttcatt cagctccggt tcccaacgat caaggcgagt 4620
tacatgatcc cccatgttgt gcaaaaaagc ggttagctcc ttcggtcctc cgatcgttgt 4680
cagaagtaag ttggccgcag tgttatcact catggttatg gcagcactgc ataattctct 4740
tactgtcatg ccatccgtaa gatgcttttc tgtgactggt gagtactcaa ccaagtcatt 4800
ctgagaatag tgtatgcggc gaccgagttg ctcttgcccg gcgtcaatac gggataatag 4860
tgtatcacat agcagaactt taaaagtgct catcattgga aaacgttctt cggggcgaaa 4920
actctcaagg atcttaccgc tgttgagatc cagttcgatg taacccactc gtgcacccaa 4980
ctgatcttca gcatctttta ctttcaccag cgtttctggg tgagcaaaaa caggaaggca 5040
aaatgccgca aaaaagggaa taagggcgac acggaaatgt tgaatactca tactcttcct 5100
ttttcaatgg gtaataactg atataattaa attgaagctc taatttgtga gtttagtata 5160
catgcattta cttataatac agttttttag ttttgctggc cgcatcttct caaatatgct 5220
tcccagcctg cttttctgta acgttcaccc tctaccttag catcccttcc ctttgcaaat 5280
agtcctcttc caacaataat aatgtcagat cctgtagaga ccacatcatc cacggttcta 5340
tactgttgac ccaatgcgtc tcccttgtca tctaaaccca caccgggtgt cataatcaac 5400
caatcgtaac cttcatctct tccacccatg tctctttgag caataaagcc gataacaaaa 5460
tctttgtcgc tcttcgcaat gtcaacagta cccttagtat attctccagt agatagggag 5520
cccttgcatg acaattctgc taacatcaaa aggcctctag gttcctttgt tacttcttct 5580
gccgcctgct tcaaaccgct aacaatacct gggcccacca caccgtgtgc attcgtaatg 5640
tctgcccatt ctgctattct gtatacaccc gcagagtact gcaatttgac tgtattacca 5700
atgtcagcaa attttctgtc ttcg 5724

<210> SEQ ID NO 22
<211> LENGTH: 5724
<212> TYPE: DNA
<213> ORGANISM: Artificial Sequence
<220> FEATURE:
<223> OTHER INFORMATION: OAC-V28A/V31G/Y41T/G43SILENT(=GGG)/K44V/T68R/
I74R/V84R/R100E/G102R

<400> SEQUENCE: 22
aagagtaaaa aattgtactt ggcggataat gcctttagcg gcttaactgt gccctccatg 60
gaaaaatcag tcaagatatc cacatgtgtt tttagtaaac aaattttggg acctaatgct 120
tcaactaact ccagtaattc cttggtggta cgaacatcca atgaagcaca caagtttgtt 180
tgcttttcgt gcatgatatt aaatagcttg gcagcaacag gactaggatg agtagcagca 240
cgttccttat atgtagcttt cgacatgatt tatcttcgtt tcctgcaggt tttgttctg 300 tgcagttggg ttaagaatac tgggcaattt catgtttctt caacactaca tatgcgtata 360

-continued

```
tataccaatc taagtctgtg ctccttcctt cgttcttcct tctgttcgga gattaccgaa    420
tcaaaaaaat ttcaaagaaa ccgaaatcaa aaaaaagaat aaaaaaaaaa tgatgaattg    480
aattgaaaag ctagcttatc gatgataagc tgtcaaagat gagaattaat tccacggact    540
atagactata ctagatactc cgtctactgt acgatacact tccgctcagg tccttgtcct    600
ttaacgaggc cttaccactc ttttgttact ctattgatcc agctcagcaa aggcagtgtg    660
atctaagatt ctatcttcgc gatgtagtaa aactagctag accgagaaag agactagaaa    720
tgcaaaaggc acttctacaa tggctgccat cattattatc cgatgtgacg ctgcagcttc    780
tcaatgatat tcgaatacgc tttgaggaga tacagcctaa tatccgacaa actgttttac    840
agatttacga tcgtacttgt tacccatcat tgaattttga acatccgaac ctgggagttt    900
tccctgaaac agatagtata tttgaacctg tataataata tatagtctag cgctttacgg    960
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc ttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcatttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gtttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
```

-continued

```
cccaaaagga agaattcttc aaaacttacg cgaacttggg gaacatcatt cctgctatga   2760
aggacgtcac gtggggggtg gatgtcactc aaaaaaacaa ggaagaaggt tatacccaca   2820
tcgttgaagt caccttcgaa tctgttgaac ggattcaaga ctacatcagg cacccagctc   2880
acgtcggttt cggtgatagg tacagatctt tctgggaaaa attgttgatc ttcgactaca   2940
ccccagagaa gcggtaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct ttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
tactgtcatg ccatccgtaa gatgcttttc tgtgactggt gagtactcaa ccaagtcatt   4800
ctgagaatag tgtatgcggc gaccgagttg ctcttgcccg gcgtcaatac gggataatag   4860
tgtatcacat agcagaactt taaaagtgct catcattgga aaacgttctt cggggcgaaa   4920
actctcaagg atcttaccgc tgttgagatc cagttcgatg taacccactc gtgcacccaa   4980
ctgatcttca gcatctttta ctttcaccag cgtttctggg tgagcaaaaa caggaaggca   5040
aaatgccgca aaaaagggaa taagggcgac acggaaatgt tgaatactca tactcttcct   5100
```

```
ttttcaatgg gtaataactg atataattaa attgaagctc taatttgtga gtttagtata   5160

catgcattta cttataatac agttttttag ttttgctggc cgcatcttct caaatatgct   5220

tcccagcctg cttttctgta acgttcaccc tctaccttag catcccttcc ctttgcaaat   5280

agtcctcttc caacaataat aatgtcagat cctgtagaga ccacatcatc cacggttcta   5340

tactgttgac ccaatgcgtc tcccttgtca tctaaaccca caccgggtgt cataatcaac   5400

caatcgtaac cttcatctct tccacccatg tctctttgag caataaagcc gataacaaaa   5460

tctttgtcgc tcttcgcaat gtcaacagta cccttagtat attctccagt agatagggag   5520

cccttgcatg acaattctgc taacatcaaa aggcctctag gttcctttgt tacttcttct   5580

gccgcctgct tcaaaccgct aacaatacct gggcccacca caccgtgtgc attcgtaatg   5640

tctgcccatt ctgctattct gtatacaccc gcagagtact gcaatttgac tgtattacca   5700

atgtcagcaa attttctgtc ttcg                                          5724
```

<210> SEQ ID NO 23
<211> LENGTH: 5724
<212> TYPE: DNA
<213> ORGANISM: Artificial Sequence
<220> FEATURE:
<223> OTHER INFORMATION: OAC-V31G/Y41S/G43SILENT(=GGG)/K44V/T68R/V84R/R100E

<400> SEQUENCE: 23

```
aagagtaaaa aattgtactt ggcggataat gcctttagcg gcttaactgt gccctccatg     60

gaaaaatcag tcaagatatc cacatgtgtt tttagtaaac aaattttggg acctaatgct    120

tcaactaact ccagtaattc cttggtggta cgaacatcca atgaagcaca caagtttgtt    180

tgcttttcgt gcatgatatt aaatagcttg gcagcaacag gactaggatg agtagcagca    240

cgttccttat atgtagcttt cgacatgatt tatcttcgtt tcctgcaggt ttttgttctg    300

tgcagttggg ttaagaatac tgggcaattt catgtttctt caacactaca tatgcgtata    360

tataccaatc taagtctgtg ctccttcctt cgttcttcct tctgttcgga gattaccgaa    420

tcaaaaaaat ttcaaagaaa ccgaaatcaa aaaaaagaat aaaaaaaaaa tgatgaattg    480

aattgaaaag ctagcttatc gatgataagc tgtcaaagat gagaattaat tccacggact    540

atagactata ctagatactc cgtctactgt acgatacact tccgctcagg tccttgtcct    600

ttaacgaggc cttaccactc ttttgttact ctattgatcc agctcagcaa aggcagtgtg    660

atctaagatt ctatcttcgc gatgtagtaa aactagctag accgagaaag agactagaaa    720

tgcaaaaggc acttctacaa tggctgccat cattattatc cgatgtgacg ctgcagcttc    780

tcaatgatat tcgaatacgc tttgaggaga tacagcctaa tatccgacaa actgttttac    840

agatttacga tcgtacttgt tacccatcat tgaattttga acatccgaac ctgggagttt    900

tccctgaaac agatagtata tttgaacctg tataataata tatagtctag cgctttacgg    960

aagacaatgt atgtatttcg gttcctggag aaactattgc atctattgca taggtaatct   1020

tgcacgtcgc atccccggtt cattttctgc gtttccatct tgcacttcaa tagcatatct   1080

ttgttcgctt gcctgtaact tacacgcgcc tcgtatcttt taatgatgga ataatttggg   1140

aatttactct gtgtttattt atttttatgt tttgtatttg gattttagaa agtaaataaa   1200

gaaggtagaa gagttacgga atgaagaaaa aaaaataaac aaaggtttaa aaaatttcaa   1260

caaaaagcgt actttacata tatatttatt agacaagaaa agcagattaa atagatatac   1320

attcgattaa cgataagtaa aatgtaaaat cacaggattt tcgtgtgtgg tcttctacac   1380
```

agacaagatg aaacaattcg gcattaatac ctgagagcag gaagagcaag ataaaaggta 1440
gtatttgttg gcgatccccc tagagtcttt tacatcttcg gaaaacaaaa actatttttt 1500
ctttaatttc ttttttttact ttctattttt aatttatata tttatattaa aaaatttaaa 1560
ttataattat ttttatagca cgtgatgaaa aggaccggga agctccaccc cggttgataa 1620
tcagaaaagc cccaaaaaca ggaagattgt ataagcaaat atttaaattg taaacgttaa 1680
tattttgtta aaattcgcgt taaatttttg ttaaatcagc tcatttttta acgaatagcc 1740
cgaaatcggc aaaatccctt ataaatcaaa agaatagacc gagatagggt tgagtgttgt 1800
tccagtttcc aacaagagtc cactattaaa gaacgtggac tccaacgtca aagggcgaaa 1860
aagggtctat cagggcgatg gcccactacg tgaaccatca ccctaatcaa gttttttggg 1920
gtcgaggtgc cgtaaagcag taaatcggaa gggtaaacgg atgcccccat ttagagcttg 1980
acggggaaag ccggcgaacg tggcgagaaa ggaagggaag aaagcgaaag gagcgggggc 2040
tagggcggtg ggaagtgtag gggtcacgct gggcgtaacc accacacccg ccgcgcttaa 2100
tggggcgcta cagggcgcgt ggggatgatc cactagtacg gattagaagc cgccgagcgg 2160
gtgacagccc tccgaaggaa gactctcctc cgtgcgtcct cgtcttcacc ggtcgcgttc 2220
ctgaaacgca gatgtgcctc gcgccgcact gctccgaaca ataaagattc tacaatacta 2280
gcttttatgg ttatgaagag gaaaaattgg cagtaacctg gccccacaaa ccttcaaatg 2340
aacgaatcaa attaacaacc ataggatgat aatgcgatta gttttttagc cttatttctg 2400
gggtaattaa tcagcgaagc gatgattttt gatctattaa cagatatata aatgcaaaaa 2460
ctgcataacc actttaacta atactttcaa cattttcggt ttgtattact tcttattcaa 2520
atgtaataaa agtatcaaca aaaaattgtt aatatacctc tatactttaa cgtcaaggag 2580
aaaaaacccc ggatcggact actagcagct gtaatacgac tcactatagg gaatattaag 2640
cttaaacaat ggccgtcaag cacttgatcg tcttaaagtt taaggacgag atcactgaag 2700
cccaaaagga agaattcttc aaaacttacg ttaacttggg gaacatcatt cctgctatga 2760
aggacgtctc ctggggggtg gatgtcactc aaaaaaaacaa ggaagaaggt tatacccaca 2820
tcgttgaagt caccttcgaa tctgttgaac ggattcaaga ctacatcatt cacccagctc 2880
acgtcggttt cggtgatagg tacagatctt tctgggaaaa attgttgatc ttcgactaca 2940
ccccagagaa gggctaactc gagcatgcat ctagagggcc gcatcatgta attagttatg 3000
tcacgcttac attcacgccc tccccccaca tccgctctaa ccgaaaagga aggagttaga 3060
caacctgaag tctaggtccc tatttatttt tttatagtta tgttagtatt aagaacgtta 3120
tttatatttc aaatttttct tttttttctg tacagacgcg tgtacgcatg taacattata 3180
ctgaaaacct tgcttgagaa ggttttggga cgctcgaagg ctttaatttg cggccctgca 3240
ttaatgaatc ggccaacgcg cggggagagg cggtttgcgt attgggcgct cttccgcttc 3300
ctcgctcact gactcgctgc gctcggtcgt tcggctgcgg cgagcggtat cagctcactc 3360
aaaggcggta atacggttat ccacagaatc aggggataac gcaggaaaga acatgtgagc 3420
aaaaggccag caaaagccca ggaaccgtaa aaaggccgcg ttgctggcgt ttttccatag 3480
gctccgcccc cctgacgagc atcacaaaaa tcgacgctca agtcagaggt ggcgaaaccc 3540
gacaggacta taaagatacc aggcgtttcc ccctggaagc tccctcgtgc gctctcctgt 3600
tccgaccctg ccgcttaccg gatacctgtc cgcctttctc ccttcgggaa gcgtggcgct 3660
ttctcatagc tcacgctgta ggtatctcag ttcggtgtag gtcgttcgct ccaagctggg 3720

-continued

```
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
tactgtcatg ccatccgtaa gatgcttttc tgtgactggt gagtactcaa ccaagtcatt   4800
ctgagaatag tgtatgcggc gaccgagttg ctcttgcccg gcgtcaatac gggataatag   4860
tgtatcacat agcagaactt taaaagtgct catcattgga aaacgttctt cggggcgaaa   4920
actctcaagg atcttaccgc tgttgagatc cagttcgatg taacccactc gtgcacccaa   4980
ctgatcttca gcatctttta ctttcaccag cgtttctggg tgagcaaaaa caggaaggca   5040
aaatgccgca aaaaagggaa taagggcgac acggaaatgt tgaatactca tactcttcct   5100
ttttcaatgg gtaataactg atataattaa attgaagctc taatttgtga gtttagtata   5160
catgcattta cttataatac agttttttag ttttgctggc cgcatcttct caaatatgct   5220
tcccagcctg cttttctgta acgttcaccc tctaccttag catcccttcc ctttgcaaat   5280
agtcctcttc caacaataat aatgtcagat cctgtagaga ccacatcatc cacggttcta   5340
tactgttgac ccaatgcgtc tcccttgtca tctaaaccca caccgggtgt cataatcaac   5400
caatcgtaac cttcatctct tccacccatg tctctttgag caataaagcc gataacaaaa   5460
tctttgtcgc tcttcgcaat gtcaacagta cccttagtat attctccagt agatagggag   5520
cccttgcatg acaattctgc taacatcaaa aggcctctag gttcctttgt tacttcttct   5580
gccgcctgct tcaaaccgct aacaatacct gggcccacca caccgtgtgc attcgtaatg   5640
tctgcccatt ctgctattct gtatacaccc gcagagtact gcaatttgac tgtattacca   5700
atgtcagcaa attttctgtc ttcg                                          5724
```

<210> SEQ ID NO 24
<211> LENGTH: 5724
<212> TYPE: DNA
<213> ORGANISM: Artificial Sequence
<220> FEATURE:
<223> OTHER INFORMATION: OAC-V28A/Y41V/G43SILENT(=GGG)/T68L/I74D/R100E/
G102STOP

<400> SEQUENCE: 24

-continued

```
aagagtaaaa aattgtactt ggcggataat gcctttagcg gcttaactgt gccctccatg     60
gaaaaatcag tcaagatatc cacatgtgtt tttagtaaac aaattttggg acctaatgct    120
tcaactaact ccagtaattc cttggtggta cgaacatcca atgaagcaca caagtttgtt    180
tgcttttcgt gcatgatatt aaatagcttg gcagcaacag gactaggatg agtagcagca    240
cgttccttat atgtagcttt cgacatgatt tatcttcgtt tcctgcaggt tttgttctg     300
tgcagttggg ttaagaatac tgggcaattt catgtttctt caacactaca tatgcgtata    360
tataccaatc taagtctgtg ctccttcctt cgttcttcct tctgttcgga gattaccgaa    420
tcaaaaaaat ttcaaagaaa ccgaaatcaa aaaaaagaat aaaaaaaaaa tgatgaattg    480
aattgaaaag ctagcttatc gatgataagc tgtcaaagat gagaattaat tccacggact    540
atagactata ctagatactc cgtctactgt acgatacact tccgctcagg tccttgtcct    600
ttaacgaggc cttaccactc ttttgttact ctattgatcc agctcagcaa aggcagtgtg    660
atctaagatt ctatcttcgc gatgtagtaa aactagctag accgagaaag agactagaaa    720
tgcaaaaggc acttctacaa tggctgccat cattattatc cgatgtgacg ctgcagcttc    780
tcaatgatat tcgaatacgc tttgaggaga tacagcctaa tatccgacaa actgttttac    840
agatttacga tcgtacttgt tacccatcat tgaattttga acatccgaac ctgggagttt    900
tccctgaaac agatagtata tttgaacctg tataataata tatagtctag cgctttacgg    960
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc tttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcatttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gtttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttttagc cttatttctg   2400
```

```
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggt taacatcatt cctgctatga   2760
aggacgtcgt gtgggggaag gatgtcactc aaaaaaacaa ggaagaaggt tatacccaca   2820
tcgttgaagt caccttcgaa tctgttgaac tgattcaaga ctacatcgac cacccagctc   2880
acgtcggttt cggtgatgtt tacagatctt tctgggaaaa attgttgatc ttcgactaca   2940
ccccagagaa gtaataactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct ttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
```

```
tactgtcatg ccatccgtaa gatgcttttc tgtgactggt gagtactcaa ccaagtcatt   4800

ctgagaatag tgtatgcggc gaccgagttg ctcttgcccg gcgtcaatac gggataatag   4860

tgtatcacat agcagaactt taaaagtgct catcattgga aaacgttctt cggggcgaaa   4920

actctcaagg atcttaccgc tgttgagatc cagttcgatg taacccactc gtgcacccaa   4980

ctgatcttca gcatctttta ctttcaccag cgtttctggg tgagcaaaaa caggaaggca   5040

aaatgccgca aaaaagggaa taagggcgac acggaaatgt tgaatactca tactcttcct   5100

ttttcaatgg gtaataactg atataattaa attgaagctc taatttgtga gtttagtata   5160

catgcattta cttataatac agttttttag ttttgctggc cgcatcttct caaatatgct   5220

tcccagcctg cttttctgta acgttcaccc tctaccttag catcccttcc ctttgcaaat   5280

agtcctcttc caacaataat aatgtcagat cctgtagaga ccacatcatc cacggttcta   5340

tactgttgac ccaatgcgtc tcccttgtca tctaaaccca caccgggtgt cataatcaac   5400

caatcgtaac cttcatctct tccacccatg tctctttgag caataaagcc gataacaaaa   5460

tctttgtcgc tcttcgcaat gtcaacagta cccttagtat attctccagt agatagggag   5520

cccttgcatg acaattctgc taacatcaaa aggcctctag gttcctttgt tacttcttct   5580

gccgcctgct tcaaaccgct aacaatacct gggcccacca caccgtgtgc attcgtaatg   5640

tctgcccatt ctgctattct gtatacaccc gcagagtact gcaatttgac tgtattacca   5700

atgtcagcaa attttctgtc ttcg                                          5724
```

<210> SEQ ID NO 25
<211> LENGTH: 5724
<212> TYPE: DNA
<213> ORGANISM: Artificial Sequence
<220> FEATURE:
<223> OTHER INFORMATION: OAC-V28A/Y41V/G43SILENT(=GGG)/T68R/I74G/V84R/
      R100M/G102R

<400> SEQUENCE: 25

```
aagagtaaaa aattgtactt ggcggataat gcctttagcg gcttaactgt gccctccatg     60

gaaaaatcag tcaagatatc cacatgtgtt tttagtaaac aaattttggg acctaatgct    120

tcaactaact ccagtaattc cttggtggta cgaacatcca atgaagcaca caagtttgtt    180

tgcttttcgt gcatgatatt aaatagcttg gcagcaacag gactaggatg agtagcagca    240

cgttccttat atgtagcttt cgacatgatt tatcttcgtt tcctgcaggt ttttgttctg    300

tgcagttggg ttaagaatac tggcaattt catgtttctt caacactaca tatgcgtata    360

tataccaatc taagtctgtg ctccttcctt cgttcttcct tctgttcgga gattaccgaa    420

tcaaaaaaat ttcaaagaaa ccgaaatcaa aaaaaagaat aaaaaaaaaa tgatgaattg    480

aattgaaaag ctagcttatc gatgataagc tgtcaaagat gagaattaat tccacggact    540

atagactata ctagatactc cgtctactgt acgatacact tccgctcagg tccttgtcct    600

ttaacgaggc cttaccactc ttttgttact ctattgatcc agctcagcaa aggcagtgtg    660

atctaagatt ctatcttcgc gatgtagtaa aactagctag accgagaaag agactagaaa    720

tgcaaaaggc acttctacaa tggctgccat cattattatc cgatgtgacg ctgcagcttc    780

tcaatgatat tcgaatacgc tttgaggaga tacagcctaa tatccgacaa actgttttac    840

agatttacga tcgtacttgt tacccatcat tgaattttga acatccgaac ctgggagttt    900

tccctgaaac agatagtata tttgaacctg tataataata tatagtctag cgctttacgg    960

aagacaatgt atgtatttcg gttcctggag aaactattgc atctattgca taggtaatct   1020
```

```
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc tttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcatttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggt taacatcatt cctgctatga   2760
aggacgtcgt gtgggggaag gatgtcactc aaaaaaacaa ggaagaaggt tatacccaca   2820
tcgttgaagt caccttcgaa tctgttgaac ggattcaaga ctacatcggg cacccagctc   2880
acgtcggttt cggtgatagg tacagatctt tctgggaaaa attgttgatc ttcgactaca   2940
ccccaatgaa gcggtaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct ttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
```

```
aaaaggccag caaaagccca ggaaccgtaa aaaggccgcg ttgctggcgt ttttccatag    3480

gctccgcccc cctgacgagc atcacaaaaa tcgacgctca agtcagaggt ggcgaaaccc    3540

gacaggacta taaagatacc aggcgtttcc ccctggaagc tccctcgtgc gctctcctgt    3600

tccgaccctg ccgcttaccg gatacctgtc cgcctttctc ccttcgggaa gcgtggcgct    3660

ttctcatagc tcacgctgta ggtatctcag ttcggtgtag gtcgttcgct ccaagctggg    3720

ctgtgtgcac gaaccccccg ttcagcccga ccgctgcgcc ttatccggta actatcgtct    3780

tgagtccaac ccggtaagac acgacttatc gccactggca gcagccactg gtaacaggat    3840

tagcagagcg aggtatgtag gcggtgctac agagttcttg aagtggtggc ctaactacgg    3900

ctacactaga agaacagtat ttggtatctg cgctctgctg aagccagtta ccttcggaaa    3960

aagagttggt agctcttgat ccggcaaaca aaccaccgct ggtagcggtg gtttttttgt    4020

ttgcaagcag cagattacgc gcagaaaaaa aggatctcaa gaagatcctt tgatcttttc    4080

tacggggtct gacgctcagt ggaacgaaaa ctcacgttaa gggattttgg tcatgagatt    4140

atcaaaaagg atcttcacct agatcctttt aaattaaaaa tgaagtttta aatcaatcta    4200

aagtatatat gagtaaactt ggtctgacag ttaccaatgc ttaatcagtg aggcaccctat   4260

ctcagcgatc tgtctatttc gttcatccat agttgcctga ctccccgtcg tgtagataac    4320

tacgatacgg gagcgcttac catctggccc cagtgctgca atgataccgc gagacccacg    4380

ctcaccggct ccagatttat cagcaataaa ccagccagcc ggaagggccg agcgcagaag    4440

tggtcctgca actttatccg cctccattca gtctattaat tgttgccggg aagctagagt    4500

aagtagttcg ccagttaata gtttgcgcaa cgttgttggc attgctacag gcatcgtggt    4560

gtcactctcg tcgtttggta tggcttcatt cagctccggt tcccaacgat caaggcgagt    4620

tacatgatcc cccatgttgt gcaaaaaagc ggttagctcc ttcggtcctc cgatcgttgt    4680

cagaagtaag ttggccgcag tgttatcact catggttatg gcagcactgc ataattctct    4740

tactgtcatg ccatccgtaa gatgcttttc tgtgactggt gagtactcaa ccaagtcatt    4800

ctgagaatag tgtatgcggc gaccgagttg ctcttgcccg gcgtcaatac gggataatag    4860

tgtatcacat agcagaactt taaaagtgct catcattgga aaacgttctt cggggcgaaa    4920

actctcaagg atcttaccgc tgttgagatc cagttcgatg taacccactc gtgcacccaa    4980

ctgatcttca gcatctttta ctttcaccag cgtttctggg tgagcaaaaa caggaaggca    5040

aaatgccgca aaaaagggaa taagggcgac acggaaatgt tgaatactca tactcttcct    5100

ttttcaatgg gtaataactg atataattaa attgaagctc taatttgtga gtttagtata    5160

catgcattta cttataatac agttttttag ttttgctggc cgcatcttct caaatatgct    5220

tcccagcctg cttttctgta acgttcaccc tctaccttag catcccttcc ctttgcaaat    5280

agtcctcttc caacaataat aatgtcagat cctgtagaga ccacatcatc cacggttcta    5340

tactgttgac ccaatgcgtc tcccttgtca tctaaaccca caccgggtgt cataatcaac    5400

caatcgtaac cttcatctct tccacccatg tctctttgag caataaagcc gataacaaaa    5460

tctttgtcgc tcttcgcaat gtcaacagta cccttagtat attctccagt agatagggag    5520

cccttgcatg acaattctgc taacatcaaa aggcctctag gttcctttgt tacttcttct    5580

gccgcctgct tcaaaccgct aacaatacct gggcccacca caccgtgtgc attcgtaatg    5640

tctgcccatt ctgctattct gtatacaccc gcagagtact gcaatttgac tgtattacca    5700

atgtcagcaa attttctgtc ttcg                                           5724
```

<210> SEQ ID NO 26
<211> LENGTH: 5724
<212> TYPE: DNA
<213> ORGANISM: Artificial Sequence
<220> FEATURE:
<223> OTHER INFORMATION: OAC-V31G/G43SILENT(=GGG)/I74G/V84R/R100E

<400> SEQUENCE: 26

```
aagagtaaaa aattgtactt ggcggataat gcctttagcg gcttaactgt gccctccatg     60
gaaaaatcag tcaagatatc cacatgtgtt tttagtaaac aaattttggg acctaatgct    120
tcaactaact ccagtaattc cttggtggta cgaacatcca atgaagcaca caagtttgtt    180
tgcttttcgt gcatgatatt aaatagcttg gcagcaacag gactaggatg agtagcagca    240
cgttccttat atgtagcttt cgacatgatt tatcttcgtt tcctgcaggt ttttgttctg    300
tgcagttggg ttaagaatac tggcaattt catgtttctt caacactaca tatgcgtata    360
tataccaatc taagtctgtg ctccttcctt cgttcttcct tctgttcgga gattaccgaa    420
tcaaaaaaat ttcaaagaaa ccgaaatcaa aaaaaagaat aaaaaaaaaa tgatgaattg    480
aattgaaaag ctagcttatc gatgataagc tgtcaaagat gagaattaat tccacggact    540
atagactata ctagatactc cgtctactgt acgatacact tccgctcagg tccttgtcct    600
ttaacgaggc cttaccactc ttttgttact ctattgatcc agctcagcaa aggcagtgtg    660
atctaagatt ctatcttcgc gatgtagtaa aactagctag accgagaaag agactagaaa    720
tgcaaaaggc acttctacaa tggctgccat cattattatc cgatgtgacg ctgcagcttc    780
tcaatgatat tcgaatacgc tttgaggaga tacagcctaa tatccgacaa actgttttac    840
agatttacga tcgtacttgt tacccatcat tgaattttga acatccgaac ctgggagttt    900
tccctgaaac agatagtata tttgaacctg tataataata tatagtctag cgctttacgg    960
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc ttttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcatttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gtttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
```

tggggcgcta cagggcgcgt ggggatgatc cactagtacg gattagaagc cgccgagcgg 2160
gtgacagccc tccgaaggaa gactctcctc cgtgcgtcct cgtcttcacc ggtcgcgttc 2220
ctgaaacgca gatgtgcctc gcgccgcact gctccgaaca ataaagattc tacaatacta 2280
gcttttatgg ttatgaagag gaaaaattgg cagtaacctg gccccacaaa ccttcaaatg 2340
aacgaatcaa attaacaacc ataggatgat aatgcgatta gtttttttagc cttatttctg 2400
gggtaattaa tcagcgaagc gatgattttt gatctattaa cagatatata aatgcaaaaa 2460
ctgcataacc actttaacta atactttcaa cattttcggt ttgtattact tcttattcaa 2520
atgtaataaa agtatcaaca aaaaattgtt aatatacctc tatactttaa cgtcaaggag 2580
aaaaaacccc ggatcggact actagcagct gtaatacgac tcactatagg gaatattaag 2640
cttaaacaat ggccgtcaag cacttgatcg tcttaaagtt taaggacgag atcactgaag 2700
cccaaaagga agaattcttc aaaacttacg ttaacttggg gaacatcatt cctgctatga 2760
aggacgtcta ctgggggaag gatgtcactc aaaaaaacaa ggaagaaggt tatacccaca 2820
tcgttgaagt caccttcgaa tctgttgaaa ctattcaaga ctacatcggg cacccagctc 2880
acgtcggttt cggtgatagg tacagatctt tctgggaaaa attgttgatc ttcgactaca 2940
ccccagagaa gggctaactc gagcatgcat ctagagggcc gcatcatgta attagttatg 3000
tcacgcttac attcacgccc tccccccaca tccgctctaa ccgaaaagga aggagttaga 3060
caacctgaag tctaggtccc tatttatttt tttatagtta tgttagtatt aagaacgtta 3120
tttatatttc aaatttttct tttttttctg tacagacgcg tgtacgcatg taacattata 3180
ctgaaaacct tgcttgagaa ggttttggga cgctcgaagg ctttaatttg cggccctgca 3240
ttaatgaatc ggccaacgcg cggggagagg cggtttgcgt attgggcgct cttccgcttc 3300
ctcgctcact gactcgctgc gctcggtcgt tcggctgcgg cgagcggtat cagctcactc 3360
aaaggcggta atacggttat ccacagaatc aggggataac gcaggaaaga acatgtgagc 3420
aaaaggccag caaaagccca ggaaccgtaa aaaggccgcg ttgctggcgt ttttccatag 3480
gctccgcccc cctgacgagc atcacaaaaa tcgacgctca agtcagaggt ggcgaaaccc 3540
gacaggacta taaagatacc aggcgtttcc ccctggaagc tccctcgtgc gctctcctgt 3600
tccgaccctg ccgcttaccg gatacctgtc cgcctttctc ccttcgggaa gcgtggcgct 3660
ttctcatagc tcacgctgta ggtatctcag ttcggtgtag gtcgttcgct ccaagctggg 3720
ctgtgtgcac gaaccccccg ttcagcccga ccgctgcgcc ttatccggta actatcgtct 3780
tgagtccaac ccggtaagac acgacttatc gccactggca gcagccactg gtaacaggat 3840
tagcagagcg aggtatgtag gcggtgctac agagttcttg aagtggtggc ctaactacgg 3900
ctacactaga agaacagtat ttggtatctg cgctctgctg aagccagtta ccttcggaaa 3960
aagagttggt agctcttgat ccggcaaaca aaccaccgct ggtagcggtg gtttttttgt 4020
ttgcaagcag cagattacgc gcagaaaaaa aggatctcaa gaagatcctt tgatcttttc 4080
tacggggtct gacgctcagt ggaacgaaaa ctcacgttaa gggattttgg tcatgagatt 4140
atcaaaaagg atcttcacct agatcctttt aaattaaaaa tgaagtttta aatcaatcta 4200
aagtatatat gagtaaactt ggtctgacag ttaccaatgc ttaatcagtg aggcacctat 4260
ctcagcgatc tgtctatttc gttcatccat agttgcctga ctccccgtcg tgtagataac 4320
tacgatacgg gagcgcttac catctggccc cagtgctgca atgataccgc gagacccacg 4380
ctcaccggct ccagatttat cagcaataaa ccagccagcc ggaagggccg agcgcagaag 4440

```
tggtcctgca actttatccg cctccattca gtctattaat tgttgccggg aagctagagt   4500

aagtagttcg ccagttaata gtttgcgcaa cgttgttggc attgctacag gcatcgtggt   4560

gtcactctcg tcgtttggta tggcttcatt cagctccggt tcccaacgat caaggcgagt   4620

tacatgatcc cccatgttgt gcaaaaaagc ggttagctcc ttcggtcctc cgatcgttgt   4680

cagaagtaag ttggccgcag tgttatcact catggttatg gcagcactgc ataattctct   4740

tactgtcatg ccatccgtaa gatgcttttc tgtgactggt gagtactcaa ccaagtcatt   4800

ctgagaatag tgtatgcggc gaccgagttg ctcttgcccg gcgtcaatac gggataatag   4860

tgtatcacat agcagaactt taaaagtgct catcattgga aaacgttctt cggggcgaaa   4920

actctcaagg atcttaccgc tgttgagatc cagttcgatg taacccactc gtgcacccaa   4980

ctgatcttca gcatctttta ctttcaccag cgtttctggg tgagcaaaaa caggaaggca   5040

aaatgccgca aaaaagggaa taagggcgac acggaaatgt tgaatactca tactcttcct   5100

ttttcaatgg gtaataactg atataattaa attgaagctc taatttgtga gtttagtata   5160

catgcattta cttataatac agttttttag ttttgctggc cgcatcttct caaatatgct   5220

tcccagcctg cttttctgta acgttcaccc tctaccttag catcccttcc ctttgcaaat   5280

agtcctcttc caacaataat aatgtcagat cctgtagaga ccacatcatc cacggttcta   5340

tactgttgac ccaatgcgtc tcccttgtca tctaaaccca caccgggtgt cataatcaac   5400

caatcgtaac cttcatctct tccacccatg tctctttgag caataaagcc gataacaaaa   5460

tctttgtcgc tcttcgcaat gtcaacagta cccttagtat attctccagt agatagggag   5520

cccttgcatg acaattctgc taacatcaaa aggcctctag gttcctttgt tacttcttct   5580

gccgcctgct tcaaaccgct aacaatacct gggcccacca caccgtgtgc attcgtaatg   5640

tctgcccatt ctgctattct gtatacaccc gcagagtact gcaatttgac tgtattacca   5700

atgtcagcaa attttctgtc ttcg                                         5724
```

<210> SEQ ID NO 27
<211> LENGTH: 5724
<212> TYPE: DNA
<213> ORGANISM: Artificial Sequence
<220> FEATURE:
<223> OTHER INFORMATION: OAC-V28A/Y41S/G43SILENT(=GGG)/K44V/T68R/I74R/
V84R/R100M/G102R

<400> SEQUENCE: 27

```
aagagtaaaa aattgtactt ggcggataat gcctttagcg gcttaactgt gccctccatg     60

gaaaaatcag tcaagatatc cacatgtgtt tttagtaaac aaattttggg acctaatgct    120

tcaactaact ccagtaattc cttggtggta cgaacatcca atgaagcaca caagtttgtt    180

tgcttttcgt gcatgatatt aaatagcttg gcagcaacag gactaggatg agtagcagca    240

cgttccttat atgtagcttt cgacatgatt tatcttcgtt tcctgcaggt ttttgttctg    300

tgcagttggg ttaagaatac tggcaattt catgtttctt caacactaca tatgcgtata    360

tataccaatc taagtctgtg ctccttcctt cgttcttcct tctgttcgga gattaccgaa    420

tcaaaaaaat ttcaaagaaa ccgaaatcaa aaaaaagaat aaaaaaaaaa tgatgaattg    480

aattgaaaag ctagcttatc gatgataagc tgtcaaagat gagaattaat tccacggact    540

atagactata ctagatactc cgtctactgt acgatacact tccgctcagg tccttgtcct    600

ttaacgaggc cttaccactc ttttgttact ctattgatcc agctcagcaa aggcagtgtg    660

atctaagatt ctatcttcgc gatgtagtaa aactagctag accgagaaag agactagaaa    720
```

```
tgcaaaaggc acttctacaa tggctgccat cattattatc cgatgtgacg ctgcagcttc    780
tcaatgatat tcgaatacgc tttgaggaga tacagcctaa tatccgacaa actgttttac    840
agatttacga tcgtacttgt tacccatcat tgaattttga acatccgaac ctgggagttt    900
tccctgaaac agatagtata tttgaacctg tataataata tatagtctag cgctttacgg    960
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc ttttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcattttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggt taacatcatt cctgctatga   2760
aggacgtctc ctggggggtg gatgtcactc aaaaaaaacaa ggaagaaggt tatacccaca   2820
tcgttgaagt caccttcgaa tctgttgaac ggattcaaga ctacatcagg cacccagctc   2880
acgtcggttt cggtgatagg tacagatctt tctgggaaaa attgttgatc ttcgactaca   2940
ccccaatgaa gcggtaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
```

```
tttatatttc aaatttttct ttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
tactgtcatg ccatccgtaa gatgcttttc tgtgactggt gagtactcaa ccaagtcatt   4800
ctgagaatag tgtatgcggc gaccgagttg ctcttgcccg gcgtcaatac gggataatag   4860
tgtatcacat agcagaactt taaaagtgct catcattgga aaacgttctt cggggcgaaa   4920
actctcaagg atcttaccgc tgttgagatc cagttcgatg taacccactc gtgcacccaa   4980
ctgatcttca gcatctttta ctttcaccag cgtttctggg tgagcaaaaa caggaaggca   5040
aaatgccgca aaaaagggaa taagggcgac acggaaatgt tgaatactca tactcttcct   5100
ttttcaatgg gtaataactg atataattaa attgaagctc taatttgtga gtttagtata   5160
catgcattta cttataatac agttttttag ttttgctggc cgcatcttct caaatatgct   5220
tcccagcctg cttttctgta acgttcaccc tctaccttag catcccttcc ctttgcaaat   5280
agtcctcttc caacaataat aatgtcagat cctgtagaga ccacatcatc cacggttcta   5340
tactgttgac ccaatgcgtc tcccttgtca tctaaaccca caccgggtgt cataatcaac   5400
caatcgtaac cttcatctct tccacccatg tctctttgag caataaagcc gataacaaaa   5460
```

-continued

```
tctttgtcgc tcttcgcaat gtcaacagta cccttagtat attctccagt agatagggag   5520

cccttgcatg acaattctgc taacatcaaa aggcctctag gttcctttgt tacttcttct   5580

gccgcctgct tcaaaccgct aacaatacct gggcccacca caccgtgtgc attcgtaatg   5640

tctgcccatt ctgctattct gtatacaccc gcagagtact gcaatttgac tgtattacca   5700

atgtcagcaa attttctgtc ttcg                                          5724


<210> SEQ ID NO 28
<211> LENGTH: 5724
<212> TYPE: DNA
<213> ORGANISM: Artificial Sequence
<220> FEATURE:
<223> OTHER INFORMATION: OAC-V28A/V31G/Y41V/G43SILENT(=GGG)/K44V/T68L/
      I74G/V84R

<400> SEQUENCE: 28

aagagtaaaa aattgtactt ggcggataat gcctttagcg gcttaactgt gccctccatg     60

gaaaaatcag tcaagatatc cacatgtgtt tttagtaaac aaattttggg acctaatgct    120

tcaactaact ccagtaattc cttggtggta cgaacatcca atgaagcaca caagtttgtt    180

tgcttttcgt gcatgatatt aaatagcttg gcagcaacag gactaggatg agtagcagca    240

cgttccttat atgtagcttt cgacatgatt tatcttcgtt tcctgcaggt ttttgttctg    300

tgcagttggg ttaagaatac tgggcaattt catgtttctt caacactaca tatgcgtata    360

tataccaatc taagtctgtg ctccttcctt cgttcttcct tctgttcgga gattaccgaa    420

tcaaaaaaat ttcaaagaaa ccgaaatcaa aaaaaagaat aaaaaaaaaa tgatgaattg    480

aattgaaaag ctagcttatc gatgataagc tgtcaaagat gagaattaat tccacggact    540

atagactata ctagatactc cgtctactgt acgatacact tccgctcagg tccttgtcct    600

ttaacgaggc cttaccactc ttttgttact ctattgatcc agctcagcaa aggcagtgtg    660

atctaagatt ctatcttcgc gatgtagtaa aactagctag accgagaaag agactagaaa    720

tgcaaaaggc acttctacaa tggctgccat cattattatc cgatgtgacg ctgcagcttc    780

tcaatgatat tcgaatacgc tttgaggaga tacagcctaa tatccgacaa actgttttac    840

agatttacga tcgtacttgt tacccatcat tgaattttga acatccgaac ctgggagttt    900

tccctgaaac agatagtata tttgaacctg tataataata tatagtctag cgctttacgg    960

aagacaatgt atgtatttcg gttcctggag aaactattgc atctattgca taggtaatct   1020

tgcacgtcgc atccccggtt cattttctgc gtttccatct tgcacttcaa tagcatatct   1080

ttgttcgctt gcctgtaact tacacgcgcc tcgtatcttt taatgatgga ataatttggg   1140

aatttactct gtgtttattt atttttatgt tttgtatttg gattttagaa agtaaataaa   1200

gaaggtagaa gagttacgga atgaagaaaa aaaaataaac aaaggtttaa aaaatttcaa   1260

caaaaagcgt actttacata tatatttatt agacaagaaa agcagattaa atagatatac   1320

attcgattaa cgataagtaa aatgtaaaat cacaggattt tcgtgtgtgg tcttctacac   1380

agacaagatg aaacaattcg gcattaatac ctgagagcag gaagagcaag ataaaaggta   1440

gtatttgttg gcgatccccc tagagtcttt tacatcttcg gaaaacaaaa actatttttt   1500

ctttaatttc ttttttttact ttctattttt aatttatata tttatattaa aaaatttaaa   1560

ttataattat ttttatagca cgtgatgaaa aggaccggga agctccaccc cggttgataa   1620

tcagaaaagc cccaaaaaca ggaagattgt ataagcaaat atttaaattg taaacgttaa   1680

tattttgtta aaattcgcgt taaatttttg ttaaatcagc tcattttttta acgaatagcc   1740
```

```
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gtttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggg gaacatcatt cctgctatga   2760
aggacgtcgt gtgggggtg gatgtcactc aaaaaaacaa ggaagaaggt tatacccaca   2820
tcgttgaagt caccttcgaa tctgttgaac tgattcaaga ctacatcggg cacccagctc   2880
acgtcggttt cggtgatagg tacagatctt tctgggaaaa attgttgatc ttcgactaca   2940
ccccaagaaa gggctaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct tttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
```

```
atcaaaaagg atcttcacct agatcctttt aaattaaaaa tgaagtttta aatcaatcta   4200

aagtatatat gagtaaactt ggtctgacag ttaccaatgc ttaatcagtg aggcacctat   4260

ctcagcgatc tgtctatttc gttcatccat agttgcctga ctccccgtcg tgtagataac   4320

tacgatacgg gagcgcttac catctggccc cagtgctgca atgataccgc gagacccacg   4380

ctcaccggct ccagatttat cagcaataaa ccagccagcc ggaagggccg agcgcagaag   4440

tggtcctgca actttatccg cctccattca gtctattaat tgttgccggg aagctagagt   4500

aagtagttcg ccagttaata gtttgcgcaa cgttgttggc attgctacag gcatcgtggt   4560

gtcactctcg tcgtttggta tggcttcatt cagctccggt tcccaacgat caaggcgagt   4620

tacatgatcc cccatgttgt gcaaaaaagc ggttagctcc ttcggtcctc cgatcgttgt   4680

cagaagtaag ttggccgcag tgttatcact catggttatg gcagcactgc ataattctct   4740

tactgtcatg ccatccgtaa gatgcttttc tgtgactggt gagtactcaa ccaagtcatt   4800

ctgagaatag tgtatgcggc gaccgagttg ctcttgcccg gcgtcaatac gggataatag   4860

tgtatcacat agcagaactt taaaagtgct catcattgga aaacgttctt cggggcgaaa   4920

actctcaagg atcttaccgc tgttgagatc cagttcgatg taacccactc gtgcacccaa   4980

ctgatcttca gcatctttta ctttcaccag cgtttctggg tgagcaaaaa caggaaggca   5040

aaatgccgca aaaaagggaa taagggcgac acggaaatgt tgaatactca tactcttcct   5100

ttttcaatgg gtaataactg atataattaa attgaagctc taatttgtga gtttagtata   5160

catgcattta cttataatac agttttttag ttttgctggc cgcatcttct caaatatgct   5220

tcccagcctg cttttctgta acgttcaccc tctaccttag catcccttcc ctttgcaaat   5280

agtcctcttc caacaataat aatgtcagat cctgtagaga ccacatcatc cacggttcta   5340

tactgttgac ccaatgcgtc tcccttgtca tctaaaccca caccgggtgt cataatcaac   5400

caatcgtaac cttcatctct tccacccatg tctctttgag caataaagcc gataacaaaa   5460

tctttgtcgc tcttcgcaat gtcaacagta cccttagtat attctccagt agatagggag   5520

cccttgcatg acaattctgc taacatcaaa aggcctctag gttcctttgt tacttcttct   5580

gccgcctgct tcaaaccgct aacaatacct gggcccacca caccgtgtgc attcgtaatg   5640

tctgcccatt ctgctattct gtatacaccc gcagagtact gcaatttgac tgtattacca   5700

atgtcagcaa attttctgtc ttcg                                          5724
```

```
<210> SEQ ID NO 29
<211> LENGTH: 5724
<212> TYPE: DNA
<213> ORGANISM: Artificial Sequence
<220> FEATURE:
<223> OTHER INFORMATION: OAC-V28A/Y41V/G43SILENT(=GGG)/K44V/T68L/I74G/
      V84R/R100M/G102R

<400> SEQUENCE: 29
```

```
aagagtaaaa aattgtactt ggcggataat gcctttagcg gcttaactgt gccctccatg     60

gaaaaatcag tcaagatatc cacatgtgtt tttagtaaac aaattttggg acctaatgct    120

tcaactaact ccagtaattc cttggtggta cgaacatcca atgaagcaca caagtttgtt    180

tgcttttcgt gcatgatatt aaatagcttg gcagcaacag gactaggatg agtagcagca    240

cgttccttat atgtagcttt cgacatgatt tatcttcgtt tcctgcaggt tttgttctg     300

tgcagttggg ttaagaatac tgggcaattt catgtttctt caacactaca tatgcgtata    360

tataccaatc taagtctgtg ctccttcctt cgttcttcct tctgttcgga gattaccgaa    420
```

```
tcaaaaaaat ttcaaagaaa ccgaaatcaa aaaaaagaat aaaaaaaaaa tgatgaattg    480
aattgaaaag ctagcttatc gatgataagc tgtcaaagat gagaattaat tccacggact    540
atagactata ctagatactc cgtctactgt acgatacact tccgctcagg tccttgtcct    600
ttaacgaggc cttaccactc ttttgttact ctattgatcc agctcagcaa aggcagtgtg    660
atctaagatt ctatcttcgc gatgtagtaa aactagctag accgagaaag agactagaaa    720
tgcaaaaggc acttctacaa tggctgccat cattattatc cgatgtgacg ctgcagcttc    780
tcaatgatat tcgaatacgc tttgaggaga tacagcctaa tatccgacaa actgttttac    840
agatttacga tcgtacttgt tacccatcat tgaattttga acatccgaac ctgggagttt    900
tccctgaaac agatagtata tttgaacctg tataataata tatagtctag cgctttacgg    960
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc ttttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcattttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gtttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggcgc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggt taacatcatt cctgctatga   2760
```

```
aggacgtcgt gtgggggggtg gatgtcactc aaaaaaacaa ggaagaaggt tatacccaca   2820
tcgttgaagt caccttcgaa tctgttgaac tgattcaaga ctacatcggg cacccagctc   2880
acgtcggttt cggtgatagg tacagatctt tctgggaaaa attgttgatc ttcgactaca   2940
ccccaatgaa gcggtaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct tttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
tactgtcatg ccatccgtaa gatgcttttc tgtgactggt gagtactcaa ccaagtcatt   4800
ctgagaatag tgtatgcggc gaccgagttg ctcttgcccg gcgtcaatac gggataatag   4860
tgtatcacat agcagaactt taaaagtgct catcattgga aaacgttctt cggggcgaaa   4920
actctcaagg atcttaccgc tgttgagatc cagttcgatg taacccactc gtgcacccaa   4980
ctgatcttca gcatctttta ctttcaccag cgtttctggg tgagcaaaaa caggaaggca   5040
aaatgccgca aaaaagggaa taagggcgac acggaaatgt tgaatactca tactcttcct   5100
ttttcaatgg gtaataactg atataattaa attgaagctc taatttgtga gtttagtata   5160
```

```
catgcattta cttataatac agttttttag ttttgctggc cgcatcttct caaatatgct   5220

tcccagcctg cttttctgta acgttcaccc tctaccttag catcccttcc ctttgcaaat   5280

agtcctcttc caacaataat aatgtcagat cctgtagaga ccacatcatc cacggttcta   5340

tactgttgac ccaatgcgtc tcccttgtca tctaaaccca caccgggtgt cataatcaac   5400

caatcgtaac cttcatctct tccacccatg tctctttgag caataaagcc gataacaaaa   5460

tctttgtcgc tcttcgcaat gtcaacagta cccttagtat attctccagt agatagggag   5520

cccttgcatg acaattctgc taacatcaaa aggcctctag gttcctttgt tacttcttct   5580

gccgcctgct tcaaaccgct aacaatacct gggcccacca caccgtgtgc attcgtaatg   5640

tctgcccatt ctgctattct gtatacaccc gcagagtact gcaatttgac tgtattacca   5700

atgtcagcaa attttctgtc ttcg                                          5724
```

<210> SEQ ID NO 30
<211> LENGTH: 5724
<212> TYPE: DNA
<213> ORGANISM: Artificial Sequence
<220> FEATURE:
<223> OTHER INFORMATION: OAC-V28A/V31G/G43SILENT(=GGG)/T68L/I74R/V84R/
R100E/G102R

<400> SEQUENCE: 30

```
aagagtaaaa aattgtactt ggcggataat gcctttagcg gcttaactgt gccctccatg     60

gaaaaatcag tcaagatatc cacatgtgtt tttagtaaac aaattttggg acctaatgct    120

tcaactaact ccagtaattc cttggtggta cgaacatcca atgaagcaca caagtttgtt    180

tgcttttcgt gcatgatatt aaatagcttg gcagcaacag gactaggatg agtagcagca    240

cgttccttat atgtagcttt cgacatgatt tatcttcgtt tcctgcaggt ttttgttctg    300

tgcagttggg ttaagaatac tgggcaattt catgtttctt caacactaca tatgcgtata    360

tataccaatc taagtctgtg ctccttcctt cgttcttcct tctgttcgga gattaccgaa    420

tcaaaaaaat ttcaaagaaa ccgaaatcaa aaaaaagaat aaaaaaaaaa tgatgaattg    480

aattgaaaag ctagcttatc gatgataagc tgtcaaagat gagaattaat tccacggact    540

atagactata ctagatactc cgtctactgt acgatacact tccgctcagg tccttgtcct    600

ttaacgaggc cttaccactc ttttgttact ctattgatcc agctcagcaa aggcagtgtg    660

atctaagatt ctatcttcgc gatgtagtaa aactagctag accgagaaag agactagaaa    720

tgcaaaaggc acttctacaa tggctgccat cattattatc cgatgtgacg ctgcagcttc    780

tcaatgatat tcgaatacgc tttgaggaga tacagcctaa tatccgacaa actgttttac    840

agatttacga tcgtacttgt tacccatcat tgaattttga acatccgaac ctgggagttt    900

tccctgaaac agatagtata tttgaacctg tataataata tatagtctag cgctttacgg    960

aagacaatgt atgtatttcg gttcctggag aaactattgc atctattgca taggtaatct   1020

tgcacgtcgc atccccggtt cattttctgc gtttccatct tgcacttcaa tagcatatct   1080

ttgttcgctt gcctgtaact tacacgcgcc tcgtatcttt taatgatgga ataatttggg   1140

aatttactct gtgtttattt atttttatgt tttgtatttg gattttagaa agtaaataaa   1200

gaaggtagaa gagttacgga atgaagaaaa aaaaataaac aaaggtttaa aaaatttcaa   1260

caaaaagcgt actttacata tatatttatt agacaagaaa agcagattaa atagatatac   1320

attcgattaa cgataagtaa aatgtaaaat cacaggattt tcgtgtgtgg tcttctacac   1380

agacaagatg aaacaattcg gcattaatac ctgagagcag gaagagcaag ataaaaggta   1440
```

gtatttgttg gcgatccccc tagagtcttt tacatcttcg gaaaacaaaa actatttttt 1500
ctttaatttc tttttttact ttctattttt aatttatata tttatattaa aaaatttaaa 1560
ttataattat ttttatagca cgtgatgaaa aggaccggga agctccaccc cggttgataa 1620
tcagaaaagc cccaaaaaca ggaagattgt ataagcaaat atttaaattg taaacgttaa 1680
tattttgtta aaattcgcgt taaatttttg ttaaatcagc tcatttttta acgaatagcc 1740
cgaaatcggc aaaatccctt ataaatcaaa agaatagacc gagatagggt tgagtgttgt 1800
tccagtttcc aacaagagtc cactattaaa gaacgtggac tccaacgtca aagggcgaaa 1860
aagggtctat cagggcgatg gcccactacg tgaaccatca ccctaatcaa gttttttggg 1920
gtcgaggtgc cgtaaagcag taaatcggaa gggtaaacgg atgcccccat ttagagcttg 1980
acggggaaag ccggcgaacg tggcgagaaa ggaagggaag aaagcgaaag gagcgggggc 2040
tagggcggtg ggaagtgtag gggtcacgct gggcgtaacc accacacccg ccgcgcttaa 2100
tggggcgcta cagggcgcgt ggggatgatc cactagtacg gattagaagc cgccgagcgg 2160
gtgacagccc tccgaaggaa gactctcctc cgtgcgtcct cgtcttcacc ggtcgcgttc 2220
ctgaaacgca gatgtgcctc gcgccgcact gctccgaaca ataaagattc tacaatacta 2280
gcttttatgg ttatgaagag gaaaaattgg cagtaacctg gccccacaaa ccttcaaatg 2340
aacgaatcaa attaacaacc ataggatgat aatgcgatta gtttttttagc cttatttctg 2400
gggtaattaa tcagcgaagc gatgattttt gatctattaa cagatatata aatgcaaaaa 2460
ctgcataacc actttaacta atactttcaa cattttcggt ttgtattact tcttattcaa 2520
atgtaataaa agtatcaaca aaaaattgtt aatatacctc tatactttaa cgtcaaggag 2580
aaaaaacccc ggatcggact actagcagct gtaatacgac tcactatagg gaatattaag 2640
cttaaacaat ggccgtcaag cacttgatcg tcttaaagtt taaggacgag atcactgaag 2700
cccaaaagga agaattcttc aaaacttacg cgaacttggg gaacatcatt cctgctatga 2760
aggacgtcta ctgggggaag gatgtcactc aaaaaaacaa ggaagaaggt tatacccaca 2820
tcgttgaagt caccttcgaa tctgttgaac tgattcaaga ctacatcagg cacccagctc 2880
acgtcggttt cggtgatagg tacagatctt tctgggaaaa attgttgatc ttcgactaca 2940
ccccagagaa gcggtaactc gagcatgcat ctagagggcc gcatcatgta attagttatg 3000
tcacgcttac attcacgccc tccccccaca tccgctctaa ccgaaaagga aggagttaga 3060
caacctgaag tctaggtccc tatttatttt tttatagtta tgttagtatt aagaacgtta 3120
tttatatttc aaatttttct ttttttctg tacagacgcg tgtacgcatg taacattata 3180
ctgaaaacct tgcttgagaa ggttttggga cgctcgaagg ctttaatttg cggccctgca 3240
ttaatgaatc ggccaacgcg cggggagagg cggtttgcgt attgggcgct cttccgcttc 3300
ctcgctcact gactcgctgc gctcggtcgt tcggctgcgg cgagcggtat cagctcactc 3360
aaaggcggta atacggttat ccacagaatc aggggataac gcaggaaaga acatgtgagc 3420
aaaaggccag caaaagccca ggaaccgtaa aaaggccgcg ttgctggcgt ttttccatag 3480
gctccgcccc cctgacgagc atcacaaaaa tcgacgctca agtcagaggt ggcgaaaccc 3540
gacaggacta taaagatacc aggcgtttcc ccctggaagc tccctcgtgc gctctcctgt 3600
tccgaccctg ccgcttaccg gatacctgtc cgcctttctc ccttcgggaa gcgtggcgct 3660
ttctcatagc tcacgctgta ggtatctcag ttcggtgtag gtcgttcgct ccaagctggg 3720
ctgtgtgcac gaaccccccg ttcagcccga ccgctgcgcc ttatccggta actatcgtct 3780

-continued

```
tgagtccaac ccggtaagac acgacttatc gccactggca gcagccactg gtaacaggat   3840

tagcagagcg aggtatgtag gcggtgctac agagttcttg aagtggtggc ctaactacgg   3900

ctacactaga agaacagtat ttggtatctg cgctctgctg aagccagtta ccttcggaaa   3960

aagagttggt agctcttgat ccggcaaaca aaccaccgct ggtagcggtg gtttttttgt   4020

ttgcaagcag cagattacgc gcagaaaaaa aggatctcaa gaagatcctt tgatcttttc   4080

tacggggtct gacgctcagt ggaacgaaaa ctcacgttaa gggattttgg tcatgagatt   4140

atcaaaaagg atcttcacct agatcctttt aaattaaaaa tgaagtttta aatcaatcta   4200

aagtatatat gagtaaactt ggtctgacag ttaccaatgc ttaatcagtg aggcacctat   4260

ctcagcgatc tgtctatttc gttcatccat agttgcctga ctccccgtcg tgtagataac   4320

tacgatacgg gagcgcttac catctggccc cagtgctgca atgataccgc gagacccacg   4380

ctcaccggct ccagatttat cagcaataaa ccagccagcc ggaagggccg agcgcagaag   4440

tggtcctgca actttatccg cctccattca gtctattaat tgttgccggg aagctagagt   4500

aagtagttcg ccagttaata gtttgcgcaa cgttgttggc attgctacag gcatcgtggt   4560

gtcactctcg tcgtttggta tggcttcatt cagctccggt tcccaacgat caaggcgagt   4620

tacatgatcc cccatgttgt gcaaaaaagc ggttagctcc ttcggtcctc cgatcgttgt   4680

cagaagtaag ttggccgcag tgttatcact catggttatg gcagcactgc ataattctct   4740

tactgtcatg ccatccgtaa gatgcttttc tgtgactggt gagtactcaa ccaagtcatt   4800

ctgagaatag tgtatgcggc gaccgagttg ctcttgcccg gcgtcaatac gggataatag   4860

tgtatcacat agcagaactt taaaagtgct catcattgga aaacgttctt cggggcgaaa   4920

actctcaagg atcttaccgc tgttgagatc cagttcgatg taacccactc gtgcacccaa   4980

ctgatcttca gcatctttta ctttcaccag cgtttctggg tgagcaaaaa caggaaggca   5040

aaatgccgca aaaaagggaa taagggcgac acggaaatgt tgaatactca tactcttcct   5100

ttttcaatgg gtaataactg atataattaa attgaagctc taatttgtga gtttagtata   5160

catgcattta cttataatac agttttttag ttttgctggc cgcatcttct caaatatgct   5220

tcccagcctg cttttctgta acgttcaccc tctaccttag catcccttcc ctttgcaaat   5280

agtcctcttc caacaataat aatgtcagat cctgtagaga ccacatcatc cacggttcta   5340

tactgttgac ccaatgcgtc tcccttgtca tctaaaccca caccgggtgt cataatcaac   5400

caatcgtaac cttcatctct tccacccatg tctctttgag caataaagcc gataacaaaa   5460

tctttgtcgc tcttcgcaat gtcaacagta cccttagtat attctccagt agatagggag   5520

cccttgcatg acaattctgc taacatcaaa aggcctctag gttcctttgt tacttcttct   5580

gccgcctgct tcaaaccgct aacaatacct gggcccacca caccgtgtgc attcgtaatg   5640

tctgcccatt ctgctattct gtatacaccc gcagagtact gcaatttgac tgtattacca   5700

atgtcagcaa attttctgtc ttcg                                          5724
```

```
<210> SEQ ID NO 31
<211> LENGTH: 5724
<212> TYPE: DNA
<213> ORGANISM: Artificial Sequence
<220> FEATURE:
<223> OTHER INFORMATION: OAC-V31G/Y41V/G43SILENT(=GGG)/K44V/T68L/I74R/
      V84R/R100E/G102STOP

<400> SEQUENCE: 31

aagagtaaaa aattgtactt ggcggataat gcctttagcg gcttaactgt gccctccatg     60
```

-continued

```
gaaaaatcag tcaagatatc cacatgtgtt tttagtaaac aaattttggg acctaatgct    120
tcaactaact ccagtaattc cttggtggta cgaacatcca atgaagcaca caagtttgtt    180
tgcttttcgt gcatgatatt aaatagcttg gcagcaacag gactaggatg agtagcagca    240
cgttccttat atgtagcttt cgacatgatt tatcttcgtt tcctgcaggt ttttgttctg    300
tgcagttggg ttaagaatac tgggcaattt catgtttctt caacactaca tatgcgtata    360
tataccaatc taagtctgtg ctccttcctt cgttcttcct tctgttcgga gattaccgaa    420
tcaaaaaaat ttcaaagaaa ccgaaatcaa aaaaaagaat aaaaaaaaaa tgatgaattg    480
aattgaaaag ctagcttatc gatgataagc tgtcaaagat gagaattaat tccacggact    540
atagactata ctagatactc cgtctactgt acgatacact tccgctcagg tccttgtcct    600
ttaacgaggc cttaccactc ttttgttact ctattgatcc agctcagcaa aggcagtgtg    660
atctaagatt ctatcttcgc gatgtagtaa aactagctag accgagaaag agactagaaa    720
tgcaaaaggc acttctacaa tggctgccat cattattatc cgatgtgacg ctgcagcttc    780
tcaatgatat tcgaatacgc tttgaggaga tacagcctaa tatccgacaa actgttttac    840
agatttacga tcgtacttgt tacccatcat tgaattttga acatccgaac ctgggagttt    900
tccctgaaac agatagtata tttgaacctg tataataata tatagtctag cgctttacgg    960
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc tttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcattttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gtttttgggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttttagc cttatttctg   2400
gggtaattaa tcagcgaagc gatgattttt gatctattaa cagatatata aatgcaaaaa   2460
```

```
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg ttaacttggg gaacatcatt cctgctatga   2760
aggacgtcgt gtggggggtg gatgtcactc aaaaaaacaa ggaagaaggt tatacccaca   2820
tcgttgaagt caccttcgaa tctgttgaac tgattcaaga ctacatcagg cacccagctc   2880
acgtcggttt cggtgatagg tacagatctt tctgggaaaa attgttgatc ttcgactaca   2940
ccccagagaa gtaataactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct tttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
tactgtcatg ccatccgtaa gatgcttttc tgtgactggt gagtactcaa ccaagtcatt   4800
```

```
ctgagaatag tgtatgcggc gaccgagttg ctcttgcccg gcgtcaatac gggataatag   4860

tgtatcacat agcagaactt taaaagtgct catcattgga aaacgttctt cggggcgaaa   4920

actctcaagg atcttaccgc tgttgagatc cagttcgatg taacccactc gtgcacccaa   4980

ctgatcttca gcatctttta ctttcaccag cgtttctggg tgagcaaaaa caggaaggca   5040

aaatgccgca aaaaagggaa taagggcgac acggaaatgt tgaatactca tactcttcct   5100

ttttcaatgg gtaataactg atataattaa attgaagctc taatttgtga gtttagtata   5160

catgcattta cttataatac agttttttag ttttgctggc cgcatcttct caaatatgct   5220

tcccagcctg cttttctgta acgttcaccc tctaccttag catcccttcc ctttgcaaat   5280

agtcctcttc caacaataat aatgtcagat cctgtagaga ccacatcatc cacggttcta   5340

tactgttgac ccaatgcgtc tcccttgtca tctaaaccca caccgggtgt cataatcaac   5400

caatcgtaac cttcatctct tccacccatg tctctttgag caataaagcc gataacaaaa   5460

tctttgtcgc tcttcgcaat gtcaacagta cccttagtat attctccagt agatagggag   5520

cccttgcatg acaattctgc taacatcaaa aggcctctag gttcctttgt tacttcttct   5580

gccgcctgct tcaaaccgct aacaatacct gggcccacca caccgtgtgc attcgtaatg   5640

tctgcccatt ctgctattct gtatacaccc gcagagtact gcaatttgac tgtattacca   5700

atgtcagcaa attttctgtc ttcg                                          5724
```

<210> SEQ ID NO 32
<211> LENGTH: 5724
<212> TYPE: DNA
<213> ORGANISM: Artificial Sequence
<220> FEATURE:
<223> OTHER INFORMATION: OAC-V31G/Y41T/G43SILENT(=GGG)/K44V/T68R/I74D/
V84R/G102R

<400> SEQUENCE: 32

```
aagagtaaaa aattgtactt ggcggataat gcctttagcg gcttaactgt gccctccatg     60

gaaaaatcag tcaagatatc cacatgtgtt tttagtaaac aaattttggg acctaatgct    120

tcaactaact ccagtaattc cttggtggta cgaacatcca atgaagcaca caagtttgtt    180

tgcttttcgt gcatgatatt aaatagcttg gcagcaacag gactaggatg agtagcagca    240

cgttccttat atgtagcttt cgacatgatt tatcttcgtt tcctgcaggt ttttgttctg    300

tgcagttggg ttaagaatac tgggcaattt catgtttctt caacactaca tatgcgtata    360

tataccaatc taagtctgtg ctccttcctt cgttcttcct tctgttcgga gattaccgaa    420

tcaaaaaaat ttcaaagaaa ccgaaatcaa aaaaaagaat aaaaaaaaaa tgatgaattg    480

aattgaaaag ctagcttatc gatgataagc tgtcaaagat gagaattaat tccacggact    540

atagactata ctagatactc cgtctactgt acgatacact tccgctcagg tccttgtcct    600

ttaacgaggc cttaccactc ttttgttact ctattgatcc agctcagcaa aggcagtgtg    660

atctaagatt ctatcttcgc gatgtagtaa aactagctag accgagaaag agactagaaa    720

tgcaaaaggc acttctacaa tggctgccat cattattatc cgatgtgacg ctgcagcttc    780

tcaatgatat tcgaatacgc tttgaggaga tacagcctaa tatccgacaa actgttttac    840

agatttacga tcgtacttgt tacccatcat tgaattttga acatccgaac ctgggagttt    900

tccctgaaac agatagtata tttgaacctg tataataata tatagtctag cgctttacgg    960

aagacaatgt atgtatttcg gttcctggag aaactattgc atctattgca taggtaatct   1020

tgcacgtcgc atccccggtt cattttctgc gtttccatct tgcacttcaa tagcatatct   1080
```

ttgttcgctt gcctgtaact tacacgcgcc tcgtatcttt taatgatgga ataatttggg 1140
aatttactct gtgtttattt atttttatgt tttgtatttg gattttagaa agtaaataaa 1200
gaaggtagaa gagttacgga atgaagaaaa aaaaataaac aaaggtttaa aaaatttcaa 1260
caaaaagcgt actttacata tatatttatt agacaagaaa agcagattaa atagatatac 1320
attcgattaa cgataagtaa aatgtaaaat cacaggattt tcgtgtgtgg tcttctacac 1380
agacaagatg aaacaattcg gcattaatac ctgagagcag gaagagcaag ataaaaggta 1440
gtatttgttg gcgatccccc tagagtcttt tacatcttcg gaaaacaaaa actatttttt 1500
ctttaatttc tttttttact ttctattttt aatttatata tttatattaa aaaatttaaa 1560
ttataattat ttttatagca cgtgatgaaa aggaccggga agctccaccc cggttgataa 1620
tcagaaaagc cccaaaaaca ggaagattgt ataagcaaat atttaaattg taaacgttaa 1680
tattttgtta aaattcgcgt taaatttttg ttaaatcagc tcatttttta acgaatagcc 1740
cgaaatcggc aaaatccctt ataaatcaaa agaatagacc gagatagggt tgagtgttgt 1800
tccagtttcc aacaagagtc cactattaaa gaacgtggac tccaacgtca aagggcgaaa 1860
aagggtctat cagggcgatg gcccactacg tgaaccatca ccctaatcaa gtttttggg 1920 gtcgaggtgc cgtaaagcag taaatcggaa gggtaaacgg atgcccccat ttagagcttg 1980
acggggaaag ccggcgaacg tggcgagaaa ggaagggaag aaagcgaaag gagcgggggc 2040
tagggcggtg ggaagtgtag gggtcacgct gggcgtaacc accacacccg ccgcgcttaa 2100
tggggcgcta cagggcgcgt ggggatgatc cactagtacg gattagaagc cgccgagcgg 2160
gtgacagccc tccgaaggaa gactctcctc cgtgcgtcct cgtcttcacc ggtcgcgttc 2220
ctgaaacgca gatgtgcctc gcgccgcact gctccgaaca ataaagattc tacaatacta 2280
gcttttatgg ttatgaagag gaaaaattgg cagtaacctg gccccacaaa ccttcaaatg 2340
aacgaatcaa attaacaacc ataggatgat aatgcgatta gtttttagc cttatttctg 2400 gggtaattaa tcagcgaagc gatgattttt gatctattaa cagatatata aatgcaaaaa 2460
ctgcataacc actttaacta atactttcaa cattttcggt ttgtattact tcttattcaa 2520
atgtaataaa agtatcaaca aaaaattgtt aatatacctc tatactttaa cgtcaaggag 2580
aaaaaacccc ggatcggact actagcagct gtaatacgac tcactatagg gaatattaag 2640
cttaaacaat ggccgtcaag cacttgatcg tcttaaagtt taaggacgag atcactgaag 2700
cccaaaagga agaattcttc aaaacttacg ttaacttggg gaacatcatt cctgctatga 2760
aggacgtcac gtggggggtg gatgtcactc aaaaaaacaa ggaagaaggt tatacccaca 2820
tcgttgaagt caccttcgaa tctgttgaac ggattcaaga ctacatcgac cacccagctc 2880
acgtcggttt cggtgatagg tacagatctt tctgggaaaa attgttgatc ttcgactaca 2940
ccccaagaaa gcggtaactc gagcatgcat ctagagggcc gcatcatgta attagttatg 3000
tcacgcttac attcacgccc tccccccaca tccgctctaa ccgaaaagga aggagttaga 3060
caacctgaag tctaggtccc tatttatttt tttatagtta tgttagtatt aagaacgtta 3120
tttatatttc aaatttttct ttttttctg tacagacgcg tgtacgcatg taacattata 3180
ctgaaaacct tgcttgagaa ggttttggga cgctcgaagg ctttaatttg cggccctgca 3240
ttaatgaatc ggccaacgcg cggggagagg cggtttgcgt attgggcgct cttccgcttc 3300
ctcgctcact gactcgctgc gctcggtcgt tcggctgcgg cgagcggtat cagctcactc 3360
aaaggcggta atacggttat ccacagaatc aggggataac gcaggaaaga acatgtgagc 3420
aaaaggccag caaaagccca ggaaccgtaa aaaggccgcg ttgctggcgt ttttccatag 3480

```
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
tactgtcatg ccatccgtaa gatgcttttc tgtgactggt gagtactcaa ccaagtcatt   4800
ctgagaatag tgtatgcggc gaccgagttg ctcttgcccg gcgtcaatac gggataatag   4860
tgtatcacat agcagaactt taaaagtgct catcattgga aaacgttctt cggggcgaaa   4920
actctcaagg atcttaccgc tgttgagatc cagttcgatg taacccactc gtgcacccaa   4980
ctgatcttca gcatctttta ctttcaccag cgtttctggg tgagcaaaaa caggaaggca   5040
aaatgccgca aaaaagggaa taagggcgac acggaaatgt tgaatactca tactcttcct   5100
ttttcaatgg gtaataactg atataattaa attgaagctc taatttgtga gtttagtata   5160
catgcattta cttataatac agtttttag ttttgctggc cgcatcttct caaatatgct   5220
tcccagcctg cttttctgta acgttcaccc tctaccttag catcccttcc ctttgcaaat   5280
agtcctcttc caacaataat aatgtcagat cctgtagaga ccacatcatc cacggttcta   5340
tactgttgac ccaatgcgtc tcccttgtca tctaaaccca caccgggtgt cataatcaac   5400
caatcgtaac cttcatctct tccacccatg tctctttgag caataaagcc gataacaaaa   5460
tctttgtcgc tcttcgcaat gtcaacagta cccttagtat attctccagt agatagggag   5520
cccttgcatg acaattctgc taacatcaaa aggcctctag gttcctttgt tacttcttct   5580
gccgcctgct tcaaaccgct aacaatacct gggcccacca caccgtgtgc attcgtaatg   5640
tctgcccatt ctgctattct gtatacaccc gcagagtact gcaatttgac tgtattacca   5700
atgtcagcaa attttctgtc ttcg                                          5724
```

<210> SEQ ID NO 33

<211> LENGTH: 5724
<212> TYPE: DNA
<213> ORGANISM: Artificial Sequence
<220> FEATURE:
<223> OTHER INFORMATION: OAC-V31G/Y41T/G43SILENT(=GGG)/K44V/T68R/I74D/
V84R/R100E/G102R

<400> SEQUENCE: 33
aagagtaaaa aattgtactt ggcggataat gcctttagcg gcttaactgt gccctccatg 60
gaaaaatcag tcaagatatc cacatgtgtt tttagtaaac aaattttggg acctaatgct 120
tcaactaact ccagtaattc cttggtggta cgaacatcca atgaagcaca caagtttgtt 180
tgcttttcgt gcatgatatt aaatagcttg gcagcaacag gactaggatg agtagcagca 240
cgttccttat atgtagcttt cgacatgatt tatcttcgtt tcctgcaggt tttgttctg 300
tgcagttggg ttaagaatac tgggcaattt catgtttctt caacactaca tatgcgtata 360
tataccaatc taagtctgtg ctccttcctt cgttcttcct tctgttcgga gattaccgaa 420
tcaaaaaaat ttcaaagaaa ccgaaatcaa aaaaaagaat aaaaaaaaaa tgatgaattg 480
aattgaaaag ctagcttatc gatgataagc tgtcaaagat gagaattaat tccacggact 540
atagactata ctagatactc cgtctactgt acgatacact tccgctcagg tccttgtcct 600
ttaacgaggc cttaccactc ttttgttact ctattgatcc agctcagcaa aggcagtgtg 660
atctaagatt ctatcttcgc gatgtagtaa aactagctag accgagaaag agactagaaa 720
tgcaaaaggc acttctacaa tggctgccat cattattatc cgatgtgacg ctgcagcttc 780
tcaatgatat tcgaatacgc tttgaggaga tacagcctaa tatccgacaa actgttttac 840
agatttacga tcgtacttgt tacccatcat tgaattttga acatccgaac ctgggagttt 900
tccctgaaac agatagtata tttgaacctg tataataata tatagtctag cgctttacgg 960
aagacaatgt atgtatttcg gttcctggag aaactattgc atctattgca taggtaatct 1020
tgcacgtcgc atccccggtt cattttctgc gtttccatct tgcacttcaa tagcatatct 1080
ttgttcgctt gcctgtaact tacacgcgcc tcgtatcttt taatgatgga ataatttggg 1140
aatttactct gtgtttattt atttttatgt tttgtatttg gattttagaa agtaaataaa 1200
gaaggtagaa gagttacgga atgaagaaaa aaaaataaac aaaggtttaa aaaatttcaa 1260
caaaaagcgt actttacata tatatttatt agacaagaaa agcagattaa atagatatac 1320
attcgattaa cgataagtaa aatgtaaaat cacaggattt tcgtgtgtgg tcttctacac 1380
agacaagatg aaacaattcg gcattaatac ctgagagcag gaagagcaag ataaaaggta 1440
gtatttgttg gcgatccccc tagagtcttt tacatcttcg gaaaacaaaa actatttttt 1500
ctttaatttc tttttttact ttctattttt aatttatata tttatattaa aaaatttaaa 1560
ttataattat ttttatagca cgtgatgaaa aggaccggga agctccaccc cggttgataa 1620
tcagaaaagc cccaaaaaca ggaagattgt ataagcaaat atttaaattg taaacgttaa 1680
tattttgtta aaattcgcgt taaatttttg ttaaatcagc tcatttttta acgaatagcc 1740
cgaaatcggc aaaatccctt ataaatcaaa agaatagacc gagatagggt tgagtgttgt 1800
tccagtttcc aacaagagtc cactattaaa gaacgtggac tccaacgtca aagggcgaaa 1860
aagggtctat cagggcgatg gcccactacg tgaaccatca ccctaatcaa gtttttt ggg 1920
gtcgaggtgc cgtaaagcag taaatcggaa gggtaaacgg atgcccccat ttagagcttg 1980
acggggaaag ccggcgaacg tggcgagaaa ggaagggaag aaagcgaaag gagcgggggc 2040
tagggcggtg ggaagtgtag gggtcacgct gggcgtaacc accacacccg ccgcgcttaa 2100

-continued tggggcgcta cagggcgcgt ggggatgatc cactagtacg gattagaagc cgccgagcgg 2160
gtgacagccc tccgaaggaa gactctcctc cgtgcgtcct cgtcttcacc ggtcgcgttc 2220
ctgaaacgca gatgtgcctc gcgccgcact gctccgaaca ataaagattc tacaatacta 2280
gcttttatgg ttatgaagag gaaaaattgg cagtaacctg gccccacaaa ccttcaaatg 2340
aacgaatcaa attaacaacc ataggatgat aatgcgatta gtttttttagc cttatttctg 2400
gggtaattaa tcagcgaagc gatgattttt gatctattaa cagatatata aatgcaaaaa 2460
ctgcataacc actttaacta atactttcaa cattttcggt ttgtattact tcttattcaa 2520
atgtaataaa agtatcaaca aaaaattgtt aatatacctc tatactttaa cgtcaaggag 2580
aaaaaacccc ggatcggact actagcagct gtaatacgac tcactatagg gaatattaag 2640
cttaaacaat ggccgtcaag cacttgatcg tcttaaagtt taaggacgag atcactgaag 2700
cccaaaagga agaattcttc aaaacttacg ttaacttggg gaacatcatt cctgctatga 2760
aggacgtcac gtggggggtg gatgtcactc aaaaaaacaa ggaagaaggt tatacccaca 2820
tcgttgaagt caccttcgaa tctgttgaac ggattcaaga ctacatcgac cacccagctc 2880
acgtcggttt cggtgatagg tacagatctt tctgggaaaa attgttgatc ttcgactaca 2940
ccccagagaa gcggtaactc gagcatgcat ctagagggcc gcatcatgta attagttatg 3000
tcacgcttac attcacgccc tccccccaca tccgctctaa ccgaaaagga aggagttaga 3060
caacctgaag tctaggtccc tatttatttt tttatagtta tgttagtatt aagaacgtta 3120
tttatatttc aaatttttct tttttttctg tacagacgcg tgtacgcatg taacattata 3180
ctgaaaacct tgcttgagaa ggttttggga cgctcgaagg ctttaatttg cggccctgca 3240
ttaatgaatc ggccaacgcg cggggagagg cggtttgcgt attgggcgct cttccgcttc 3300
ctcgctcact gactcgctgc gctcggtcgt tcggctgcgg cgagcggtat cagctcactc 3360
aaaggcggta atacggttat ccacagaatc aggggataac gcaggaaaga acatgtgagc 3420
aaaaggccag caaaagccca ggaaccgtaa aaaggccgcg ttgctggcgt ttttccatag 3480
gctccgcccc cctgacgagc atcacaaaaa tcgacgctca agtcagaggt ggcgaaaccc 3540
gacaggacta taaagatacc aggcgtttcc ccctggaagc tccctcgtgc gctctcctgt 3600
tccgaccctg ccgcttaccg gatacctgtc cgcctttctc ccttcgggaa gcgtggcgct 3660
ttctcatagc tcacgctgta ggtatctcag ttcggtgtag gtcgttcgct ccaagctggg 3720
ctgtgtgcac gaaccccccg ttcagcccga ccgctgcgcc ttatccggta actatcgtct 3780
tgagtccaac ccggtaagac acgacttatc gccactggca gcagccactg gtaacaggat 3840
tagcagagcg aggtatgtag gcggtgctac agagttcttg aagtggtggc ctaactacgg 3900
ctacactaga agaacagtat ttggtatctg cgctctgctg aagccagtta ccttcggaaa 3960
aagagttggt agctcttgat ccggcaaaca aaccaccgct ggtagcggtg gtttttttgt 4020
ttgcaagcag cagattacgc gcagaaaaaa aggatctcaa gaagatcctt tgatcttttc 4080
tacggggtct gacgctcagt ggaacgaaaa ctcacgttaa gggattttgg tcatgagatt 4140
atcaaaaagg atcttcacct agatcctttt aaattaaaaa tgaagtttta aatcaatcta 4200
aagtatatat gagtaaactt ggtctgacag ttaccaatgc ttaatcagtg aggcacctat 4260
ctcagcgatc tgtctatttc gttcatccat agttgcctga ctccccgtcg tgtagataac 4320
tacgatacgg gagcgcttac catctggccc cagtgctgca atgataccgc gagacccacg 4380
ctcaccggct ccagatttat cagcaataaa ccagccagcc ggaagggccg agcgcagaag 4440
tggtcctgca actttatccg cctccattca gtctattaat tgttgccggg aagctagagt 4500
aagtagttcg ccagttaata gtttgcgcaa cgttgttggc attgctacag gcatcgtggt 4560
gtcactctcg tcgtttggta tggcttcatt cagctccggt tcccaacgat caaggcgagt 4620
tacatgatcc cccatgttgt gcaaaaaagc ggttagctcc ttcggtcctc cgatcgttgt 4680
cagaagtaag ttggccgcag tgttatcact catggttatg gcagcactgc ataattctct 4740
tactgtcatg ccatccgtaa gatgcttttc tgtgactggt gagtactcaa ccaagtcatt 4800
ctgagaatag tgtatgcggc gaccgagttg ctcttgcccg gcgtcaatac gggataatag 4860
tgtatcacat agcagaactt taaaagtgct catcattgga aaacgttctt cggggcgaaa 4920
actctcaagg atcttaccgc tgttgagatc cagttcgatg taacccactc gtgcacccaa 4980
ctgatcttca gcatctttta ctttcaccag cgtttctggg tgagcaaaaa caggaaggca 5040
aaatgccgca aaaaagggaa taagggcgac acggaaatgt tgaatactca tactcttcct 5100
ttttcaatgg gtaataactg atataattaa attgaagctc taatttgtga gtttagtata 5160
catgcattta cttataatac agttttttag ttttgctggc cgcatcttct caaatatgct 5220
tcccagcctg cttttctgta acgttcaccc tctaccttag catcccttcc ctttgcaaat 5280
agtcctcttc caacaataat aatgtcagat cctgtagaga ccacatcatc cacggttcta 5340
tactgttgac ccaatgcgtc tcccttgtca tctaaaccca caccgggtgt cataatcaac 5400
caatcgtaac cttcatctct tccacccatg tctctttgag caataaagcc gataacaaaa 5460
tctttgtcgc tcttcgcaat gtcaacagta cccttagtat attctccagt agatagggag 5520
cccttgcatg acaattctgc taacatcaaa aggcctctag gttcctttgt tacttcttct 5580
gccgcctgct tcaaaccgct aacaatacct gggcccacca caccgtgtgc attcgtaatg 5640
tctgcccatt ctgctattct gtatacaccc gcagagtact gcaatttgac tgtattacca 5700
atgtcagcaa attttctgtc ttcg 5724

<210> SEQ ID NO 34
<211> LENGTH: 5724
<212> TYPE: DNA
<213> ORGANISM: Artificial Sequence
<220> FEATURE:
<223> OTHER INFORMATION: OAC-V28A/Y41S/G43SILENT(=GGG)/K44V/T68R/I74G/
V84R/R100M/G102R

<400> SEQUENCE: 34
aagagtaaaa aattgtactt ggcggataat gcctttagcg gcttaactgt gccctccatg 60
gaaaaatcag tcaagatatc cacatgtgtt tttagtaaac aaattttggg acctaatgct 120
tcaactaact ccagtaattc cttggtggta cgaacatcca atgaagcaca caagtttgtt 180
tgcttttcgt gcatgatatt aaatagcttg gcagcaacag gactaggatg agtagcagca 240
cgttccttat atgtagcttt cgacatgatt tatcttcgtt tcctgcaggt ttttgttctg 300
tgcagttggg ttaagaatac tgggcaattt catgtttctt caacactaca tatgcgtata 360
tataccaatc taagtctgtg ctccttcctt cgttcttcct tctgttcgga gattaccgaa 420
tcaaaaaaat ttcaaagaaa ccgaaatcaa aaaaaagaat aaaaaaaaaa tgatgaattg 480
aattgaaaag ctagcttatc gatgataagc tgtcaaagat gagaattaat tccacggact 540
atagactata ctagatactc cgtctactgt acgatacact tccgctcagg tccttgtcct 600
ttaacgaggc cttaccactc ttttgttact ctattgatcc agctcagcaa aggcagtgtg 660
atctaagatt ctatcttcgc gatgtagtaa aactagctag accgagaaag agactagaaa 720
tgcaaaaggc acttctacaa tggctgccat cattattatc cgatgtgacg ctgcagcttc 780

```
tcaatgatat tcgaatacgc tttgaggaga tacagcctaa tatccgacaa actgttttac    840
agatttacga tcgtacttgt tacccatcat tgaattttga acatccgaac ctgggagttt    900
tccctgaaac agatagtata tttgaacctg tataataata tatagtctag cgctttacgg    960
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc tttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcatttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gtttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggt taacatcatt cctgctatga   2760
aggacgtctc ctggggggtg gatgtcactc aaaaaaacaa ggaagaaggt tatacccaca   2820
tcgttgaagt caccttcgaa tctgttgaac ggattcaaga ctacatcggg cacccagctc   2880
acgtcggttt cggtgatagg tacagatctt tctgggaaaa attgttgatc ttcgactaca   2940
ccccaatgaa gcggtaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
```

-continued

```
tttatatttc aaatttttct ttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
tactgtcatg ccatccgtaa gatgcttttc tgtgactggt gagtactcaa ccaagtcatt   4800
ctgagaatag tgtatgcggc gaccgagttg ctcttgcccg gcgtcaatac gggataatag   4860
tgtatcacat agcagaactt taaaagtgct catcattgga aaacgttctt cggggcgaaa   4920
actctcaagg atcttaccgc tgttgagatc cagttcgatg taacccactc gtgcacccaa   4980
ctgatcttca gcatctttta ctttcaccag cgtttctggg tgagcaaaaa caggaaggca   5040
aaatgccgca aaaaagggaa taagggcgac acggaaatgt tgaatactca tactcttcct   5100
ttttcaatgg gtaataactg atataattaa attgaagctc taatttgtga gtttagtata   5160
catgcattta cttataatac agttttttag ttttgctggc cgcatcttct caaatatgct   5220
tcccagcctg cttttctgta acgttcaccc tctaccttag catcccttcc ctttgcaaat   5280
agtcctcttc caacaataat aatgtcagat cctgtagaga ccacatcatc cacggttcta   5340
tactgttgac ccaatgcgtc tcccttgtca tctaaaccca caccgggtgt cataatcaac   5400
caatcgtaac cttcatctct tccacccatg tctctttgag caataaagcc gataacaaaa   5460
tctttgtcgc tcttcgcaat gtcaacagta cccttagtat attctccagt agatagggag   5520
```

cccttgcatg acaattctgc taacatcaaa aggcctctag gttcctttgt tacttcttct 5580
gccgcctgct tcaaaccgct aacaatacct gggcccacca caccgtgtgc attcgtaatg 5640
tctgcccatt ctgctattct gtatacaccc gcagagtact gcaatttgac tgtattacca 5700
atgtcagcaa attttctgtc ttcg 5724

<210> SEQ ID NO 35
<211> LENGTH: 5724
<212> TYPE: DNA
<213> ORGANISM: Artificial Sequence
<220> FEATURE:
<223> OTHER INFORMATION: OAC-V28A/Y41V/G43SILENT(=GGG)/K44V/I74R/R100E/
G102STOP

<400> SEQUENCE: 35
aagagtaaaa aattgtactt ggcggataat gcctttagcg gcttaactgt gccctccatg 60
gaaaaatcag tcaagatatc cacatgtgtt tttagtaaac aaattttggg acctaatgct 120
tcaactaact ccagtaattc cttggtggta cgaacatcca atgaagcaca caagtttgtt 180
tgcttttcgt gcatgatatt aaatagcttg gcagcaacag gactaggatg agtagcagca 240
cgttccttat atgtagcttt cgacatgatt tatcttcgtt tcctgcaggt ttttgttctg 300
tgcagttggg ttaagaatac tgggcaattt catgtttctt caacactaca tatgcgtata 360
tataccaatc taagtctgtg ctccttcctt cgttcttcct tctgttcgga gattaccgaa 420
tcaaaaaaat ttcaaagaaa ccgaaatcaa aaaaaagaat aaaaaaaaaa tgatgaattg 480
aattgaaaag ctagcttatc gatgataagc tgtcaaagat gagaattaat tccacggact 540
atagactata ctagatactc cgtctactgt acgatacact tccgctcagg tccttgtcct 600
ttaacgaggc cttaccactc ttttgttact ctattgatcc agctcagcaa aggcagtgtg 660
atctaagatt ctatcttcgc gatgtagtaa aactagctag accgagaaag agactagaaa 720
tgcaaaaggc acttctacaa tggctgccat cattattatc cgatgtgacg ctgcagcttc 780
tcaatgatat tcgaatacgc tttgaggaga tacagcctaa tatccgacaa actgttttac 840
agatttacga tcgtacttgt tacccatcat tgaattttga acatccgaac ctgggagttt 900
tccctgaaac agatagtata tttgaacctg tataataata tatagtctag cgctttacgg 960
aagacaatgt atgtatttcg gttcctggag aaactattgc atctattgca taggtaatct 1020
tgcacgtcgc atccccggtt cattttctgc gtttccatct tgcacttcaa tagcatatct 1080
ttgttcgctt gcctgtaact tacacgcgcc tcgtatcttt taatgatgga ataatttggg 1140
aatttactct gtgtttattt atttttatgt tttgtatttg gattttagaa agtaaataaa 1200
gaaggtagaa gagttacgga atgaagaaaa aaaaataaac aaaggtttaa aaaatttcaa 1260
caaaaagcgt actttacata tatatttatt agacaagaaa agcagattaa atagatatac 1320
attcgattaa cgataagtaa aatgtaaaat cacaggattt tcgtgtgtgg tcttctacac 1380
agacaagatg aaacaattcg gcattaatac ctgagagcag gaagagcaag ataaaaggta 1440
gtatttgttg gcgatccccc tagagtcttt tacatcttcg gaaaacaaaa actatttttt 1500
ctttaatttc ttttttttact ttctattttt aatttatata tttatattaa aaaatttaaa 1560
ttataattat ttttatagca cgtgatgaaa aggaccggga agctccaccc cggttgataa 1620
tcagaaaagc cccaaaaaca ggaagattgt ataagcaaat atttaaattg taaacgttaa 1680
tattttgtta aaattcgcgt taaatttttg ttaaatcagc tcattttttta acgaatagcc 1740 cgaaatcggc aaaatccctt ataaatcaaa agaatagacc gagatagggt tgagtgttgt 1800

-continued

```
tccagtttcc aacaagagtc cactattaaa gaacgtggac tccaacgtca aagggcgaaa   1860
aagggtctat cagggcgatg gcccactacg tgaaccatca ccctaatcaa gtttttggg    1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttagc cttatttctg    2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggt taacatcatt cctgctatga   2760
aggacgtcgt gtgggggtg gatgtcactc aaaaaaacaa ggaagaaggt tatacccaca    2820
tcgttgaagt caccttcgaa tctgttgaaa ctattcaaga ctacatcagg cacccagctc   2880
acgtcggttt cggtgatgtt tacagatctt tctgggaaaa attgttgatc ttcgactaca   2940
ccccagagaa gtaataactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct tttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gttttttgt    4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
```

```
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
tactgtcatg ccatccgtaa gatgcttttc tgtgactggt gagtactcaa ccaagtcatt   4800
ctgagaatag tgtatgcggc gaccgagttg ctcttgcccg gcgtcaatac gggataatag   4860
tgtatcacat agcagaactt taaaagtgct catcattgga aaacgttctt cggggcgaaa   4920
actctcaagg atcttaccgc tgttgagatc cagttcgatg taacccactc gtgcacccaa   4980
ctgatcttca gcatctttta ctttcaccag cgtttctggg tgagcaaaaa caggaaggca   5040
aaatgccgca aaaaagggaa taagggcgac acggaaatgt tgaatactca tactcttcct   5100
ttttcaatgg gtaataactg atataattaa attgaagctc taatttgtga gtttagtata   5160
catgcattta cttataatac agttttttag ttttgctggc cgcatcttct caaatatgct   5220
tcccagcctg cttttctgta acgttcaccc tctaccttag catcccttcc ctttgcaaat   5280
agtcctcttc caacaataat aatgtcagat cctgtagaga ccacatcatc cacggttcta   5340
tactgttgac ccaatgcgtc tcccttgtca tctaaaccca caccgggtgt cataatcaac   5400
caatcgtaac cttcatctct tccacccatg tctctttgag caataaagcc gataacaaaa   5460
tctttgtcgc tcttcgcaat gtcaacagta cccttagtat attctccagt agatagggag   5520
cccttgcatg acaattctgc taacatcaaa aggcctctag gttcctttgt tacttcttct   5580
gccgcctgct tcaaaccgct aacaatacct gggcccacca caccgtgtgc attcgtaatg   5640
tctgcccatt ctgctattct gtatacaccc gcagagtact gcaatttgac tgtattacca   5700
atgtcagcaa attttctgtc ttcg                                          5724
```

<210> SEQ ID NO 36
<211> LENGTH: 5724
<212> TYPE: DNA
<213> ORGANISM: Artificial Sequence
<220> FEATURE:
<223> OTHER INFORMATION: OAC-V28A/V31G/Y41T/G43SILENT(=GGG)/K44V/I74E/
V84R/R100M/G102R

<400> SEQUENCE: 36

```
aagagtaaaa aattgtactt ggcggataat gcctttagcg gcttaactgt gccctccatg     60
gaaaaatcag tcaagatatc cacatgtgtt tttagtaaac aaattttggg acctaatgct    120
tcaactaact ccagtaattc cttggtggta cgaacatcca atgaagcaca caagtttgtt    180
tgcttttcgt gcatgatatt aaatagcttg gcagcaacag gactaggatg agtagcagca    240
cgttccttat atgtagcttt cgacatgatt tatcttcgtt tcctgcaggt ttttgttctg    300
tgcagttggg ttaagaatac tgggcaattt catgtttctt caacactaca tatgcgtata    360
tataccaatc taagtctgtg ctccttcctt cgttcttcct tctgttcgga gattaccgaa    420
```

-continued

```
tcaaaaaaat ttcaaagaaa ccgaaatcaa aaaaaagaat aaaaaaaaaa tgatgaattg    480
aattgaaaag ctagcttatc gatgataagc tgtcaaagat gagaattaat tccacggact    540
atagactata ctagatactc cgtctactgt acgatacact tccgctcagg tccttgtcct    600
ttaacgaggc cttaccactc ttttgttact ctattgatcc agctcagcaa aggcagtgtg    660
atctaagatt ctatcttcgc gatgtagtaa aactagctag accgagaaag agactagaaa    720
tgcaaaaggc acttctacaa tggctgccat cattattatc cgatgtgacg ctgcagcttc    780
tcaatgatat tcgaatacgc tttgaggaga tacagcctaa tatccgacaa actgttttac    840
agatttacga tcgtacttgt tacccatcat tgaattttga acatccgaac ctgggagttt    900
tccctgaaac agatagtata tttgaacctg tataataata tatagtctag cgctttacgg    960
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc tttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcatttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggg gaacatcatt cctgctatga   2760
aggacgtcac gtggggggtg gatgtcactc aaaaaaacaa ggaagaaggt tatacccaca   2820
```

tcgttgaagt caccttcgaa tctgttgaaa ctattcaaga ctacatcgag cacccagctc 2880
acgtcggttt cggtgatagg tacagatctt tctgggaaaa attgttgatc ttcgactaca 2940
ccccaatgaa gcggtaactc gagcatgcat ctagagggcc gcatcatgta attagttatg 3000
tcacgcttac attcacgccc tccccccaca tccgctctaa ccgaaaagga aggagttaga 3060
caacctgaag tctaggtccc tatttatttt tttatagtta tgttagtatt aagaacgtta 3120
tttatatttc aaatttttct tttttttctg tacagacgcg tgtacgcatg taacattata 3180
ctgaaaacct tgcttgagaa ggttttggga cgctcgaagg ctttaatttg cggccctgca 3240
ttaatgaatc ggccaacgcg cggggagagg cggtttgcgt attgggcgct cttccgcttc 3300
ctcgctcact gactcgctgc gctcggtcgt tcggctgcgg cgagcggtat cagctcactc 3360
aaaggcggta atacggttat ccacagaatc aggggataac gcaggaaaga acatgtgagc 3420
aaaaggccag caaaagccca ggaaccgtaa aaaggccgcg ttgctggcgt ttttccatag 3480
gctccgcccc cctgacgagc atcacaaaaa tcgacgctca agtcagaggt ggcgaaaccc 3540
gacaggacta taaagatacc aggcgtttcc ccctggaagc tccctcgtgc gctctcctgt 3600
tccgaccctg ccgcttaccg gatacctgtc cgcctttctc ccttcgggaa gcgtggcgct 3660
ttctcatagc tcacgctgta ggtatctcag ttcggtgtag gtcgttcgct ccaagctggg 3720
ctgtgtgcac gaaccccccg ttcagcccga ccgctgcgcc ttatccggta actatcgtct 3780
tgagtccaac ccggtaagac acgacttatc gccactggca gcagccactg gtaacaggat 3840
tagcagagcg aggtatgtag gcggtgctac agagttcttg aagtggtggc ctaactacgg 3900
ctacactaga agaacagtat ttggtatctg cgctctgctg aagccagtta ccttcggaaa 3960
aagagttggt agctcttgat ccggcaaaca aaccaccgct ggtagcggtg gtttttttgt 4020
ttgcaagcag cagattacgc gcagaaaaaa aggatctcaa gaagatcctt tgatcttttc 4080
tacggggtct gacgctcagt ggaacgaaaa ctcacgttaa gggattttgg tcatgagatt 4140
atcaaaaagg atcttcacct agatcctttt aaattaaaaa tgaagtttta aatcaatcta 4200
aagtatatat gagtaaactt ggtctgacag ttaccaatgc ttaatcagtg aggcacctat 4260
ctcagcgatc tgtctatttc gttcatccat agttgcctga ctccccgtcg tgtagataac 4320
tacgatacgg gagcgcttac catctggccc cagtgctgca atgataccgc gagacccacg 4380
ctcaccggct ccagatttat cagcaataaa ccagccagcc ggaagggccg agcgcagaag 4440
tggtcctgca actttatccg cctccattca gtctattaat tgttgccggg aagctagagt 4500
aagtagttcg ccagttaata gtttgcgcaa cgttgttggc attgctacag gcatcgtggt 4560
gtcactctcg tcgtttggta tggcttcatt cagctccggt tcccaacgat caaggcgagt 4620
tacatgatcc cccatgttgt gcaaaaaagc ggttagctcc ttcggtcctc cgatcgttgt 4680
cagaagtaag ttggccgcag tgttatcact catggttatg gcagcactgc ataattctct 4740
tactgtcatg ccatccgtaa gatgcttttc tgtgactggt gagtactcaa ccaagtcatt 4800
ctgagaatag tgtatgcggc gaccgagttg ctcttgcccg gcgtcaatac gggataatag 4860
tgtatcacat agcagaactt taaaagtgct catcattgga aaacgttctt cggggcgaaa 4920
actctcaagg atcttaccgc tgttgagatc cagttcgatg taacccactc gtgcacccaa 4980
ctgatcttca gcatctttta ctttcaccag cgtttctggg tgagcaaaaa caggaaggca 5040
aaatgccgca aaaaagggaa taagggcgac acggaaatgt tgaatactca tactcttcct 5100
ttttcaatgg gtaataactg atataattaa attgaagctc taatttgtga gtttagtata 5160
catgcattta cttataatac agttttttag ttttgctggc cgcatcttct caaatatgct 5220
tcccagcctg cttttctgta acgttcaccc tctaccttag catcccttcc ctttgcaaat 5280
agtcctcttc caacaataat aatgtcagat cctgtagaga ccacatcatc cacggttcta 5340
tactgttgac ccaatgcgtc tcccttgtca tctaaaccca caccgggtgt cataatcaac 5400
caatcgtaac cttcatctct tccacccatg tctctttgag caataaagcc gataacaaaa 5460
tctttgtcgc tcttcgcaat gtcaacagta cccttagtat attctccagt agatagggag 5520
cccttgcatg acaattctgc taacatcaaa aggcctctag gttcctttgt tacttcttct 5580
gccgcctgct tcaaaccgct aacaatacct gggcccacca caccgtgtgc attcgtaatg 5640
tctgcccatt ctgctattct gtatacaccc gcagagtact gcaatttgac tgtattacca 5700
atgtcagcaa attttctgtc ttcg 5724

<210> SEQ ID NO 37
<211> LENGTH: 5724
<212> TYPE: DNA
<213> ORGANISM: Artificial Sequence
<220> FEATURE:
<223> OTHER INFORMATION: OAC-V28A/G43SILENT(=GGG)/K44V/T68R/I74E/V84R/
R100E/G102STOP

<400> SEQUENCE: 37
aagagtaaaa aattgtactt ggcggataat gcctttagcg gcttaactgt gccctccatg 60
gaaaaatcag tcaagatatc cacatgtgtt tttagtaaac aaattttggg acctaatgct 120
tcaactaact ccagtaattc cttggtggta cgaacatcca atgaagcaca caagtttgtt 180
tgcttttcgt gcatgatatt aaatagcttg gcagcaacag gactaggatg agtagcagca 240
cgttccttat atgtagcttt cgacatgatt tatcttcgtt tcctgcaggt ttttgttctg 300
tgcagttggg ttaagaatac tgggcaattt catgtttctt caacactaca tatgcgtata 360
tataccaatc taagtctgtg ctccttcctt cgttcttcct tctgttcgga gattaccgaa 420
tcaaaaaaat ttcaaagaaa ccgaaatcaa aaaaaagaat aaaaaaaaaa tgatgaattg 480
aattgaaaag ctagcttatc gatgataagc tgtcaaagat gagaattaat tccacggact 540
atagactata ctagatactc cgtctactgt acgatacact tccgctcagg tccttgtcct 600
ttaacgaggc cttaccactc ttttgttact ctattgatcc agctcagcaa aggcagtgtg 660
atctaagatt ctatcttcgc gatgtagtaa aactagctag accgagaaag agactagaaa 720
tgcaaaaggc acttctacaa tggctgccat cattattatc cgatgtgacg ctgcagcttc 780
tcaatgatat tcgaatacgc tttgaggaga tacagcctaa tatccgacaa actgttttac 840
agatttacga tcgtacttgt tacccatcat tgaattttga acatccgaac ctgggagttt 900
tccctgaaac agatagtata tttgaacctg tataataata tatagtctag cgctttacgg 960
aagacaatgt atgtatttcg gttcctggag aaactattgc atctattgca taggtaatct 1020
tgcacgtcgc atccccggtt cattttctgc gtttccatct tgcacttcaa tagcatatct 1080
ttgttcgctt gcctgtaact tacacgcgcc tcgtatcttt taatgatgga ataatttggg 1140
aatttactct gtgtttattt atttttatgt tttgtatttg gattttagaa agtaaataaa 1200
gaaggtagaa gagttacgga atgaagaaaa aaaaataaac aaaggtttaa aaaatttcaa 1260
caaaaagcgt actttacata tatatttatt agacaagaaa agcagattaa atagatatac 1320
attcgattaa cgataagtaa aatgtaaaat cacaggattt tcgtgtgtgg tcttctacac 1380
agacaagatg aaacaattcg gcattaatac ctgagagcag gaagagcaag ataaaaggta 1440

-continued

```
gtatttgttg gcgatccccc tagagtcttt tacatcttcg gaaaacaaaa actatttttt   1500
ctttaatttc tttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcatttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg cgaacttggt taacatcatt cctgctatga   2760
aggacgtcta ctgggggggtg gatgtcactc aaaaaaacaa ggaagaaggt tatacccaca   2820
tcgttgaagt caccttcgaa tctgttgaac ggattcaaga ctacatcgag cacccagctc   2880
acgtcggttt cggtgatagg tacagatctt tctgggaaaa attgttgatc ttcgactaca   2940
ccccagagaa gtaataactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct ttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
```

tagcagagcg aggtatgtag gcggtgctac agagttcttg aagtggtggc ctaactacgg 3900
ctacactaga agaacagtat ttggtatctg cgctctgctg aagccagtta ccttcggaaa 3960
aagagttggt agctcttgat ccggcaaaca aaccaccgct ggtagcggtg gtttttttgt 4020
ttgcaagcag cagattacgc gcagaaaaaa aggatctcaa gaagatcctt tgatcttttc 4080
tacggggtct gacgctcagt ggaacgaaaa ctcacgttaa gggattttgg tcatgagatt 4140
atcaaaaagg atcttcacct agatcctttt aaattaaaaa tgaagtttta aatcaatcta 4200
aagtatatat gagtaaactt ggtctgacag ttaccaatgc ttaatcagtg aggcacctat 4260
ctcagcgatc tgtctatttc gttcatccat agttgcctga ctccccgtcg tgtagataac 4320
tacgatacgg gagcgcttac catctggccc cagtgctgca atgataccgc gagacccacg 4380
ctcaccggct ccagatttat cagcaataaa ccagccagcc ggaagggccg agcgcagaag 4440
tggtcctgca actttatccg cctccattca gtctattaat tgttgccggg aagctagagt 4500
aagtagttcg ccagttaata gtttgcgcaa cgttgttggc attgctacag gcatcgtggt 4560
gtcactctcg tcgtttggta tggcttcatt cagctccggt tcccaacgat caaggcgagt 4620
tacatgatcc cccatgttgt gcaaaaaagc ggttagctcc ttcggtcctc cgatcgttgt 4680
cagaagtaag ttggccgcag tgttatcact catggttatg gcagcactgc ataattctct 4740
tactgtcatg ccatccgtaa gatgcttttc tgtgactggt gagtactcaa ccaagtcatt 4800
ctgagaatag tgtatgcggc gaccgagttg ctcttgcccg gcgtcaatac gggataatag 4860
tgtatcacat agcagaactt taaaagtgct catcattgga aaacgttctt cggggcgaaa 4920
actctcaagg atcttaccgc tgttgagatc cagttcgatg taacccactc gtgcacccaa 4980
ctgatcttca gcatctttta ctttcaccag cgtttctggg tgagcaaaaa caggaaggca 5040
aaatgccgca aaaaagggaa taagggcgac acggaaatgt tgaatactca tactcttcct 5100
ttttcaatgg gtaataactg atataattaa attgaagctc taatttgtga gtttagtata 5160
catgcattta cttataatac agttttttag ttttgctggc cgcatcttct caaatatgct 5220
tcccagcctg cttttctgta acgttcaccc tctaccttag catcccttcc ctttgcaaat 5280
agtcctcttc caacaataat aatgtcagat cctgtagaga ccacatcatc cacggttcta 5340
tactgttgac ccaatgcgtc tcccttgtca tctaaaccca caccgggtgt cataatcaac 5400
caatcgtaac cttcatctct tccacccatg tctctttgag caataaagcc gataacaaaa 5460
tctttgtcgc tcttcgcaat gtcaacagta cccttagtat attctccagt agatagggag 5520
cccttgcatg acaattctgc taacatcaaa aggcctctag gttcctttgt tacttcttct 5580
gccgcctgct tcaaaccgct aacaatacct gggcccacca caccgtgtgc attcgtaatg 5640
tctgcccatt ctgctattct gtatacaccc gcagagtact gcaatttgac tgtattacca 5700
atgtcagcaa attttctgtc ttcg 5724

<210> SEQ ID NO 38
<211> LENGTH: 5724
<212> TYPE: DNA
<213> ORGANISM: Artificial Sequence
<220> FEATURE:
<223> OTHER INFORMATION: OAC-V31G/Y41T/G43SILENT(=GGG)/K44V/T68L/I74D/
V84R/G102R

<400> SEQUENCE: 38
aagagtaaaa aattgtactt ggcggataat gcctttagcg gcttaactgt gccctccatg 60
gaaaaatcag tcaagatatc cacatgtgtt tttagtaaac aaattttggg acctaatgct 120

```
tcaactaact ccagtaattc cttggtggta cgaacatcca atgaagcaca caagtttgtt    180
tgcttttcgt gcatgatatt aaatagcttg gcagcaacag gactaggatg agtagcagca    240
cgttccttat atgtagcttt cgacatgatt tatcttcgtt tcctgcaggt ttttgttctg    300
tgcagttggg ttaagaatac tgggcaattt catgtttctt caacactaca tatgcgtata    360
tataccaatc taagtctgtg ctccttcctt cgttcttcct tctgttcgga gattaccgaa    420
tcaaaaaaat ttcaaagaaa ccgaaatcaa aaaaaagaat aaaaaaaaaa tgatgaattg    480
aattgaaaag ctagcttatc gatgataagc tgtcaaagat gagaattaat tccacggact    540
atagactata ctagatactc cgtctactgt acgatacact tccgctcagg tccttgtcct    600
ttaacgaggc cttaccactc ttttgttact ctattgatcc agctcagcaa aggcagtgtg    660
atctaagatt ctatcttcgc gatgtagtaa aactagctag accgagaaag agactagaaa    720
tgcaaaaggc acttctacaa tggctgccat cattattatc cgatgtgacg ctgcagcttc    780
tcaatgatat tcgaatacgc tttgaggaga tacagcctaa tatccgacaa actgttttac    840
agatttacga tcgtacttgt tacccatcat tgaattttga acatccgaac ctgggagttt    900
tccctgaaac agatagtata tttgaacctg tataataata tatagtctag cgctttacgg    960
aagacaatgt atgtatttcg gttcctggag aaactattgc atctattgca taggtaatct   1020
tgcacgtcgc atccccggtt cattttctgc gtttccatct tgcacttcaa tagcatatct   1080
ttgttcgctt gcctgtaact tacacgcgcc tcgtatcttt taatgatgga ataatttggg   1140
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc tttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcattttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gtttttggg    1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttagc cttatttctg    2400
gggtaattaa tcagcgaagc gatgattttt gatctattaa cagatatata aatgcaaaaa   2460
```

-continued

```
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg ttaacttggg gaacatcatt cctgctatga   2760
aggacgtcac gtggggggtg gatgtcactc aaaaaaacaa ggaagaaggt tatacccaca   2820
tcgttgaagt caccttcgaa tctgttgaac tgattcaaga ctacatcgac cacccagctc   2880
acgtcggttt cggtgatagg tacagatctt tctgggaaaa attgttgatc ttcgactaca   2940
ccccaagaaa gcggtaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaatttttct tttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
gctccgcccc cctgacgagc atcacaaaaa tcgacgctca agtcagaggt ggcgaaaccc   3540
gacaggacta taaagatacc aggcgtttcc ccctggaagc tccctcgtgc gctctcctgt   3600
tccgaccctg ccgcttaccg gatacctgtc cgcctttctc ccttcgggaa gcgtggcgct   3660
ttctcatagc tcacgctgta ggtatctcag ttcggtgtag gtcgttcgct ccaagctggg   3720
ctgtgtgcac gaaccccccg ttcagcccga ccgctgcgcc ttatccggta actatcgtct   3780
tgagtccaac ccggtaagac acgacttatc gccactggca gcagccactg gtaacaggat   3840
tagcagagcg aggtatgtag gcggtgctac agagttcttg aagtggtggc ctaactacgg   3900
ctacactaga agaacagtat ttggtatctg cgctctgctg aagccagtta ccttcggaaa   3960
aagagttggt agctcttgat ccggcaaaca aaccaccgct ggtagcggtg gtttttttgt   4020
ttgcaagcag cagattacgc gcagaaaaaa aggatctcaa gaagatcctt tgatcttttc   4080
tacggggtct gacgctcagt ggaacgaaaa ctcacgttaa gggattttgg tcatgagatt   4140
atcaaaaagg atcttcacct agatcctttt aaattaaaaa tgaagtttta aatcaatcta   4200
aagtatatat gagtaaactt ggtctgacag ttaccaatgc ttaatcagtg aggcacctat   4260
ctcagcgatc tgtctatttc gttcatccat agttgcctga ctccccgtcg tgtagataac   4320
tacgatacgg gagcgcttac catctggccc cagtgctgca atgataccgc gagacccacg   4380
ctcaccggct ccagatttat cagcaataaa ccagccagcc ggaagggccg agcgcagaag   4440
tggtcctgca actttatccg cctccattca gtctattaat tgttgccggg aagctagagt   4500
aagtagttcg ccagttaata gtttgcgcaa cgttgttggc attgctacag gcatcgtggt   4560
gtcactctcg tcgtttggta tggcttcatt cagctccggt tcccaacgat caaggcgagt   4620
tacatgatcc cccatgttgt gcaaaaaagc ggttagctcc ttcggtcctc cgatcgttgt   4680
cagaagtaag ttggccgcag tgttatcact catggttatg gcagcactgc ataattctct   4740
tactgtcatg ccatccgtaa gatgcttttc tgtgactggt gagtactcaa ccaagtcatt   4800
ctgagaatag tgtatgcggc gaccgagttg ctcttgcccg gcgtcaatac gggataatag   4860
```

tgtatcacat agcagaactt taaaagtgct catcattgga aaacgttctt cggggcgaaa 4920
actctcaagg atcttaccgc tgttgagatc cagttcgatg taacccactc gtgcacccaa 4980
ctgatcttca gcatctttta ctttcaccag cgtttctggg tgagcaaaaa caggaaggca 5040
aaatgccgca aaaaagggaa taagggcgac acggaaatgt tgaatactca tactcttcct 5100
ttttcaatgg gtaataactg atataattaa attgaagctc taatttgtga gtttagtata 5160
catgcattta cttataatac agttttttag ttttgctggc cgcatcttct caaatatgct 5220
tcccagcctg cttttctgta acgttcaccc tctaccttag catcccttcc ctttgcaaat 5280
agtcctcttc caacaataat aatgtcagat cctgtagaga ccacatcatc cacggttcta 5340
tactgttgac ccaatgcgtc tcccttgtca tctaaaccca caccgggtgt cataatcaac 5400
caatcgtaac cttcatctct tccacccatg tctctttgag caataaagcc gataacaaaa 5460
tctttgtcgc tcttcgcaat gtcaacagta cccttagtat attctccagt agatagggag 5520
cccttgcatg acaattctgc taacatcaaa aggcctctag gttcctttgt tacttcttct 5580
gccgcctgct tcaaaccgct aacaatacct gggcccacca caccgtgtgc attcgtaatg 5640
tctgcccatt ctgctattct gtatacaccc gcagagtact gcaatttgac tgtattacca 5700
atgtcagcaa attttctgtc ttcg 5724

<210> SEQ ID NO 39
<211> LENGTH: 5724
<212> TYPE: DNA
<213> ORGANISM: Artificial Sequence
<220> FEATURE:
<223> OTHER INFORMATION: OAC-Y41V/G43SILENT(=GGG)/K44V/T68L/I74R/V84R/
G102R

<400> SEQUENCE: 39
aagagtaaaa aattgtactt ggcggataat gcctttagcg gcttaactgt gccctccatg 60
gaaaaatcag tcaagatatc cacatgtgtt tttagtaaac aaattttggg acctaatgct 120
tcaactaact ccagtaattc cttggtggta cgaacatcca atgaagcaca caagtttgtt 180
tgcttttcgt gcatgatatt aaatagcttg gcagcaacag gactaggatg agtagcagca 240
cgttccttat atgtagcttt cgacatgatt tatcttcgtt tcctgcaggt ttttgttctg 300
tgcagttggg ttaagaatac tgggcaattt catgtttctt caacactaca tatgcgtata 360
tataccaatc taagtctgtg ctccttcctt cgttcttcct tctgttcgga gattaccgaa 420
tcaaaaaaat ttcaaagaaa ccgaaatcaa aaaaaagaat aaaaaaaaaa tgatgaattg 480
aattgaaaag ctagcttatc gatgataagc tgtcaaagat gagaattaat tccacggact 540
atagactata ctagatactc cgtctactgt acgatacact tccgctcagg tccttgtcct 600
ttaacgaggc cttaccactc ttttgttact ctattgatcc agctcagcaa aggcagtgtg 660
atctaagatt ctatcttcgc gatgtagtaa aactagctag accgagaaag agactagaaa 720
tgcaaaaggc acttctacaa tggctgccat cattattatc cgatgtgacg ctgcagcttc 780
tcaatgatat tcgaatacgc tttgaggaga tacagcctaa tatccgacaa actgttttac 840
agatttacga tcgtacttgt tacccatcat tgaattttga acatccgaac ctgggagttt 900
tccctgaaac agatagtata tttgaacctg tataataata tatagtctag cgctttacgg 960
aagacaatgt atgtatttcg gttcctggag aaactattgc atctattgca taggtaatct 1020
tgcacgtcgc atccccggtt cattttctgc gtttccatct tgcacttcaa tagcatatct 1080
ttgttcgctt gcctgtaact tacacgcgcc tcgtatcttt taatgatgga ataatttggg 1140

```
aatttactct gtgtttattt atttttatgt tttgtatttg gattttagaa agtaaataaa   1200
gaaggtagaa gagttacgga atgaagaaaa aaaaataaac aaaggtttaa aaaatttcaa   1260
caaaaagcgt actttacata tatatttatt agacaagaaa agcagattaa atagatatac   1320
attcgattaa cgataagtaa aatgtaaaat cacaggattt tcgtgtgtgg tcttctacac   1380
agacaagatg aaacaattcg gcattaatac ctgagagcag gaagagcaag ataaaaggta   1440
gtatttgttg gcgatccccc tagagtcttt tacatcttcg gaaaacaaaa actatttttt   1500
ctttaatttc ttttttttact ttctattttt aatttatata tttatattaa aaaatttaaa   1560
ttataattat ttttatagca cgtgatgaaa aggaccggga agctccaccc cggttgataa   1620
tcagaaaagc cccaaaaaca ggaagattgt ataagcaaat atttaaattg taaacgttaa   1680
tattttgtta aaattcgcgt taaatttttg ttaaatcagc tcattttttta acgaatagcc   1740
cgaaatcggc aaaatccctt ataaatcaaa agaatagacc gagatagggt tgagtgttgt   1800
tccagtttcc aacaagagtc cactattaaa gaacgtggac tccaacgtca aagggcgaaa   1860
aagggtctat cagggcgatg gcccactacg tgaaccatca ccctaatcaa gtttttttggg   1920
gtcgaggtgc cgtaaagcag taaatcggaa gggtaaacgg atgcccccat ttagagcttg   1980
acggggaaag ccggcgaacg tggcgagaaa ggaagggaag aaagcgaaag gagcgggggc   2040
tagggcggtg ggaagtgtag gggtcacgct gggcgtaacc accacacccg ccgcgcttaa   2100
tggggcgcta cagggcgcgt ggggatgatc cactagtacg gattagaagc cgccgagcgg   2160
gtgacagccc tccgaaggaa gactctcctc cgtgcgtcct cgtcttcacc ggtcgcgttc   2220
ctgaaacgca gatgtgcctc gcgccgcact gctccgaaca ataaagattc tacaatacta   2280
gcttttatgg ttatgaagag gaaaaattgg cagtaacctg gccccacaaa ccttcaaatg   2340
aacgaatcaa attaacaacc ataggatgat aatgcgatta gtttttttagc cttatttctg   2400
gggtaattaa tcagcgaagc gatgattttt gatctattaa cagatatata aatgcaaaaa   2460
ctgcataacc actttaacta atactttcaa cattttcggt ttgtattact tcttattcaa   2520
atgtaataaa agtatcaaca aaaaattgtt aatatacctc tatactttaa cgtcaaggag   2580
aaaaaacccc ggatcggact actagcagct gtaatacgac tcactatagg gaatattaag   2640
cttaaacaat ggccgtcaag cacttgatcg tcttaaagtt taaggacgag atcactgaag   2700
cccaaaagga agaattcttc aaaacttacg ttaacttggt taacatcatt cctgctatga   2760
aggacgtcgt gtggggggtg gatgtcactc aaaaaaacaa ggaagaaggt tatacccaca   2820
tcgttgaagt caccttcgaa tctgttgaac tgattcaaga ctacatcagg cacccagctc   2880
acgtcggttt cggtgatagg tacagatctt tctgggaaaa attgttgatc ttcgactaca   2940
ccccaagaaa gcggtaactc gagcatgcat ctagagggcc gcatcatgta attagttatg   3000
tcacgcttac attcacgccc tccccccaca tccgctctaa ccgaaaagga aggagttaga   3060
caacctgaag tctaggtccc tatttatttt tttatagtta tgttagtatt aagaacgtta   3120
tttatatttc aaattttttct tttttttctg tacagacgcg tgtacgcatg taacattata   3180
ctgaaaacct tgcttgagaa ggttttggga cgctcgaagg ctttaatttg cggccctgca   3240
ttaatgaatc ggccaacgcg cggggagagg cggtttgcgt attgggcgct cttccgcttc   3300
ctcgctcact gactcgctgc gctcggtcgt tcggctgcgg cgagcggtat cagctcactc   3360
aaaggcggta atacggttat ccacagaatc aggggataac gcaggaaaga acatgtgagc   3420
aaaaggccag caaaagccca ggaaccgtaa aaaggccgcg ttgctggcgt ttttccatag   3480
```

gctccgcccc cctgacgagc atcacaaaaa tcgacgctca agtcagaggt ggcgaaaccc 3540
gacaggacta taaagatacc aggcgtttcc ccctggaagc tccctcgtgc gctctcctgt 3600
tccgaccctg ccgcttaccg gatacctgtc cgcctttctc ccttcgggaa gcgtggcgct 3660
ttctcatagc tcacgctgta ggtatctcag ttcggtgtag gtcgttcgct ccaagctggg 3720
ctgtgtgcac gaaccccccg ttcagcccga ccgctgcgcc ttatccggta actatcgtct 3780
tgagtccaac ccggtaagac acgacttatc gccactggca gcagccactg gtaacaggat 3840
tagcagagcg aggtatgtag gcggtgctac agagttcttg aagtggtggc ctaactacgg 3900
ctacactaga agaacagtat ttggtatctg cgctctgctg aagccagtta ccttcggaaa 3960
aagagttggt agctcttgat ccggcaaaca aaccaccgct ggtagcggtg gtttttttgt 4020
ttgcaagcag cagattacgc gcagaaaaaa aggatctcaa gaagatcctt tgatcttttc 4080
tacggggtct gacgctcagt ggaacgaaaa ctcacgttaa gggattttgg tcatgagatt 4140
atcaaaaagg atcttcacct agatcctttt aaattaaaaa tgaagtttta aatcaatcta 4200
aagtatatat gagtaaactt ggtctgacag ttaccaatgc ttaatcagtg aggcacctat 4260
ctcagcgatc tgtctatttc gttcatccat agttgcctga ctccccgtcg tgtagataac 4320
tacgatacgg gagcgcttac catctggccc cagtgctgca atgataccgc gagacccacg 4380
ctcaccggct ccagatttat cagcaataaa ccagccagcc ggaagggccg agcgcagaag 4440
tggtcctgca actttatccg cctccattca gtctattaat tgttgccggg aagctagagt 4500
aagtagttcg ccagttaata gtttgcgcaa cgttgttggc attgctacag gcatcgtggt 4560
gtcactctcg tcgtttggta tggcttcatt cagctccggt tcccaacgat caaggcgagt 4620
tacatgatcc cccatgttgt gcaaaaaagc ggttagctcc ttcggtcctc cgatcgttgt 4680
cagaagtaag ttggccgcag tgttatcact catggttatg gcagcactgc ataattctct 4740
tactgtcatg ccatccgtaa gatgcttttc tgtgactggt gagtactcaa ccaagtcatt 4800
ctgagaatag tgtatgcggc gaccgagttg ctcttgcccg gcgtcaatac gggataatag 4860
tgtatcacat agcagaactt taaaagtgct catcattgga aaacgttctt cggggcgaaa 4920
actctcaagg atcttaccgc tgttgagatc cagttcgatg taacccactc gtgcacccaa 4980
ctgatcttca gcatctttta ctttcaccag cgtttctggg tgagcaaaaa caggaaggca 5040
aaatgccgca aaaaagggaa taagggcgac acggaaatgt tgaatactca tactcttcct 5100
ttttcaatgg gtaataactg atataattaa attgaagctc taatttgtga gtttagtata 5160
catgcattta cttataatac agttttttag ttttgctggc cgcatcttct caaatatgct 5220
tcccagcctg cttttctgta acgttcaccc tctaccttag catcccttcc ctttgcaaat 5280
agtcctcttc caacaataat aatgtcagat cctgtagaga ccacatcatc cacggttcta 5340
tactgttgac ccaatgcgtc tcccttgtca tctaaaccca caccgggtgt cataatcaac 5400
caatcgtaac cttcatctct tccacccatg tctctttgag caataaagcc gataacaaaa 5460
tctttgtcgc tcttcgcaat gtcaacagta cccttagtat attctccagt agatagggag 5520
cccttgcatg acaattctgc taacatcaaa aggcctctag gttcctttgt tacttcttct 5580
gccgcctgct tcaaaccgct aacaatacct gggcccacca caccgtgtgc attcgtaatg 5640
tctgcccatt ctgctattct gtatacaccc gcagagtact gcaatttgac tgtattacca 5700
atgtcagcaa attttctgtc ttcg 5724

<210> SEQ ID NO 40
<211> LENGTH: 102

```
<212> TYPE: PRT
<213> ORGANISM: Artificial Sequence
<220> FEATURE:
<223> OTHER INFORMATION: OAC-V28A/Y41T/G43SILENT(=GGG)/T68L/I74E/V84R/
      R100M/G102R

<400> SEQUENCE: 40

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Ala Asn Leu Val Asn
            20                  25                  30

Ile Ile Pro Ala Met Lys Asp Val Thr Trp Gly Lys Asp Val Thr Gln
        35                  40                  45

Lys Asn Lys Glu Glu Gly Tyr Thr His Ile Val Glu Val Thr Phe Glu
    50                  55                  60

Ser Val Glu Leu Ile Gln Asp Tyr Ile Glu His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Met Lys Arg
            100


<210> SEQ ID NO 41
<211> LENGTH: 102
<212> TYPE: PRT
<213> ORGANISM: Artificial Sequence
<220> FEATURE:
<223> OTHER INFORMATION: OAC-Y41S/G43SILENT(=GGG)/K44V/T68R/I74R/V84R

<400> SEQUENCE: 41

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Val Asn
            20                  25                  30

Ile Ile Pro Ala Met Lys Asp Val Ser Trp Gly Val Asp Val Thr Gln
        35                  40                  45

Lys Asn Lys Glu Glu Gly Tyr Thr His Ile Val Glu Val Thr Phe Glu
    50                  55                  60

Ser Val Glu Arg Ile Gln Asp Tyr Ile Arg His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Arg Lys Gly
            100


<210> SEQ ID NO 42
<211> LENGTH: 102
<212> TYPE: PRT
<213> ORGANISM: Artificial Sequence
<220> FEATURE:
<223> OTHER INFORMATION: OAC-V28A/V31G/Y41S/G43SILENT(=GGG)/K44V/T68L/
      I74R/V84R/R100E/G102R

<400> SEQUENCE: 42

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Ala Asn Leu Gly Asn
            20                  25                  30

Ile Ile Pro Ala Met Lys Asp Val Ser Trp Gly Val Asp Val Thr Gln
        35                  40                  45
```

Lys Asn Lys Glu Glu Gly Tyr Thr His Ile Val Glu Val Thr Phe Glu
50 55 60

Ser Val Glu Leu Ile Gln Asp Tyr Ile Arg His Pro Ala His Val Gly
65 70 75 80

Phe Gly Asp Arg Tyr Arg Ser Phe Trp Glu Lys Leu Leu Ile Phe Asp
85 90 95

Tyr Thr Pro Glu Lys Arg
100

<210> SEQ ID NO 43
<211> LENGTH: 102
<212> TYPE: PRT
<213> ORGANISM: Artificial Sequence
<220> FEATURE:
<223> OTHER INFORMATION: OAC-V28A/Y41T/G43SILENT(=GGG)/T68L/I74G/V84R/R100E

<400> SEQUENCE: 43

Met Ala Val Lys His Leu Ile Val Leu Lys Phe Lys Asp Glu Ile Thr
1 5 10 15

Glu Ala Gln Lys Glu Glu Phe Phe Lys Thr Tyr Ala Asn Leu Val Asn
20 25 30

Ile Ile Pro Ala Met Lys Asp Val Thr Trp Gly Lys Asp Val Thr Gln
35 40 45

Lys Asn Lys Glu Glu Gly Tyr Thr His Ile Val Glu Val Thr Phe Glu
50 55 60

Ser Val Glu Leu Ile Gln Asp Tyr Ile Gly His Pro Ala His Val Gly
65 70 75 80

Phe Gly Asp Arg Tyr Arg Ser Phe Trp Glu Lys Leu Leu Ile Phe Asp
85 90 95

Tyr Thr Pro Glu Lys Gly
100

<210> SEQ ID NO 44
<211> LENGTH: 102
<212> TYPE: PRT
<213> ORGANISM: Artificial Sequence
<220> FEATURE:
<223> OTHER INFORMATION: OAC-V28A/Y41T/G43SILENT(=GGG)/K44V/T68L/I74D/V84R/R100M/G102R

<400> SEQUENCE: 44

Met Ala Val Lys His Leu Ile Val Leu Lys Phe Lys Asp Glu Ile Thr
1 5 10 15

Glu Ala Gln Lys Glu Glu Phe Phe Lys Thr Tyr Ala Asn Leu Val Asn
20 25 30

Ile Ile Pro Ala Met Lys Asp Val Thr Trp Gly Val Asp Val Thr Gln
35 40 45

Lys Asn Lys Glu Glu Gly Tyr Thr His Ile Val Glu Val Thr Phe Glu
50 55 60

Ser Val Glu Leu Ile Gln Asp Tyr Ile Asp His Pro Ala His Val Gly
65 70 75 80

Phe Gly Asp Arg Tyr Arg Ser Phe Trp Glu Lys Leu Leu Ile Phe Asp
85 90 95

Tyr Thr Pro Met Lys Arg
100

<210> SEQ ID NO 45

<211> LENGTH: 102
<212> TYPE: PRT
<213> ORGANISM: Artificial Sequence
<220> FEATURE:
<223> OTHER INFORMATION: OAC-V28A/Y41T/G43SILENT(=GGG)/T68L/I74D/V84R/
G102R

<400> SEQUENCE: 45

```
Met Ala Val Lys His Leu Ile Val Leu Lys Phe Lys Asp Glu Ile Thr
1               5                   10                  15

Glu Ala Gln Lys Glu Glu Phe Phe Lys Thr Tyr Ala Asn Leu Val Asn
            20                  25                  30

Ile Ile Pro Ala Met Lys Asp Val Thr Trp Gly Lys Asp Val Thr Gln
        35                  40                  45

Lys Asn Lys Glu Glu Gly Tyr Thr His Ile Val Glu Val Thr Phe Glu
    50                  55                  60

Ser Val Glu Leu Ile Gln Asp Tyr Ile Asp His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Arg Lys Arg
            100
```

<210> SEQ ID NO 46
<211> LENGTH: 102
<212> TYPE: PRT
<213> ORGANISM: Artificial Sequence
<220> FEATURE:
<223> OTHER INFORMATION: OAC-V28A/Y41T/G43SILENT(=GGG)/K44V/T68L/I74R/
V84R/R100E/G102R

<400> SEQUENCE: 46

```
Met Ala Val Lys His Leu Ile Val Leu Lys Phe Lys Asp Glu Ile Thr
1               5                   10                  15

Glu Ala Gln Lys Glu Glu Phe Phe Lys Thr Tyr Ala Asn Leu Val Asn
            20                  25                  30

Ile Ile Pro Ala Met Lys Asp Val Thr Trp Gly Val Asp Val Thr Gln
        35                  40                  45

Lys Asn Lys Glu Glu Gly Tyr Thr His Ile Val Glu Val Thr Phe Glu
    50                  55                  60

Ser Val Glu Leu Ile Gln Asp Tyr Ile Arg His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Glu Lys Arg
            100
```

<210> SEQ ID NO 47
<211> LENGTH: 101
<212> TYPE: PRT
<213> ORGANISM: Artificial Sequence
<220> FEATURE:
<223> OTHER INFORMATION: OAC-Y41T/G43SILENT(=GGG)/T68R/I74R/V84R/R100M/
G102STOP

<400> SEQUENCE: 47

```
Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Val Asn
            20                  25                  30
```

```
Ile Ile Pro Ala Met Lys Asp Val Thr Trp Gly Lys Asp Val Thr Gln
        35                  40                  45

Lys Asn Lys Glu Glu Gly Tyr Thr His Ile Val Glu Val Thr Phe Glu
    50                  55                  60

Ser Val Glu Arg Ile Gln Asp Tyr Ile Arg His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Met Lys
            100


<210> SEQ ID NO 48
<211> LENGTH: 102
<212> TYPE: PRT
<213> ORGANISM: Artificial Sequence
<220> FEATURE:
<223> OTHER INFORMATION:
      OAC-V28A/Y41V/G43SILENT(=GGG)/K44V/T68L/I74G/V84R/R100E/G102R

<400> SEQUENCE: 48

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Ala Asn Leu Val Asn
            20                  25                  30

Ile Ile Pro Ala Met Lys Asp Val Val Trp Gly Val Asp Val Thr Gln
        35                  40                  45

Lys Asn Lys Glu Glu Gly Tyr Thr His Ile Val Glu Val Thr Phe Glu
    50                  55                  60

Ser Val Glu Leu Ile Gln Asp Tyr Ile Gly His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Glu Lys Arg
            100


<210> SEQ ID NO 49
<211> LENGTH: 101
<212> TYPE: PRT
<213> ORGANISM: Artificial Sequence
<220> FEATURE:
<223> OTHER INFORMATION: OAC-V28A/Y41T/G43SILENT(=GGG)/K44V/T68R/I74G/
      V84R/G102STOP

<400> SEQUENCE: 49

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Ala Asn Leu Val Asn
            20                  25                  30

Ile Ile Pro Ala Met Lys Asp Val Thr Trp Gly Val Asp Val Thr Gln
        35                  40                  45

Lys Asn Lys Glu Glu Gly Tyr Thr His Ile Val Glu Val Thr Phe Glu
    50                  55                  60

Ser Val Glu Arg Ile Gln Asp Tyr Ile Gly His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Arg Lys
            100
```

<210> SEQ ID NO 50
<211> LENGTH: 101
<212> TYPE: PRT
<213> ORGANISM: Artificial Sequence
<220> FEATURE:
<223> OTHER INFORMATION: OAC-V28A/Y41V/G43SILENT(=GGG)/K44V/T68L/I74R/V84R/R100E/G102STOP

<400> SEQUENCE: 50

Met Ala Val Lys His Leu Ile Val Leu Lys Phe Lys Asp Glu Ile Thr
1 5 10 15

Glu Ala Gln Lys Glu Glu Phe Phe Lys Thr Tyr Ala Asn Leu Val Asn
20 25 30

Ile Ile Pro Ala Met Lys Asp Val Val Trp Gly Val Asp Val Thr Gln
35 40 45

Lys Asn Lys Glu Glu Gly Tyr Thr His Ile Val Glu Val Thr Phe Glu
50 55 60

Ser Val Glu Leu Ile Gln Asp Tyr Ile Arg His Pro Ala His Val Gly
65 70 75 80

Phe Gly Asp Arg Tyr Arg Ser Phe Trp Glu Lys Leu Leu Ile Phe Asp
85 90 95

Tyr Thr Pro Glu Lys
100

<210> SEQ ID NO 51
<211> LENGTH: 102
<212> TYPE: PRT
<213> ORGANISM: Artificial Sequence
<220> FEATURE:
<223> OTHER INFORMATION: OAC-V28A/V31G/Y41T/G43SILENT(=GGG)/K44V/T68R/I74E/V84R/R100E

<400> SEQUENCE: 51

Met Ala Val Lys His Leu Ile Val Leu Lys Phe Lys Asp Glu Ile Thr
1 5 10 15

Glu Ala Gln Lys Glu Glu Phe Phe Lys Thr Tyr Ala Asn Leu Gly Asn
20 25 30

Ile Ile Pro Ala Met Lys Asp Val Thr Trp Gly Val Asp Val Thr Gln
35 40 45

Lys Asn Lys Glu Glu Gly Tyr Thr His Ile Val Glu Val Thr Phe Glu
50 55 60

Ser Val Glu Arg Ile Gln Asp Tyr Ile Glu His Pro Ala His Val Gly
65 70 75 80

Phe Gly Asp Arg Tyr Arg Ser Phe Trp Glu Lys Leu Leu Ile Phe Asp
85 90 95

Tyr Thr Pro Glu Lys Gly
100

<210> SEQ ID NO 52
<211> LENGTH: 101
<212> TYPE: PRT
<213> ORGANISM: Artificial Sequence
<220> FEATURE:
<223> OTHER INFORMATION: OAC-V28A/Y41S/G43SILENT(=GGG)/T68R/I74R/V84R/R100M/G102STOP

<400> SEQUENCE: 52

Met Ala Val Lys His Leu Ile Val Leu Lys Phe Lys Asp Glu Ile Thr
1 5 10 15

Glu Ala Gln Lys Glu Glu Phe Phe Lys Thr Tyr Ala Asn Leu Val Asn

```
            20                  25                  30

Ile Ile Pro Ala Met Lys Asp Val Ser Trp Gly Lys Asp Val Thr Gln
        35                  40                  45

Lys Asn Lys Glu Glu Gly Tyr Thr His Ile Val Glu Val Thr Phe Glu
    50                  55                  60

Ser Val Glu Arg Ile Gln Asp Tyr Ile Arg His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Met Lys
            100


<210> SEQ ID NO 53
<211> LENGTH: 102
<212> TYPE: PRT
<213> ORGANISM: Artificial Sequence
<220> FEATURE:
<223> OTHER INFORMATION: OAC-Y41T/G43SILENT(=GGG)/K44V/T68L/I74G/V84R/
      G102R

<400> SEQUENCE: 53

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Val Asn
            20                  25                  30

Ile Ile Pro Ala Met Lys Asp Val Thr Trp Gly Val Asp Val Thr Gln
        35                  40                  45

Lys Asn Lys Glu Glu Gly Tyr Thr His Ile Val Glu Val Thr Phe Glu
    50                  55                  60

Ser Val Glu Leu Ile Gln Asp Tyr Ile Gly His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Arg Lys Arg
            100


<210> SEQ ID NO 54
<211> LENGTH: 102
<212> TYPE: PRT
<213> ORGANISM: Artificial Sequence
<220> FEATURE:
<223> OTHER INFORMATION: OAC-V28A/Y41T/G43SILENT(=GGG)/K44V/T68R/I74R/
      V84R/R100E/G102R

<400> SEQUENCE: 54

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Ala Asn Leu Val Asn
            20                  25                  30

Ile Ile Pro Ala Met Lys Asp Val Thr Trp Gly Val Asp Val Thr Gln
        35                  40                  45

Lys Asn Lys Glu Glu Gly Tyr Thr His Ile Val Glu Val Thr Phe Glu
    50                  55                  60

Ser Val Glu Arg Ile Gln Asp Tyr Ile Arg His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Glu Lys Arg
```

100

<210> SEQ ID NO 55
<211> LENGTH: 102
<212> TYPE: PRT
<213> ORGANISM: Artificial Sequence
<220> FEATURE:
<223> OTHER INFORMATION: OAC-V28A/V31G/Y41S/G43SILENT(=GGG)/K44V/T68R/
I74R/V84R

<400> SEQUENCE: 55

Met Ala Val Lys His Leu Ile Val Leu Lys Phe Lys Asp Glu Ile Thr
1 5 10 15

Glu Ala Gln Lys Glu Glu Phe Phe Lys Thr Tyr Ala Asn Leu Gly Asn
20 25 30

Ile Ile Pro Ala Met Lys Asp Val Ser Trp Gly Val Asp Val Thr Gln
35 40 45

Lys Asn Lys Glu Glu Gly Tyr Thr His Ile Val Glu Val Thr Phe Glu
50 55 60

Ser Val Glu Arg Ile Gln Asp Tyr Ile Arg His Pro Ala His Val Gly
65 70 75 80

Phe Gly Asp Arg Tyr Arg Ser Phe Trp Glu Lys Leu Leu Ile Phe Asp
85 90 95

Tyr Thr Pro Arg Lys Gly
100

<210> SEQ ID NO 56
<211> LENGTH: 102
<212> TYPE: PRT
<213> ORGANISM: Artificial Sequence
<220> FEATURE:
<223> OTHER INFORMATION: OAC-V28A/G43SILENT(=GGG)/K44V/I74D/V84R/R100E/
G102R(=CGC)

<400> SEQUENCE: 56

Met Ala Val Lys His Leu Ile Val Leu Lys Phe Lys Asp Glu Ile Thr
1 5 10 15

Glu Ala Gln Lys Glu Glu Phe Phe Lys Thr Tyr Ala Asn Leu Val Asn
20 25 30

Ile Ile Pro Ala Met Lys Asp Val Tyr Trp Gly Val Asp Val Thr Gln
35 40 45

Lys Asn Lys Glu Glu Gly Tyr Thr His Ile Val Glu Val Thr Phe Glu
50 55 60

Ser Val Glu Thr Ile Gln Asp Tyr Ile Asp His Pro Ala His Val Gly
65 70 75 80

Phe Gly Asp Arg Tyr Arg Ser Phe Trp Glu Lys Leu Leu Ile Phe Asp
85 90 95

Tyr Thr Pro Glu Lys Arg
100

<210> SEQ ID NO 57
<211> LENGTH: 102
<212> TYPE: PRT
<213> ORGANISM: Artificial Sequence
<220> FEATURE:
<223> OTHER INFORMATION: OAC-V28A/Y41V/G43SILENT(=GGG)/K44V/T68L/I74G/
V84R/G102R

<400> SEQUENCE: 57

Met Ala Val Lys His Leu Ile Val Leu Lys Phe Lys Asp Glu Ile Thr
1 5 10 15

Glu Ala Gln Lys Glu Glu Phe Phe Lys Thr Tyr Ala Asn Leu Val Asn
20 25 30

Ile Ile Pro Ala Met Lys Asp Val Val Trp Gly Val Asp Val Thr Gln
35 40 45

Lys Asn Lys Glu Glu Gly Tyr Thr His Ile Val Glu Val Thr Phe Glu
50 55 60

Ser Val Glu Leu Ile Gln Asp Tyr Ile Gly His Pro Ala His Val Gly
65 70 75 80

Phe Gly Asp Arg Tyr Arg Ser Phe Trp Glu Lys Leu Leu Ile Phe Asp
85 90 95

Tyr Thr Pro Arg Lys Arg
100

<210> SEQ ID NO 58
<211> LENGTH: 102
<212> TYPE: PRT
<213> ORGANISM: Artificial Sequence
<220> FEATURE:
<223> OTHER INFORMATION: OAC-Y41T/G43SILENT(=GGG)/T68L/I74G/V84R/R100M/
G102R

<400> SEQUENCE: 58

Met Ala Val Lys His Leu Ile Val Leu Lys Phe Lys Asp Glu Ile Thr
1 5 10 15

Glu Ala Gln Lys Glu Glu Phe Phe Lys Thr Tyr Val Asn Leu Val Asn
20 25 30

Ile Ile Pro Ala Met Lys Asp Val Thr Trp Gly Lys Asp Val Thr Gln
35 40 45

Lys Asn Lys Glu Glu Gly Tyr Thr His Ile Val Glu Val Thr Phe Glu
50 55 60

Ser Val Glu Leu Ile Gln Asp Tyr Ile Gly His Pro Ala His Val Gly
65 70 75 80

Phe Gly Asp Arg Tyr Arg Ser Phe Trp Glu Lys Leu Leu Ile Phe Asp
85 90 95

Tyr Thr Pro Met Lys Arg
100

<210> SEQ ID NO 59
<211> LENGTH: 102
<212> TYPE: PRT
<213> ORGANISM: Artificial Sequence
<220> FEATURE:
<223> OTHER INFORMATION: OAC-V28A/V31G/Y41T/G43SILENT(=GGG)/K44V/T68R/
I74R/V84R/R100E/G102R

<400> SEQUENCE: 59

Met Ala Val Lys His Leu Ile Val Leu Lys Phe Lys Asp Glu Ile Thr
1 5 10 15

Glu Ala Gln Lys Glu Glu Phe Phe Lys Thr Tyr Ala Asn Leu Gly Asn
20 25 30

Ile Ile Pro Ala Met Lys Asp Val Thr Trp Gly Val Asp Val Thr Gln
35 40 45

Lys Asn Lys Glu Glu Gly Tyr Thr His Ile Val Glu Val Thr Phe Glu
50 55 60

Ser Val Glu Arg Ile Gln Asp Tyr Ile Arg His Pro Ala His Val Gly
65 70 75 80

Phe Gly Asp Arg Tyr Arg Ser Phe Trp Glu Lys Leu Leu Ile Phe Asp
85 90 95

```
Tyr Thr Pro Glu Lys Arg
            100


<210> SEQ ID NO 60
<211> LENGTH: 102
<212> TYPE: PRT
<213> ORGANISM: Artificial Sequence
<220> FEATURE:
<223> OTHER INFORMATION: OAC-V31G/Y41S/G43SILENT(=GGG)/K44V/T68R/V84R/
      R100E

<400> SEQUENCE: 60

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Gly Asn
            20                  25                  30

Ile Ile Pro Ala Met Lys Asp Val Ser Trp Gly Val Asp Val Thr Gln
        35                  40                  45

Lys Asn Lys Glu Glu Gly Tyr Thr His Ile Val Glu Val Thr Phe Glu
    50                  55                  60

Ser Val Glu Arg Ile Gln Asp Tyr Ile Ile His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Glu Lys Gly
            100


<210> SEQ ID NO 61
<211> LENGTH: 101
<212> TYPE: PRT
<213> ORGANISM: Artificial Sequence
<220> FEATURE:
<223> OTHER INFORMATION: OAC-V28A/Y41V/G43SILENT(=GGG)/T68L/I74D/R100E/
      G102STOP

<400> SEQUENCE: 61

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Ala Asn Leu Val Asn
            20                  25                  30

Ile Ile Pro Ala Met Lys Asp Val Val Trp Gly Lys Asp Val Thr Gln
        35                  40                  45

Lys Asn Lys Glu Glu Gly Tyr Thr His Ile Val Glu Val Thr Phe Glu
    50                  55                  60

Ser Val Glu Leu Ile Gln Asp Tyr Ile Asp His Pro Ala His Val Gly
65                  70                  75                  80

Phe Gly Asp Val Tyr Arg Ser Phe Trp Glu Lys Leu Leu Ile Phe Asp
                85                  90                  95

Tyr Thr Pro Glu Lys
            100


<210> SEQ ID NO 62
<211> LENGTH: 102
<212> TYPE: PRT
<213> ORGANISM: Artificial Sequence
<220> FEATURE:
<223> OTHER INFORMATION: OAC-V28A/Y41V/G43SILENT(=GGG)/T68R/I74G/V84R/
      R100M/G102R

<400> SEQUENCE: 62
```

```
Met Ala Val Lys His Leu Ile Val Leu Lys Phe Lys Asp Glu Ile Thr
1               5                   10                  15

Glu Ala Gln Lys Glu Glu Phe Phe Lys Thr Tyr Ala Asn Leu Val Asn
            20                  25                  30

Ile Ile Pro Ala Met Lys Asp Val Val Trp Gly Lys Asp Val Thr Gln
        35                  40                  45

Lys Asn Lys Glu Glu Gly Tyr Thr His Ile Val Glu Val Thr Phe Glu
    50                  55                  60

Ser Val Glu Arg Ile Gln Asp Tyr Ile Gly His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Met Lys Arg
            100


<210> SEQ ID NO 63
<211> LENGTH: 102
<212> TYPE: PRT
<213> ORGANISM: Artificial Sequence
<220> FEATURE:
<223> OTHER INFORMATION: OAC-V31G/G43SILENT(=GGG)/I74G/V84R/R100E

<400> SEQUENCE: 63

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Gly Asn
            20                  25                  30

Ile Ile Pro Ala Met Lys Asp Val Tyr Trp Gly Lys Asp Val Thr Gln
        35                  40                  45

Lys Asn Lys Glu Glu Gly Tyr Thr His Ile Val Glu Val Thr Phe Glu
    50                  55                  60

Ser Val Glu Thr Ile Gln Asp Tyr Ile Gly His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Glu Lys Gly
            100


<210> SEQ ID NO 64
<211> LENGTH: 102
<212> TYPE: PRT
<213> ORGANISM: Artificial Sequence
<220> FEATURE:
<223> OTHER INFORMATION: OAC-V28A/Y41S/G43SILENT(=GGG)/K44V/T68R/I74R/
      V84R/R100M/G102R

<400> SEQUENCE: 64

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Ala Asn Leu Val Asn
            20                  25                  30

Ile Ile Pro Ala Met Lys Asp Val Ser Trp Gly Val Asp Val Thr Gln
        35                  40                  45

Lys Asn Lys Glu Glu Gly Tyr Thr His Ile Val Glu Val Thr Phe Glu
    50                  55                  60

Ser Val Glu Arg Ile Gln Asp Tyr Ile Arg His Pro Ala His Val Gly
65                  70                  75                  80

Phe Gly Asp Arg Tyr Arg Ser Phe Trp Glu Lys Leu Leu Ile Phe Asp
```

```
                85                  90                  95

Tyr Thr Pro Met Lys Arg
            100


<210> SEQ ID NO 65
<211> LENGTH: 102
<212> TYPE: PRT
<213> ORGANISM: Artificial Sequence
<220> FEATURE:
<223> OTHER INFORMATION: OAC-V28A/V31G/Y41V/G43SILENT(=GGG)/K44V/T68L/
      I74G/V84

<400> SEQUENCE: 65

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Ala Asn Leu Gly Asn
            20                  25                  30

Ile Ile Pro Ala Met Lys Asp Val Val Trp Gly Val Asp Val Thr Gln
        35                  40                  45

Lys Asn Lys Glu Glu Gly Tyr Thr His Ile Val Glu Val Thr Phe Glu
    50                  55                  60

Ser Val Glu Leu Ile Gln Asp Tyr Ile Gly His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Arg Lys Gly
            100


<210> SEQ ID NO 66
<211> LENGTH: 102
<212> TYPE: PRT
<213> ORGANISM: Artificial Sequence
<220> FEATURE:
<223> OTHER INFORMATION: OAC-V28A/Y41V/G43SILENT(=GGG)/K44V/T68L/I74G/
      V84R/R100M/G102R

<400> SEQUENCE: 66

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Ala Asn Leu Val Asn
            20                  25                  30

Ile Ile Pro Ala Met Lys Asp Val Val Trp Gly Val Asp Val Thr Gln
        35                  40                  45

Lys Asn Lys Glu Glu Gly Tyr Thr His Ile Val Glu Val Thr Phe Glu
    50                  55                  60

Ser Val Glu Leu Ile Gln Asp Tyr Ile Gly His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Met Lys Arg
            100


<210> SEQ ID NO 67
<211> LENGTH: 102
<212> TYPE: PRT
<213> ORGANISM: Artificial Sequence
<220> FEATURE:
<223> OTHER INFORMATION:
      OAC-V28A/V31G/G43SILENT(=GGG)/T68L/I74R/V84R/R100E/G102R

<400> SEQUENCE: 67
```

Met Ala Val Lys His Leu Ile Val Leu Lys Phe Lys Asp Glu Ile Thr
1 5 10 15

Glu Ala Gln Lys Glu Glu Phe Phe Lys Thr Tyr Ala Asn Leu Gly Asn
20 25 30

Ile Ile Pro Ala Met Lys Asp Val Tyr Trp Gly Lys Asp Val Thr Gln
35 40 45

Lys Asn Lys Glu Glu Gly Tyr Thr His Ile Val Glu Val Thr Phe Glu
50 55 60

Ser Val Glu Leu Ile Gln Asp Tyr Ile Arg His Pro Ala His Val Gly
65 70 75 80

Phe Gly Asp Arg Tyr Arg Ser Phe Trp Glu Lys Leu Leu Ile Phe Asp
85 90 95

Tyr Thr Pro Glu Lys Arg
100

<210> SEQ ID NO 68
<211> LENGTH: 101
<212> TYPE: PRT
<213> ORGANISM: Artificial Sequence
<220> FEATURE:
<223> OTHER INFORMATION: OAC-V31G/Y41V/G43SILENT(=GGG)/K44V/T68L/I74R/
V84R/R100E/G102STOP

<400> SEQUENCE: 68

Met Ala Val Lys His Leu Ile Val Leu Lys Phe Lys Asp Glu Ile Thr
1 5 10 15

Glu Ala Gln Lys Glu Glu Phe Phe Lys Thr Tyr Val Asn Leu Gly Asn
20 25 30

Ile Ile Pro Ala Met Lys Asp Val Val Trp Gly Val Asp Val Thr Gln
35 40 45

Lys Asn Lys Glu Glu Gly Tyr Thr His Ile Val Glu Val Thr Phe Glu
50 55 60

Ser Val Glu Leu Ile Gln Asp Tyr Ile Arg His Pro Ala His Val Gly
65 70 75 80

Phe Gly Asp Arg Tyr Arg Ser Phe Trp Glu Lys Leu Leu Ile Phe Asp
85 90 95

Tyr Thr Pro Glu Lys
100

<210> SEQ ID NO 69
<211> LENGTH: 102
<212> TYPE: PRT
<213> ORGANISM: Artificial Sequence
<220> FEATURE:
<223> OTHER INFORMATION: OAC-V31G/Y41T/G43SILENT(=GGG)/K44V/T68R/I74D/
V84R/G102R

<400> SEQUENCE: 69

Met Ala Val Lys His Leu Ile Val Leu Lys Phe Lys Asp Glu Ile Thr
1 5 10 15

Glu Ala Gln Lys Glu Glu Phe Phe Lys Thr Tyr Val Asn Leu Gly Asn
20 25 30

Ile Ile Pro Ala Met Lys Asp Val Thr Trp Gly Val Asp Val Thr Gln
35 40 45

Lys Asn Lys Glu Glu Gly Tyr Thr His Ile Val Glu Val Thr Phe Glu
50 55 60

Ser Val Glu Arg Ile Gln Asp Tyr Ile Asp His Pro Ala His Val Gly
65 70 75 80

Phe Gly Asp Arg Tyr Arg Ser Phe Trp Glu Lys Leu Leu Ile Phe Asp
85 90 95

Tyr Thr Pro Arg Lys Arg
100

<210> SEQ ID NO 70
<211> LENGTH: 102
<212> TYPE: PRT
<213> ORGANISM: Artificial Sequence
<220> FEATURE:
<223> OTHER INFORMATION: OAC-V31G/Y41T/G43SILENT(=GGG)/K44V/T68R/I74D/V84R/R100E/G102R

<400> SEQUENCE: 70

Met Ala Val Lys His Leu Ile Val Leu Lys Phe Lys Asp Glu Ile Thr
1 5 10 15

Glu Ala Gln Lys Glu Glu Phe Phe Lys Thr Tyr Val Asn Leu Gly Asn
20 25 30

Ile Ile Pro Ala Met Lys Asp Val Thr Trp Gly Val Asp Val Thr Gln
35 40 45

Lys Asn Lys Glu Glu Gly Tyr Thr His Ile Val Glu Val Thr Phe Glu
50 55 60

Ser Val Glu Arg Ile Gln Asp Tyr Ile Asp His Pro Ala His Val Gly
65 70 75 80

Phe Gly Asp Arg Tyr Arg Ser Phe Trp Glu Lys Leu Leu Ile Phe Asp
85 90 95

Tyr Thr Pro Glu Lys Arg
100

<210> SEQ ID NO 71
<211> LENGTH: 102
<212> TYPE: PRT
<213> ORGANISM: Artificial Sequence
<220> FEATURE:
<223> OTHER INFORMATION: OAC-V28A/Y41S/G43SILENT(=GGG)/K44V/T68R/I74G/V84R/R100M/G102R

<400> SEQUENCE: 71

Met Ala Val Lys His Leu Ile Val Leu Lys Phe Lys Asp Glu Ile Thr
1 5 10 15

Glu Ala Gln Lys Glu Glu Phe Phe Lys Thr Tyr Ala Asn Leu Val Asn
20 25 30

Ile Ile Pro Ala Met Lys Asp Val Ser Trp Gly Val Asp Val Thr Gln
35 40 45

Lys Asn Lys Glu Glu Gly Tyr Thr His Ile Val Glu Val Thr Phe Glu
50 55 60

Ser Val Glu Arg Ile Gln Asp Tyr Ile Gly His Pro Ala His Val Gly
65 70 75 80

Phe Gly Asp Arg Tyr Arg Ser Phe Trp Glu Lys Leu Leu Ile Phe Asp
85 90 95

Tyr Thr Pro Met Lys Arg
100

<210> SEQ ID NO 72
<211> LENGTH: 101
<212> TYPE: PRT
<213> ORGANISM: Artificial Sequence
<220> FEATURE:
<223> OTHER INFORMATION: OAC-V28A/Y41V/G43SILENT(=GGG)/K44V/I74R/R100E/G102STOP

<400> SEQUENCE: 72

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Ala Asn Leu Val Asn
            20                  25                  30

Ile Ile Pro Ala Met Lys Asp Val Val Trp Gly Val Asp Val Thr Gln
        35                  40                  45

Lys Asn Lys Glu Glu Gly Tyr Thr His Ile Val Glu Val Thr Phe Glu
    50                  55                  60

Ser Val Glu Thr Ile Gln Asp Tyr Ile Arg His Pro Ala His Val Gly
65                  70                  75                  80

Phe Gly Asp Val Tyr Arg Ser Phe Trp Glu Lys Leu Leu Ile Phe Asp
                85                  90                  95

Tyr Thr Pro Glu Lys
            100

<210> SEQ ID NO 73
<211> LENGTH: 102
<212> TYPE: PRT
<213> ORGANISM: Artificial Sequence
<220> FEATURE:
<223> OTHER INFORMATION: OAC-V28A/V31G/Y41T/G43SILENT(=GGG)/K44V/I74E/
      V84R/R100M/G102R

<400> SEQUENCE: 73

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Ala Asn Leu Gly Asn
            20                  25                  30

Ile Ile Pro Ala Met Lys Asp Val Thr Trp Gly Val Asp Val Thr Gln
        35                  40                  45

Lys Asn Lys Glu Glu Gly Tyr Thr His Ile Val Glu Val Thr Phe Glu
    50                  55                  60

Ser Val Glu Thr Ile Gln Asp Tyr Ile Glu His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Met Lys Arg
            100

<210> SEQ ID NO 74
<211> LENGTH: 101
<212> TYPE: PRT
<213> ORGANISM: Artificial Sequence
<220> FEATURE:
<223> OTHER INFORMATION: OAC-V28A/G43SILENT(=GGG)/K44V/T68R/I74E/V84R/
      R100E/G102STOP

<400> SEQUENCE: 74

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Ala Asn Leu Val Asn
            20                  25                  30

Ile Ile Pro Ala Met Lys Asp Val Tyr Trp Gly Val Asp Val Thr Gln
        35                  40                  45

Lys Asn Lys Glu Glu Gly Tyr Thr His Ile Val Glu Val Thr Phe Glu
    50                  55                  60

```
Ser Val Glu Arg Ile Gln Asp Tyr Ile Glu His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Glu Lys
            100


<210> SEQ ID NO 75
<211> LENGTH: 102
<212> TYPE: PRT
<213> ORGANISM: Artificial Sequence
<220> FEATURE:
<223> OTHER INFORMATION: OAC-V31G/Y41T/G43SILENT(=GGG)/K44V/T68L/I74D/
      V84R/G102R

<400> SEQUENCE: 75

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Gly Asn
            20                  25                  30

Ile Ile Pro Ala Met Lys Asp Val Thr Trp Gly Val Asp Val Thr Gln
        35                  40                  45

Lys Asn Lys Glu Glu Gly Tyr Thr His Ile Val Glu Val Thr Phe Glu
    50                  55                  60

Ser Val Glu Leu Ile Gln Asp Tyr Ile Asp His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Arg Lys Arg
            100


<210> SEQ ID NO 76
<211> LENGTH: 102
<212> TYPE: PRT
<213> ORGANISM: Artificial Sequence
<220> FEATURE:
<223> OTHER INFORMATION: OAC-Y41V/G43SILENT(=GGG)/K44V/T68L/I74R/V84R/
      G102R

<400> SEQUENCE: 76

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Val Asn
            20                  25                  30

Ile Ile Pro Ala Met Lys Asp Val Val Trp Gly Val Asp Val Thr Gln
        35                  40                  45

Lys Asn Lys Glu Glu Gly Tyr Thr His Ile Val Glu Val Thr Phe Glu
    50                  55                  60

Ser Val Glu Leu Ile Gln Asp Tyr Ile Arg His Pro Ala His Val Gly
65                  70                  75                  80

Phe Gly Asp Arg Tyr Arg Ser Phe Trp Glu Lys Leu Leu Ile Phe Asp
                85                  90                  95

Tyr Thr Pro Arg Lys Arg
            100


<210> SEQ ID NO 77
<211> LENGTH: 3564
<212> TYPE: DNA
<213> ORGANISM: Artificial Sequence
<220> FEATURE:
```

<223> OTHER INFORMATION: NpgA DNA

<400> SEQUENCE: 77

```
tcaatcaaag caacccacaa atcctaggct gaatcatgat atcgatggaa gcaatcaaca     60
attttatcaa gaccgcacca aagcacgact atctgacagg cggagttcat cattctggta    120
atgtagacgt gttacaatta agcggcaata aagaagatgg tagtttagta tggaaccata    180
cttttgttga tgtagacaac aatgtggtag ctaagtttga agacgctctc gaaaaacttg    240
aaagtttgca ccggcgctca tcctcatcca caggcaatga agaacacgct aacgtttaac    300
cgaggggagt cacttcataa tgatgtgaga aataagtgaa tattgtaata attgttggga    360
ctccattgtc aacaaaagct ataatgtagg tatacagtat atactagaag ttctcctcga    420
ggatcttgga atccacaaaa gggagtcgat aaatctatat aataaaaatt actttatctt    480
ctttcgtttt atacgttgtc gtttattatc ctattacgtt atcaatcttc gcatttcagc    540
tttcattaga tttgatgact gtttctcaaa ctttatgtca ttttcttaca ccgcataaac    600
aacaaataat cataaaaatt ttagaactag acataaagca acaggcgcgt tggactttta    660
attttcgagg accgcgaatc cttacatcac acccaatccc ccacaagtga tcccccacac    720
accatagctt caaaatgttt ctactccttt tttactcttc cagattttct cggactccgc    780
gcatcgccgt accacttcaa aacacccaag cacagcatac taaatttccc ctctttcttc    840
ctctagggtg tcgttaatta cccgtactaa aggtttggaa aagaaaaaag agaccgcctc    900
gtttcttttt cttcgtcgaa aaaggcaata aaaattttta tcacgtttct ttttcttgaa    960
aatttttttt tttgattttt ttctctttcg atgacctccc attgatattt aagttaataa   1020
acggtcttca atttctcaag tttcagtttc atttttcttg ttctattaca acttttttta   1080
cttcttgctc attagaaaga aagcatagca atctaatcta agttttaatc tagaaaattt   1140
attataaaag gaagagaaat aattaaacaa tggttcaaga tacctcttct gcttctacct   1200
ctccaatttt gactagatgg tacattgata ccagaccatt gactgcttct actgctgctt   1260
tgccattatt ggaaacttta caaccagccg atcaaatctc cgttcaaaag tactatcact   1320
tgaaggacaa gcacatgtct ttggcttcta acttgttgaa gtacttgttc gttcacagaa   1380
actgcagaat tccatggtcc tctatcgtta tttctagaac tccagatcca catagaaggc   1440
catgttatat tccaccatct ggttctcaag aggattcttt taaagatggt tacaccggta   1500
tcaacgtcga gtttaatgtt tctcatcaag cctccatggt tgctattgct ggtactgctt   1560
ttactccaaa ttctggtggt gattctaagt tgaaaccaga agttggtatc gatattacct   1620
gcgtcaacga aagacaaggt agaaatggtg aagaaaggtc cttggaatct ttgagacagt   1680
acatcgatat cttctccgaa gtttttctcta ctgctgaaat ggccaacatt agaagattgg   1740
atggtgtctc ttcttcctca ttgtctgctg atagattggt tgattatggc tacaggttgt   1800
tctatactta ctgggctttg aaagaagcct acattaagat gactggtgaa gccttgttgg   1860
ctccatggtt gagagaattg gaattctcta atgttgttgc tccagctgct gttgctgaat   1920
ctggtgattc tgctggtgat tttggtgaac catatactgg tgttagaacc accttgtaca   1980
agaacttggt tgaagatgtt agaattgaag ttgctgcttt gggtggtgat tacttgtttg   2040
ctactgctgc tagaggtggt ggtattggtg cttcttctag accaggtggt ggtccagatg   2100
gttctggtat tagatctcaa gatccttgga ggccattcaa gaagttggat attgaaaggg   2160
atattcaacc atgtgctact ggtgtatgta actgcttgtc ttaaagacat aaaactgaaa   2220
caacaccaat taataataga ctttacagaa gacgggagac actagcacac aactttacca   2280
```

ggcaaggtat ttgacgctag catgtgtcca attcagtgtc atttatgatt ttttgtagta 2340
ggatataaat atatacagcg ctccaaatag tgcggttgcc ccaaaaacac cacggaacct 2400
catctgttct cgtactttgt tgtgacaaag tagctcactg ccttattatc acattttcat 2460
tatgcaacgc ttcggaaaat acgatgttga aaatgcctct agagatgaaa aacaatcgta 2520
aaagggtcct gcgtaattga aacatttgat cagtatgcag tggcacagaa acaaccagga 2580
atactatagt cataggcaat acaaggtata tattggctat gcagacccct ccagaaagta 2640
ccgacgtcaa gttagataca cttaacgaac ctagtgcaca tttaattgag aaaaatgtgg 2700
ctcttcctaa ggacatattc cgttcgtact tgagttattg gatctatgaa atcgctcgct 2760
atacaccagt catgattttg tccttaaata acatactcat cactaaacat tcttaacaat 2820
cagaaaatgc aaccgataaa acattataaa tcttcgcggt tatctggcat tgttattaac 2880
caaaaaaatg ccggcctatt acaagctact gttcaataaa tattgttgta atgaagacgg 2940
tccaactgta caaatacagc aaactgtcat atataaggtg tcttatgtga cagcacttgc 3000
gttattgtca gccggagtat gtctttgtcg cattctgggc tttttacttt ctgctcagaa 3060
ggaagtacga acaagaaaaa aaaatcacca atgcttccct tttcagtatt agtttcatat 3120
ttgtttacgt tcaaactcgt cgtttgcgcg ataacctcta aaaaagtcag ttacgtaact 3180
atatcaatca gagaatgcaa aaagcactat cataaaaatg tctctagggg atgtgagaca 3240
tgtcaattat aagaagtgat ggtgtcatag tatatatatc ataaatgatt atcaaagttt 3300
caatcctttg tattttctag tttagcgcca acttttgaca aaacctaaac tttagataat 3360
catcattctt acaattttta tctggatggc aataatctcc tatataaagc ccagataaac 3420
tgtaaaaaga atccatcact atttgaaaaa aagtcatctg gcacgtttaa ttatcagagc 3480
agaaatgatg aagggtgtta gcgccgtcca ttgatgcgcc tggtagtcat gatttacgta 3540
taactaacac atcatgagga cggc 3564

<210> SEQ ID NO 78
<211> LENGTH: 11114
<212> TYPE: DNA
<213> ORGANISM: Artificial Sequence
<220> FEATURE:
<223> OTHER INFORMATION: SEQ ID NO:78 (DiPKS-1)

<400> SEQUENCE: 78
tggaccactt cttcttggac ttcttaccac cagcaagagc ggcagcggct ttggcagctt 60
tagacaattg ttgctttgga ggcatgttat attatgttct gagacgtaag aaagggtgaa 120
aattgatgtt agtgtcaaaa attatattac aaaatacgca gagatattct agttcctttg 180
atgaatgaat ctttcagaaa aaaaagtcaa agcaaaagca aaatggcctg cagactaaac 240
tgtatggtgg tcttggaatg ataaagatct gtttaataga tttagtagat acaatagcac 300
atctcattac ccagttatga ttgacgtcat tctgagttac aatgatctta agcaacaggc 360
gcgttggact tttaatttc gaggaccgcg aatccttaca tcacacccaa tcccccacaa 420
gtgatccccc acacaccata gcttcaaaat gtttctactc ctttttact cttccagatt 480 ttctcggact ccgcgcatcg ccgtaccact tcaaaacacc caagcacagc atactaaatt 540
tcccctcttt cttcctctag ggtgtcgtta attacccgta ctaaaggttt ggaaaagaaa 600
aaagagaccg cctcgtttct ttttcttcgt cgaaaaaggc aataaaaatt tttatcacgt 660
ttctttttct tgaaaatttt tttttttgat ttttttctct ttcgatgacc tcccattgat 720
atttaagtta ataaacggtc ttcaatttct caagtttcag tttcattttt cttgttctat 780
tacaactttt tttacttctt gctcattaga aagaaagcat agcaatctaa tctaagtttt 840
aataaacaat gaacaagaac tccaaaatcc agtccccaaa ctcttctgat gttgctgtta 900
ttggtgttgg ttttagattc ccaggtaact ctaatgaccc agaatctttg tggaacaact 960
tgttggatgg tttcgatgct attacccaag tcccaaaaga aagatgggct acttctttta 1020
gagagatggg tttgatcaag aacaagttcg gtggtttctt gaaggattct gaatggaaga 1080
atttcgaccc tttgttcttt ggtatcggtc caaaagaagc tccattcatt gatccacaac 1140
aaaggttgtt gttgtccatc gtttgggaat ctttggaaga tgcttacatc agaccagatg 1200
aattgagagg ttctaacact ggtgttttca tcggtgtttc taacaacgat tacaccaagt 1260
tgggtttcca agacaactac tctatttctc catacactat gaccggctct aactcttcat 1320
tgaactccaa cagaatttcc tactgcttcg attttagagg tccatccatt actgttgata 1380
ccgcttgttc ttcttccttg gtttctgtta atttgggtgt ccaatccatc caaatgggtg 1440
aatgtaagat tgctatttgc ggtggtgtta acgctttgtt tgatccatct acatctgttg 1500
ccttttccaa gttgggtgtt ttgtctgaaa atggcagatg caactctttt agtgatcaag 1560
cctctggtta cgttagatct gaaggtgctg gtgttgttgt tttgaagtct ttggaacaag 1620
ctaagttgga tggtgataga atctacggtg ttatcaaggg tgtttcctct aatgaagatg 1680
gtgcttctaa tggtgacaag aactctttga ctactccatc ttgtgaagcc caatccatta 1740
acatttctaa ggctatggaa aaggcctcct tgtctccatc tgatatctat tacattgaag 1800
cccatggtac tggtactcca gttggtgatc caattgaagt taaggccttg tccaagatct 1860
tctccaactc taacaacaac cagttgaaca acttctctac cgatggtaat gataacgatg 1920
atgatgatga cgataacacc tctccagaac cattattgat tggctcattc aagtccaaca 1980
tcggtcattt ggaatctgct gctggtattg cttctttgat taagtgttgc ttgatgttga 2040
agaacaggat gttggttcca tccattaact gctctaattt gaacccatcc attccattcg 2100
atcagtacaa catctccgtt atcagagaaa tcagacaatt cccaaccgat aagttggtta 2160
acatcggtat caattctttc ggtttcggtg gttctaactg ccatttgatt attcaagagt 2220
acaacaacaa cttcaagaac aactctacca tctgcaataa caacaacaac aacaataaca 2280
acatcgacta cttgatccca atctcctcta agactaagaa gtccttggat aagtacttga 2340
ttttgatcaa gaccaactcc aactaccaca aggatatttc tttcgatgac ttcgtcaagt 2400
tccaaatcaa gtctaagcag tacaacttgt ccaacagaat gactaccatt gctaacgatt 2460
ggaactcctt cattaagggt tctaacgaat tccacaactt gatcgaatct aaggatggtg 2520
aaggtggttc ttcatcttct aacagaggta ttgattccgc caatcaaatc aacactacta 2580
ctacctctac catcaacgat atcgaacctt tgttggtttt cgttttctgt ggtcaaggtc 2640
cacaatggaa tggtatgatt aagaccttgt acaactccga gaacgttttc aagaacaccg 2700
ttgatcatgt tgacagcatc ttgtacaagt acttcggtta ctccattttg aacgtcttgt 2760
ctaagatcga tgataacgac gattccatca accatccaat agttgctcaa ccatctttgt 2820
tcttgttgca aattggtttg gtcgagttgt ttaagtactg ggtatctac ccatctatct 2880
ctgttggtca ttctttcggt gaagtctctt cttattactt gtccggtatc atctctttgg 2940
aaaccgcttg taaaatcgtc tacgtcagat cctctaatca gaacaaaact atgggttccg 3000
gtaagatgtt ggttgtttct atgggtttta agcaatggaa cgatcaattc tctgctgaat 3060
ggtccgatat tgaaattgct tgttacaacg ctccagattc catagttgtt actggtaacg 3120
aagaaagatt gaaagaattg tccatcaagt tgtccgacga atccaatcaa attttcaaca 3180
ccttcttgag gtccccatgt tcttttcatt cttcccatca agaagtcatc aagggttcta 3240
tgttcgaaga gttgtctaac ttgcaatcta ctggtgaaac cgaaatccct ttgttctcta 3300
ctgttactgg tagacaagtt ttgtctggtc atgttactgc tcaacacatc tacgataatg 3360
ttagagaacc agtcttgttc caaaagacga ttgaatccat tacctcctac atcaagtctc 3420
actacccatc caatcaaaag gttatctacg ttgaaattgc tccacaccca accttgtttt 3480
cattgatcaa aaagtccatc ccatcctcca acaagaattc ctcttctgtt ttgtgtccat 3540
tgaacagaaa agaaaactcc aacaactcct acaagaagtt cgtttctcag ttgtacttca 3600
acggtgttaa cgttgacttc aacttccagt tgaactccat ttgcgataac gttaacaacg 3660
atcaccattt gaacaacgtc aagcaaaact ccttcaaaga gactaccaat tccttgccaa 3720
gataccaatg ggaacaagat gaatattggt ccgaaccatt gatctccaga aagaatagat 3780
tggaaggtcc aactacttcc ttgttgggtc atagaattat ctacagcttc ccagttttcc 3840
aatccgtttt ggacttgcaa tctgacaact acaaatactt gttggaccac ttggttaacg 3900
gtaagccagt tttccaggt gctggttatt tggatatcat catcgaattc ttcgactacc 3960
aaaagcagca gttgaattcc tctgattcct ctaactccta catcatcaac gttgacaaga 4020
tccaattctt gaacccaatt cacttgaccg aaaacaagtt gcaaaccttg caatcttctt 4080
tcgaacctat cgttactaag aagtctgcct tctctgttaa cttcttcatc aaggataccg 4140
tcgaggatca atctaaggtt aagtctatgt ctgacgaaac ttggactaac acttgtaagg 4200
ctaccatttc cttggaacaa caacagccat ctccatcttc tactttgact ttgtctaaga 4260
agcaagactt gcagatcttg agaaacagat gcgatattag caagctagac aagtttgagt 4320
tgtacgacaa gatctctaag aatttgggct tgcagtacaa ctccttgttt caagttgttg 4380
ataccatcga aactggtaag gattgctctt ttgctacttt gtctttgcca gaagatactt 4440
tgttcaccac cattttgaac ccatgcttgt tggataactg tttccatggt ttgttgacct 4500
tgatcaacga aaagggttct ttcgttgtcg agtccatttc ttctgtttct atctacttgg 4560
agaacatcgg ttccttcaat caaacttctg ttggtaacgt ccagttctac ttgtacacca 4620
ctatttctaa agccacctcc tttagttctg aaggtacttg taagttgttc accaaggatg 4680
gttccttgat tttgtctatc ggtaagttca tcatcaagtc caccaatcca aagtctacta 4740
agaccaacga aactatcgaa tctccattgg acgaaacctt ctctattgaa tggcaatcta 4800
aggattctcc aattccaacc ccacaacaaa tccaacaaca atctccattg aactctaacc 4860
catccttcat tagatctacc atcttgaagg acatccagtt cgaacaatac tgctcctcca 4920
ttatccacaa agaattgatc aaccacgaaa agtacaagaa ccagcaatcc ttcgatatca 4980
actccttgga aaaccacttg aacgatgacc aattgatgga atccttgtcc atctccaaag 5040
aatacttgag attcttcacc aggatcatct ccatcattaa gcaataccca aagatcttga 5100
acgaaaaaga gctaaaagaa ttgaaagaaa tcatcgaatt gaagtaccca tccgaagttc 5160
agttgttgga attcgaagtt atcgagaagg tgtccatgat tatcccaaag ttgttgttcg 5220
aaaacgacaa gcaatcttcc atgaccttgt tccaagataa cttgttgacc aggttctact 5280
ccaattctaa ctctaccaga ttctacttgg aaagggtttc cgaaatggtc ttggaatcta 5340
ttagaccaat cgtcagagaa aagagggtgt tcagaatttt agagatcggt gctcgtacag 5400
gctctttgtc taatgttgtt ttgactaagt tgaacaccta cttgtccacc ttgaattcta 5460

-continued

```
atggtggttc tggttacaac atcatcattg agtacacctt caccgatatt tccgccaact   5520
tcattattgg tgaaatccaa gaaaccatgt gcaacttgta cccaaacgtt actttcaagt   5580
tctccgtctt ggacttggag aaagagatta ttaactcctc cgatttcttg atgggtgatt   5640
acgatatagt tttgatggcc tacgttatcc atgccgtttc taacattaag ttctccatcg   5700
aacagttgta caagttgttg tctccaagag gttggttgtt gtgtattgaa cctaagtcca   5760
acgttgtgtt ctccgatttg gttttcggtt gttttaatca gtggtggaac tactacgatg   5820
atattagaac tacccactgc tccttgtctg aatctcaatg gaatcagttg ttgttgaacc   5880
agtccttgaa caacgaatcc tcttcttctt ctaactgtta cggtggtttc tccaacgttt   5940
cttttattgg tggtgaaaag gatgtcgact cccattcttt catattgcac tgccaaaaag   6000
aatccatctc ccaaatgaag ttagccacca ctattaacaa cggtttgtca tctggttcca   6060
tcgttatcgt tttgaactct caacaattga ccaacatgaa gtcctaccca aaggttattg   6120
agtatattca agaggctacc tctttgtgca agaccattga aattatcgat tccaaggacg   6180
tcttgaactc taccaattca gttttggaaa agatccaaaa gtccttgttg gtgttctgtt   6240
tgttgggtta tgacttgttg gagaacaact accaagaaca gtctttcgaa tacgttaagt   6300
tgttgaactt gatctctact accgcctctt catctaatga taagaaacca ccaaaggtct   6360
tgttgatcac caagcaatct gaaagaatct ccaggtcttt ctactccaga tccttgattg   6420
gtatttccag aacctctatg aacgagtacc caaatttgtc cattacctct atcgatttgg   6480
ataccaacga ctactcattg cagtctttgt tgaagccaat cttcagcaac tctaagtttt   6540
ccgacaacga gttcatcttc aaaaagggct tgatgttcgt gtccaggatc tttaagaaca   6600
agcagttgct agaatcctcc aacgcttttg aaactgactc ttctaacttg tactgtaagg   6660
cctcttctga cttgtcttac aagtacgcta ttaagcagtc tatgttgacc gaaaatcaga   6720
tcgaaatcaa ggttgaatgc gtcggtatta acttcaagga caacctattc tacaagggct   6780
tgttgccaca agaaattttc agaatgggtg acatctacaa tccaccatat ggtttggaat   6840
gctctggtgt tattaccaga attggttcta acgtcaccga atactcagtt ggtcaaaatg   6900
tttttggttt cgccagacat tctttgggtt ctcatgttgt taccaacaag gatttggtta   6960
tcttgaagcc agataccatc tcattttctg aagctgcttc tatcccagtt gtttactgta   7020
ctgcttggta ctccttgttc aacattggtc agttgtctaa cgaagaatcc atcctaattc   7080
attctgctac tggtggtgta ggtttggctt ctttgaattt gttgaaaatg aagaatcagc   7140
aacagcaacc attgaccaat gtttatgcta ctgttggctc taacgagaag aagaagttct   7200
tgatcgataa cttcaacaac ttgttcaaag aggacggcga aaacattttc tctaccagag   7260
acaaagaata ctccaaccag ttggaatcca agatcgatgt tattttgaac accttgtccg   7320
gtgaattcgt cgaatctaat ttcaagtcct tgagatcctt cggtagattg attgatttgt   7380
ctgctactca cgtttacgcc aatcaacaaa ttggtctagg taacttcaag ttcgaccact   7440
tgtattctgc tgttgacttg gaaagattga tcgacgaaaa acctaagttg ttgcagtcca   7500
tcttgcaaag aattaccaac tctatcgtca acggttcctt ggaaaaaatt ccaattacca   7560
tcttcccatc caccgaaact aaggatgcta tcgaattatt gtccaagaga tcccatatcg   7620
gtaaagttgt tgtagattgc accgatatct ctaagtgtaa tcctgttggt gatgtgatca   7680
ccaacttctc tatgagattg ccaaagccaa actaccagtt gaatttgaac tccaccttgt   7740
tgattactgg tcagtctggt ttgtctatcc ctttgttgaa ttggttgttg tctaagtctg   7800
gtggtaacgt taagaacgtt gtcatcattt ctaagtccac catgaagtgg aagttgcaga   7860
```

```
ctatgatttc ccatttcgtt tccggtttcg gtatccattt taactacgtt caagtcgaca   7920
tctccaacta cgatgctttg tctgaagcta ttaagcaatt gccatctgat ttgccaccaa   7980
tcacctctgt ttttcatttg gctgctatct acaacgatgt tccaatggat caagttacca   8040
tgtctaccgt tgaatctgtt cataacccta aagttttggg tgccgttaac ttgcatagaa   8100
tctctgtttc ttttggttgg aagttgaacc acttcgtctt gttctcttct attactgcta   8160
ttaccggtta cccagaccaa tctatctaca attctgccaa ctctattttg gacgctttgt   8220
ccaactttag aaggtttatg ggtttgccat ccttctccat taacttgggt ccaatgaagg   8280
atgaaggtaa ggtttctacc aacaagagca tcaagaagct attcaagtct agaggtttgc   8340
caagcctatc cttgaacaag ttatttggtt tgttggaggt cgtcatcaac aacccatcta   8400
atcatgttat cccatcccaa ttgatttgct ccccaatcga tttcaagacc tacatcgaat   8460
ctttctcaac tatgaggcca aagttgttac acttgcaacc taccatttcc aagcagcaat   8520
cttctatcat taacgattct accaaggctt cctccaacat ttcattgcaa gataagatca   8580
cctccaaggt gtctgatttg ttgtccattc caatctccaa gatcaacttc gatcatccat   8640
tgaaacacta cggcttggat tctttgttga ccgttcaatt caaatcctgg atcgacaaag   8700
aattcgaaaa gaacttgttc acccatatcc aattggccac catctctatt aactcattct   8760
tggaaaaggt gaacggcttg tctacaaaca ataacaacaa caacaattcc aacgtcaagt   8820
cctctccatc cattgtcaaa gaagaaatcg ttaccttgga caaggatcaa caaccattgc   8880
tattgaaaga acaccagcac attatcatct ccccagatat tagaatcaac aagccaaaga   8940
gggaatcctt gattagaacc ccaatcttga acaaattcaa ccagatcacc gaatccatta   9000
tcactccatc tacaccatct ttgtcccaat ccgatgtttt gaaaactcca ccaatcaagt   9060
ctttgaacaa cactaagaac tccagcttga ttaacacccc accaattcaa tctgtccaac   9120
aacatcaaaa gcaacaacaa aaggtccaag tcatccaaca acagcaacaa ccattatcca   9180
gattgtccta caagagcaac aacaactctt tcgttttggg tatcggtatt tctgttccag   9240
gtgaacctat ttcccaacaa tccttgaaag actccatctc caatgacttt tctgataagg   9300
ctgaaactaa cgagaaggtc aagagaatct ttgagcaatc tcaaatcaag accagacact   9360
tggttagaga ttacactaag ccagagaact ccatcaagtt cagacatttg gaaaccatta   9420
ccgatgtgaa caaccagttc aagaaagttg ttccagattt ggctcaacaa gcctgtttga   9480
gagctttgaa agattggggt ggtgataagg gtgatattac ccatatagtt tctgttacct   9540
ccaccggtat tatcatccca gatgttaatt tcaagttgat cgacttgttg ggcttgaaca   9600
aggatgttga aagagtgtct ttgaacctaa tgggttgttt ggctggtttg agttctttga   9660
gaactgctgc ttctttggct aaggcttctc caagaaatag aattttggtt gtctgtaccg   9720
aagtctgctc cttgcatttt tctaatactg atggtggtga tcaaatggtc gcctcttcta   9780
tttttgctga tggttctgct gcttacatta ttggttgtaa cccaagaatt gaagaaaccc   9840
cattatacga agtcatgtgc tccattaaca gatctttccc aaataccgaa aacgccatgg   9900
tttgggattt ggaaaaagaa ggttggaact tgggtttgga tgcttctatt ccaattgtca   9960
ttggttctgg tattgaagcc ttcgttgata ctttgttgga taaggctaag ttgcaaactt  10020
ccactgctat ttctgctaag gattgcgaat tcttgattca tactggtggc aagtccatct  10080
tgatgaacat cgaaaattcc ttgggtatcg acccaaagca aactaagaat acttgggatg  10140
tttaccatgc ctacggcaat atgtcatctg cctctgttat tttcgttatg gatcatgcca  10200
```

gaaagtccaa gtctttgcca acttactcaa tttctttggc ttttggtcca ggtttggctt 10260
ttgaaggttg tttcttgaag aacgtcgtct gaacagaaga cgggagacac tagcacacaa 10320
ctttaccagg caaggtattt gacgctagca tgtgtccaat tcagtgtcat ttatgatttt 10380
ttgtagtagg atataaatat atacagcgct ccaaatagtg cggttgcccc aaaaacacca 10440
cggaacctca tctgttctcg tactttgttg tgacaaagta gctcactgcc ttattatcac 10500
attttcatta tgcaacgctt cggaaaatac gatgttgaaa atgcctctag agatgaaaaa 10560
caatcgtaaa agggtcctgc gtaattgaaa catttgatca gtatgcagtg gcacagaaac 10620
aaccaggaat actatagtca taggcaatac aaggtatata ttggctatgc agacccctcc 10680
agaaagtacc gacgtcaagt tagatacact taacgaacct agtgcacatt taattgagaa 10740
aaatgtggct cttcctatgg acatattccg ttcgtacttg agttattgga tctatgaaat 10800
cgctcgctat acaccagtca tgattttgtc gaagttatta tccaggaggc acggatgcaa 10860
aagatagaag acaaattaat ttccttaaaa ttcaaaatgc tcattattgt cacgctgtat 10920
gagcatttgg tgaagatttc actgggaaat gttgcaataa tttgataatc gttcgtattg 10980
gatgaaactg taacatcatc tgtttattaa gtatccgtgt tattagtata tcatcacata 11040
cggtgtaaga agataacata aagattgaga aacagtcatc aaatataatg gaagctgaaa 11100
tgcgaggatt gatg 11114

<210> SEQ ID NO 79
<211> LENGTH: 10890
<212> TYPE: DNA
<213> ORGANISM: Artificial Sequence
<220> FEATURE:
<223> OTHER INFORMATION: DiPKS-2

<400> SEQUENCE: 79
acgatgattc agttcgcctt ctatcctttg tttacgtatt tgtttatata tataacttta 60
ttttttttta ttaattgggc tgcaagacaa ttttgttgtc agtgatgcct caatccttct 120
tttgcttcca tatttaccat gtggaccctt tcaaaacaga gttgtatctc tgcaggatgc 180
cctttttgac gtattgaatg gcataattgc actgtcaaag caacaggcgc gttggacttt 240
taattttcga ggaccgcgaa tccttacatc acacccaatc ccccacaagt gatcccccac 300
acaccatagc ttcaaaatgt ttctactcct tttttactct tccagatttt ctcggactcc 360
gcgcatcgcc gtaccacttc aaaacaccca agcacagcat actaaatttc ccctctttct 420
tcctctaggg tgtcgttaat tacccgtact aaaggtttgg aaaagaaaaa agagaccgcc 480
tcgtttcttt ttcttcgtcg aaaaaggcaa taaaaatttt tatcacgttt ctttttcttg 540
aaaatttttt tttttgattt ttttctcttt cgatgacctc ccattgatat ttaagttaat 600
aaacggtctt caatttctca agtttcagtt tcatttttct tgttctatta caactttttt 660
tacttcttgc tcattagaaa gaaagcatag caatctaatc taagttttaa taaacaatga 720
acaagaactc caaaatccag tccccaaact cttctgatgt tgctgttatt ggtgttggtt 780
ttagattccc aggtaactct aatgacccag aatctttgtg gaacaacttg ttggatggtt 840
tcgatgctat tacccaagtc ccaaaagaaa gatgggctac ttcttttaga gagatgggtt 900
tgatcaagaa caagttcggt ggtttcttga aggattctga atggaagaat ttcgaccctt 960
tgttctttgg tatcggtcca aaagaagctc cattcattga tccacaacaa aggttgttgt 1020
tgtccatcgt ttgggaatct ttggaagatg cttacatcag accagatgaa ttgagaggtt 1080
ctaacactgg tgttttcatc ggtgtttcta acaacgatta caccaagttg ggtttccaag 1140
acaactactc tatttctcca tacactatga ccggctctaa ctcttcattg aactccaaca 1200
gaatttccta ctgcttcgat tttagaggtc catccattac tgttgatacc gcttgttctt 1260
cttccttggt ttctgttaat ttgggtgtcc aatccatcca aatgggtgaa tgtaagattg 1320
ctatttgcgg tggtgttaac gctttgtttg atccatctac atctgttgcc ttttccaagt 1380
tgggtgtttt gtctgaaaat ggcagatgca actcttttag tgatcaagcc tctggttacg 1440
ttagatctga aggtgctggt gttgttgttt tgaagtcttt ggaacaagct aagttggatg 1500
gtgatagaat ctacggtgtt atcaagggtg tttcctctaa tgaagatggt gcttctaatg 1560
gtgacaagaa ctctttgact actccatctt gtgaagccca atccattaac atttctaagg 1620
ctatggaaaa ggcctccttg tctccatctg atatctatta cattgaagcc catggtactg 1680
gtactccagt tggtgatcca attgaagtta aggccttgtc caagatcttc tccaactcta 1740
acaacaacca gttgaacaac ttctctaccg atggtaatga taacgatgat gatgatgacg 1800
ataacacctc tccagaacca ttattgattg gctcattcaa gtccaacatc ggtcatttgg 1860
aatctgctgc tggtattgct tctttgatta agtgttgctt gatgttgaag aacaggatgt 1920
tggttccatc cattaactgc tctaatttga acccatccat tccattcgat cagtacaaca 1980
tctccgttat cagagaaatc agacaattcc caaccgataa gttggttaac atcggtatca 2040
attctttcgg tttcggtggt tctaactgcc atttgattat tcaagagtac aacaacaact 2100
tcaagaacaa ctctaccatc tgcaataaca acaacaacaa caataacaac atcgactact 2160
tgatcccaat ctcctctaag actaagaagt ccttggataa gtacttgatt ttgatcaaga 2220
ccaactccaa ctaccacaag gatatttctt tcgatgactt cgtcaagttc caaatcaagt 2280
ctaagcagta caacttgtcc aacagaatga ctaccattgc taacgattgg aactccttca 2340
ttaagggttc taacgaattc cacaacttga tcgaatctaa ggatggtgaa ggtggttctt 2400
catcttctaa cagaggtatt gattccgcca atcaaatcaa cactactact acctctacca 2460
tcaacgatat cgaacctttg ttggttttcg ttttctgtgg tcaaggtcca caatggaatg 2520
gtatgattaa gaccttgtac aactccgaga acgttttcaa gaacaccgtt gatcatgttg 2580
acagcatctt gtacaagtac ttcggttact ccattttgaa cgtcttgtct aagatcgatg 2640
ataacgacga ttccatcaac catccaatag ttgctcaacc atctttgttc ttgttgcaaa 2700
ttggtttggt cgagttgttt aagtactggg gtatctaccc atctatctct gttggtcatt 2760
ctttcggtga agtctcttct tattacttgt ccggtatcat ctctttggaa accgcttgta 2820
aaatcgtcta cgtcagatcc tctaatcaga acaaaactat gggttccggt aagatgttgg 2880
ttgtttctat gggttttaag caatggaacg atcaattctc tgctgaatgg tccgatattg 2940
aaattgcttg ttacaacgct ccagattcca tagttgttac tggtaacgaa gaaagattga 3000
aagaattgtc catcaagttg tccgacgaat ccaatcaaat tttcaacacc ttcttgaggt 3060
ccccatgttc ttttcattct tcccatcaag aagtcatcaa gggttctatg ttcgaagagt 3120
tgtctaactt gcaatctact ggtgaaaccg aaatcccttt gttctctact gttactggta 3180
gacaagtttt gtctggtcat gttactgctc aacacatcta cgataatgtt agagaaccag 3240
tcttgttcca aaagacgatt gaatccatta cctcctacat caagtctcac tacccatcca 3300
atcaaaaggt tatctacgtt gaaattgctc cacacccaac cttgttttca ttgatcaaaa 3360
agtccatccc atcctccaac aagaattcct cttctgtttt gtgtccattg aacagaaaag 3420
aaaactccaa caactcctac aagaagttcg tttctcagtt gtacttcaac ggtgttaacg 3480

```
ttgacttcaa cttccagttg aactccattt gcgataacgt taacaacgat caccatttga   3540
acaacgtcaa gcaaaactcc ttcaaagaga ctaccaattc cttgccaaga taccaatggg   3600
aacaagatga atattggtcc gaaccattga tctccagaaa gaatagattg gaaggtccaa   3660
ctacttcctt gttgggtcat agaattatct acagcttccc agttttccaa tccgttttgg   3720
acttgcaatc tgacaactac aaatacttgt tggaccactt ggttaacggt aagccagttt   3780
ttccaggtgc tggttatttg gatatcatca tcgaattctt cgactaccaa aagcagcagt   3840
tgaattcctc tgattcctct aactcctaca tcatcaacgt tgacaagatc caattcttga   3900
acccaattca cttgaccgaa aacaagttgc aaaccttgca atcttctttc gaacctatcg   3960
ttactaagaa gtctgccttc tctgttaact tcttcatcaa ggataccgtc gaggatcaat   4020
ctaaggttaa gtctatgtct gacgaaactt ggactaacac ttgtaaggct accatttcct   4080
tggaacaaca acagccatct ccatcttcta ctttgacttt gtctaagaag caagacttgc   4140
agatcttgag aaacagatgc gatattagca agctagacaa gtttgagttg tacgacaaga   4200
tctctaagaa tttgggcttg cagtacaact ccttgtttca agttgttgat accatcgaaa   4260
ctggtaagga ttgctctttt gctactttgt ctttgccaga agatactttg ttcaccacca   4320
ttttgaaccc atgcttgttg gataactgtt tccatggttt gttgaccttg atcaacgaaa   4380
agggttcttt cgttgtcgag tccatttctt ctgtttctat ctacttggag aacatcggtt   4440
ccttcaatca aacttctgtt ggtaacgtcc agttctactt gtacaccact atttctaaag   4500
ccacctcctt tagttctgaa ggtacttgta agttgttcac caaggatggt tccttgattt   4560
tgtctatcgg taagttcatc atcaagtcca ccaatccaaa gtctactaag accaacgaaa   4620
ctatcgaatc tccattggac gaaaccttct ctattgaatg gcaatctaag gattctccaa   4680
ttccaacccc acaacaaatc caacaacaat ctccattgaa ctctaaccca tccttcatta   4740
gatctaccat cttgaaggac atccagttcg aacaatactg ctcctccatt atccacaaag   4800
aattgatcaa ccacgaaaag tacaagaacc agcaatcctt cgatatcaac tccttggaaa   4860
accacttgaa cgatgaccaa ttgatggaat ccttgtccat ctccaaagaa tacttgagat   4920
tcttcaccag gatcatctcc atcattaagc aatacccaaa gatcttgaac gaaaaagagc   4980
taaaagaatt gaaagaaatc atcgaattga agtacccatc cgaagttcag ttgttggaat   5040
tcgaagttat cgagaaggtg tccatgatta tcccaaagtt gttgttcgaa aacgacaagc   5100
aatcttccat gaccttgttc caagataact tgttgaccag gttctactcc aattctaact   5160
ctaccagatt ctacttggaa agggtttccg aaatggtctt ggaatctatt agaccaatcg   5220
tcagagaaaa gagggtgttc agaattttag agatcggtgc tcgtacaggc tctttgtcta   5280
atgttgtttt gactaagttg aacacctact tgtccacctt gaattctaat ggtggttctg   5340
gttacaacat catcattgag tacaccttca ccgatatttc cgccaacttc attattggtg   5400
aaatccaaga aaccatgtgc aacttgtacc caaacgttac tttcaagttc tccgtcttgg   5460
acttggagaa agagattatt aactcctccg atttcttgat gggtgattac gatatagttt   5520
tgatggccta cgttatccat gccgtttcta acattaagtt ctccatcgaa cagttgtaca   5580
agttgttgtc tccaagaggt tggttgttgt gtattgaacc taagtccaac gttgtgttct   5640
ccgatttggt tttcggttgt tttaatcagt ggtggaacta ctacgatgat attagaacta   5700
cccactgctc cttgtctgaa tctcaatgga atcagttgtt gttgaaccag tccttgaaca   5760
acgaatcctc ttcttcttct aactgttacg gtggtttctc caacgtttct tttattggtg   5820
gtgaaaagga tgtcgactcc cattctttca tattgcactg ccaaaaagaa tccatctccc   5880
```

aaatgaagtt agccaccact attaacaacg gtttgtcatc tggttccatc gttatcgttt 5940
tgaactctca acaattgacc aacatgaagt cctacccaaa ggttattgag tatattcaag 6000
aggctacctc tttgtgcaag accattgaaa ttatcgattc caaggacgtc ttgaactcta 6060
ccaattcagt tttggaaaag atccaaaagt ccttgttggt gttctgtttg ttgggttatg 6120
acttgttgga gaacaactac caagaacagt ctttcgaata cgttaagttg ttgaacttga 6180
tctctactac cgcctcttca tctaatgata agaaaccacc aaaggtcttg ttgatcacca 6240
agcaatctga aagaatctcc aggtctttct actccagatc cttgattggt atttccagaa 6300
cctctatgaa cgagtaccca aatttgtcca ttacctctat cgatttggat accaacgact 6360
actcattgca gtctttgttg aagccaatct tcagcaactc taagttttcc gacaacgagt 6420
tcatcttcaa aaagggcttg atgttcgtgt ccaggatctt taagaacaag cagttgctag 6480
aatcctccaa cgcttttgaa actgactctt ctaacttgta ctgtaaggcc tcttctgact 6540
tgtcttacaa gtacgctatt aagcagtcta tgttgaccga aaatcagatc gaaatcaagg 6600
ttgaatgcgt cggtattaac ttcaaggaca acctattcta caagggcttg ttgccacaag 6660
aaattttcag aatgggtgac atctacaatc caccatatgg tttggaatgc tctggtgtta 6720
ttaccagaat tggttctaac gtcaccgaat actcagttgg tcaaaatgtt tttggtttcg 6780
ccagacattc tttgggttct catgttgtta ccaacaagga tttggttatc ttgaagccag 6840
ataccatctc attttctgaa gctgcttcta tcccagttgt ttactgtact gcttggtact 6900
ccttgttcaa cattggtcag ttgtctaacg aagaatccat cctaattcat tctgctactg 6960
gtggtgtagg tttggcttct ttgaatttgt tgaaaatgaa gaatcagcaa cagcaaccat 7020
tgaccaatgt ttatgctact gttggctcta acgagaagaa gaagttcttg atcgataact 7080
tcaacaactt gttcaaagag gacggcgaaa acattttctc taccagagac aaagaatact 7140
ccaaccagtt ggaatccaag atcgatgtta ttttgaacac cttgtccggt gaattcgtcg 7200
aatctaattt caagtccttg agatccttcg gtagattgat tgatttgtct gctactcacg 7260
tttacgccaa tcaacaaatt ggtctaggta acttcaagtt cgaccacttg tattctgctg 7320
ttgacttgga aagattgatc gacgaaaaac ctaagttgtt gcagtccatc ttgcaaagaa 7380
ttaccaactc tatcgtcaac ggttccttgg aaaaaattcc aattaccatc ttcccatcca 7440
ccgaaactaa ggatgctatc gaattattgt ccaagagatc ccatatcggt aaagttgttg 7500
tagattgcac cgatatctct aagtgtaatc ctgttggtga tgtgatcacc aacttctcta 7560
tgagattgcc aaagccaaac taccagttga atttgaactc caccttgttg attactggtc 7620
agtctggttt gtctatccct ttgttgaatt ggttgttgtc taagtctggt ggtaacgtta 7680
agaacgttgt catcatttct aagtccacca tgaagtggaa gttgcagact atgatttccc 7740
atttcgtttc cggtttcggt atccatttta actacgttca agtcgacatc tccaactacg 7800
atgctttgtc tgaagctatt aagcaattgc catctgattt gccaccaatc acctctgttt 7860
ttcatttggc tgctatctac aacgatgttc caatggatca agttaccatg tctaccgttg 7920
aatctgttca taaccctaaa gttttgggtg ccgttaactt gcatagaatc tctgtttctt 7980
ttggttggaa gttgaaccac ttcgtcttgt tctcttctat tactgctatt accggttacc 8040
cagaccaatc tatctacaat tctgccaact ctattttgga cgctttgtcc aactttagaa 8100
ggtttatggg tttgccatcc ttctccatta acttgggtcc aatgaaggat gaaggtaagg 8160
tttctaccaa caagagcatc aagaagctat tcaagtctag aggtttgcca agcctatcct 8220

-continued

```
tgaacaagtt atttggtttg ttggaggtcg tcatcaacaa cccatctaat catgttatcc   8280
catcccaatt gatttgctcc ccaatcgatt tcaagaccta catcgaatct ttctcaacta   8340
tgaggccaaa gttgttacac ttgcaaccta ccatttccaa gcagcaatct tctatcatta   8400
acgattctac caaggcttcc tccaacattt cattgcaaga taagatcacc tccaaggtgt   8460
ctgatttgtt gtccattcca atctccaaga tcaacttcga tcatccattg aaacactacg   8520
gcttggattc tttgttgacc gttcaattca aatcctggat cgacaaagaa ttcgaaaaga   8580
acttgttcac ccatatccaa ttggccacca tctctattaa ctcattcttg gaaaaggtga   8640
acggcttgtc tacaaacaat aacaacaaca acaattccaa cgtcaagtcc tctccatcca   8700
ttgtcaaaga agaaatcgtt accttggaca aggatcaaca accattgcta ttgaaagaac   8760
accagcacat tatcatctcc ccagatatta gaatcaacaa gccaaagagg gaatccttga   8820
ttagaacccc aatcttgaac aaattcaacc agatcaccga atccattatc actccatcta   8880
caccatcttt gtcccaatcc gatgttttga aaactccacc aatcaagtct ttgaacaaca   8940
ctaagaactc cagcttgatt aacaccccac caattcaatc tgtccaacaa catcaaaagc   9000
aacaacaaaa ggtccaagtc atccaacaac agcaacaacc attatccaga ttgtcctaca   9060
agagcaacaa caactctttc gttttgggta tcggtatttc tgttccaggt gaacctattt   9120
cccaacaatc cttgaaagac tccatctcca atgacttttc tgataaggct gaaactaacg   9180
agaaggtcaa gagaatcttt gagcaatctc aaatcaagac cagacacttg gttagagatt   9240
acactaagcc agagaactcc atcaagttca gacatttgga aaccattacc gatgtgaaca   9300
accagttcaa gaaagttgtt ccagatttgg ctcaacaagc ctgtttgaga gctttgaaag   9360
attggggtgg tgataagggt gatattaccc atatagtttc tgttacctcc accggtatta   9420
tcatcccaga tgttaatttc aagttgatcg acttgttggg cttgaacaag gatgttgaaa   9480
gagtgtcttt gaacctaatg ggttgtttgg ctggtttgag ttctttgaga actgctgctt   9540
ctttggctaa ggcttctcca agaaatagaa ttttggttgt ctgtaccgaa gtctgctcct   9600
tgcatttttc taatactgat ggtggtgatc aaatggtcgc ctcttctatt tttgctgatg   9660
gttctgctgc ttacattatt ggttgtaacc caagaattga agaaacccca ttatacgaag   9720
tcatgtgctc cattaacaga tctttcccaa ataccgaaaa cgccatggtt tgggatttgg   9780
aaaaagaagg ttggaacttg ggtttggatg cttctattcc aattgtcatt ggttctggta   9840
ttgaagcctt cgttgatact ttgttggata aggctaagtt gcaaacttcc actgctattt   9900
ctgctaagga ttgcgaattc ttgattcata ctggtggcaa gtccatcttg atgaacatcg   9960
aaaattcctt gggtatcgac ccaaagcaaa ctaagaatac ttgggatgtt taccatgcct  10020
acggcaatat gtcatctgcc tctgttattt tcgttatgga tcatgccaga aagtccaagt  10080
ctttgccaac ttactcaatt tctttggctt ttggtccagg tttggctttt gaaggttgtt  10140
tcttgaagaa cgtcgtctga acagaagacg ggagacacta gcacacaact ttaccaggca  10200
aggtatttga cgctagcatg tgtccaattc agtgtcattt atgatttttt gtagtaggat  10260
ataaatatat acagcgctcc aaatagtgcg gttgccccaa aaacaccacg gaacctcatc  10320
tgttctcgta ctttgttgtg acaaagtagc tcactgcctt attatcacat tttcattatg  10380
caacgcttcg gaaaatacga tgttgaaaat gcctctagag atgaaaaaca atcgtaaaag  10440
ggtcctgcgt aattgaaaca tttgatcagt atgcagtggc acagaaacaa ccaggaatac  10500
tatagtcata ggcaatacaa ggtatatatt ggctatgcag acccctccag aaagtaccga  10560
cgtcaagtta gatacactta acgaacctag tgcacattta attgagaaaa atgtggctct  10620
```

```
tcctaaggac atattccgtt cgtacttgag ttattggatc tatgaaatcg ctcgctatac  10680

accagtcatg attttgtcta tgtgttgctc ttaaaatatt tggatacgac atcctttatc  10740

ttttttcctt taagagcagg atataagcca tcaagtttct gaaaatcaaa atggtagcaa  10800

caataatgca gacgacaaca actgtgctga cgacagtcgc cgcaatgtct actaccttag  10860

catcaaatta catatcttcg caagctagtt                                   10890


<210> SEQ ID NO 80
<211> LENGTH: 11300
<212> TYPE: DNA
<213> ORGANISM: Artificial Sequence
<220> FEATURE:
<223> OTHER INFORMATION: DiPKS-3

<400> SEQUENCE: 80

cgggttacag tcatcgttga aaacgatgga aaaacatgtc gagattcctc aatccataca     60

ccattatagt ccgttttatc agcttccact aattttttaa atctcagttt cttcttgaaa    120

tttagcatcg tgcatgggat agcggctagt aaaaaagaaa attaatatct cattaacaaa    180

gttattgtac ataatccggt acaatattct tcaatgtact ctctaatatc gagcacactg    240

gcaatattca tgcacacatt cgcctaatgc tgacgaatgc ttaatcagtg caattaagca    300

acaggcgcgt tggactttta attttcgagg accgcgaatc cttacatcac acccaatccc    360

ccacaagtga tcccccacac accatagctt caaaatgttt ctactccttt tttactcttc    420

cagattttct cggactccgc gcatcgccgt accacttcaa aacacccaag cacagcatac    480

taaatttccc ctctttcttc ctctagggtg tcgttaatta cccgtactaa aggtttggaa    540

aagaaaaaag agaccgcctc gtttcttttt cttcgtcgaa aaaggcaata aaaattttta    600

tcacgtttct ttttcttgaa aatttttttt tttgattttt ttctctttcg atgacctccc    660

attgatattt aagttaataa acggtcttca atttctcaag tttcagtttc atttttcttg    720

ttctattaca actttttta cttcttgctc attagaaaga aagcatagca atctaatcta    780

agttttaata aacaatgaac aagaactcca aaatccagtc cccaaactct tctgatgttg    840

ctgttattgg tgttggtttt agattcccag gtaactctaa tgacccagaa tctttgtgga    900

acaacttgtt ggatggtttc gatgctatta cccaagtccc aaaagaaaga tgggctactt    960

cttttagaga gatgggtttg atcaagaaca agttcggtgg tttcttgaag gattctgaat   1020

ggaagaattt cgaccctttg ttctttggta tcggtccaaa agaagctcca ttcattgatc   1080

cacaacaaag gttgttgttg tccatcgttt gggaatcttt ggaagatgct tacatcagac   1140

cagatgaatt gagaggttct aacactggtg ttttcatcgg tgtttctaac aacgattaca   1200

ccaagttggg tttccaagac aactactcta tttctccata cactatgacc ggctctaact   1260

cttcattgaa ctccaacaga atttcctact gcttcgattt tagaggtcca tccattactg   1320

ttgataccgc ttgttcttct tccttggttt ctgttaattt gggtgtccaa tccatccaaa   1380

tgggtgaatg taagattgct atttgcggtg gtgttaacgc tttgtttgat ccatctacat   1440

ctgttgcctt ttccaagttg ggtgttttgt ctgaaaatgg cagatgcaac tcttttagtg   1500

atcaagcctc tggttacgtt agatctgaag gtgctggtgt tgttgttttg aagtctttgg   1560

aacaagctaa gttggatggt gatagaatct acggtgttat caagggtgtt tcctctaatg   1620

aagatggtgc ttctaatggt gacaagaact ctttgactac tccatcttgt gaagcccaat   1680

ccattaacat ttctaaggct atggaaaagg cctccttgtc tccatctgat atctattaca   1740
```

-continued

```
ttgaagccca tggtactggt actccagttg gtgatccaat tgaagttaag gccttgtcca   1800
agatcttctc caactctaac aacaaccagt tgaacaactt ctctaccgat ggtaatgata   1860
acgatgatga tgatgacgat aacacctctc cagaaccatt attgattggc tcattcaagt   1920
ccaacatcgg tcatttggaa tctgctgctg gtattgcttc tttgattaag tgttgcttga   1980
tgttgaagaa caggatgttg gttccatcca ttaactgctc taatttgaac ccatccattc   2040
cattcgatca gtacaacatc tccgttatca gagaaatcag acaattccca accgataagt   2100
tggttaacat cggtatcaat tctttcggtt tcggtggttc taactgccat ttgattattc   2160
aagagtacaa caacaacttc aagaacaact ctaccatctg caataacaac aacaacaaca   2220
ataacaacat cgactacttg atcccaatct cctctaagac taagaagtcc ttggataagt   2280
acttgatttt gatcaagacc aactccaact accacaagga tatttctttc gatgacttcg   2340
tcaagttcca aatcaagtct aagcagtaca acttgtccaa cagaatgact accattgcta   2400
acgattggaa ctccttcatt aagggttcta acgaattcca caacttgatc gaatctaagg   2460
atggtgaagg tggttcttca tcttctaaca gaggtattga ttccgccaat caaatcaaca   2520
ctactactac ctctaccatc aacgatatcg aacctttgtt ggttttcgtt ttctgtggtc   2580
aaggtccaca atggaatggt atgattaaga ccttgtacaa ctccgagaac gttttcaaga   2640
acaccgttga tcatgttgac agcatcttgt acaagtactt cggttactcc attttgaacg   2700
tcttgtctaa gatcgatgat aacgacgatt ccatcaacca tccaatagtt gctcaaccat   2760
ctttgttctt gttgcaaatt ggtttggtcg agttgtttaa gtactggggt atctacccat   2820
ctatctctgt tggtcattct ttcggtgaag tctcttctta ttacttgtcc ggtatcatct   2880
ctttggaaac cgcttgtaaa atcgtctacg tcagatcctc taatcagaac aaaactatgg   2940
gttccggtaa gatgttggtt gtttctatgg gttttaagca atggaacgat caattctctg   3000
ctgaatggtc cgatattgaa attgcttgtt acaacgctcc agattccata gttgttactg   3060
gtaacgaaga aagattgaaa gaattgtcca tcaagttgtc cgacgaatcc aatcaaattt   3120
tcaacacctt cttgaggtcc ccatgttctt ttcattcttc ccatcaagaa gtcatcaagg   3180
gttctatgtt cgaagagttg tctaacttgc aatctactgg tgaaaccgaa atccctttgt   3240
tctctactgt tactggtaga caagttttgt ctggtcatgt tactgctcaa cacatctacg   3300
ataatgttag agaaccagtc ttgttccaaa agacgattga atccattacc tcctacatca   3360
agtctcacta cccatccaat caaaaggtta tctacgttga aattgctcca cacccaacct   3420
tgttttcatt gatcaaaaag tccatcccat cctccaacaa gaattcctct tctgttttgt   3480
gtccattgaa cagaaaagaa aactccaaca actcctacaa gaagttcgtt tctcagttgt   3540
acttcaacgg tgttaacgtt gacttcaact tccagttgaa ctccatttgc gataacgtta   3600
acaacgatca ccatttgaac aacgtcaagc aaaactcctt caaagagact accaattcct   3660
tgccaagata ccaatgggaa caagatgaat attggtccga accattgatc tccagaaaga   3720
atagattgga aggtccaact acttccttgt tgggtcatag aattatctac agcttcccag   3780
ttttccaatc cgttttggac ttgcaatctg acaactacaa atacttgttg gaccacttgg   3840
ttaacggtaa gccagttttt ccaggtgctg gttatttgga tatcatcatc gaattcttcg   3900
actaccaaaa gcagcagttg aattcctctg attcctctaa ctcctacatc atcaacgttg   3960
acaagatcca attcttgaac ccaattcact tgaccgaaaa caagttgcaa accttgcaat   4020
cttctttcga acctatcgtt actaagaagt ctgccttctc tgttaacttc ttcatcaagg   4080
ataccgtcga ggatcaatct aaggttaagt ctatgtctga cgaaacttgg actaacactt   4140
```

-continued

```
gtaaggctac catttccttg gaacaacaac agccatctcc atcttctact ttgactttgt   4200
ctaagaagca agacttgcag atcttgagaa acagatgcga tattagcaag ctagacaagt   4260
ttgagttgta cgacaagatc tctaagaatt tgggcttgca gtacaactcc ttgtttcaag   4320
ttgttgatac catcgaaact ggtaaggatt gctcttttgc tactttgtct ttgccagaag   4380
atactttgtt caccaccatt ttgaacccat gcttgttgga taactgtttc catggtttgt   4440
tgaccttgat caacgaaaag ggttctttcg ttgtcgagtc catttcttct gtttctatct   4500
acttggagaa catcggttcc ttcaatcaaa cttctgttgg taacgtccag ttctacttgt   4560
acaccactat ttctaaagcc acctccttta gttctgaagg tacttgtaag ttgttcacca   4620
aggatggttc cttgattttg tctatcggta agttcatcat caagtccacc aatccaaagt   4680
ctactaagac caacgaaact atcgaatctc cattggacga aaccttctct attgaatggc   4740
aatctaagga ttctccaatt ccaaccccac aacaaatcca acaacaatct ccattgaact   4800
ctaacccatc cttcattaga tctaccatct tgaaggacat ccagttcgaa caatactgct   4860
cctccattat ccacaaagaa ttgatcaacc acgaaaagta caagaaccag caatccttcg   4920
atatcaactc cttggaaaac cacttgaacg atgaccaatt gatggaatcc ttgtccatct   4980
ccaaagaata cttgagattc ttcaccagga tcatctccat cattaagcaa tacccaaaga   5040
tcttgaacga aaaagagcta aaagaattga aagaaatcat cgaattgaag tacccatccg   5100
aagttcagtt gttggaattc gaagttatcg agaaggtgtc catgattatc ccaaagttgt   5160
tgttcgaaaa cgacaagcaa tcttccatga ccttgttcca agataacttg ttgaccaggt   5220
tctactccaa ttctaactct accagattct acttggaaag ggtttccgaa atggtcttgg   5280
aatctattag accaatcgtc agagaaaaga gggtgttcag aattttagag atcggtgctc   5340
gtacaggctc tttgtctaat gttgttttga ctaagttgaa cacctacttg tccaccttga   5400
attctaatgg tggttctggt tacaacatca tcattgagta caccttcacc gatatttccg   5460
ccaacttcat tattggtgaa atccaagaaa ccatgtgcaa cttgtaccca aacgttactt   5520
tcaagttctc cgtcttggac ttggagaaag agattattaa ctcctccgat ttcttgatgg   5580
gtgattacga tatagttttg atggcctacg ttatccatgc cgtttctaac attaagttct   5640
ccatcgaaca gttgtacaag ttgttgtctc caagaggttg gttgttgtgt attgaaccta   5700
agtccaacgt tgtgttctcc gatttggttt tcggttgttt taatcagtgg tggaactact   5760
acgatgatat tagaactacc cactgctcct tgtctgaatc tcaatggaat cagttgttgt   5820
tgaaccagtc cttgaacaac gaatcctctt cttcttctaa ctgttacggt ggtttctcca   5880
acgtttcttt tattggtggt gaaaaggatg tcgactccca ttctttcata ttgcactgcc   5940
aaaaagaatc catctcccaa atgaagttag ccaccactat taacaacggt ttgtcatctg   6000
gttccatcgt tatcgttttg aactctcaac aattgaccaa catgaagtcc tacccaaagg   6060
ttattgagta tattcaagag gctacctctt tgtgcaagac cattgaaatt atcgattcca   6120
aggacgtctt gaactctacc aattcagttt tggaaaagat ccaaaagtcc ttgttggtgt   6180
tctgtttgtt gggttatgac ttgttggaga acaactacca agaacagtct ttcgaatacg   6240
ttaagttgtt gaacttgatc tctactaccg cctcttcatc taatgataag aaaccaccaa   6300
aggtcttgtt gatcaccaag caatctgaaa gaatctccag gtctttctac tccagatcct   6360
tgattggtat ttccagaacc tctatgaacg agtacccaaa tttgtccatt acctctatcg   6420
atttggatac caacgactac tcattgcagt ctttgttgaa gccaatcttc agcaactcta   6480
```

agttttccga caacgagttc atcttcaaaa agggcttgat gttcgtgtcc aggatcttta 6540
agaacaagca gttgctagaa tcctccaacg cttttgaaac tgactcttct aacttgtact 6600
gtaaggcctc ttctgacttg tcttacaagt acgctattaa gcagtctatg ttgaccgaaa 6660
atcagatcga aatcaaggtt gaatgcgtcg gtattaactt caaggacaac ctattctaca 6720
agggcttgtt gccacaagaa attttcagaa tgggtgacat ctacaatcca ccatatggtt 6780
tggaatgctc tggtgttatt accagaattg gttctaacgt caccgaatac tcagttggtc 6840
aaaatgtttt tggtttcgcc agacattctt tgggttctca tgttgttacc aacaaggatt 6900
tggttatctt gaagccagat accatctcat tttctgaagc tgcttctatc ccagttgttt 6960
actgtactgc ttggtactcc ttgttcaaca ttggtcagtt gtctaacgaa gaatccatcc 7020
taattcattc tgctactggt ggtgtaggtt tggcttcttt gaatttgttg aaaatgaaga 7080
atcagcaaca gcaaccattg accaatgttt atgctactgt tggctctaac gagaagaaga 7140
agttcttgat cgataacttc aacaacttgt tcaaagagga cggcgaaaac attttctcta 7200
ccagagacaa agaatactcc aaccagttgg aatccaagat cgatgttatt ttgaacacct 7260
tgtccggtga attcgtcgaa tctaatttca agtccttgag atccttcggt agattgattg 7320
atttgtctgc tactcacgtt tacgccaatc aacaaattgg tctaggtaac ttcaagttcg 7380
accacttgta ttctgctgtt gacttggaaa gattgatcga cgaaaaacct aagttgttgc 7440
agtccatctt gcaaagaatt accaactcta tcgtcaacgg ttccttggaa aaaattccaa 7500
ttaccatctt cccatccacc gaaactaagg atgctatcga attattgtcc aagagatccc 7560
atatcggtaa agttgttgta gattgcaccg atatctctaa gtgtaatcct gttggtgatg 7620
tgatcaccaa cttctctatg agattgccaa agccaaacta ccagttgaat ttgaactcca 7680
ccttgttgat tactggtcag tctggtttgt ctatcccttt gttgaattgg ttgttgtcta 7740
agtctggtgg taacgttaag aacgttgtca tcatttctaa gtccaccatg aagtggaagt 7800
tgcagactat gatttcccat ttcgtttccg gtttcggtat ccattttaac tacgttcaag 7860
tcgacatctc caactacgat gctttgtctg aagctattaa gcaattgcca tctgatttgc 7920
caccaatcac ctctgttttt catttggctg ctatctacaa cgatgttcca atggatcaag 7980
ttaccatgtc taccgttgaa tctgttcata accctaaagt tttgggtgcc gttaacttgc 8040
atagaatctc tgtttctttt ggttggaagt tgaaccactt cgtcttgttc tcttctatta 8100
ctgctattac cggttaccca gaccaatcta tctacaattc tgccaactct attttggacg 8160
ctttgtccaa ctttagaagg tttatgggtt tgccatcctt ctccattaac ttgggtccaa 8220
tgaaggatga aggtaaggtt tctaccaaca agagcatcaa gaagctattc aagtctagag 8280
gtttgccaag cctatccttg aacaagttat ttggtttgtt ggaggtcgtc atcaacaacc 8340
catctaatca tgttatccca tcccaattga tttgctcccc aatcgatttc aagacctaca 8400
tcgaatcttt ctcaactatg aggccaaagt tgttacactt gcaacctacc atttccaagc 8460
agcaatcttc tatcattaac gattctacca aggcttcctc caacatttca ttgcaagata 8520
agatcacctc caaggtgtct gatttgttgt ccattccaat ctccaagatc aacttcgatc 8580
atccattgaa acactacggc ttggattctt tgttgaccgt tcaattcaaa tcctggatcg 8640
acaaagaatt cgaaaagaac ttgttcaccc atatccaatt ggccaccatc tctattaact 8700
cattcttgga aaaggtgaac ggcttgtcta caaacaataa caacaacaac aattccaacg 8760
tcaagtcctc tccatccatt gtcaaagaag aaatcgttac cttggacaag gatcaacaac 8820
cattgctatt gaaagaacac cagcacatta tcatctcccc agatattaga atcaacaagc 8880

```
caaagaggga atccttgatt agaaccccaa tcttgaacaa attcaaccag atcaccgaat   8940
ccattatcac tccatctaca ccatctttgt cccaatccga tgttttgaaa actccaccaa   9000
tcaagtcttt gaacaacact aagaactcca gcttgattaa caccccacca attcaatctg   9060
tccaacaaca tcaaaagcaa caacaaaagg tccaagtcat ccaacaacag caacaaccat   9120
tatccagatt gtcctacaag agcaacaaca actctttcgt tttgggtatc ggtatttctg   9180
ttccaggtga acctatttcc caacaatcct tgaaagactc catctccaat gacttttctg   9240
ataaggctga aactaacgag aaggtcaaga gaatctttga gcaatctcaa atcaagacca   9300
gacacttggt tagagattac actaagccag agaactccat caagttcaga catttggaaa   9360
ccattaccga tgtgaacaac cagttcaaga aagttgttcc agatttggct caacaagcct   9420
gtttgagagc tttgaaagat tggggtggtg ataagggtga tattacccat atagtttctg   9480
ttacctccac cggtattatc atcccagatg ttaatttcaa gttgatcgac ttgttgggct   9540
tgaacaagga tgttgaaaga gtgtctttga acctaatggg ttgtttggct ggtttgagtt   9600
ctttgagaac tgctgcttct ttggctaagg cttctccaag aaatagaatt ttggttgtct   9660
gtaccgaagt ctgctccttg cattttttcta atactgatgg tggtgatcaa atggtcgcct   9720
cttctatttt tgctgatggt tctgctgctt acattattgg ttgtaaccca agaattgaag   9780
aaaccccatt atacgaagtc atgtgctcca ttaacagatc tttcccaaat accgaaaacg   9840
ccatggtttg ggatttggaa aaagaaggtt ggaacttggg tttggatgct tctattccaa   9900
ttgtcattgg ttctggtatt gaagccttcg ttgatacttt gttggataag gctaagttgc   9960
aaacttccac tgctatttct gctaaggatt gcgaattctt gattcatact ggtggcaagt  10020
ccatcttgat gaacatcgaa aattccttgg gtatcgaccc aaagcaaact aagaatactt  10080
gggatgttta ccatgcctac ggcaatatgt catctgcctc tgttattttc gttatggatc  10140
atgccagaaa gtccaagtct ttgccaactt actcaatttc tttggctttt ggtccaggtt  10200
tggcttttga aggttgtttc ttgaagaacg tcgtctgaac agaagacggg agacactagc  10260
acacaacttt accaggcaag gtatttgacg ctagcatgtg tccaattcag tgtcatttat  10320
gatttttttgt agtaggatat aaatatatac agcgctccaa atagtgcggt tgccccaaaa  10380
acaccacgga acctcatctg ttctcgtact ttgttgtgac aaagtagctc actgccttat  10440
tatcacattt tcattatgca acgcttcgga aaatacgatg ttgaaaatgc ctctagagat  10500
gaaaaacaat cgtaaaaggg tcctgcgtaa ttgaaacatt tgatcagtat gcagtggcac  10560
agaaacaacc aggaatacta tagtcatagg caatacaagg tatatattgg ctatgcagac  10620
ccctccagaa agtaccgacg tcaagttaga tacacttaac gaacctagtg cacatttaat  10680
tgagaaaaat gtggctcttc ctaaggacat attccgttcg tacttgagtt attggatcta  10740
tgaaatcgct cgctatacac cagtcatgat tttgtctgag atcgacttgc atcaaccttt  10800
gaaaaatata aggatgagaa agtgaaatcg gtttttttttt tccattgtcg tcatcaacat  10860
gatttttttaa ataaataaat acgatttttt attttttttc ccttctttgt ttttgttttg  10920
cttattccca tcttcattat taaattcttc cgctcttaat aaaggagttt ttttattatc  10980
ttcttgtgta atcatccttt ttctttaatt ttcttccttt tctttttctc tttactggtt  11040
tttttacttc tttattctca accatctaaa gaatattatt gctttctacc aataaaatct  11100
gttaattcta tttggattgt cgtctactca agtctcgcct agtaaataaa cgataaacaa  11160
atttgaagta agaataacaa tatagggaga gaaatttttc tatttttaat ttcgaaacag  11220
```

-continued gtaccaaaaa atctaagttc actttagcac tatttgggaa agcttttata taaaaaatct 11280
gaaacaaaat catatcaaag 11300

<210> SEQ ID NO 81
<211> LENGTH: 11140
<212> TYPE: DNA
<213> ORGANISM: Artificial Sequence
<220> FEATURE:
<223> OTHER INFORMATION: DiPKS-4

<400> SEQUENCE: 81
cggcacccac cataaagatt actttagcgt tggggttgct tttcatatga gcagcgatct 60
tcctaaccga catctctgta gaggcggtag aaacagacat cgaaacacgg agagatcgcg 120
gtacgtctgg ttggtagctc agtgacgggc acagatagcg acatttactg atacagagac 180
agttacgaaa gatggaaaca catgcagaga atgtggtcta ttccttattc ttaagatcgg 240
cgaagctaac agagttaatg ctgggccata gctggacggc agaaagcacg caggaagcaa 300
caggcgcgtt ggacttttaa ttttcgagga ccgcgaatcc ttacatcaca cccaatcccc 360
cacaagtgat cccccacaca ccatagcttc aaaatgtttc tactcctttt ttactcttcc 420
agattttctc ggactccgcg catcgccgta ccacttcaaa acacccaagc acagcatact 480
aaatttcccc tctttcttcc tctagggtgt cgttaattac ccgtactaaa ggtttggaaa 540
agaaaaaaga gaccgcctcg tttctttttc ttcgtcgaaa aaggcaataa aaatttttat 600
cacgtttctt tttcttgaaa attttttttt ttgatttttt tctctttcga tgacctccca 660
ttgatattta agttaataaa cggtcttcaa tttctcaagt ttcagtttca tttttcttgt 720
tctattacaa cttttttttac ttcttgctca ttagaaagaa agcatagcaa tctaatctaa 780
gttttaataa acaatgaaca agaactccaa aatccagtcc ccaaactctt ctgatgttgc 840
tgttattggt gttggtttta gattcccagg taactctaat gacccagaat ctttgtggaa 900
caacttgttg gatggtttcg atgctattac ccaagtccca aaagaaagat gggctacttc 960
ttttagagag atgggtttga tcaagaacaa gttcggtggt ttcttgaagg attctgaatg 1020
gaagaatttc gaccctttgt tctttggtat cggtccaaaa gaagctccat tcattgatcc 1080
acaacaaagg ttgttgttgt ccatcgtttg ggaatctttg gaagatgctt acatcagacc 1140
agatgaattg agaggttcta acactggtgt tttcatcggt gtttctaaca acgattacac 1200
caagttgggt ttccaagaca actactctat ttctccatac actatgaccg gctctaactc 1260
ttcattgaac tccaacagaa tttcctactg cttcgatttt agaggtccat ccattactgt 1320
tgataccgct tgttcttctt ccttggtttc tgttaatttg ggtgtccaat ccatccaaat 1380
gggtgaatgt aagattgcta tttgcggtgg tgttaacgct ttgtttgatc catctacatc 1440
tgttgccttt tccaagttgg gtgttttgtc tgaaaatggc agatgcaact cttttagtga 1500
tcaagcctct ggttacgtta gatctgaagg tgctggtgtt gttgttttga agtctttgga 1560
acaagctaag ttggatggtg atagaatcta cggtgttatc aagggtgttt cctctaatga 1620
agatggtgct tctaatggtg acaagaactc tttgactact ccatcttgtg aagcccaatc 1680
cattaacatt tctaaggcta tggaaaaggc ctccttgtct ccatctgata tctattacat 1740
tgaagcccat ggtactggta ctccagttgg tgatccaatt gaagttaagg ccttgtccaa 1800
gatcttctcc aactctaaca acaaccagtt gaacaacttc tctaccgatg gtaatgataa 1860
cgatgatgat gatgacgata acacctctcc agaaccatta ttgattggct cattcaagtc 1920
caacatcggt catttggaat ctgctgctgg tattgcttct ttgattaagt gttgcttgat 1980

```
gttgaagaac aggatgttgg ttccatccat taactgctct aatttgaacc catccattcc   2040
attcgatcag tacaacatct ccgttatcag agaaatcaga caattcccaa ccgataagtt   2100
ggttaacatc ggtatcaatt ctttcggttt cggtggttct aactgccatt tgattattca   2160
agagtacaac aacaacttca agaacaactc taccatctgc aataacaaca acaacaacaa   2220
taacaacatc gactacttga tcccaatctc ctctaagact aagaagtcct tggataagta   2280
cttgattttg atcaagacca actccaacta ccacaaggat atttctttcg atgacttcgt   2340
caagttccaa atcaagtcta agcagtacaa cttgtccaac agaatgacta ccattgctaa   2400
cgattggaac tccttcatta agggttctaa cgaattccac aacttgatcg aatctaagga   2460
tggtgaaggt ggttcttcat cttctaacag aggtattgat tccgccaatc aaatcaacac   2520
tactactacc tctaccatca acgatatcga acctttgttg gttttcgttt tctgtggtca   2580
aggtccacaa tggaatggta tgattaagac cttgtacaac tccgagaacg ttttcaagaa   2640
caccgttgat catgttgaca gcatcttgta caagtacttc ggttactcca ttttgaacgt   2700
cttgtctaag atcgatgata acgacgattc catcaaccat ccaatagttg ctcaaccatc   2760
tttgttcttg ttgcaaattg gtttggtcga gttgtttaag tactggggta tctacccatc   2820
tatctctgtt ggtcattctt tcggtgaagt ctcttcttat tacttgtccg gtatcatctc   2880
tttggaaacc gcttgtaaaa tcgtctacgt cagatcctct aatcagaaca aaactatggg   2940
ttccggtaag atgttggttg tttctatggg ttttaagcaa tggaacgatc aattctctgc   3000
tgaatggtcc gatattgaaa ttgcttgtta caacgctcca gattccatag ttgttactgg   3060
taacgaagaa agattgaaag aattgtccat caagttgtcc gacgaatcca atcaaatttt   3120
caacaccttc ttgaggtccc catgttcttt tcattcttcc catcaagaag tcatcaaggg   3180
ttctatgttc gaagagttgt ctaacttgca atctactggt gaaaccgaaa tccctttgtt   3240
ctctactgtt actggtagac aagttttgtc tggtcatgtt actgctcaac acatctacga   3300
taatgttaga gaaccagtct tgttccaaaa gacgattgaa tccattacct cctacatcaa   3360
gtctcactac ccatccaatc aaaaggttat ctacgttgaa attgctccac acccaacctt   3420
gttttcattg atcaaaaagt ccatcccatc ctccaacaag aattcctctt ctgttttgtg   3480
tccattgaac agaaaagaaa actccaacaa ctcctacaag aagttcgttt ctcagttgta   3540
cttcaacggt gttaacgttg acttcaactt ccagttgaac tccatttgcg ataacgttaa   3600
caacgatcac catttgaaca acgtcaagca aaactccttc aaagagacta ccaattcctt   3660
gccaagatac caatgggaac aagatgaata ttggtccgaa ccattgatct ccagaaagaa   3720
tagattggaa ggtccaacta cttccttgtt gggtcataga attatctaca gcttcccagt   3780
tttccaatcc gttttggact tgcaatctga caactacaaa tacttgttgg accacttggt   3840
taacggtaag ccagtttttc caggtgctgg ttatttggat atcatcatcg aattcttcga   3900
ctaccaaaag cagcagttga attcctctga ttcctctaac tcctacatca tcaacgttga   3960
caagatccaa ttcttgaacc caattcactt gaccgaaaac aagttgcaaa ccttgcaatc   4020
ttctttcgaa cctatcgtta ctaagaagtc tgccttctct gttaacttct tcatcaagga   4080
taccgtcgag gatcaatcta aggttaagtc tatgtctgac gaaacttgga ctaacacttg   4140
taaggctacc atttccttgg aacaacaaca gccatctcca tcttctactt tgactttgtc   4200
taagaagcaa gacttgcaga tcttgagaaa cagatgcgat attagcaagc tagacaagtt   4260
tgagttgtac gacaagatct ctaagaattt gggcttgcag tacaactcct tgtttcaagt   4320
```

-continued

```
tgttgatacc atcgaaactg gtaaggattg ctcttttgct actttgtctt tgccagaaga   4380
tactttgttc accaccattt tgaacccatg cttgttggat aactgtttcc atggtttgtt   4440
gaccttgatc aacgaaaagg gttctttcgt tgtcgagtcc atttcttctg tttctatcta   4500
cttggagaac atcggttcct tcaatcaaac ttctgttggt aacgtccagt tctacttgta   4560
caccactatt tctaaagcca cctcctttag ttctgaaggt acttgtaagt tgttcaccaa   4620
ggatggttcc ttgattttgt ctatcggtaa gttcatcatc aagtccacca atccaaagtc   4680
tactaagacc aacgaaacta tcgaatctcc attggacgaa accttctcta ttgaatggca   4740
atctaaggat tctccaattc caaccccaca acaaatccaa caacaatctc cattgaactc   4800
taacccatcc ttcattagat ctaccatctt gaaggacatc cagttcgaac aatactgctc   4860
ctccattatc cacaaagaat tgatcaacca cgaaaagtac aagaaccagc aatccttcga   4920
tatcaactcc ttggaaaacc acttgaacga tgaccaattg atggaatcct tgtccatctc   4980
caaagaatac ttgagattct tcaccaggat catctccatc attaagcaat acccaaagat   5040
cttgaacgaa aaagagctaa aagaattgaa agaaatcatc gaattgaagt acccatccga   5100
agttcagttg ttggaattcg aagttatcga gaaggtgtcc atgattatcc caaagttgtt   5160
gttcgaaaac gacaagcaat cttccatgac cttgttccaa gataacttgt tgaccaggtt   5220
ctactccaat tctaactcta ccagattcta cttggaaagg gtttccgaaa tggtcttgga   5280
atctattaga ccaatcgtca gagaaaagag ggtgttcaga attttagaga tcggtgctcg   5340
tacaggctct ttgtctaatg ttgttttgac taagttgaac acctacttgt ccaccttgaa   5400
ttctaatggt ggttctggtt acaacatcat cattgagtac accttcaccg atatttccgc   5460
caacttcatt attggtgaaa tccaagaaac catgtgcaac ttgtacccaa acgttacttt   5520
caagttctcc gtcttggact tggagaaaga gattattaac tcctccgatt tcttgatggg   5580
tgattacgat atagttttga tggcctacgt tatccatgcc gtttctaaca ttaagttctc   5640
catcgaacag ttgtacaagt tgttgtctcc aagaggttgg ttgttgtgta ttgaacctaa   5700
gtccaacgtt gtgttctccg atttggtttt cggttgtttt aatcagtggt ggaactacta   5760
cgatgatatt agaactaccc actgctcctt gtctgaatct caatggaatc agttgttgtt   5820
gaaccagtcc ttgaacaacg aatcctcttc ttcttctaac tgttacggtg gtttctccaa   5880
cgtttctttt attggtggtg aaaaggatgt cgactcccat tctttcatat tgcactgcca   5940
aaaagaatcc atctcccaaa tgaagttagc caccactatt aacaacggtt tgtcatctgg   6000
ttccatcgtt atcgttttga actctcaaca attgaccaac atgaagtcct acccaaaggt   6060
tattgagtat attcaagagg ctacctcttt gtgcaagacc attgaaatta tcgattccaa   6120
ggacgtcttg aactctacca attcagtttt ggaaaagatc caaaagtcct tgttggtgtt   6180
ctgtttgttg ggttatgact tgttggagaa caactaccaa gaacagtctt tcgaatacgt   6240
taagttgttg aacttgatct ctactaccgc ctcttcatct aatgataaga aaccaccaaa   6300
ggtcttgttg atcaccaagc aatctgaaag aatctccagg tctttctact ccagatcctt   6360
gattggtatt tccagaacct ctatgaacga gtacccaaat ttgtccatta cctctatcga   6420
tttggatacc aacgactact cattgcagtc tttgttgaag ccaatcttca gcaactctaa   6480
gttttccgac aacgagttca tcttcaaaaa gggcttgatg ttcgtgtcca ggatctttaa   6540
gaacaagcag ttgctagaat cctccaacgc ttttgaaact gactcttcta acttgtactg   6600
taaggcctct tctgacttgt cttacaagta cgctattaag cagtctatgt tgaccgaaaa   6660
tcagatcgaa atcaaggttg aatgcgtcgg tattaacttc aaggacaacc tattctacaa   6720
```

```
gggcttgttg ccacaagaaa ttttcagaat gggtgacatc tacaatccac catatggttt   6780
ggaatgctct ggtgttatta ccagaattgg ttctaacgtc accgaatact cagttggtca   6840
aaatgttttt ggtttcgcca gacattcttt gggttctcat gttgttacca acaaggattt   6900
ggttatcttg aagccagata ccatctcatt ttctgaagct gcttctatcc cagttgttta   6960
ctgtactgct tggtactcct tgttcaacat tggtcagttg tctaacgaag aatccatcct   7020
aattcattct gctactggtg gtgtaggttt ggcttctttg aatttgttga aaatgaagaa   7080
tcagcaacag caaccattga ccaatgttta tgctactgtt ggctctaacg agaagaagaa   7140
gttcttgatc gataacttca acaacttgtt caaagaggac ggcgaaaaca ttttctctac   7200
cagagacaaa gaatactcca accagttgga atccaagatc gatgttattt tgaacacctt   7260
gtccggtgaa ttcgtcgaat ctaatttcaa gtccttgaga tccttcggta gattgattga   7320
tttgtctgct actcacgttt acgccaatca acaaattggt ctaggtaact tcaagttcga   7380
ccacttgtat tctgctgttg acttggaaag attgatcgac gaaaaaccta agttgttgca   7440
gtccatcttg caaagaatta ccaactctat cgtcaacggt tccttggaaa aaattccaat   7500
taccatcttc ccatccaccg aaactaagga tgctatcgaa ttattgtcca agagatccca   7560
tatcggtaaa gttgttgtag attgcaccga tatctctaag tgtaatcctg ttggtgatgt   7620
gatcaccaac ttctctatga gattgccaaa gccaaactac cagttgaatt tgaactccac   7680
cttgttgatt actggtcagt ctggtttgtc tatccctttg ttgaattggt tgttgtctaa   7740
gtctggtggt aacgttaaga acgttgtcat catttctaag tccaccatga agtggaagtt   7800
gcagactatg atttcccatt tcgtttccgg tttcggtatc cattttaact acgttcaagt   7860
cgacatctcc aactacgatg ctttgtctga agctattaag caattgccat ctgatttgcc   7920
accaatcacc tctgtttttc atttggctgc tatctacaac gatgttccaa tggatcaagt   7980
taccatgtct accgttgaat ctgttcataa ccctaaagtt ttgggtgccg ttaacttgca   8040
tagaatctct gtttcttttg gttggaagtt gaaccacttc gtcttgttct cttctattac   8100
tgctattacc ggttacccag accaatctat ctacaattct gccaactcta ttttggacgc   8160
tttgtccaac tttagaaggt ttatgggttt gccatccttc tccattaact tgggtccaat   8220
gaaggatgaa ggtaaggttt ctaccaacaa gagcatcaag aagctattca agtctagagg   8280
tttgccaagc ctatccttga acaagttatt tggtttgttg gaggtcgtca tcaacaaccc   8340
atctaatcat gttatcccat cccaattgat ttgctcccca atcgatttca agacctacat   8400
cgaatctttc tcaactatga ggccaaagtt gttacacttg caacctacca tttccaagca   8460
gcaatcttct atcattaacg attctaccaa ggcttcctcc aacatttcat tgcaagataa   8520
gatcacctcc aaggtgtctg atttgttgtc cattccaatc tccaagatca acttcgatca   8580
tccattgaaa cactacggct tggattcttt gttgaccgtt caattcaaat cctggatcga   8640
caaagaattc gaaaagaact tgttcaccca tatccaattg gccaccatct ctattaactc   8700
attcttggaa aaggtgaacg gcttgtctac aaacaataac aacaacaaca attccaacgt   8760
caagtcctct ccatccattg tcaaagaaga aatcgttacc ttggacaagg atcaacaacc   8820
attgctattg aaagaacacc agcacattat catctcccca gatattagaa tcaacaagcc   8880
aaagagggaa tccttgatta gaaccccaat cttgaacaaa ttcaaccaga tcaccgaatc   8940
cattatcact ccatctacac catctttgtc ccaatccgat gttttgaaaa ctccaccaat   9000
caagtctttg aacaacacta agaactccag cttgattaac accccaccaa ttcaatctgt   9060
```

-continued ccaacaacat caaaagcaac aacaaaaggt ccaagtcatc caacaacagc aacaaccatt 9120
atccagattg tcctacaaga gcaacaacaa ctctttcgtt ttgggtatcg gtatttctgt 9180
tccaggtgaa cctatttccc aacaatcctt gaaagactcc atctccaatg acttttctga 9240
taaggctgaa actaacgaga aggtcaagag aatctttgag caatctcaaa tcaagaccag 9300
acacttggtt agagattaca ctaagccaga gaactccatc aagttcagac atttggaaac 9360
cattaccgat gtgaacaacc agttcaagaa agttgttcca gatttggctc aacaagcctg 9420
tttgagagct ttgaaagatt ggggtggtga taagggtgat attacccata tagtttctgt 9480
tacctccacc ggtattatca tcccagatgt taatttcaag ttgatcgact tgttgggctt 9540
gaacaaggat gttgaaagag tgtctttgaa cctaatgggt tgtttggctg gtttgagttc 9600
tttgagaact gctgcttctt tggctaaggc ttctccaaga aatagaattt tggttgtctg 9660
taccgaagtc tgctccttgc atttttctaa tactgatggt ggtgatcaaa tggtcgcctc 9720
ttctattttt gctgatggtt ctgctgctta cattattggt tgtaacccaa gaattgaaga 9780
aaccccatta tacgaagtca tgtgctccat taacagatct ttcccaaata ccgaaaacgc 9840
catggtttgg gatttggaaa aagaaggttg gaacttgggt ttggatgctt ctattccaat 9900
tgtcattggt tctggtattg aagccttcgt tgatactttg ttggataagg ctaagttgca 9960
aacttccact gctatttctg ctaaggattg cgaattcttg attcatactg gtggcaagtc 10020
catcttgatg aacatcgaaa attccttggg tatcgaccca aagcaaacta agaatacttg 10080
ggatgtttac catgcctacg gcaatatgtc atctgcctct gttattttcg ttatggatca 10140
tgccagaaag tccaagtctt tgccaactta ctcaatttct ttggcttttg gtccaggttt 10200
ggcttttgaa ggttgtttct tgaagaacgt cgtctgaaca gaagacggga gacactagca 10260
cacaacttta ccaggcaagg tatttgacgc tagcatgtgt ccaattcagt gtcatttatg 10320
attttttgta gtaggatata aatatataca gcgctccaaa tagtgcggtt gccccaaaaa 10380
caccacggaa cctcatctgt tctcgtactt tgttgtgaca aagtagctca ctgccttatt 10440
atcacatttt cattatgcaa cgcttcggaa aatacgatgt tgaaaatgcc tctagagatg 10500
aaaaacaatc gtaaaagggt cctgcgtaat tgaaacattt gatcagtatg cagtggcaca 10560
gaaacaacca ggaatactat agtcataggc aatacaaggt atatattggc tatgcagacc 10620
cctccagaaa gtaccgacgt caagttagat acacttaacg aacctagtgc acatttaatt 10680
gagaaaaatg tggctcttcc taaggacata ttccgttcgt acttgagtta ttggatctat 10740
gaaatcgctc gctatacacc agtcatgatt ttgtcgaaga catatgccca ctttgggaaa 10800
tagaaatggt cattttaagc tcaagtgaag cgaaaaaagg aggtatactc ctttacgcgt 10860
cacccaatct ggataggcac gtcaaactca ttaggtctca tcaagaacta gtgtagaaat 10920
gacgcttgaa ctccgaactt taaacaaagt tctgtttttg tttctgtttc tgtttcctgt 10980
tgctgtctct gtttctattt ttttcgtata gctctatttc ccttgtagat aaacatatat 11040
aagaatgcta ttatagaagc gtgtattttc ctccccctag cttcaacctg taattccctt 11100
cttagtaaag cgaactagaa ccagtttaat aggatataga 11140

<210> SEQ ID NO 82
<211> LENGTH: 11637
<212> TYPE: DNA
<213> ORGANISM: Artificial Sequence
<220> FEATURE:
<223> OTHER INFORMATION: DiPKS-5

<400> SEQUENCE: 82

-continued

```
atgaacgcta atatatgggt ggctgcttca gatggtaatt tggaccgagt ggaacatatc     60
ctccgcgaga gtaaaggcgc catgaccccg caatccaagg acattaacgg ctacactcca    120
atgcatgctg ccgccgcata cggccacctg gatttgctga agaaaatgtg caatgagtac    180
aatggagaca ttaatgtgtt ggacaacgac ggcgataccc cgttgcacca tgtggaggat    240
gtggccactg ccaggttgat cgtggaagag ctgggtggag acttcactat caggaatgtg    300
gagggccaaa cgccatacga ctcgttcgtc gagaacggtg aagatggtga gctaatcgag    360
tacatgagga ttaagtccgg cgtggccgat gttcacggag tggacggcgt gcagggtgag    420
ggtgtcatcg acagcaaatt gctggaagag ttcaaggaca acgtgagata caccttggaa    480
aatgaccctg aggaaggagc cgatgaggcc actctgcaac gcaggaggca gttggaacag    540
atcattacgg gagacaacgc tgaggaggag ttggaaaggt acatccgtgc tatggtcaga    600
gagcagatgc tgggccaggg ctccatggcg ggttccgggg acgaaccaga ttccaagaga    660
agaaaataac gaaagcaaca ggcgcgttgg acttttaatt ttcgaggacc gcgaatcctt    720
acatcacacc caatccccca caagtgatcc cccacacacc atagcttcaa aatgtttcta    780
ctcctttttt actcttccag attttctcgg actccgcgca tcgccgtacc acttcaaaac    840
acccaagcac agcatactaa atttcccctc tttcttcctc tagggtgtcg ttaattaccc    900
gtactaaagg tttggaaaag aaaaaagaga ccgcctcgtt tctttttctt cgtcgaaaaa    960
ggcaataaaa atttttatca cgtttctttt tcttgaaaat tttttttttt gatttttttc   1020
tctttcgatg acctcccatt gatatttaag ttaataaacg gtcttcaatt tctcaagttt   1080
cagtttcatt tttcttgttc tattacaact ttttttactt cttgctcatt agaaagaaag   1140
catagcaatc taatctaagt tttaataaac aatgaacaag aactccaaaa tccagtcccc   1200
aaactcttct gatgttgctg ttattggtgt tggttttaga ttcccaggta actctaatga   1260
cccagaatct ttgtggaaca acttgttgga tggtttcgat gctattaccc aagtcccaaa   1320
agaaagatgg gctacttctt ttagagagat gggtttgatc aagaacaagt tcggtggttt   1380
cttgaaggat tctgaatgga agaatttcga ccctttgttc tttggtatcg gtccaaaaga   1440
agctccattc attgatccac aacaaaggtt gttgttgtcc atcgtttggg aatctttgga   1500
agatgcttac atcagaccag atgaattgag aggttctaac actggtgttt tcatcggtgt   1560
ttctaacaac gattacacca agttgggttt ccaagacaac tactctattt ctccatacac   1620
tatgaccggc tctaactctt cattgaactc caacagaatt tcctactgct tcgattttag   1680
aggtccatcc attactgttg ataccgcttg ttcttcttcc ttggtttctg ttaatttggg   1740
tgtccaatcc atccaaatgg gtgaatgtaa gattgctatt tgcggtggtg ttaacgcttt   1800
gtttgatcca tctacatctg ttgccttttc caagttgggt gttttgtctg aaaatggcag   1860
atgcaactct tttagtgatc aagcctctgg ttacgttaga tctgaaggtg ctggtgttgt   1920
tgttttgaag tctttggaac aagctaagtt ggatggtgat agaatctacg gtgttatcaa   1980
gggtgtttcc tctaatgaag atggtgcttc taatggtgac aagaactctt tgactactcc   2040
atcttgtgaa gcccaatcca ttaacatttc taaggctatg gaaaaggcct ccttgtctcc   2100
atctgatatc tattacattg aagcccatgg tactggtact ccagttggtg atccaattga   2160
agttaaggcc ttgtccaaga tcttctccaa ctctaacaac aaccagttga acaacttctc   2220
taccgatggt aatgataacg atgatgatga tgacgataac acctctccag aaccattatt   2280
gattggctca ttcaagtcca acatcggtca tttggaatct gctgctggta ttgcttcttt   2340
```

```
gattaagtgt tgcttgatgt tgaagaacag gatgttggtt ccatccatta actgctctaa   2400
tttgaaccca tccattccat tcgatcagta caacatctcc gttatcagag aaatcagaca   2460
attcccaacc gataagttgg ttaacatcgg tatcaattct ttcggtttcg gtggttctaa   2520
ctgccatttg attattcaag agtacaacaa caacttcaag aacaactcta ccatctgcaa   2580
taacaacaac aacaacaata acaacatcga ctacttgatc ccaatctcct ctaagactaa   2640
gaagtccttg gataagtact tgattttgat caagaccaac tccaactacc acaaggatat   2700
ttctttcgat gacttcgtca agttccaaat caagtctaag cagtacaact tgtccaacag   2760
aatgactacc attgctaacg attggaactc cttcattaag ggttctaacg aattccacaa   2820
cttgatcgaa tctaaggatg gtgaaggtgg ttcttcatct tctaacagag gtattgattc   2880
cgccaatcaa atcaacacta ctactacctc taccatcaac gatatcgaac ctttgttggt   2940
tttcgttttc tgtggtcaag gtccacaatg gaatggtatg attaagacct tgtacaactc   3000
cgagaacgtt ttcaagaaca ccgttgatca tgttgacagc atcttgtaca agtacttcgg   3060
ttactccatt ttgaacgtct tgtctaagat cgatgataac gacgattcca tcaaccatcc   3120
aatagttgct caaccatctt tgttcttgtt gcaaattggt ttggtcgagt tgtttaagta   3180
ctggggtatc tacccatcta tctctgttgg tcattctttc ggtgaagtct cttcttatta   3240
cttgtccggt atcatctctt tggaaaccgc ttgtaaaatc gtctacgtca gatcctctaa   3300
tcagaacaaa actatgggtt ccggtaagat gttggttgtt tctatgggtt ttaagcaatg   3360
gaacgatcaa ttctctgctg aatggtccga tattgaaatt gcttgttaca acgctccaga   3420
ttccatagtt gttactggta acgaagaaag attgaaagaa ttgtccatca agttgtccga   3480
cgaatccaat caaattttca acaccttctt gaggtcccca tgttcttttc attcttccca   3540
tcaagaagtc atcaagggtt ctatgttcga agagttgtct aacttgcaat ctactggtga   3600
aaccgaaatc cctttgttct ctactgttac tggtagacaa gttttgtctg gtcatgttac   3660
tgctcaacac atctacgata atgttagaga accagtcttg ttccaaaaga cgattgaatc   3720
cattacctcc tacatcaagt ctcactaccc atccaatcaa aaggttatct acgttgaaat   3780
tgctccacac ccaaccttgt tttcattgat caaaaagtcc atcccatcct ccaacaagaa   3840
ttcctcttct gttttgtgtc cattgaacag aaaagaaaac tccaacaact cctacaagaa   3900
gttcgtttct cagttgtact tcaacggtgt taacgttgac ttcaacttcc agttgaactc   3960
catttgcgat aacgttaaca acgatcacca tttgaacaac gtcaagcaaa actccttcaa   4020
agagactacc aattccttgc caagatacca atgggaacaa gatgaatatt ggtccgaacc   4080
attgatctcc agaaagaata gattggaagg tccaactact tccttgttgg gtcatagaat   4140
tatctacagc ttcccagttt tccaatccgt tttggacttg caatctgaca actacaaata   4200
cttgttggac cacttggtta acggtaagcc agtttttcca ggtgctggtt atttggatat   4260
catcatcgaa ttcttcgact accaaaagca gcagttgaat tcctctgatt cctctaactc   4320
ctacatcatc aacgttgaca agatccaatt cttgaaccca attcacttga ccgaaaacaa   4380
gttgcaaacc ttgcaatctt ctttcgaacc tatcgttact aagaagtctg ccttctctgt   4440
taacttcttc atcaaggata ccgtcgagga tcaatctaag gttaagtcta tgtctgacga   4500
aacttggact aacacttgta aggctaccat ttccttggaa caacaacagc catctccatc   4560
ttctactttg actttgtcta agaagcaaga cttgcagatc ttgagaaaca gatgcgatat   4620
tagcaagcta gacaagtttg agttgtacga caagatctct aagaatttgg gcttgcagta   4680
caactccttg tttcaagttg ttgataccat cgaaactggt aaggattgct cttttgctac   4740
```

-continued

```
tttgtctttg ccagaagata ctttgttcac caccattttg aacccatgct tgttggataa   4800
ctgtttccat ggtttgttga ccttgatcaa cgaaaagggt tctttcgttg tcgagtccat   4860
ttcttctgtt tctatctact tggagaacat cggttccttc aatcaaactt ctgttggtaa   4920
cgtccagttc tacttgtaca ccactatttc taaagccacc tcctttagtt ctgaaggtac   4980
ttgtaagttg ttcaccaagg atggttcctt gattttgtct atcggtaagt tcatcatcaa   5040
gtccaccaat ccaaagtcta ctaagaccaa cgaaactatc gaatctccat tggacgaaac   5100
cttctctatt gaatggcaat ctaaggattc tccaattcca accccacaac aaatccaaca   5160
acaatctcca ttgaactcta acccatcctt cattagatct accatcttga aggacatcca   5220
gttcgaacaa tactgctcct ccattatcca caaagaattg atcaaccacg aaaagtacaa   5280
gaaccagcaa tccttcgata tcaactcctt ggaaaaccac ttgaacgatg accaattgat   5340
ggaatccttg tccatctcca aagaatactt gagattcttc accaggatca tctccatcat   5400
taagcaatac ccaaagatct tgaacgaaaa agagctaaaa gaattgaaag aaatcatcga   5460
attgaagtac ccatccgaag ttcagttgtt ggaattcgaa gttatcgaga aggtgtccat   5520
gattatccca aagttgttgt tcgaaaacga caagcaatct tccatgacct tgttccaaga   5580
taacttgttg accaggttct actccaattc taactctacc agattctact tggaaagggt   5640
ttccgaaatg gtcttggaat ctattagacc aatcgtcaga gaaaagaggg tgttcagaat   5700
tttagagatc ggtgctcgta caggctcttt gtctaatgtt gttttgacta agttgaacac   5760
ctacttgtcc accttgaatt ctaatggtgg ttctggttac aacatcatca ttgagtacac   5820
cttcaccgat atttccgcca acttcattat tggtgaaatc caagaaacca tgtgcaactt   5880
gtacccaaac gttactttca agttctccgt cttggacttg gagaaagaga ttattaactc   5940
ctccgatttc ttgatgggtg attacgatat agttttgatg gcctacgtta tccatgccgt   6000
ttctaacatt aagttctcca tcgaacagtt gtacaagttg ttgtctccaa gaggttggtt   6060
gttgtgtatt gaacctaagt ccaacgttgt gttctccgat ttggttttcg gttgttttaa   6120
tcagtggtgg aactactacg atgatattag aactacccac tgctccttgt ctgaatctca   6180
atggaatcag ttgttgttga accagtcctt gaacaacgaa tcctcttctt cttctaactg   6240
ttacggtggt ttctccaacg tttcttttat tggtggtgaa aaggatgtcg actcccattc   6300
tttcatattg cactgccaaa aagaatccat ctcccaaatg aagttagcca ccactattaa   6360
caacggtttg tcatctggtt ccatcgttat cgttttgaac tctcaacaat tgaccaacat   6420
gaagtcctac ccaaaggtta ttgagtatat tcaagaggct acctctttgt gcaagaccat   6480
tgaaattatc gattccaagg acgtcttgaa ctctaccaat tcagttttgg aaaagatcca   6540
aaagtccttg ttggtgttct gtttgttggg ttatgacttg ttggagaaca actaccaaga   6600
acagtctttc gaatacgtta agttgttgaa cttgatctct actaccgcct cttcatctaa   6660
tgataagaaa ccaccaaagg tcttgttgat caccaagcaa tctgaaagaa tctccaggtc   6720
tttctactcc agatccttga ttggtatttc cagaacctct atgaacgagt acccaaattt   6780
gtccattacc tctatcgatt tggataccaa cgactactca ttgcagtctt tgttgaagcc   6840
aatcttcagc aactctaagt tttccgacaa cgagttcatc ttcaaaaagg gcttgatgtt   6900
cgtgtccagg atctttaaga acaagcagtt gctagaatcc tccaacgctt ttgaaactga   6960
ctcttctaac ttgtactgta aggcctcttc tgacttgtct tacaagtacg ctattaagca   7020
gtctatgttg accgaaaatc agatcgaaat caaggttgaa tgcgtcggta ttaacttcaa   7080
```

-continued

```
ggacaaccta ttctacaagg gcttgttgcc acaagaaatt ttcagaatgg gtgacatcta   7140
caatccacca tatggtttgg aatgctctgg tgttattacc agaattggtt ctaacgtcac   7200
cgaatactca gttggtcaaa atgtttttgg tttcgccaga cattctttgg gttctcatgt   7260
tgttaccaac aaggatttgg ttatcttgaa gccagatacc atctcatttt ctgaagctgc   7320
ttctatccca gttgtttact gtactgcttg gtactccttg ttcaacattg gtcagttgtc   7380
taacgaagaa tccatcctaa ttcattctgc tactggtggt gtaggtttgg cttctttgaa   7440
tttgttgaaa atgaagaatc agcaacagca accattgacc aatgtttatg ctactgttgg   7500
ctctaacgag aagaagaagt tcttgatcga taacttcaac aacttgttca aagaggacgg   7560
cgaaaacatt ttctctacca gagacaaaga atactccaac cagttggaat ccaagatcga   7620
tgttattttg aacaccttgt ccggtgaatt cgtcgaatct aatttcaagt ccttgagatc   7680
cttcggtaga ttgattgatt tgtctgctac tcacgtttac gccaatcaac aaattggtct   7740
aggtaacttc aagttcgacc acttgtattc tgctgttgac ttggaaagat tgatcgacga   7800
aaaacctaag ttgttgcagt ccatcttgca aagaattacc aactctatcg tcaacggttc   7860
cttggaaaaa attccaatta ccatcttccc atccaccgaa actaaggatg ctatcgaatt   7920
attgtccaag agatcccata tcggtaaagt tgttgtagat tgcaccgata tctctaagtg   7980
taatcctgtt ggtgatgtga tcaccaactt ctctatgaga ttgccaaagc caaactacca   8040
gttgaatttg aactccacct tgttgattac tggtcagtct ggtttgtcta tccctttgtt   8100
gaattggttg ttgtctaagt ctggtggtaa cgttaagaac gttgtcatca tttctaagtc   8160
caccatgaag tggaagttgc agactatgat ttcccatttc gtttccggtt tcggtatcca   8220
ttttaactac gttcaagtcg acatctccaa ctacgatgct ttgtctgaag ctattaagca   8280
attgccatct gatttgccac caatcacctc tgtttttcat ttggctgcta tctacaacga   8340
tgttccaatg gatcaagtta ccatgtctac cgttgaatct gttcataacc ctaaagtttt   8400
gggtgccgtt aacttgcata gaatctctgt ttcttttggt tggaagttga accacttcgt   8460
cttgttctct tctattactg ctattaccgg ttacccagac caatctatct acaattctgc   8520
caactctatt ttggacgctt tgtccaactt tagaaggttt atgggtttgc catccttctc   8580
cattaacttg ggtccaatga aggatgaagg taaggtttct accaacaaga gcatcaagaa   8640
gctattcaag tctagaggtt tgccaagcct atccttgaac aagttatttg gtttgttgga   8700
ggtcgtcatc aacaacccat ctaatcatgt tatcccatcc caattgattt gctccccaat   8760
cgatttcaag acctacatcg aatctttctc aactatgagg ccaaagttgt tacacttgca   8820
acctaccatt tccaagcagc aatcttctat cattaacgat tctaccaagg cttcctccaa   8880
catttcattg caagataaga tcacctccaa ggtgtctgat ttgttgtcca ttccaatctc   8940
caagatcaac ttcgatcatc cattgaaaca ctacggcttg gattctttgt tgaccgttca   9000
attcaaatcc tggatcgaca aagaattcga aaagaacttg ttcacccata tccaattggc   9060
caccatctct attaactcat tcttggaaaa ggtgaacggc ttgtctacaa acaataacaa   9120
caacaacaat tccaacgtca agtcctctcc atccattgtc aaagaagaaa tcgttacctt   9180
ggacaaggat caacaaccat tgctattgaa agaacaccag cacattatca tctccccaga   9240
tattagaatc aacaagccaa agagggaatc cttgattaga accccaatct tgaacaaatt   9300
caaccagatc accgaatcca ttatcactcc atctacacca tctttgtccc aatccgatgt   9360
tttgaaaact ccaccaatca agtctttgaa caacactaag aactccagct tgattaacac   9420
cccaccaatt caatctgtcc aacaacatca aaagcaacaa caaaaggtcc aagtcatcca   9480
```

-continued acaacagcaa caaccattat ccagattgtc ctacaagagc aacaacaact ctttcgtttt 9540
gggtatcggt atttctgttc caggtgaacc tatttcccaa caatccttga aagactccat 9600
ctccaatgac ttttctgata aggctgaaac taacgagaag gtcaagagaa tctttgagca 9660
atctcaaatc aagaccagac acttggttag agattacact aagccagaga actccatcaa 9720
gttcagacat ttggaaacca ttaccgatgt gaacaaccag ttcaagaaag ttgttccaga 9780
tttggctcaa caagcctgtt tgagagcttt gaaagattgg ggtggtgata agggtgatat 9840
tacccatata gtttctgtta cctccaccgg tattatcatc ccagatgtta atttcaagtt 9900
gatcgacttg ttgggcttga acaaggatgt tgaaagagtg tctttgaacc taatgggttg 9960
tttggctggt ttgagttctt tgagaactgc tgcttctttg gctaaggctt ctccaagaaa 10020
tagaattttg gttgtctgta ccgaagtctg ctccttgcat tttctaata ctgatggtgg 10080 tgatcaaatg gtcgcctctt ctatttttgc tgatggttct gctgcttaca ttattggttg 10140
taacccaaga attgaagaaa ccccattata cgaagtcatg tgctccatta acagatcttt 10200
cccaaatacc gaaaacgcca tggtttggga tttggaaaaa gaaggttgga acttgggttt 10260
ggatgcttct attccaattg tcattggttc tggtattgaa gccttcgttg atactttgtt 10320
ggataaggct aagttgcaaa cttccactgc tatttctgct aaggattgcg aattcttgat 10380
tcatactggt ggcaagtcca tcttgatgaa catcgaaaat tccttgggta tcgacccaaa 10440
gcaaactaag aatacttggg atgtttacca tgcctacggc aatatgtcat ctgcctctgt 10500
tattttcgtt atggatcatg ccagaaagtc caagtctttg ccaacttact caatttcttt 10560
ggcttttggt ccaggtttgg cttttgaagg ttgtttcttg aagaacgtcg tctgaacaga 10620
agacgggaga cactagcaca caactttacc aggcaaggta tttgacgcta gcatgtgtcc 10680
aattcagtgt catttatgat tttttgtagt aggatataaa tatatacagc gctccaaata 10740
gtgcggttgc cccaaaaaca ccacggaacc tcatctgttc tcgtactttg ttgtgacaaa 10800
gtagctcact gccttattat cacattttca ttatgcaacg cttcggaaaa tacgatgttg 10860
aaaatgcctc tagagatgaa aaacaatcgt aaaagggtcc tgcgtaattg aaacatttga 10920
tcagtatgca gtggcacaga aacaaccagg aatactatag tcataggcaa tacaaggtat 10980
atattggcta tgcagacccc tccagaaagt accgacgtca agttagatac acttaacgaa 11040
cctagtgcac atttaattga gaaaaatgtg gctcttccta aggacatatt ccgttcgtac 11100
ttgagttatt ggatctatga aatcgctcgc tatacaccag tcatgatttt gtctaataga 11160
cgttcttaca aggtaaaatt tcaccgcgtt tttaaataga atgaaaaaaa cgttgtagag 11220
tgaaagaaaa gcaacaaata tacagttcac aaggcagctt cgtatagtaa tacagcacga 11280
aaaacagctc atagaaatgg taacacagac caatccggtc cctgttacat atccaacgga 11340
tgcttatatc cccacgtatc tgcccgatga taaggtctcc aatctggcag atttgaaaaa 11400
attgatagaa atggattcca gactagattt gtatctgaca agaaggaggc tggatacgtc 11460
catcaattta cctacaaaca ccaagaccaa ggaccatccc cccaataaag agatgctgag 11520
gatttacgtc tacaacacta cggaaagcag ccctcgcagc gattctggca ccccagcgga 11580
ctcaggcaag actacatgga cactgagaat agaaggtaag cttctgcacg agtccgc 11637

<210> SEQ ID NO 83
<211> LENGTH: 7114
<212> TYPE: DNA
<213> ORGANISM: Artificial Sequence
<220> FEATURE:

<223> OTHER INFORMATION: PDH

<400> SEQUENCE: 83

```
caccggagct tggatatgat aaacgaaata ttcttgaatc gtgagatcgc ctgttttcaa     60
aaccgttgga ggcagaaaca attttgtcac aagatgggca ttctacccca tccttgctgt    120
attattgtag tctcgctttc ttttatgctg gacaaatgag actactgcac atttttatac    180
gttcttggtt ttttttaaag gtgtggtttc ggcattatcc tgccgcacgt ttcttggata    240
attcatcctg attctctatt ttaaacgctt cagcctatca ggatttggtt ttgatacata    300
ctgcaagagt gtatctcggg aacagtcatt tattccgcaa caaacttaat tgcggaacgc    360
gttaggcgat ttctagcata tatcaaatac cgttcgcgat ttcttctggg ttcgtctctt    420
ttcttttaaa tacttattaa cgtactcaaa caactacact tcgttgtatc tcagaatgag    480
atccctcagt atgacaatac atcattctaa acgttcgtaa aacacatatg aaacaacttt    540
ataacaaagc gaacaaaatg ggcaacatga gatgaaactc cgcgtccctt agctgaacta    600
cccaaacgta cgaatgcctg aacaattagt ttagatccga gattccgcgc ttccatcatt    660
tagtataatc catattttat ataatatata ggataagtaa cagcccgcga aaaacaacaa    720
ataatcataa aaattttaga actagacata tcgagtttat cattatcaat actgccattt    780
caaagaatac gtaaataatt aatagtagtg attttcctaa ctttatttag tcaaaaaatt    840
agccttttaa ttctgctgta acccgtacat gcccaaaata gggggcgggt tacacagaat    900
atataacatc gtaggtgtct gggtgaacag tttattcctg gcatccacta aatataatgg    960
agcccgcttt ttaagctggc atccagaaaa aaaaagaatc ccagcaccaa aatattgttt   1020
tcttcaccaa ccatcagttc ataggtccat tctcttagcg caactacaga gaacaggggc   1080
acaaacaggc aaaaaacggg cacaacctca atggagtgat gcaacctgcc tggagtaaat   1140
gatgacacaa ggcaattgac ccacgcatgt atctatctca ttttcttaca ccttctatta   1200
ccttctgctc tctctgattt ggaaaaagct gaaaaaaaag gttgaaacca gttccctgaa   1260
attattcccc tacttgacta ataagtatat aaagacggta ggtattgatt gtaattctgt   1320
aaatctattt cttaaacttc ttaaattcta cttttatagt tagtcttttt tttagtttta   1380
aaacaccaag aacttagttt cgactagaaa atttattata aaaggaagag aaataattaa   1440
acaatgacta agctacactt tgacactgct gaaccagtca agatcacact tccaaatggt   1500
ttgacatacg agcaaccaac cggtctattc attaacaaca agtttatgaa agctcaagac   1560
ggtaagacct atcccgtcga agatccttcc actgaaaaca ccgtttgtga ggtctcttct   1620
gccaccactg aagatgttga atatgctatc gaatgtgccg accgtgcttt ccacgacact   1680
gaatgggcta cccaagaccc aagagaaaga ggccgtctac taagtaagtt ggctgacgaa   1740
ttggaaagcc aaattgactt ggtttcttcc attgaagctt tggacaatgg taaaactttg   1800
gccttagccc gtggggatgt taccattgca atcaactgtc taagagatgc tgctgcctat   1860
gccgacaaag tcaacggtag aacaatcaac accggtgacg gctacatgaa cttcaccacc   1920
ttagagccaa tcggtgtctg tggtcaaatt attccatgga actttccaat aatgatgttg   1980
gcttggaaga tcgccccagc attggccatg ggtaacgtct gtatcttgaa acccgctgct   2040
gtcacacctt taaatgccct atactttgct tctttatgta agaaggttgg tattccagct   2100
ggtgtcgtca acatcgttcc aggtcctggt agaactgttg gtgctgcttt gaccaacgac   2160
ccaagaatca gaaagctggc ttttaccggt tctacagaag tcggtaagag tgttgctgtc   2220
gactcttctg aatctaactt gaagaaaatc actttggaac taggtggtaa gtccgcccat   2280
```

ttggtctttg acgatgctaa cattaagaag actttaccaa atctagtaaa cggtattttc 2340
aagaacgctg gtcaaatttg ttcctctggt tctagaattt acgttcaaga aggtatttac 2400
gacgaactat tggctgcttt caaggcttac ttggaaaccg aaatcaaagt tggtaatcca 2460
tttgacaagg ctaacttcca aggtgctatc actaaccgtc aacaattcga cacaattatg 2520
aactacatcg atatcggtaa gaaagaaggc gccaagatct taactggtgg cgaaaaagtt 2580
ggtgacaagg gttacttcat cagaccaacc gttttctacg atgttaatga agacatgaga 2640
attgttaagg aagaaatttt tggaccagtt gtcactgtcg caaagttcaa gactttagaa 2700
gaaggtgtcg aaatggctaa cagctctgaa ttcggtctag gttctatggg tatcgaaaca 2760
gaatctttga gcacaggttt gaaggtggcc aagatgttga aggccggtac cgtctggatc 2820
aacacataca acgattttga ctccagagtt ccattcggtg gtgttaagca atctggttac 2880
ggtagagaaa tgggtgaaga agtctaccat gcatacactg aagtaaaagc tgtcagaatt 2940
aagttgtaaa gacataaaac tgaaacaaca ccaattaata atagactttt ggacttcttc 3000
gccagaggtt tggtcaagtc tccaatcaag gttgtcggct tgtctacctt gccagaaatt 3060
tacgaaaaga tggaaaaggg tcaaatcgtt ggtagatacg ttgttgacac ttctaaataa 3120
gcgaatttct tatgatttat gatttttatt attaaataag ttataaaaaa aataagtgta 3180
tacaaatttt aaagtgactc ttaggtttta aaacgaaaat tcttattctt gagtaactct 3240
ttcctgtagg tcaggttgct ttctcaggta tagcatgagg tcgctcttat tgaccacacc 3300
tctaccggca tggcttaaat aacatactca tcactaaaca ttcttaacaa tcaaagcaac 3360
aggcgcgttg gacttttaat tttcgaggac cgcgaatcct tacatcacac ccaatccccc 3420
acaagtgatc ccccacacac catagcttca aaatgtttct actccttttt tactcttcca 3480
gattttctcg gactccgcgc atcgccgtac cacttcaaaa cacccaagca cagcatacta 3540
aatttcccct ctttcttcct ctagggtgtc gttaattacc cgtactaaag gtttggaaaa 3600
gaaaaaagag accgcctcgt ttcttttct tcgtcgaaaa aggcaataaa aatttttatc 3660
acgtttcttt ttcttgaaaa tttttttttt tgattttttt ctctttcgat gacctcccat 3720
tgatatttaa gttaataaac ggtcttcaat ttctcaagtt tcagtttcat ttttcttgtt 3780
ctattacaac ttttttact tcttgctcat tagaaagaaa gcatagcaat ctaatctaag 3840
ttttaataca tctaccagtc aacagccaac aattaactaa ttaaacaatg tcccaaactc 3900
ataagcacgc tattccagct aatattgctg atagatgctt gatcaaccca gaacagtacg 3960
aaactaagta caagcaatcc atcaacgatc cagatacttt ttggggtgaa caaggtaaga 4020
ttttggattg gattacccca taccaaaagg tcaagaatac ttcttttgct ccaggcaacg 4080
tttccattaa gtggtatgaa gatggtactt tgaacttggc tgctaactgt ttggatagac 4140
acttgcaaga aaacggtgat agaaccgcta ttatttggga aggtgatgat acctcccaat 4200
ccaaacatat ctcttacaga gaattgcaca gagatgtctg tagattcgct aacactttgt 4260
tggatttggg catcaaaaag ggtgatgttg ttgctatcta tatgccaatg gttcctgaag 4320
ctgctgttgc tatgttggct tgtgctagaa ttggtgctgt tcattctgtt attttcggtg 4380
gtttttcacc agaagctgtt gccggtagaa ttatcgattc ttcatccaga ttggttatca 4440
ccgctgatga aggtgttaga gctggtagat ctattccatt gaaaaagaac gttgatgacg 4500
ccttgaagaa cccaaatgtt acttctgttg aacacgtcat cgttttgaag agaactggtt 4560
ctgatatcga ttggcaagag ggtagagatt tgtggtggag agatttgatt gaaaaggctt 4620

-continued

```
ctccagaaca tcaaccagaa gctatgaacg ctgaagatcc tttgtttatc ttgtacactt   4680
ctggttctac tggtaagcca aaaggtgttt tacacactac tggtggttat ttggtttacg   4740
ctgctactac tttcaagtac gttttcgatt atcacccagg tgatatctat tggtgtactg   4800
ctgatgttgg ttgggttact ggtcattctt atttgttgta tggtccattg gcttgtggtg   4860
ctactacatt gatgtttgaa ggtgttccaa attggccaac tccagctaga atgtgtcaag   4920
ttgttgacaa acaccaagtc aacatcttgt atactgctcc aactgctatt agagctttga   4980
tggctgaagg tgataaggct attgaaggta ctgatagatc ctccttgaga atcttgggtt   5040
ctgttggtga acctattaac cctgaagcct gggaatggta ttggaagaaa attggtaaag   5100
aaaagtgccc agttgttgat acttggtggc aaactgaaac tggtggtttt atgattactc   5160
cattgccagg tgctattgaa ttgaaagctg gttctgctac tagaccattt tttggtgttc   5220
aaccagcttt ggttgataac gaaggtcatc cacaagaagg tgctactgaa ggtaatttgg   5280
ttattactga ttcttggcca ggtcaagcta gaactttgtt tggtgatcac gaaagattcg   5340
aacagactta cttctctacc ttcaagaaca tgtacttctc tggtgatggt gctagaagag   5400
atgaagatgg ttactattgg attaccggta gagttgatga tgtcttgaat gtttctggtc   5460
acagattagg tactgccgaa attgaatctg ctttggttgc tcatccaaag attgctgaag   5520
ctgcagttgt tggtattcca catgctatta agggtcaagc tatctacgct tacgttactt   5580
tgaatcatgg tgaagaacca tctccagaat tatacgctga agttagaaac tgggtcagaa   5640
aagaaattgg tccattagct accccagatg ttttacattg gactgattct ttgccaaaga   5700
ccagatcagg taagatcatg agaagaatct tgagaaagat tgctgctggt gatacttcta   5760
acttgggtga tacttcaaca ttagctgatc caggtgttgt tgaaaagcct ttggaagaaa   5820
aacaagctat tgccatgcca tcctaataat taaatactat tttcaaaatt ctacttaaaa   5880
ataacagaag acgggagaca ctagcacaca actttaccag gcaaggtatt tgacgctagc   5940
atgtgtccaa ttcagtgtca tttatgattt tttgtagtag gatataaata tatacagcgc   6000
tccaaatagt gcggttgccc caaaaacacc acggaacctc atctgttctc gtactttgtt   6060
gtgacaaagt agctcactgc cttattatca cattttcatt atgcaacgct tcggaaaata   6120
cgatgttgaa aatgcctcta gagatgaaaa acaatcgtaa aagggtcctg cgtaattgaa   6180
acatttgatc agtatgcagt ggcacagaaa caaccaggaa tactatagtc ataggcaata   6240
caaggtatat attggctatg cagacccctc cagaaagtac cgacgtcaag ttagatacac   6300
ttaacgaacc tagtgcacat ttaattgaga aaaatgtggc tcttcctaag gacatattcc   6360
gttcgtactt gagttattgg atctatgaaa tcgctcgcta tacaccagtc atgattttgt   6420
cattgcgaag actatactga tatatgaatt taaactagag cggaccaact atcatccgct   6480
aattactgac attaccaaat gagatctgtg aatgggcaag ataaaaaaca aaaattgaaa   6540
tgtttgacgt tatgtaaaac tattaattcc ttcgctttcg gcggtcacag aatttgcgtg   6600
tagctgactc ttgttcaatc aatatcattt gttactttat ttgaaagtct gtattactgc   6660
gcctattgtc atccgtacca aagaacgtca aaaagaaaca agataatttt tgtgcttaca   6720
ccatttatag atcactgagc ccagaatatc gctggagctc agtgtaagtg gcatgaacac   6780
aactctgact gatcgcacat attgccgtta tcataaatac tagttgtact tgtcaatgcg   6840
acgaatggca tcatgcctat tattacgttc ctctttttcc gtttcatgtt tccagaatgc   6900
tattgaatct aacacttcaa ttataaaaaa gaataaatcc gcaataattt taggctaatt   6960
gttgtactgt caagcgaacc taatggttaa aattcagagg aaccttcgac gtagtctgat   7020
```

cgctacttct atatcttatg ttcccagtca atcaaaagtt gatactataa tagctgccat 7080
ttatacctgt tagttatggc gatcgtttat cacg 7114

<210> SEQ ID NO 84
<211> LENGTH: 3256
<212> TYPE: DNA
<213> ORGANISM: Artificial Sequence
<220> FEATURE:
<223> OTHER INFORMATION: Maf1

<400> SEQUENCE: 84
aatgatttaa gcgtgcgtga agataacact acaatccatt ttaaagcaac atccacattg 60
agtgtataca ccacaaaggt tttttcaggg cgtttttctc gccactttat gttgaccaaa 120
attattaatg gaacttacaa cgtttccaaa agttagttaa atacatacgt ctatttacta 180
agcaagaaat atatcatgac aagcccaaat attatattgt tatgtttaca aaaaaaaaat 240
ggctatatac atcaagtctg gaggcttttt ataacaagca agtggggtaa cttagacata 300
agattgactt ctttgaattc aacaaaaata catacttttg atgatttcaa tggtagaagc 360
ataaacaaca aataatcata aaaattttag aactagacat aaagcaacag gcgcgttgga 420
cttttaattt tcgaggaccg cgaatcctta catcacaccc aatcccccac aagtgatccc 480
ccacacacca tagcttcaaa atgtttctac tcctttttta ctcttccaga ttttctcgga 540
ctccgcgcat cgccgtacca cttcaaaaca cccaagcaca gcatactaaa tttcccctct 600
ttcttcctct agggtgtcgt taattacccg tactaaaggt ttggaaaaga aaaaagagac 660
cgcctcgttt ctttttcttc gtcgaaaaag gcaataaaaa tttttatcac gtttcttttt 720
cttgaaaatt tttttttttg atttttttct ctttcgatga cctcccattg atatttaagt 780
taataaacgg tcttcaattt ctcaagtttc agtttcattt ttcttgttct attacaactt 840
tttttacttc ttgctcatta gaaagaaagc atagcaatct aatctaagtt ttaatctaga 900
aaatttatta taaaaggaag agaaataatt aaacaatgaa atttattgat gagctagata 960
tagagagagt gaatcaaact ctcaatttcg agacaaatga ctgtaaaatc gtgggcagtt 1020
gcgatatttt cacaacaaag gcggttgcat cagatagaaa attatataaa actattgatc 1080
agcatttgga tactatttta caggaaaatg agaattacaa tgctaccctt cagcaacagc 1140
tagctgctcc cgaaacaaac caatcaccct gctcgtcgcc attttattct aataggaggg 1200
atagcaactc tttttgggag caaaagagaa gaatatcttt tagtgaatac aatagcaata 1260
ataacactaa caacagtaat ggcaatagca gtaataacaa taactattct ggacctaatg 1320
gttcttctcc agcaactttt cccaaaagtg ccaagctaaa tgaccaaaat ttaaaagaat 1380
tagtctcgaa ttacgattct ggctctatga gctcatcgtc tcttgattct tcttctaaga 1440
atgatgagag gataagaaga aggagcagta gcagtattag cagtttcaaa agtggtaaat 1500
catcgaacaa taattacagt tctggtacag caaccaacaa tgttaacaaa agaagaaaat 1560
cttcgataaa cgaaaggcca agcaatttaa gtttgggtcc gtttggtccc ataaacgaac 1620
cgtcaagccg caaaatattt gcttatctga ttgctatcct caacgcttct tatcctgacc 1680
atgatttttc atcggttgag ccaacggatt ttgtcaaaac atcattgaaa acttttattt 1740
ccaaatttga aaacacctta tattctcttg gtagacaacc agaggaatgg gtctgggagg 1800
taattaattc tcacatgact ctttctgatt gcgtcctttt tcaatattca ccttcaaact 1860 ctttttttgga agatgagcct ggctatcttt ggaatcttat aggttttctt tacaacagga 1920

```
aaaggaaaag agtggcttac ctttacttga tttgctcgcg tctaaattcg agtacaggcg   1980
aagtggaaga tgccttggca aaaaaacctc agggaaagct tataatagat gatggctcaa   2040
atgaatacga aggagaatac gatttcactt atgatgagaa tgtaatagat gataaatcag   2100
atcaagaaga atccctacag tagagacata aaactgaaac aacaccaatt aataatagac   2160
tttacagaag acgggagaca ctagcacaca actttaccag gcaaggtatt tgacgctagc   2220
atgtgtccaa ttcagtgtca tttatgattt tttgtagtag gatataaata tatacagcgc   2280
tccaaatagt gcggttgccc caaaaacacc acggaacctc atctgttctc gtactttgtt   2340
gtgacaaagt agctcactgc cttattatca cattttcatt atgcaacgct tcggaaaata   2400
cgatgttgaa aatgcctcta gagatgaaaa acaatcgtaa aagggtcctg cgtaattgaa   2460
acatttgatc agtatgcagt ggcacagaaa caaccaggaa tactatagtc ataggcaata   2520
caaggtatat attggctatg cagacccctc cagaaagtac cgacgtcaag ttagatacac   2580
ttaacgaacc tagtgcacat ttaattgaga aaaatgtggc tcttcctaag gacatattcc   2640
gttcgtactt gagttattgg atctatgaaa tcgctcgcta tacaccagtc atgattttgt   2700
ccttaaataa catactcatc actaaacatt cttaacaatc agaaaacaac gcgtcatgaa   2760
aaagagttac tgaaccttca gatcctactt attgtaatgc ttcgcgacat ccaatccatt   2820
taataatcaa tttaaaacta gagttggtag agttccttgt tgaacgtgat aacccaaaag   2880
cataatacga gtaatgtttc agtattgcta ttatatgttt acacaaggaa aacatataat   2940
aacaaacctc taatccggta gtacttaaga aactatagtt tctatgtaca aaaaggtaac   3000
tatgtaattc ttacatttac ataacatata gaagggtcca ataaacttac taaacttact   3060
accttgttgt atataggcta gatcgtaatc cactacgtca acataaaaaa aacttaagga   3120
gtttgaattt tatgtacaaa cagattgtta aaatataata taagattatg gaaacgaact   3180
tgctctaaaa aaaatttaaa gttttataaa atcctcgcac tatcgctgtt atacatgatg   3240
tccccaaagc gtgtac                                                    3256
```

<210> SEQ ID NO 85
<211> LENGTH: 4538
<212> TYPE: DNA
<213> ORGANISM: Artificial Sequence
<220> FEATURE:
<223> OTHER INFORMATION: Erg20K197E

<400> SEQUENCE: 85

```
ggccgcgttg ctggcgtttt tccataggct ccgcccccct gacgagcatc acaaaaatcg     60
acgctcaagt cagaggtggc gaaacccgac aggactataa agataccagg cgtttccccc    120
tggaagctcc ctcgtgcgct ctcctgttcc gaccctgccg cttaccggat acctgtccgc    180
ctttctccct tcgggaagcg tggcgctttc tcaatgctca cgctgtaggt atctcagttc    240
ggtgtaggtc gttcgctcca agctgggctg tgtgcacgaa ccccccgttc agcccgaccg    300
ctgcgcctta tccggtaact atcgtcttga gtccaacccg gtaagacacg acttatcgcc    360
actggcagca gccactggta acaggattag cagagcgagg tatgtaggcg gtgctacaga    420
gttcttgaag tggtggccta actacggcta cactagaagg acagtatttg gtatctgcgc    480
tctgctgaag ccagttacct tcggaaaaag agttggtagc tcttgatccg gcaaacaaac    540
caccgctggt agcggtggtt tttttgtttg caagcagcag attacgcgca gaaaaaaagg    600
atctcaagaa gatcctttga tcttttctac ggggtctgac gctcagtgga acgaaaactc    660
acgttaaggg attttggtca tgaacgcatc tacgactgtg ggtcccgtgg agaaatgtat    720
```

```
gaaaccctgt atggagagtg attagcttgc ctcgtccccg ccgggtcacc cggccagcga     780
catggaggcc cagaataccc tccttgacag tcttgacgtg cgcagctcag gggcatgatg     840
tgactgtcgc ccgtacattt agcccataca tccccatgta taatcatttg catccataca     900
ttttgatggc cgcacggcgc gaagcaaaaa ttacggctcc tcgctgcaga cctgcgagca     960
gggaaacgct cccctcacag acgcgttgaa ttgtccccac gccgcgcccc tgtagagaaa    1020
tataaaaggt taggatttgc cactgaggtt cttctttcat atacttcctt ttaaaatctt    1080
gctaggatac agttctcaca tcacatccga acataaacaa ccatgggtaa ggaaaagact    1140
cacgtttcga ggccgcgatt aaattccaac atggatgctg atttatatgg gtataaatgg    1200
gctcgcgata atgtcgggca atcaggtgcg acaatctatc gattgtatgg gaagcccgat    1260
gcgccagagt tgtttctgaa acatggcaaa ggtagcgttg ccaatgatgt tacagatgag    1320
atggtcagac taaactggct gacggaattt atgcctcttc cgaccatcaa gcattttatc    1380
cgtactcctg atgatgcatg gttactcacc actgcgatcc ccggcaaaac agcattccag    1440
gtattagaag aatatcctga ttcaggtgaa aatattgttg atgcgctggc agtgttcctg    1500
cgccggttgc attcgattcc tgtttgtaat tgtcctttta acagcgatcg cgtatttcgt    1560
ctcgctcagg cgcaatcacg aatgaataac ggtttggttg atgcgagtga ttttgatgac    1620
gagcgtaatg gctggcctgt tgaacaagtc tggaaagaaa tgcataagct tttgccattc    1680
tcaccggatt cagtcgtcac tcatggtgat ttctcacttg ataaccttat ttttgacgag    1740
gggaaattaa taggttgtat tgatgttgga cgagtcggaa tcgcagaccg ataccaggat    1800
cttgccatcc tatggaactg cctcggtgag ttttctcctt cattacagaa acggcttttt    1860
caaaaatatg gtattgataa tcctgatatg aataaattgc agtttcattt gatgctcgat    1920
gagtttttct aatcagtact gacaataaaa agattcttgt tttcaagaac ttgtcatttg    1980
tatagttttt ttatattgta gttgttctat tttaatcaaa tgttagcgtg atttatattt    2040
tttttcgcct cgacatcatc tgcccagatg cgaagttaag tgcgcagaaa gtaatatcat    2100
gcgtcaatcg tatgtgaatg ctggtcgcta tactgctgtc gattcgatac taacgccgcc    2160
atccagtgtc gaaaacgagc tctcgagaac ccttaatcat acgttgaaac tacggcaaag    2220
gattggtcag atcgcttcat acaggggtat cccggcataa ccctcactaa agggaacaaa    2280
agctggagct cgtttaaaag caacaggcgc gttggacttt taattttcga ggaccgcgaa    2340
tccttacatc acacccaatc ccccacaagt gatcccccac acaccatagc ttcaaaatgt    2400
ttctactcct tttttactct tccagatttt ctcggactcc gcgcatcgcc gtaccacttc    2460
aaaacaccca agcacagcat actaaatttc ccctctttct tcctctaggg tgtcgttaat    2520
tacccgtact aaaggtttgg aaaagaaaaa agagaccgcc tcgtttcttt ttcttcgtcg    2580
aaaaaggcaa taaaaatttt tatcacgttt ctttttcttg aaaatttttt tttttgattt    2640
ttttctcttt cgatgacctc ccattgatat ttaagttaat aaacggtctt caatttctca    2700
agtttcagtt tcatttttct tgttctatta caactttttt tacttcttgc tcattagaaa    2760
gaaagcatag caatctaatc taagttttaa tggcgggggt cggaatgatt aaagaaaggg    2820
gctgtgggcg agattgaaac aatggcttca gaaaaagaaa ttaggagaga gagattcttg    2880
aacgttttcc ctaaattagt agaggaattg aacgcatcgc ttttggctta cggtatgcct    2940
aaggaagcat gtgactggta tgcccactca ttgaactaca acactccagg cggtaagcta    3000
aatagaggtt tgtccgttgt ggacacgtat gctattctct ccaacaagac cgttgaacaa    3060
```

ttggggcaag aagaatacga aaaggttgcc attctaggtt ggtgcattga gttgttgcag 3120
gcttacttct tggtcgccga tgatatgatg gacaagtcca ttaccagaag aggccaacca 3180
tgttggtaca aggttcctga agttggggaa attgccatca atgacgcatt catgttagag 3240
gctgctatct acaagctttt gaaatctcac ttcagaaacg aaaaatacta catagatatc 3300
accgaattgt tccatgaggt caccttccaa accgaattgg gccaattgat ggacttaatc 3360
actgcacctg aagacaaagt cgacttgagt aagttctccc taaagaagca ctccttcata 3420
gttactttcg agactgctta ctattctttc tacttgcctg tcgcattggc catgtacgtt 3480
gccggtatca cggatgaaaa ggatttgaaa caagccagag atgtcttgat tccattgggt 3540
gaatacttcc aaattcaaga tgactactta gactgcttcg gtaccccaga acagatcggt 3600
aagatcggta cagatatcca agataacaaa tgttcttggg taatcaacaa ggcattggaa 3660
cttgcttccg cagaacaaag aaagacttta gacgaaaatt acggtaagaa ggactcagtc 3720
gcagaagcca aatgcaaaaa gattttcaat gacttgaaaa ttgaacagct ataccacgaa 3780
tatgaagagt ctattgccaa ggatttgaag gccaaaattt ctcaggtcga tgagtctcgt 3840
ggcttcaaag ctgatgtctt aactgcgttc ttgaacaaag tttacaagag aagcaaataa 3900
ccagttaata aaccgtggca aacatgatgg tggcctaatg gaggtcacca acagaagacg 3960
ggagacacta gcacacaact ttaccaggca aggtatttga cgctagcatg tgtccaattc 4020
agtgtcattt atgatttttt gtagtaggat ataaatatat acagcgctcc aaatagtgcg 4080
gttgccccaa aaacaccacg gaacctcatc tgttctcgta ctttgttgtg acaaagtagc 4140
tcactgcctt attatcacat tttcattatg caacgcttcg gaaaatacga tgttgaaaat 4200
gcctctagag atgaaaaaca atcgtaaaag ggtcctgcgt aattgaaaca tttgatcagt 4260
atgcagtggc acagaaacaa ccaggaatac tatagtcata ggcaatacaa ggtatatatt 4320
ggctatgcag accccctccag aaagtaccga cgtcaagtta gatacactta acgaacctag 4380
tgcacattta attgagaaaa atgtggctct tcctaaggac atattccgtt cgtacttgag 4440
ttattggatc tatgaaatcg ctcgctatac accagtcatg attttgtcgc ggccgcggta 4500
cctaataact tcgtatagca tacattatac gaagttat 4538

<210> SEQ ID NO 86
<211> LENGTH: 3503
<212> TYPE: DNA
<213> ORGANISM: Artificial Sequence
<220> FEATURE:
<223> OTHER INFORMATION: Erg1p:UB14-Erg20:deg

<400> SEQUENCE: 86
tgtgcacaaa ggccataata ttatgtctac agaatatact agatgtcctc cctataggat 60
atagtaatcc tctaaatgga accgatattt ctacataata atattacgat tattcctcct 120
tccgttttat atgtttcatt atcctagcac actatcaatc tttgcatttc agcttccatt 180
agatttgatg actatttctc aatctttatg ttatctcctt acgccgcatg tgataatata 240
ctgctagtat gactactagt tgatagaaga tagttgattt ttactccaac aaaagtaaca 300
atattattta gaactataga ttccattttg tgcattccca tattctcgag gaaaactttt 360
agtatattct gtagacataa tattatcgcc tttgtgaaca atagaatccc aacaattgtc 420
gcaaatttac caattttcta gattgcagtc accttttcaa ttaatcacta gtgtttcact 480
tgtaacattg tcgttgttgt ttaacgtatt ctgtcccgtg ccaactatga caaaaatgca 540
atgatttcag cggttaaata cgaagcgcaa caagagttag cgaaaaataa gtaccaccat 600

-continued

```
tctacgctac cattacttac tgaaattaga gacaactgtt atctattggc agatgttcat    660
acggggcttt caaatattga tgaaattatg tgatgtttag aagaagattc gaactgtttt    720
cagtagattt ggtaactgtg caaccataac tcatgcctac gttcgggatt taatcttctc    780
gcagtctgca ggcgccttga gatttgcgtt cggcctaaac gtttgctcca caaacgtgaa    840
tggtatgaac atggacatga gcgtggttca gggcactcta cgggatcgtg gcgaatggga    900
atcgttctgc aagctcttct accaaaccat cggcgaattt gcgtcgcttt aatgcgatac    960
tgccgtagcg ggccttcgta tagctcggcc gagctcgtac aaaaggcaag cagtgtatcg   1020
gacagagctg atataacaca atacgctcgt agtcgatgca tgccgtggct gctctcggtc   1080
gggtataagt cttagacaat agtcttacct cgcatgtata ataaatcttt tgtatttaat   1140
ctattatatg tttctatgct tttttttcct attgttgttt gcttttcctt ttccttattt   1200
ctttctagct tctaatttc tttctttttt tttttttttt cattgaaaat tatatatata   1260
tatatatatc agaacaattg tccagtattg aacaatacag gttatttcga acaattgaaa   1320
aaaaaaaatc acagaaaaac atatcgagaa aagggtcaaa acaatgcaga ttttcgtcaa   1380
gactttgacc ggtaaaacca taacattgga agttgaatct tccgatacca tcgacaacgt   1440
taagtcgaaa attcaagaca aggaaggtat ccctccagat caacaaagat tgatctttgc   1500
cggtaagcag ctagaagacg gtagaacgct gtctgattac aacattcaga aggagtccac   1560
cttacatctt gtgctaaggc taagaggtgg tttccacaaa tctggtgctt ggttgttgcc   1620
agtttctttg gttaagggtt ctggtgcttc agaaaaagaa attaggagag agagattctt   1680
gaacgttttc cctaaattag tagaggaatt gaacgcatcg cttttggctt acggtatgcc   1740
taaggaagca tgtgactggt atgcccactc attgaactac aacactccag gcggtaagct   1800
aaatagaggt ttgtccgttg tggacacgta tgctattctc tccaacaaga ccgttgaaca   1860
attggggcaa gaagaatacg aaaaggttgc cattctaggt tggtgcattg agttgttgca   1920
ggcttacttc ttggtcgccg atgatatgat ggacaagtcc attaccagaa gaggccaacc   1980
atgttggtac aaggttcctg aagttgggga aattgccatc aatgacgcat tcatgttaga   2040
ggctgctatc tacaagcttt tgaaatctca cttcagaaac gaaaaatact acatagatat   2100
caccgaattg ttccatgagg tcaccttcca aaccgaattg ggccaattga tggacttaat   2160
cactgcacct gaagacaaag tcgacttgag taagttctcc ctaaagaagc actccttcat   2220
agttactttc aagactgctt actattcttt ctacttgcct gtcgcattgg ccatgtacgt   2280
tgccggtatc acggatgaaa aggatttgaa acaagccaga gatgtcttga ttccattggg   2340
tgaatacttc caaattcaag atgactactt agactgcttc ggtaccccag aacagatcgg   2400
taagatcggt acagatatcc aagataacaa atgttcttgg gtaatcaaca aggcattgga   2460
acttgcttcc gcagaacaaa gaaagacttt agacgaaaat tacggtaaga aggactcagt   2520
cgcagaagcc aaatgcaaaa agattttcaa tgacttgaaa attgaacagc tataccacga   2580
atatgaagag tctattgcca aggatttgaa ggccaaaatt tctcaggtcg atgagtctcg   2640
tggcttcaaa gctgatgtct taactgcgtt cttgaacaaa gtttacaaga gaagcaaata   2700
gtggacttct tcgccagagg tttggtcaag tctccaatca aggttgtcgg cttgtctacc   2760
ttgccagaaa tttacgaaaa gatggaaaag ggtcaaatcg ttggtagata cgttgttgac   2820
acttctaaat aagcgaattt cttatgattt atgattttta ttattaaata agttataaaa   2880
aaaataagtg tatacaaatt ttaaagtgac tcttaggttt taaaacgaaa attcttattc   2940
```

ttgagtaact ctttcctgta ggtcaggttg ctttctcagg tatagcatga ggtcgctctt 3000
attgaccaca cctctaccgg catggaatcg tccccaacaa aagtgggctc tcaaaattca 3060
tcacatttaa atgcatatag gaagagcaac agttggtttg catctgatgt tccttaaaga 3120
tttcgacata atgtgcgaag tagataaaat gggtcattta ttaatagtta tttcattatt 3180
aaccagttgt ggtacaaatg caactaaaga aaaaaactac taaactatcc gggaaatgcg 3240
ccttagattg cacttcttaa ttcttatttt cgatttttat ttttcctttg ataatcataa 3300
agagaaacga cgatcatttc taaagccatt tctgctagta taccgttaaa taagaaaaat 3360
aaagccaaat attataattt ttctaatgtg aatccataaa tatcaaagca tgcaaaaagg 3420
gaaagaagta atgtcttgga tttatatagc gtatttgtct aaggggagcc agctttggcg 3480
cgcctatcga gagaccgatt aca 3503

<210> SEQ ID NO 87
<211> LENGTH: 4859
<212> TYPE: DNA
<213> ORGANISM: Artificial Sequence
<220> FEATURE:
<223> OTHER INFORMATION: tHMGr-IDI

<400> SEQUENCE: 87
ggcgcgcccg agatctttgt gttcggttac ccggctcaga tcctaacttc gtatgtttat 60
tcgtataagt tactgttgtc cacaggcaat actctgcaga aaattaaaac ggcattaatg 120
ctaggacaac cagaattgtt actactgtat gtgcgatagt tgataactgc aacattatgc 180
ccggtatatt ctcaaaaaac cctattactg catacgaaga aatcgctcga gtttatcatt 240
atcaatactg ccatttcaaa gaatacgtaa ataattaata gtagtgattt tcctaacttt 300
atttagtcaa aaaattagcc ttttaattct gctgtaaccc gtacatgccc aaaatagggg 360
gcgggttaca cagaatatat aacatcgtag gtgtctgggt gaacagttta ttcctggcat 420
ccactaaata taatggagcc cgctttttaa gctggcatcc agaaaaaaaa agaatcccag 480
caccaaaata ttgttttctt caccaaccat cagttcatag gtccattctc ttagcgcaac 540
tacagagaac aggggcacaa acaggcaaaa aacgggcaca acctcaatgg agtgatgcaa 600
cctgcctgga gtaaatgatg acacaaggca attgacccac gcatgtatct atctcatttt 660
cttacacctt ctattacctt ctgctctctc tgatttggaa aaagctgaaa aaaaaggttg 720
aaaccagttc cctgaaatta ttcccctact tgactaataa gtatataaag acggtaggta 780
ttgattgtaa ttctgtaaat ctatttctta aacttcttaa attctacttt tatagttagt 840
ctttttttta gttttaaaac accaagaact tagtttcgaa aacaatggtt ttaaccaata 900
aaacagtcat ttctggatcg aaagtcaaaa gtttatcatc tgcgcaatcg agctcatcag 960
gaccttcatc atctagtgag gaagatgatt cccgcgatat tgaaagcttg gataagaaaa 1020
tacgtccttt agaagaatta gaagcattat taagtagtgg aaatacaaaa caattgaaga 1080
acaaagaggt cgctgccttg gttattcacg gtaagttacc tttgtacgct ttggagaaaa 1140
aattaggtga tactacgaga gcggttgcgg tacgtaggaa ggctctttca attttggcag 1200
aagctcctgt attagcatct gatcgtttac catataaaaa ttatgactac gaccgcgtat 1260
ttggcgcttg ttgtgaaaat gttataggtt acatgccttt gcccgttggt gttataggcc 1320
ccttggttat cgatggtaca tcttatcata taccaatggc aactacagag ggttgtttgg 1380
tagcttctgc catgcgtggc tgtaaggcaa tcaatgctgg cggtggtgca acaactgttt 1440
taactaagga tggtatgaca agaggcccag tagtccgttt cccaactttg aaaagatctg 1500

```
gtgcctgtaa gatatggtta gactcagaag agggacaaaa cgcaattaaa aaagctttta   1560
actctacatc aagatttgca cgtctgcaac atattcaaac ttgtctagca ggagatttac   1620
tcttcatgag atttagaaca actactggtg acgcaatggg tatgaatatg atttctaaag   1680
gtgtcgaata ctcattaaag caaatggtag aagagtatgg ctgggaagat atggaggttg   1740
tctccgtttc tggtaactac tgtaccgaca aaaaaccagc tgccatcaac tggatcgaag   1800
gtcgtggtaa gagtgtcgtc gcagaagcta ctattcctgg tgatgttgtc agaaaagtgt   1860
taaaaagtga tgtttccgca ttggttgagt tgaacattgc taagaatttg gttggatctg   1920
caatggctgg gtctgttggt ggatttaacg cacatgcagc taatttagtg acagctgttt   1980
tcttggcatt aggacaagat cctgcacaaa atgttgaaag ttccaactgt ataacattga   2040
tgaaagaagt ggacggtgat ttgagaattt ccgtatccat gccatccatc gaagtaggta   2100
ccatcggtgg tggtactgtt ctagaaccac aaggtgccat gttggactta ttaggtgtaa   2160
gaggcccgca tgctaccgct cctggtacca acgcacgtca attagcaaga atagttgcct   2220
gtgccgtctt ggcaggtgaa ttatccttat gtgctgccct agcagccggc catttggttc   2280
aaagtcatat gacccacaac aggaaacctg ctgaaccaac aaaacctaac aatttggacg   2340
ccactgatat aaatcgtttg aaagatgggt ccgtcacctg cattaaatcc taatggactt   2400
cttcgccaga ggtttggtca agtctccaat caaggttgtc ggcttgtcta ccttgccaga   2460
aatttacgaa aagatggaaa agggtcaaat cgttggtaga tacgttgttg acacttctaa   2520
ataagcgaat ttcttatgat ttatgatttt tattattaaa taagttataa aaaaaataag   2580
tgtatacaaa ttttaaagtg actcttaggt tttaaaacga aaattcttat tcttgagtaa   2640
ctctttcctg taggtcaggt tgctttctca ggtatagcat gaggtcgctc ttattgacca   2700
cacctctacc ggcatgcaag caacaggcgc gttggacttt taattttcga ggaccgcgaa   2760
tccttacatc acacccaatc ccccacaagt gatcccccac acaccatagc ttcaaaatgt   2820
ttctactcct tttttactct tccagatttt ctcggactcc gcgcatcgcc gtaccacttc   2880
aaaacaccca agcacagcat actaaatttc ccctctttct tcctctaggg tgtcgttaat   2940
tacccgtact aaaggtttgg aaaagaaaaa agagaccgcc tcgtttcttt ttcttcgtcg   3000
aaaaaggcaa taaaaatttt tatcacgttt ctttttcttg aaaatttttt tttttgattt   3060
ttttctcttt cgatgacctc ccattgatat ttaagttaat aaacggtctt caatttctca   3120
agtttcagtt tcatttttct tgttctatta caactttttt tacttcttgc tcattagaaa   3180
gaaagcatag caatctaatc taagttttaa taaacaatga ctgccgacaa caatagtatg   3240
ccccatggtg cagtatctag ttacgccaaa ttagtgcaaa accaaacacc tgaagacatt   3300
ttggaagagt ttcctgaaat tattccatta caacaaagac ctaatacccg atctagtgag   3360
acgtcaaatg acgaaagcgg agaaacatgt ttttctggtc atgatgagga gcaaattaag   3420
ttaatgaatg aaaattgtat tgttttggat tgggacgata atgctattgg tgccggtacc   3480
aagaaagttt gtcatttaat ggaaaatatt gaaaagggtt tactacatcg tgcattctcc   3540
gtctttattt tcaatgaaca aggtgaatta cttttacaac aaagagccac tgaaaaaata   3600
actttccctg atctttggac taacacatgc tgctctcatc cactatgtat tgatgacgaa   3660
ttaggtttga agggtaagct agacgataag attaagggcg ctattactgc ggcggtgaga   3720
aaactagatc atgaattagg tattccagaa gatgaaacta agacaagggg taagtttcac   3780
tttttaaaca gaatccatta catggcacca agcaatgaac catggggtga acatgaaatt   3840
```

gattacatcc tattttataa gatcaacgct aaagaaaact tgactgtcaa cccaaacgtc 3900
aatgaagtta gagacttcaa atgggtttca ccaaatgatt tgaaaactat gtttgctgac 3960
ccaagttaca agtttacgcc ttggtttaag attatttgcg agaattactt attcaactgg 4020
tgggagcaat tagatgacct ttctgaagtg gaaaatgaca ggcaaattca tagaatgcta 4080
taaacagaag acgggagaca ctagcacaca actttaccag gcaaggtatt tgacgctagc 4140
atgtgtccaa ttcagtgtca tttatgattt tttgtagtag gatataaata tatacagcgc 4200
tccaaatagt gcggttgccc caaaaacacc acggaacctc atctgttctc gtactttgtt 4260
gtgacaaagt agctcactgc cttattatca cattttcatt atgcaacgct tcggaaaata 4320
cgatgttgaa aatgcctcta gagatgaaaa acaatcgtaa aagggtcctg cgtaattgaa 4380
acatttgatc agtatgcagt ggcacagaaa caaccaggaa tactatagtc ataggcaata 4440
caaggtatat attggctatg cagacccctc cagaaagtac cgacgtcaag ttagatacac 4500
ttaacgaacc tagtgcacat ttaattgaga aaaatgtggc tcttcctaag gacatattcc 4560
gttcgtactt gagttattgg atctatgaaa tcgctcgcta tacaccagtc atgattttgt 4620
cacactcgta tatgcatgtt gttgaaactc tgttacgctg aactaacaat cacacatgta 4680
gaggtcaccg ggaaaagttg cgaccccatg gaaggtcgat ctcttcgttt ggctttgctt 4740
ggctggcggc attgcgcttc ttcgcttata cccgtctctt gacgctcgag ctcgttcatt 4800
gagatacctt tattcttgca cattttctgg ctttttttcgc tactcgggta cggcgcgcc 4859

<210> SEQ ID NO 88
<211> LENGTH: 7673
<212> TYPE: DNA
<213> ORGANISM: Artificial Sequence
<220> FEATURE:
<223> OTHER INFORMATION: PGK1p:ACC1S659A,S1157A

<400> SEQUENCE: 88
caagtcgcag tcgaaattca accgctcatt gccactctct ctactgcttg gtgaactagg 60
ctatacgctc aatcagcgcc aagatatata agaagaacag cactcccagt cgtattctgg 120
cacagtatag cctagcacaa tcactgtcac aattgttatc ggttctacaa ttgttctgct 180
ctcttcaatt ttcctttcct tattctactc tttttatccc tacgcacaga tattataaca 240
tctgcataat aggcatttgc aagaattact cgtgagtaag gaaagagtga ggaactatcg 300
catacctgca tttaaagatg ccgatttggg cgcgaatcct ttattttggc ttcaccctca 360
tactattatc agggccagaa aaaggaagtg tttccctcct tcttgaattg atgttaccct 420
cataaagcac gtggcctctt atcgagaaag aaattaccgt cgctcgtgat ttgtttgcaa 480
aaagaacaaa actgaaaaaa cccagacacg ctcgacttcc tgtcttccta ttgattgcag 540
cttccaattt cgtcacacaa caaggtccta gcgacggctc acaggttttg taacaagcaa 600
tcgaaggttc tggaatggcg ggaaagggtt tagtaccaca tgctatgatg cccactgtga 660
tctccagagc aaagttcgtt cgatcgtact gttactctct ctctttcaaa cagaattgtc 720
cgaatcgtgt gacaacaaca gcctgttctc acacactctt ttcttctaac caagggggtg 780
gtttagttta gtagaacctc gtgaaactta catttacata tatataaact tgcataaatt 840
ggtcaatgca agaaatacat atttggtctt ttctaattcg tagtttttca agttcttaga 900
tgctttcttt ttctcttttt tacagatcat caaggaagta attatctact ttttacaaca 960
aatataaaac aatgagcgaa gaaagcttat tcgagtcttc tccacagaag atggagtacg 1020
aaattacaaa ctactcagaa agacatacag aacttccagg tcatttcatt ggcctcaata 1080

```
cagtagataa actagaggag tccccgttaa gggactttgt taagagtcac ggtggtcaca   1140
cggtcatatc caagatcctg atagcaaata atggtattgc cgccgtgaaa gaaattagat   1200
ccgtcagaaa atgggcatac gagacgttcg gcgatgacag aaccgtccaa ttcgtcgcca   1260
tggccacccc agaagatctg gaggccaacg cagaatatat ccgtatggcc gatcaataca   1320
ttgaagtgcc aggtggtact aataataaca actacgctaa cgtagacttg atcgtagaca   1380
tcgccgaaag agcagacgta gacgccgtat gggctggctg gggtcacgcc tccgagaatc   1440
cactattgcc tgaaaaattg tcccagtcta agaggaaagt catctttatt gggcctccag   1500
gtaacgccat gaggtcttta ggtgataaaa tctcctctac cattgtcgct caaagtgcta   1560
aagtcccatg tattccatgg tctggtaccg gtgttgacac cgttcacgtg gacgagaaaa   1620
ccggtctggt ctctgtcgac gatgacatct atcaaaaggg ttgttgtacc tctcctgaag   1680
atggtttaca aaaggccaag cgtattggtt ttcctgtcat gattaaggca tccgaaggtg   1740
gtggtggtaa aggtatcaga caagttgaac gtgaagaaga tttcatcgct ttataccacc   1800
aggcagccaa cgaaattcca ggctccccca ttttcatcat gaagttggcc ggtagagcgc   1860
gtcacttgga agttcaactg ctagcagatc agtacggtac aaatatttcc ttgttcggta   1920
gagactgttc cgttcagaga cgtcatcaaa aaattatcga agaagcacca gttacaattg   1980
ccaaggctga aacatttcac gagatggaaa aggctgccgt cagactgggg aaactagtcg   2040
gttatgtctc tgccggtacc gtggagtatc tatattctca tgatgatgga aaattctact   2100
ttttagaatt gaacccaaga ttacaagtcg agcatccaac aacggaaatg gtctccggtg   2160
ttaacttacc tgcagctcaa ttacaaatcg ctatgggtat ccctatgcat agaataagtg   2220
acattagaac tttatatggt atgaatcctc attctgcctc agaaatcgat ttcgaattca   2280
aaactcaaga tgccaccaag aaacaaagaa gacctattcc aaagggtcat tgtaccgctt   2340
gtcgtatcac atcagaagat ccaaacgatg gattcaagcc atcgggtggt actttgcatg   2400
aactaaactt ccgttcttcc tctaatgttt ggggttactt ctccgtgggt aacaatggta   2460
atattcactc cttttcggac tctcagttcg gccatatttt tgcttttggt gaaaatagac   2520
aagcttccag gaaacacatg gttgttgccc tgaaggaatt gtccattagg ggtgatttca   2580
gaactactgt ggaatacttg atcaaacttt tggaaactga agatttcgag gataacacta   2640
ttaccaccgg ttggttggac gatttgatta ctcataaaat gaccgctgaa aagcctgatc   2700
caactcttgc cgtcatttgc ggtgccgcta caaaggcttt cttagcatct gaagaagccc   2760
gccacaagta tatcgaatcc ttacaaaagg gacaagttct atctaaagac ctactgcaaa   2820
ctatgttccc tgtagatttt atccatgagg gtaaaagata caagttcacc gtagctaaat   2880
ccggtaatga ccgttacaca ttatttatca atggttctaa atgtgatatc atactgcgtc   2940
aactatctga tggtggtctt ttgattgcca taggcggtaa atcgcatacc atctattgga   3000
aagaagaagt tgctgctaca agattatccg ttgactctat gactactttg ttggaagttg   3060
aaaacgatcc aacccagttg cgtactccat cccctggtaa attggttaaa ttcttggtgg   3120
aaaatggtga acacattatc aagggccaac catatgcaga aattgaagtt atgaaaatgc   3180
aaatgccttt ggtttctcaa gaaaatggta tcgtccagtt attaaagcaa cctggttcta   3240
ccattgttgc aggtgatatc atggctatta tgactcttga cgatccatcc aaggtcaagc   3300
acgctctacc atttgaaggt atgctgccag attttggttc tccagttatc gaaggaacca   3360
aacctgccta taaattcaag tcattagtgt ctactttgga aaacattttg aagggttatg   3420
```

```
acaaccaagt tattatgaac gcttccttgc aacaattgat agaggttttg agaaatccaa   3480
aactgcctta ctcagaatgg aaactacaca tctctgcttt acattcaaga ttgcctgcta   3540
agctagatga acaaatggaa gagttagttg cacgttcttt gagacgtggt gctgttttcc   3600
cagctagaca attaagtaaa ttgattgata tggccgtgaa gaatcctgaa tacaaccccg   3660
acaaattgct gggcgccgtc gtggaaccat tggcggatat tgctcataag tactctaacg   3720
ggttagaagc ccatgaacat tctatatttg tccatttctt ggaagaatat tacgaagttg   3780
aaaagttatt caatggtcca aatgttcgtg aggaaaatat cattctgaaa ttgcgtgatg   3840
aaaaccctaa agatctagat aaagttgcgc taactgtttt gtctcattcg aaagtttcag   3900
cgaagaataa cctgatccta gctatcttga aacattatca accattgtgc aagttatctt   3960
ctaaagtttc tgccattttc tctactcctc tacaacatat tgttgaacta gaatctaagg   4020
ctaccgctaa ggtcgctcta caagcaagag aaattttgat tcaaggcgct ttaccttcgg   4080
tcaaggaaag aactgaacaa attgaacata tcttaaaatc ctctgttgtg aaggttgcct   4140
atggctcatc caatccaaag cgctctgaac cagatttgaa tatcttgaag gacttgatcg   4200
attctaatta cgttgtgttc gatgttttac ttcaattcct aacccatcaa gacccagttg   4260
tgactgctgc agctgctcaa gtctatattc gtcgtgctta tcgtgcttac accataggag   4320
atattagagt tcacgaaggt gtcacagttc caattgttga atggaaattc caactacctt   4380
cagctgcgtt ctccaccttt ccaactgtta aatctaaaat gggtatgaac agggctgttt   4440
ctgtttcaga tttgtcatat gttgcaaaca gtcagtcatc tccgttaaga gaaggtattt   4500
tgatggctgt ggatcattta gatgatgttg atgaaatttt gtcacaaagt ttggaagtta   4560
ttcctcgtca ccaatcttct tctaacggac ctgctcctga tcgttctggt agctccgcat   4620
cgttgagtaa tgttgctaat gtttgtgttg cttctacaga aggtttcgaa tctgaagagg   4680
aaattttggt aaggttgaga gaaattttgg atttgaataa gcaggaatta atcaatgctt   4740
ctatccgtcg tatcacattt atgttcggtt ttaaagatgg gtcttatcca aagtattata   4800
cttttaacgg tccaaattat aacgaaaatg aaacaattcg tcacattgag ccggctttgg   4860
ccttccaact ggaattagga agattgtcca acttcaacat taaaccaatt ttcactgata   4920
atagaaacat ccatgtctac gaagctgtta gtaagacttc tccattggat aagagattct   4980
ttacaagagg tattattaga acgggtcata tccgtgatga catttctatt caagaatatc   5040
tgacttctga agctaacaga ttgatgagtg atatattgga taatttagaa gtcaccgaca   5100
cttcaaattc tgatttgaat catatcttca tcaacttcat tgcggtgttt gatatctctc   5160
cagaagatgt cgaagccgcc ttcggtggtt tcttagaaag atttggtaag agattgttga   5220
gattgcgtgt ttcttctgcc gaaattagaa tcatcatcaa agatcctcaa acaggtgccc   5280
cagtaccatt gcgtgccttg atcaataacg tttctggtta tgttatcaaa acagaaatgt   5340
acaccgaagt caagaacgca aaaggtgaat gggtatttaa gtctttgggt aaacctggat   5400
ccatgcattt aagacctatt gctactcctt accctgttaa ggaatggttg caaccaaaac   5460
gttataaggc acacttgatg ggtaccacat atgtctatga cttcccagaa ttattccgcc   5520
aagcatcgtc atcccaatgg aaaaatttct ctgcagatgt taagttaaca gatgatttct   5580
ttatttccaa cgagttgatt gaagatgaaa acggcgaatt aactgaggtg gaaagagaac   5640
ctggtgccaa cgctattggt atggttgcct ttaagattac tgtaaagact cctgaatatc   5700
caagaggccg tcaatttgtt gttgttgcta acgatatcac attcaagatc ggttcctttg   5760
gtccacaaga agacgaattc ttcaataagg ttactgaata tgctagaaag cgtggtatcc   5820
```

caagaattta cttggctgca aactcaggtg ccagaattgg tatggctgaa gagattgttc 5880
cactatttca agttgcatgg aatgatgctg ccaatccgga caagggcttc caatacttat 5940
acttaacaag tgaaggtatg gaaactttaa agaaatttga caaagaaaat tctgttctca 6000
ctgaacgtac tgttataaac ggtgaagaaa gatttgtcat caagacaatt attggttctg 6060
aagatgggtt aggtgtcgaa tgtctacgtg gatctggttt aattgctggt gcaacgtcaa 6120
gggcttacca cgatatcttc actatcacct tagtcacttg tagatccgtc ggtatcggtg 6180
cttatttggt tcgtttgggt caaagagcta ttcaggtcga aggccagcca attattttaa 6240
ctggtgctcc tgcaatcaac aaaatgctgg gtagagaagt ttatacttct aacttacaat 6300
tgggtggtac tcaaatcatg tataacaacg gtgtttcaca tttgactgct gttgacgatt 6360
tagctggtgt agagaagatt gttgaatgga tgtcttatgt tccagccaag cgtaatatgc 6420
cagttcctat cttggaaact aaagacacat gggatagacc agttgatttc actccaacta 6480
atgatgaaac ttacgatgta agatggatga ttgaaggtcg tgagactgaa agtggatttg 6540
aatatggttt gtttgataaa gggtctttct ttgaaacttt gtcaggatgg gccaaaggtg 6600
ttgtcgttgg tagagcccgt cttggtggta ttccactggg tgttattggt gttgaaacaa 6660
gaactgtcga gaacttgatt cctgctgatc cagctaatcc aaatagtgct gaaacattaa 6720
ttcaagaacc tggtcaagtt tggcatccaa actccgcctt caagactgct caagctatca 6780
atgactttaa caacggtgaa caattgccaa tgatgatttt ggccaactgg agaggtttct 6840
ctggtggtca acgtgatatg ttcaacgaag tcttgaagta tggttcgttt attgttgacg 6900
cattggtgga ttacaaacaa ccaattatta tctatatccc acctaccggt gaactaagag 6960
gtggttcatg ggttgttgtc gatccaacta tcaacgctga ccaaatggaa atgtatgccg 7020
acgtcaacgc tagagctggt gttttggaac cacaaggtat ggttggtatc aagttccgta 7080
gagaaaaatt gctggacacc atgaacagat tggatgacaa gtacagagaa ttgagatctc 7140
aattatccaa caagagtttg gctccagaag tacatcagca aatatccaag caattagctg 7200
atcgtgagag agaactattg ccaatttacg gacaaatcag tcttcaattt gctgatttgc 7260
acgataggtc ttcacgtatg gtggccaagg gtgttatttc taaggaactg gaatggaccg 7320
aggcacgtcg tttcttcttc tggagattga gaagaagatt gaacgaagaa tatttgatta 7380
aaaggttgag ccatcaggta ggcgaagcat caagattaga aaagatcgca agaattagat 7440
cgtggtaccc tgcttcagtg gaccatgaag atgataggca agtcgcaaca tggattgaag 7500
aaaactacaa aactttggac gataaactaa agggtttgaa attagagtca ttcgctcaag 7560
acttagctaa aaagatcaga agcgaccatg acaatgctat tgatggatta tctgaagtta 7620
tcaagatgtt atctaccgat gataaagaaa aattgttgaa gactttgaaa taa 7673

<210> SEQ ID NO 89
<211> LENGTH: 4707
<212> TYPE: DNA
<213> ORGANISM: Artificial Sequence
<220> FEATURE:
<223> OTHER INFORMATION: PT254-R2S

<400> SEQUENCE: 89
agtatgacaa gttttaatcg agatagtttg acgttcgttt tttactttga atatactcgt 60
agtcttttta ctttttgagt ataaaaaaaa aatgactagc aaaataaaat tagtagtcta 120
aaaaagaaag ctcgcactca ggatcgaact aaggaccaac agatttgcaa tctgctgcgc 180

```
taccactgcg ccatacgagc ttttgaatta tggtaatttt gattatccta gaatgttata    240
tctcaatatc tcaatatatt ttggacatct atgaaacacc cataaagcag ccgctaccaa    300
acagacaaga ttcagtatgt aaggtaaata cctttttgca cagttaaact acccaaactt    360
attaaagctt gataaattac tgaaattcca cctttcagtt agattcaggc ctcatataga    420
ttagatatag ggtacgtaac attctgtcaa ccaagttgtt ggaatgaaag tctaaaatgt    480
catctattcg gtagcactca tgttactagt atactgtcac atgcggtgta acgtggggac    540
ataaaacaga catcaaatat aatggaagct gaaatgcaaa gatcgataat gtaataggaa    600
tgaaacatat aaaacgaaag gagaagtaat ggtaatatta gtatgtagaa ataccgattc    660
aattttgggg attcttatat tctcgagaga atttctagta taatctgtat acataatatt    720
ataggcttta ccaacaatgg aatttcgaca attatcatat tattcaccaa ttaatcacaa    780
gttggtaatg agtttgataa caagttactt tcttaacaac gttagtatcg tcaaaacact    840
cggttttact cgagcttgta gcacaataat accgtgtaga gttctgtatt gttcttctta    900
gtgcttgtat atgctcatcc cgaccttcca ttatgctggt ctcttcgccc gagaacctca    960
gttacttttc cttatgcgca tagacataca agtggacaga tgatgggtac gggcctctaa   1020
tacatccaac actctacgcc ctcttcaaga gctagaaggg caccctgcag ttggaaaggg   1080
aattatttcg taaggcgagc ccataccgtc attcatgcgg aagagttaac acgattggaa   1140
gtaggaatag tttcgaacca cggttactaa tcctaataac ggaacgctgt ctgaaggatg   1200
agtgtcagcg agtgtaactc gatgagctac ccagtagtcg tactggtcga gacaaccctt   1260
gccaacaggg agttcttcag agacatggag gctcaaaacg aaattattga cagcctagac   1320
atcaatagtc atacaacaga aagcgaccac ccaactttgg ctgataatag cgtataaaca   1380
atgcatactt tgtacgttca aaatacaatg cagtagatat atttatgcat attacatata   1440
atacatatca cataggaagc aacaggcgcg ttggactttt aattttcgag gaccgcgaat   1500
ccttacatca cacccaatcc cccacaagtg atcccccaca caccatagct tcaaaatgtt   1560
tctactcctt ttttactctt ccagatttc tcggactccg cgcatcgccg taccacttca    1620
aaacacccaa gcacagcata ctaaatttcc cctctttctt cctctagggt gtcgttaatt   1680
acccgtacta aaggtttgga aaagaaaaaa gacaccgcct cgtttctttt tcttcgtcga   1740
aaaaggcaat aaaaattttt atcacgtttc tttttcttga aaattttttt ttttgatttt   1800
tttctctttc gatgacctcc cattgatatt taagttaata aacggtcatc aatttctcaa   1860
gtttcagttt catttttctt gttctattac aacttttttt acttcttgct cattagaaag   1920
aaagcatagc aatctaatct aagttttaat tacaaaatga gagccggttc cgatcaaatt   1980
gaaggttctc cacatcatga atccgataac tctattgcca ccaagatttt gaacttcggt   2040
catacttgtt ggaagttgca aagaccatat gttgtcaagg gtatgatttc tattgcttgc   2100
ggtttgtttg gtcgtgagtt gtttaacaac agacacttgt tttcttgggg cttgatgtgg   2160
aaagcttttt ttgctttggt tcccatcctg tcctttaatt tctttgccgc cattatgaac   2220
cagatctacg atgttgatat cgacagaatc aacaagccag atttgccatt ggtttctggt   2280
gaaatgtcta ttgaaaccgc ctggattttg tccattatcg ttgctttgac tggtttgatc   2340
gttaccatca agttgaaatc tgctcccttg ttcgttttca tctacatctt tggtattttc   2400
gctggtttcg cttattccgt tccaccaatt agatggaaac aatacccatt caccaatttc   2460
ttgatcacca tctcttctca tgttggtttg gctttcactt cttactctgc tactacttct   2520
gctttgggtt taccatttgt ttggaggcca gctttctctt tcattattgc tttcatgacc   2580
```

```
gttatgggta tgaccattgc tttcgctaag gatatctctg atattgaagg tgatgctaag   2640
tacggtgttt ctactgttgc tacaaaattg ggtgctagaa acatgacctt tgttgtctct   2700
ggtgttctgt tgttgaacta cttggtttcc atttccattg gtatcatttg gccacaggtt   2760
ttcaagtcca acatcatgat tttgtctcat gccatcttgg ctttctgctt gatttttcaa   2820
actagagaat tggccttggc taactatgct tctgctccat ctagacaatt cttcgaattc   2880
atctggttgt tgtactacgc cgaatacttc gtctacgtgt tcattctcga gcatgcatct   2940
agagggccgc atcatgtaat tagttatgtc acgcttacat tcacgccctc cccccacatc   3000
cgctctaacc gaaaaggaag gagttagaca acctgaagtc taggtcccta tttatttttt   3060
tatagttatg ttagtattaa gaacgttatt tatatttcaa atttttcttt tttttctgta   3120
cagacgcgtg tacgcatgta acattatact gaaaaccttg cttgagaagg ttttgggacg   3180
ctcgaaggct ttaatttgcc cagctctaat gcactcaatc ccgaggcctg acgcgacata   3240
tcagcttaga ctagggcggg ggtgttgacg tttggggttg aataaatcta ttgtactaat   3300
cggcttcaac gtgccccacg ggtggcacct caggaggggc ccacagcgag gaagtaaact   3360
gttattcgtc ggcgatggtg gtagctaatt atgttccttg ccactacaat agtatctaag   3420
ccgtgtaatg ggaacatcca cactttagtg aatcgatgtg cagcttcaga ataccattcc   3480
ttgaagccgt gtccataaac aatatcgaga gaccgattac actcgagcat gcatctagag   3540
ggccgcatca tgtaattagt tatgtcacgc ttacattcac gccctccccc cacatccgct   3600
ctaaccgaaa aggaaggagt tagacaacct gaagtctagg tccctattta ttttttata   3660
gttatgttag tattaagaac gttatttata tttcaaattt ttcttttttt tctgtacaga   3720
cgcgtgtacg catgtaacat tatactgaaa accttgcttg agaaggtttt gggacgctcg   3780
aaggctttaa tttgctttgc gaaaccctat gctctgttgt tcggatttga aattttaaaa   3840
ctacattaat gtgttagttt ttctttcttt ctttctttgt cttgacgtga tttggacttc   3900
tgtcttgcat tcgcgtccat tcatctgacc caatattcct tttggttttg ttatccttat   3960
aaaaagaaag gaagcttctt agagggaaaa aaatgatgaa gagtaatgcc aaaatataaa   4020
taaataaata aatatgaaaa tcattttcta tttttaatag aataagaaga gcatcttaag   4080
attacaattt caagaaatag tttacacagt atatccaata actccaataa actactttcc   4140
tatacaaatt tctatggtgg gattaatagt aaaacttctg tacttctcta attcaccaag   4200
aaattaaggt aaacatctgg taagcactat ccagcttttt gctattacac atatggcttt   4260
tctgcaatca tttcttccca ttttgtctca agccgttagt cttgaaacca caggcggagt   4320
agagttactt gatgcggtat tttacatgcc tttttcact gcaaaaaaaa tgaaatacat   4380
atttacacga tttgcaggac agtttacgat agtgagtatg cagaatagtt aacacctttg   4440
ttttatcctt ttgtgtctta attatatgat ataaaggcgc ctggcgttat cggatagtaa   4500
tagatgctag ttatcaacat ttcacaattg aaggaaataa agttgaagta ctcaacaaaa   4560
acttacttca gaattaaatt tttgggggga acataggcat cctatgacag gtgaccacaa   4620
gcccctcaac gcaatctaat attttacaaa gtggtaaaat tctttcgttc ttcgttttaa   4680
tatacagtca tttattgatt ctattac                                       4707
```

<210> SEQ ID NO 90
<211> LENGTH: 4137
<212> TYPE: DNA
<213> ORGANISM: Artificial Sequence
<220> FEATURE:

<223> OTHER INFORMATION: Ost1-pro-alpha-f(l)-OXC53

<400> SEQUENCE: 90
caagaaggat tttctggcat ttgcttattg aaagcgtctt caattatatt aaaactaaaa 60
ttgaagtttc caaaaaagaa agatagaact gatattagca aattgtgtga caagaaagaa 120
cggatgacac agtggttaga aatttcaatt ttgatgaact gagaataata atattatgct 180
cccctggatt ttatgcgaag acactgctga aaaaatttct gatatatgca gagaaggagc 240
aaataagcca gttttaagga accgagataa gctgttttcg cccattgttc tagttctaca 300
aaatatctac agggaatcga tgaggttgta agaaatcctg aatactctat gatagtgcat 360
aacactaaaa agttgaaaga atcccgtatc atggacgatt tccttgaaca tttgagcaaa 420
gacgataaca aagcatggta tggcgcggaa gaaaccgaga gagctgcaaa attagatgca 480
atagaaacac tacttattac agatagtgta ctaaaaagga acgacgtgaa aaaacgtgaa 540
aaatacctag acctaataga gaatagtgga aacaacaatg gcaaaatatt cgtactcagt 600
acttcaaaaa tcacagtgag caacttgaca aaccaacacc ttgccaacag ggagttcttc 660
agagacatgg aggctcaaaa cgaaattatt gacagcctag acatcaatag tcatacaaca 720
gaaagcgacc acccaacttt ggctgataat agcgtataaa caatgcatac tttgtacgtt 780
caaaatacaa tgcagtagat atatttatgc atattacata taatacatat cacataggaa 840
gcaacaggcg cgttggactt ttaattttcg aggaccgcga atccttacat cacacccaat 900
cccccacaag tgatccccca cacaccatag cttcaaaatg tttctactcc tttttactc 960 ttccagattt tctcggactc cgcgcatcgc cgtaccactt caaaacaccc aagcacagca 1020
tactaaattt cccctctttc ttcctctagg gtgtcgttaa ttacccgtac taaaggtttg 1080
gaaaagaaaa aagacaccgc ctcgtttctt tttcttcgtc gaaaaaggca ataaaaattt 1140
ttatcacgtt tctttttctt gaaaattttt ttttttgatt tttttctctt tcgatgacct 1200
cccattgata tttaagttaa taaacggtca tcaatttctc aagtttcagt ttcatttttc 1260
ttgttctatt acaacttttt ttacttcttg ctcattagaa agaaagcata gcaatctaat 1320
ctaagtttta attacaaaat gaggcaggtt tggttctctt ggattgtggg attgttccta 1380 tgtttttca acgtgtcttc tgctgcttca gtcaacacta caacagaaga tgaaacggca 1440
caaattccgg ctgaagctgt catcggttac tcagatttag aaggggattt cgatgttgct 1500
gttttgccat tttccaacag cacaaataac gggttattgt ttataaatac tactattgcc 1560
agcattgctg ctaaagaaga aggggtatct ctcgagaaaa gagaggctga agctatgcca 1620
agagaaaact tcttgaagtg tttctctaag catatcccaa acaacgttgc taacccaaag 1680
ttggtctata ctcaacacga tcaattgtat atgtctattt tgaactctac tattcaaaat 1740
ttgagattca tttctgatac caccccaaaa ccattggtca ttgtcactcc ttccaacaac 1800
tcccatatcc aagctactat tttgtgttct aagaaggtcg gtttgcaaat cagaaccaga 1860
tctggtggtc acgatgccga gggtatgtcc tacatttctc aagttccttt tgtcgttgtt 1920
gatttgagaa acatgcactc catcaaaatt gatgttcact cccaaaccgc ctgggtcgaa 1980
gctggtgcca ctttgggtga agtctactac tggattaatg aaaagaatga aaatttgtcc 2040
ttcccaggtg gttactgtcc aaccgttggt gttggtggtc acttctccgg tggtggttac 2100
ggtgctttga tgagaaacta cggtttagct gctgataaca ttatcgacgc ccacttggtt 2160
aatgttgatg gtaaagtctt ggacagaaaa tctatgggtg aagatttgtt ttgggccatt 2220
agaggtggtg gtggtgagaa cttcggtatc attgctgcct ggaagatcaa attggttgct 2280

-continued

```
gttccatcta agtccactat tttttccgtt aagaagaaca tggaaatcca tggtttagtt   2340

aaattattta acaagtggca aaacattgcc tacaagtacg ataaagattt ggttttgatg   2400

acccatttca ttactaagaa tattactgac aatcacggta agaacaagac taccgttcac   2460

ggttacttct cttctatttt ccacggtggt gtcgactcct tagttgattt gatgaacaaa   2520

tcctttccag agttgggtat taagaagact gattgtaagg aattctcttg gattgacacc   2580

accatcttct actctggtgt cgtcaacttt aacactgcca actttaagaa ggaaatttta   2640

ttggatagat ccgctggtaa gaagaccgct tttccatca aattggatta cgtcaagaag   2700

ccaatccctg agactgccat ggtcaagatc ttggaaaagt tgtatgaaga agacgttggt   2760

gctggtatgt acgttttata tccatacggt ggtattatgg aagagatttc cgaatccgct   2820

attccattcc cacatagagc tggtatcatg tacgaattgt ggtacactgc ttcttgggaa   2880

aaacaagaag ataatgaaaa gcatattaac tgggttagat ccgtttacaa cttcaccact   2940

ccatatgttt ctcaaaaccc aagattggct tacttgaact atagagattt ggatttgggt   3000

aagactaacc acgcctctcc aaacaattac actcaagcta gaatctgggg tgaaaaatac   3060

ttcggtaaga acttcaacag attagtcaaa gtcaagacca aagttgaccc aaacaacttc   3120

ttcagaaacg agcaatccat tcctccattg cctccacacc atcacggcca tcatcaccat   3180

caccattagc tcgagcatgc atctagaggg ccgcatcatg taattagtta tgtcacgctt   3240

acattcacgc cctcccccca catccgctct aaccgaaaag gaaggagtta gacaacctga   3300

agtctaggtc cctatttatt tttttatagt tatgttagta ttaagaacgt tatttatatt   3360

tcaaattttt cttttttttc tgtacagacg cgtgtacgca tgtaacatta tactgaaaac   3420

cttgcttgag aaggttttgg gacgctcgaa ggctttaatt tgccaatagc ttgcagcgta   3480

gctaaactct aaaatttatc taaatcactc atataaaccg aacccttccc cttccgctta   3540

tagtacagta cctatacatt tcataaacat ggcatggcga tcagcgccaa acaatatgga   3600

aaatccacag aaagctattc attgaaaaaa tagtacaaat aagtcacatg atgatatttg   3660

attttattat atttttaaaa aaagtaaaaa ataaaaagta gtttattttt aaaaaataaa   3720

atttaaaata ttagtgtatt tgatttccga aagttaaaaa agaaatagta agaaatatat   3780

atttcattga atggatatat gaaacgttta ctggtggaag ttttgctcat atattattat   3840

tcaatagaag taataaagaa aaagttggta aagcaactta acagtaaaaa ggtaatgatt   3900

gaaaaagttt ttgaacatct aagctatatg ttgatgggtt tacaatttta ccattagtac   3960

tcatgcctat acttttctgt tcgtccttaa tgtccgcgat ttagagcaat cattgaaagt   4020

actagataca ttttagccag agaggactcg ttgacgtaga attaaaattc aaatgaattt   4080

ccgccccatt catatacccc aaataacaaa catattaaaa cttcataatt attcaaa      4137
```

<210> SEQ ID NO 91
<211> LENGTH: 102
<212> TYPE: PRT
<213> ORGANISM: Artificial Sequence
<220> FEATURE:
<223> OTHER INFORMATION: Wild Type OAC Protein

<400> SEQUENCE: 91

```
Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Val Asn
            20                  25                  30
```

Ile Ile Pro Ala Met Lys Asp Val Tyr Trp Gly Lys Asp Val Thr Gln
35 40 45

Lys Asn Lys Glu Glu Gly Tyr Thr His Ile Val Glu Val Thr Phe Glu
50 55 60

Ser Val Glu Thr Ile Gln Asp Tyr Ile Ile His Pro Ala His Val Gly
65 70 75 80

Phe Gly Asp Val Tyr Arg Ser Phe Trp Glu Lys Leu Leu Ile Phe Asp
85 90 95

Tyr Thr Pro Arg Lys Gly
100

<210> SEQ ID NO 92
<211> LENGTH: 102
<212> TYPE: PRT
<213> ORGANISM: Artificial Sequence
<220> FEATURE:
<223> OTHER INFORMATION: Variant OAC Protein - General
<220> FEATURE:
<221> NAME/KEY: MISC_FEATURE
<222> LOCATION: (1)..(102)
<223> OTHER INFORMATION: Xaa is any amino acid

<400> SEQUENCE: 92

Met Ala Val Lys His Leu Ile Val Leu Lys Phe Lys Asp Glu Ile Thr
1 5 10 15

Glu Ala Gln Lys Glu Glu Phe Phe Lys Thr Tyr Xaa Asn Leu Xaa Asn
20 25 30

Ile Ile Pro Ala Met Lys Asp Val Xaa Trp Xaa Xaa Asp Val Thr Gln
35 40 45

Lys Asn Lys Glu Glu Gly Tyr Thr His Ile Val Glu Val Thr Phe Glu
50 55 60

Ser Val Glu Xaa Ile Gln Asp Tyr Ile Xaa His Pro Ala His Val Gly
65 70 75 80

Phe Gly Asp Xaa Tyr Arg Ser Phe Trp Glu Lys Leu Leu Ile Phe Asp
85 90 95

Tyr Thr Pro Xaa Lys Xaa
100

<210> SEQ ID NO 93
<211> LENGTH: 232
<212> TYPE: PRT
<213> ORGANISM: Artificial Sequence
<220> FEATURE:
<223> OTHER INFORMATION: mScarlet Protein

<400> SEQUENCE: 93

Met Val Ser Lys Gly Glu Ala Val Ile Lys Glu Phe Met Arg Phe Lys
1 5 10 15

Val His Met Glu Gly Ser Met Asn Gly His Glu Phe Glu Ile Glu Gly
20 25 30

Glu Gly Glu Gly Arg Pro Tyr Glu Gly Thr Gln Thr Ala Lys Leu Lys
35 40 45

Val Thr Lys Gly Gly Pro Leu Pro Phe Ser Trp Asp Ile Leu Ser Pro
50 55 60

Gln Phe Met Tyr Gly Ser Arg Ala Phe Thr Lys His Pro Ala Asp Ile
65 70 75 80

Pro Asp Tyr Tyr Lys Gln Ser Phe Pro Glu Gly Phe Lys Trp Glu Arg
85 90 95

-continued

```
Val Met Asn Phe Glu Asp Gly Gly Ala Val Thr Val Thr Gln Asp Thr
            100                 105                 110

Ser Leu Glu Asp Gly Thr Leu Ile Tyr Lys Val Lys Leu Arg Gly Thr
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Glu Asp Gly Val Leu Lys Gly
145                 150                 155                 160

Asp Ile Lys Met Ala Leu Arg Leu Lys Asp Gly Gly Arg Tyr Leu Ala
                165                 170                 175

Asp Phe Lys Thr Thr Tyr Lys Ala Lys Lys Pro Val Gln Met Pro Gly
            180                 185                 190

Ala Tyr Asn Val Asp Arg Lys Leu Asp Ile Thr Ser His Asn Glu Asp
        195                 200                 205

Tyr Thr Val Val Glu Gln Tyr Glu Arg Ser Glu Gly Arg His Ser Thr
    210                 215                 220

Gly Gly Met Asp Glu Leu Tyr Lys
225                 230
```